United States Patent
Bushaboina et al.

(10) Patent No.: US 12,157,737 B2
(45) Date of Patent: *Dec. 3, 2024

(54) HETEROARYL SUBSTITUTED SPIROPIPERIDINYL DERIVATIVES AND PHARMACEUTICAL USES THEREOF

(71) Applicant: NOVARTIS AG, Basel (CH)

(72) Inventors: Mallesh Bushaboina, Bengaluru (IN); Xin Chen, Lexington, MA (US); Atwood Kim Cheung, Arlington, MA (US); Andrew James Culshaw, Norfolk (GB); Timothy Brian Hurley, Boston, MA (US); Nancy Labbe-Giguere, Arlington, MA (US); Wolfgang Miltz, Allschwil (CH); David Orain, Hesingue (FR); Tajesh Patel, Westford, MA (US); Srinivasan Rajagopalan, Bengaluru (IN); Till Roehn, Zürich (CH); David Andrew Sandham, Concord, MA (US); Gebhard Thoma, Lörrach (DE); Ritesh Bhanudasji Tichkule, Cambridge, MA (US); Rudolf Wälchli, Basel (CH)

(73) Assignee: Novartis AG, Basel (CH)

( * ) Notice: Subject to any disclaimer, the term of this patent is extended or adjusted under 35 U.S.C. 154(b) by 0 days.

This patent is subject to a terminal disclaimer.

(21) Appl. No.: 18/319,585

(22) Filed: May 18, 2023

(65) Prior Publication Data

US 2024/0043425 A1 Feb. 8, 2024

Related U.S. Application Data

(63) Continuation of application No. 17/400,458, filed on Aug. 12, 2021, now Pat. No. 11,708,366.

(30) Foreign Application Priority Data

Aug. 14, 2020 (EP) .................................... 20191191

(51) Int. Cl.
| | |
|---|---|
| *A61K 31/438* | (2006.01) |
| *A61K 31/506* | (2006.01) |
| *A61K 45/06* | (2006.01) |
| *C07D 471/10* | (2006.01) |
| *C07D 519/00* | (2006.01) |

(52) U.S. Cl.
CPC ............ *C07D 471/10* (2013.01); *A61K 45/06* (2013.01); *C07D 519/00* (2013.01)

(58) Field of Classification Search
CPC ..... A61K 31/438; A61K 31/506; A61P 11/06; A61P 9/00; A61P 29/00; A61P 37/08; A61P 17/06
USPC .................................................. 514/278, 256
See application file for complete search history.

(56) References Cited

U.S. PATENT DOCUMENTS

| | | | |
|---|---|---|---|
| 3,998,834 A | 12/1976 | Janssen et al. | |
| 11,708,366 B2 * | 7/2023 | Bushaboina | A61P 37/08 |
| | | | 514/210.16 |
| 2004/0110826 A1 | 6/2004 | Uesaka et al. | |

FOREIGN PATENT DOCUMENTS

| | | |
|---|---|---|
| WO | 2009030887 A1 | 3/2009 |
| WO | 2011076747 A1 | 6/2011 |
| WO | 2011110824 A1 | 9/2011 |
| WO | 2012055888 A1 | 5/2012 |
| WO | 2014117920 A1 | 8/2014 |
| WO | 2016071293 A1 | 5/2016 |
| WO | 2016078771 A1 | 5/2016 |
| WO | 2016177845 A1 | 11/2016 |
| WO | 2018119263 A1 | 6/2018 |

OTHER PUBLICATIONS

Vargas_Mendez_et al, An efficient synthesis of new 1-H-4-methyl-3, 4-dihydrospiro (piperidin e-4,2 (1'H)quinoline) scaffolds, Elsevier, vol. 48, pp. 2509-2512, 2007.

Database Registry, Chemical Abstracts Service, Jun. 1, 2008.

Werz, Oliver et al."Novel leukotriene biosynthesis inhibitors (2012-2016) as anti-inflammatory agents", Exptert Opinion on Therapeutic Patents, vol. 27, No. 5, pp. 607-620, 2017.

Hideo, Ago et al. "A leukotriene C4 synthase inhibitor with the backbone of 5-(5-methylene-4-oxo-4,5-dihydrothiazol-2-ylamino) isophthalic acid", Journal of Biochemistry, vol. 153, No. 5, pp. 421-429, 2013.

Kleinschmidt, Thea et al. "Tandem Benzophenone Amino Pyridines, Potent and Selective Inhibitors of Human Leukotriene C4 Synthases", Journal of Pharmacology and Experimental Therapeutics, vol. 355, No. 1, pp. 108-116, 2015.

(Continued)

*Primary Examiner* — Charanjit Aulakh
(74) *Attorney, Agent, or Firm* — Sophie Binet Cross

(57) ABSTRACT

The present invention provides a compound of formula (I) or a pharmaceutically acceptable salt thereof;

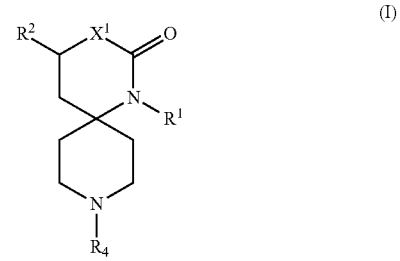

(I)

wherein $R^1$ $R^2$, $R^4$ and $X^1$ are defined herein, a method for manufacturing the compounds of the invention, and its therapeutic uses. The present invention further provides a combination of pharmacologically active agents and a pharmaceutical composition.

16 Claims, No Drawings

(56) References Cited

OTHER PUBLICATIONS

Kouznetsov Vladimir V et al, "3',4'-Dihydrospiro(piperidine-4,2'-(1'H)quinoline) Derivatives as New Antioxidant Agents with Acetylcholinesterase Inhibitory Property", Letters in Drug Design and Discovery, Bentham Science Publishers, US, vol. 7, No. 10, pp. 710-715, 2010.
Allen Charlotte E. et al. "Synthesis and evaluation of heteroaryl substituted diazaspirocycles as scaffolds to probe the ATP-binding site of protein kinases", Bioorganic & Medicinal Chemistry, vol. 21, pp. 5707-5724, 2013.
Betschart, Claudia et al Identification of a Novel Series of Orexin Receptor Antagonists with a Distinct Effect on Sleep Architecture for the Treatment of Insomnia, Journal of Medicinal Chemistry, vol. 56, No. 19, pp. 7590-7607, 2013.
Sadik et al: Experimental Dermatology, 2013, 22, 705-709; "Leukotrienes orchestrating allergic skin inflammation".
Jo-Watanabe et al. Int. J. Mol. Sci. 2019, 20, 3580 ;"The Role of leukotrienes as potential Therapeutic Targets in Allergic Disorders"—see pp. 5-6 for link between LTC4 and asthma.
Oyoshi et al. PNAS 2012, vol. 109, No. 13, 4992-4997 "Eosinophil-derived leukotriene C4 signals via type 2 cysteinyl leukotriene receptor to promote skin fibrosis in a mouse model of atopic dermatitits".

* cited by examiner

HETEROARYL SUBSTITUTED SPIROPIPERIDINYL DERIVATIVES AND PHARMACEUTICAL USES THEREOF

CROSS-REFERENCE TO RELATED APPLICATIONS

This application is a Continuation of U.S. patent application Ser. No. 17/400,458 filed Aug. 12, 2021, which claims priority to European patent application No. 20191191.4 filed on Aug. 14, 2020; the content of which is incorporated by reference in its entirety The present invention relates to novel heteroaryl substituted spiropiperidinyl compounds useful as inhibitors of leukotriene C4 synthase (LTC4S). The present invention also relates to pharmaceutical compositions comprising said compounds, methods of using said compounds in the treatment of various diseases and disorders, and processes for preparing the said novel compounds.

FIELD OF THE INVENTION

The present invention relates to compounds of formula (I) or pharmaceutically acceptable salts thereof, and to their use in inhibiting LTC4S. Hence the compounds of the invention may be useful in the treatment of diseases and/or disorders related to LTC4S. Such diseases and/or disorders typically include respiratory diseases/disorders, inflammation and/or disease/disorders having an inflammatory component. The present invention further relates to pharmaceutical compositions comprising said heteroaryl substituted spiropiperidinyl compounds of formula (I), methods of using said compounds in the treatment of various diseases and disorders, and processes for preparing the said novel compounds.

BACKGROUND OF THE INVENTION

The cysteinyl leukotrienes (cys-LTs), leukotriene C4 (LTC4) and its metabolites, LTD4 and LTE4, are proinflammatory lipid mediators in asthma and other inflammatory diseases. They are generated through the 5-lipoxygenase/LTC4 synthase (LTC4S) pathway and act via at least two distinct G protein-coupled receptors. Leukotriene (LT) $C_4$ synthase (LTC4S) catalyzes the conjugation reaction between the fatty acid $LTA_4$ and GSH to form the pro-inflammatory $LTC_4$ an important mediator of asthma.

There are many diseases/disorders that are inflammatory in their nature or have an inflammatory component. One of the major problems associated with existing treatments of inflammatory conditions is a lack of efficacy and/or the prevalence of side effects. Asthma is a chronic inflammatory disease affecting 6% to 8% of the adult population of the industrialized world. In children, the incidence is even higher, being close to 10% in most countries. Asthma is the most common cause of hospitalization for children under the age of fifteen. Treatment regimens for asthma depend upon the severity of the condition. Mild cases are either untreated or are only treated with inhaled P-agonists. Patients with more severe asthma are typically treated with anti-inflammatory compounds on a regular basis.

There is a considerable under-treatment of asthma, which is due at least in part to perceived risks with existing maintenance therapy (mainly inhaled corticosteroids). These include risks of growth retardation in children and loss of bone mineral density, resulting in unnecessary morbidity and mortality. As an alternative to steroids, LTRAs have been developed. These drugs may be given orally, but are considerably less efficacious than inhaled steroids and usually do not control airway inflammation satisfactorily. This combination of factors has led to at least 50% of all asthma patients being inadequately treated.

A similar pattern of under-treatment exists in relation to allergic disorders, where drugs are available to treat a number of common conditions but are underused in view of apparent side effects. For instance, rhinitis, conjunctivitis and dermatitis may have an allergic component, but may also arise in the absence of underlying allergy. Indeed, nonallergic conditions of this class are in many cases more difficult to treat.

Other inflammatory disorders which may be mentioned include: chronic obstructive pulmonary disease (COPD) is a common disease affecting 6% to 8% of the world population. The disease is potentially lethal, and the morbidity and mortality from the condition is considerable. At present, there is no known pharmacological treatment capable of changing the course of COPD; pulmonary fibrosis (this is less common than COPD, but is a serious disorder with a very poor prognosis); inflammatory bowel disease (a group of disorders with a high morbidity rate—today only symptomatic treatment of such disorders is available); rheumatoid arthritis and osteoarthritis (common disabling inflammatory disorders of the joints—there are currently no curative, and only moderately effective symptomatic, treatments available for the management of such conditions); diabetes, a disease affecting over 3% of the world population, and growing, causing considerable morbidity and mortality; and cardiovascular disease.

Inflammation is also a common cause of pain. Inflammatory pain may arise for numerous reasons, such as infection, surgery or other trauma. Moreover, several malignancies have inflammatory components adding to the symptomatology of the patients. Inflammation may also play a role in cancer with leukotrienes involved in cancer cell proliferation and extending cancer cell lifetimes. Thus, new and/or alternative treatments for respiratory and/or inflammatory disorders would be of benefit to all of the above-mentioned patient groups. In particular, there is a real and substantial unmet clinical need for an effective anti-inflammatory drug capable of treating inflammatory disorders, in particular asthma and atopic dermatitis, with no real or perceived side effects.

The inhibition of LTC4S may therefore be useful in the treatment of the cys-LT relevant inflammatory diseases such as asthma, allergic rhinitis, atopic dermatitis, allergic conjunctivitis, rheumatoid arthritis, chronic obstructive pulmonary disease.

For reviews on cysteinyl leukotrienes and LTC4 see B. Lam et al. Clinical and Experimental Allergy Reviews, 2004, 4, 89-95; B. Lam et al., Prostaglandins & Other Lipid Mediators, 2002, 68-69, 511-520; H.-E. Claesson et al., Journal of Internal Medicine 1999, 245, 205-277

SUMMARY OF THE INVENTION

There remains a need for new treatments and therapies for diseases or disorders related to LTC4S. The invention provides compounds, pharmaceutically acceptable salts thereof, pharmaceutical compositions thereof and combinations thereof, which compounds are LTC4S inhibitors. The invention further provides methods of treating, preventing, or ameliorating disease and/or disorders related to LTC4S, comprising administering to a subject in need thereof an effective amount of an LTC4S inhibitor.

Various embodiments of the invention are described herein.

Within certain aspects, provided herein is a compound of Formula I or a pharmaceutically acceptable salt thereof:

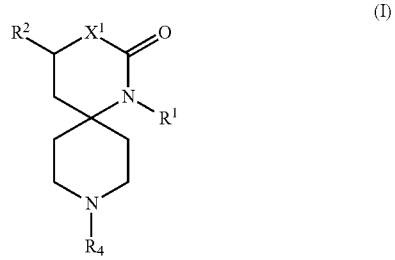

(I)

or a pharmaceutically acceptable salt thereof, wherein:
$R^1$ is phenyl optionally substituted with one or more halo substituents;
$R^2$ is H or fluoro;
$X^1$ is $CH_2$ or O;
$R^4$ is a mono or bicyclic heteroaryl, optionally substituted with one or more R3 substituents;
each $R^3$ is independently selected from $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)$NH_2$, and $NR^aR^b$, wherein $R^a$ and $R^b$ are independently H, $C_{1-6}$alkyl, $C_{3-7}$cycloalkyl, $C_{3-7}$cycloalkyl-$C_{1-6}$alkyl or halo $C_{1-6}$alkyl;
wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, C3-7cycloalkoxy, $NH_2$, $C_{1-6}$alkyl, $C_{1-6}$alkoxy, halo$C_{1-6}$alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;
$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;
wherein phenyl, heterocyclyl and $C_{3-7}$cycloakyl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl;
with the proviso that when $R^2$ is F, then $X^1$ is $CH_2$.

In another aspect, the invention provides a pharmaceutical composition comprising a therapeutically effective amount of a compound according to the definition of formula (I), or a pharmaceutically acceptable salt thereof, or subformulae thereof and one or more pharmaceutically acceptable carriers. The pharmaceutical composition is useful in the treatment of diseases and/or disorders related to LTC4S activity.

In another aspect, the invention provides a combination, in particular a pharmaceutical combination, comprising a therapeutically effective amount of the compound according to the definition of formula (I), or a pharmaceutically acceptable salt thereof, or subformulae thereof and one or more therapeutic agent.

Another aspect of the present invention relates to method of modulation LTC4S activity, more particularly inhibiting LTC4S activity. The method comprises administering to a subject in need thereof a compound of Formula (I) or subformulae thereof, or a pharmaceutically acceptable salt thereof.

Another aspect of the invention relate to method of treating a disease or a disorder selected from: respiratory diseases/disorders, inflammation and/or disease/disorders having an inflammatory component, for example allergic disorders, asthma, childhood wheezing, chronic obstructive pulmonary disease, aspirin exacerbated respiratory disease, bronchopulmonary dysplasia, cystic fibrosis, interstitial lung disease (e.g. sarcoidosis, pulmonary fibrosis, scleroderma lung disease, and usual interstitial in pneumonia), ear nose and throat diseases (e.g. sinusitis, rhinitis, nasal polyposis, rhinosinusitis, otitis media, and allergic eosinophilic esophagitis), eye diseases (e.g. conjunctivitis and giant papillary conjunctivitis), skin diseases (e.g. psoriasis, atopic dermatitis, eczema and chronic urticaria), rheumatic diseases (e.g. rheumatoid arthritis, arthrosis, psoriasis arthritis, osteoarthritis, systemic lupus erythematosus, systemic sclerosis), vasculitis (e.g. Henoch-Schonlein purpura, Loffler's syndrome and Kawasaki disease), cardiovascular diseases (e.g. atherosclerosis, cerebrovascular diseases, acute ischemic heart attacks and post-heart attack treatment), gastrointestinal diseases (e.g. eosinophilic diseases in the gastrointestinal system, inflammatory bowel disease, irritable bowel syndrome, colitis, celiaci and gastric haemorrhagia), urologic diseases (e.g. glomerulonephritis, interstitial cystitis, nephritis, nephropathy, nephrotic syndrome, hepatorenal syndrome, and nephrotoxicity), diseases of the central nervous system (e.g. cerebral ischemia, spinal cord injury, migraine, multiple sclerosis, and sleep-disordered breathing), endocrine diseases (e.g. autoimmune thyreoiditis, diabetes-related inflammation), urticaria, anaphylaxis, angioedema, oedema in Kwashiorkor, dysmenorrhoea, burn-induced oxidative injury, multiple trauma, pain (inflammatory and neuropathic), endotoxin shock, sepsis, bacterial infections (e.g. from *Helicobacter pylori, Pseudomonas aerugiosa* or *Shigella dysenteriae*), fungal infections (e.g. vulvovaginal candidasis), viral infections (e.g. hepatitis, meningitis, parainfluenza and respiratory syncytial virus), hypereosinofilic syndrome, and malignancies (e.g. Hodgkin's lymphoma, leukemia (e.g. eosinophil leukemia and chronic myelogenous leukemia), mastocytos, polycytemi vera, and ovarian carcinoma.

In particular, compounds of the invention may be useful in treating allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease. In one particular embodiment, compounds of the invention are useful in treating asthma. In another particular embodiment, compounds of the invention are useful in the treatment of atopic dermatitis or chronic urticaria.

Another aspect of the invention relates the use of a compound of Formula (I), or subformulae thereof, or a pharmaceutically acceptable salt thereof, in the manufacture of a medicament for the treatment of a disease or a disorder selected from respiratory diseases/disorders, inflammation and/or disease/disorders having an inflammatory component, for example allergic disorders, asthma, childhood wheezing, chronic obstructive pulmonary disease, aspirin exacerbated respiratory disease, bronchopulmonary dysplasia, cystic fibrosis, interstitial lung disease (e.g. sarcoidosis, pulmonary fibrosis, scleroderma lung disease, and usual interstitial in pneumonia), ear nose and throat diseases (e.g. sinusitis, rhinitis, nasal polyposis, rhinosinusitis, otitis media, and allergic eosinophilic esophagitis), eye diseases (e.g. conjunctivitis and giant papillary conjunctivitis), skin diseases (e.g. psoriasis, atopic dermatitis, eczema and chronic urticaria), rheumatic diseases (e.g. rheumatoid arthritis, arthrosis, psoriasis arthritis, osteoarthritis, systemic lupus erythematosus, systemic sclerosis), vasculitis (e.g. Henoch-Schonlein purpura, Loffler's syndrome and Kawasaki disease), cardiovascular diseases (e.g. atherosclerosis, cerebrovascular diseases, acute ischemic heart attacks and post-heart attack treatment), gastrointestinal diseases (e.g. eosinophilic diseases in the gastrointestinal system, inflammatory bowel disease, irritable bowel syndrome, colitis, celiaci and gastric haemorrhagia), urologic diseases (e.g. glomerulonephritis, interstitial cystitis, nephritis, nephropathy, nephrotic syndrome, hepatorenal syndrome, and nephrotoxicity), diseases of the central nervous system (e.g. cerebral ischemia, spinal cord injury, migraine, multiple sclerosis, and sleep-disordered breathing), endocrine diseases (e.g. autoimmune thyreoiditis, diabetes-related inflammation), urticaria, anaphylaxis, angioedema, oedema in Kwashiorkor, dysmenorrhoea, burn-induced oxidative injury, multiple trauma, pain (inflammatory and neuropathic), endotoxin shock, sepsis, bacterial infections (e.g. from *Helicobacter pylori, Pseudomonas aerugiosa* or *Shigella dysenteriae*), fungal infections (e.g. vulvovaginal candidasis), viral infections (e.g. hepatitis, meningitis, parainfluenza and respiratory syncytial virus), hypereosinofilic syndrome, and malignancies (e.g. Hodgkin's lymphoma, leukemia (e.g. eosinophil leukemia and chronic myelogenous leukemia), mastocytos, polycytemi vera, and ovarian carcinoma).

The present disclosure also provides a compound of formula I, or subformulae thereof, or a pharmaceutical acceptable salt thereof, for use in the treatment of a disease or disorder selected from respiratory diseases/disorders, inflammation and/or disease/disorders having an inflammatory component, for example allergic disorders, asthma, childhood wheezing, chronic obstructive pulmonary disease, aspirin exacerbated respiratory disease, bronchopulmonary dysplasia, cystic fibrosis, interstitial lung disease (e.g. sarcoidosis, pulmonary fibrosis, scleroderma lung disease, and usual interstitial in pneumonia), ear nose and throat diseases (e.g. sinusitis, rhinitis, nasal polyposis, rhinosinusitis, otitis media, and allergic eosinophilic esophagitis), eye diseases (e.g. conjunctivitis and giant papillary conjunctivitis), skin diseases (e.g. psoriasis, atopic dermatitis, eczema and chronic urticaria), rheumatic diseases (e.g. rheumatoid arthritis, arthrosis, psoriasis arthritis, osteoarthritis, systemic lupus erythematosus, systemic sclerosis), vasculitis (e.g. Henoch-Schonlein purpura, Loffler's syndrome and Kawasaki disease), cardiovascular diseases (e.g. atherosclerosis, cerebrovascular diseases, acute ischemic heart attacks and post-heart attack treatment), gastrointestinal diseases (e.g. eosinophilic diseases in the gastrointestinal system, inflammatory bowel disease, irritable bowel syndrome, colitis, celiaci and gastric haemorrhagia), urologic diseases (e.g. glomerulonephritis, interstitial cystitis, nephritis, nephropathy, nephrotic syndrome, hepatorenal syndrome, and nephrotoxicity), diseases of the central nervous system (e.g. cerebral ischemia, spinal cord injury, migraine, multiple sclerosis, and sleep-disordered breathing), endocrine diseases (e.g. autoimmune thyreoiditis, diabetes-related inflammation), urticaria, anaphylaxis, angioedema, oedema in Kwashiorkor, dysmenorrhoea, burn-induced oxidative injury, multiple trauma, pain (inflammatory and neuropathic), endotoxin shock, sepsis, bacterial infections (e.g. from *Helicobacter pylori, Pseudomonas aerugiosa* or *Shigella dysenteriae*), fungal infections (e.g. vulvovaginal candidasis), viral infections (e.g. hepatitis, meningitis, parainfluenza and respiratory syncytial virus), hypereosinofilic syndrome, and malignancies (e.g. Hodgkin's lymphoma, leukemia (e.g. eosinophil leukemia and chronic myelogenous leukemia), mastocytos, polycytemi vera, and ovarian carcinoma).

DETAILED DESCRIPTION OF THE INVENTION

The invention therefore provides a compound of the formula (I):

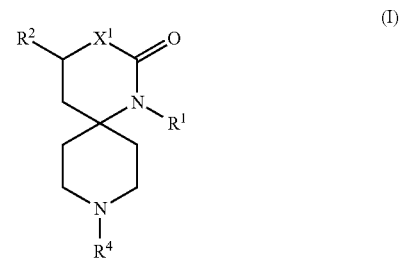

or a pharmaceutically acceptable salt thereof, wherein:
$R^1$ is phenyl optionally substituted with one or more halo substituents;
$R^2$ is H or fluoro;
$X^1$ is $CH_2$ or O;
$R^4$ is a mono or bicyclic heteroaryl, optionally substituted with one or more R3 substituents;
each $R^3$ is independently selected from $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)OC$_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein R$^a$ and R$^b$ are independently H, $C_{1-6}$alkyl, $C_{3-7}$cycloalkyl, $C_{3-7}$cycloalkyl-$C_{1-6}$alkyl or halo $C_{1-6}$alkyl;
wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, C3-7cycloalkoxy, NH$_2$, $C_{1-6}$alkyl, $C_{1-6}$alkoxy, halo$C_{1-6}$alkoxy, hydroxyC1-6alkyl, —S—C$_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;
$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkylC$_{1-6}$alkyl, phenyl, benzyl, 4-10 membered heterocyclyl, 5-10 membered heteroaryl;
wherein phenyl, heterocyclyl and $C_{3-7}$cycloakyl, $C_{3-7}$cycloalkylC$_{1-6}$alkyl, $C_{3-7}$cycloalkylC$_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl;
with the proviso that when $R^2$ is F, then $X^1$ is $CH_2$.

Unless specified otherwise, the term "compounds of the present invention" refers to compounds of formula (I) and subformulae thereof, and salts thereof, as well as all stereoisomers (including diastereoisomers and enantiomers), rotamers, tautomers and isotopically labeled compounds (including deuterium substitutions), as well as inherently formed moieties.

For purpose of the interpreting this specification, the following definitions will apply unless specified otherwise and whether appropriate, terms used in the singular will also include the plural and vice versa.

It must be noted that as used herein and in the appended claims, the singular forms "a", "an" and "the" include plural referents unless the context clearly dictates otherwise. Thus, for example, reference to "the compound" includes reference to one or more compounds; and so forth.

Definitions

As used herein, the term "$C_{1-6}$alkyl" refers to a straight or branched hydrocarbon chain radical consisting solely of carbon and hydrogen atoms, containing no unsaturation, having from one to six carbon atoms, and which is attached to the rest of the molecule by a single bond. The term "$C_{1-2}$alkyl" is to be construed accordingly. Examples of $C_{1-6}$alkyl include, but are not limited to, methyl, ethyl, n-propyl, 1-methylethyl (iso-propyl), n-butyl, n-pentyl and 1,1-dimethylethyl (t-butyl).

As used herein, the term "$C_{1-6}$alkoxy" refers to a radical of the formula —$OR_a$ where $R_a$ is a $C_{1-6}$alkyl radical as generally defined above. Examples of $C_{1-6}$alkoxy include, but are not limited to, methoxy, ethoxy, propoxy, iso-propoxy, butoxy, isobutoxy, pentoxy, and hexoxy.

As used herein, the term "$C_{3-7}$cycloalkyl" refers to a stable mono- or bicyclic saturated hydrocarbon radical consisting solely of carbon and hydrogen atoms, having from three to seven carbon atoms. $C_{3-6}$cycloalkyl is to be construed the same way. Cycloalkyl groups can include bridged rings as well as spirocyclic rings. Examples of $C_{3-7}$cycloalkyl include, but are not limited to, cyclopropyl, cyclobutyl, cyclopentyl, cyclohexyl and cycloheptyl.

"Halogen" refers to bromo, chloro, fluoro or iodo.

As used herein, the term "halo$C_{1-6}$alkyl" refers to $C_{1-6}$alkyl radical, as defined above, substituted by one or more halo radicals, as defined above. Examples of halogen$C_{1-6}$alkyl include, but are not limited to, trifluoromethyl, difluoromethyl, fluoromethyl, trichloromethyl, 2,2,2-trifluoroethyl, 1,3-dibromopropan-2-yl, 3-bromo-2-fluoropropyl and 1,4,4-trifluorobutan-2-yl.

As used herein, the term "halo$C_{1-6}$alkoxy" refers to $C_{1-6}$alkoxy radical, as defined above, substituted by one or more halo radicals, as defined above. Examples of halo$C_{1-6}$alkyl include, but are not limited to, trifluoromethoxy, difluoromethoxy, fluoromethoxy, trichloromethoxy, and 2,2,2-trifluoroethoxy.

As used herein, the term "heterocyclyl" refers to a heterocyclic group that is saturated or partially saturated and is preferably a monocyclic or a polycyclic ring (in case of a polycyclic ring particularly a bicyclic, tricyclic or spirocyclic ring); and has 3 to 24, more preferably 4 to 16, most preferably 5 to 10 and most preferably 5 or 6 ring atoms; wherein one or more, preferably one to four, especially one or two ring atoms are a heteroatom (the remaining ring atoms therefore being carbon). The term heterocyclyl excludes heteroaryl. The heterocyclic group can be attached at a heteroatom or a carbon atom. The heterocyclyl can include fused or bridged rings as well as spirocyclic rings. In one embodiment, the heterocyclyl is a 5-7 monocyclic ring containing 1 or 2 heteroatoms. In another embodiment, the heterocyclyl is a 6-10 spiroheterocyclyl. Examples of heterocycles include dihydrofuranyl, dioxolanyl, dioxanyl, dithianyl, piperazinyl, pyrrolidine, dihydropyranyl, oxathiolanyl, dithiolane, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl. A non limiting example of a spiroheterocyclyl is azaspiro[2.3]hexanyl. A non limiting example of a bridged heterocyclic ring is bicyclo[1.1.1]pentanyl.

As used herein, the term "heteroaryl" refers to a 5-14 membered monocyclic- or bicyclic-ring system, having 1 to 8 heteroatoms. Each heteroatoms is independently selected from O, N or S wherein S and N may be oxidized to various oxidation states. Typically, the heteroaryl is a 5-10 membered ring system (e.g., 5- or 6-membered monocycle or an 8-10 membered bicycle).

Typically a monocyclic heteroaryl contains from 5 or 6 ring members selected from carbon atoms and 1 to 4 heteroatoms, and. Typical monocyclic heteroaryl groups include thienyl, furyl, pyrrolyl, imidazolyl, pyrazolyl, thiazolyl, isothiazolyl, oxa-2,3-diazolyl, oxa-2,4-diazolyl, oxa-2,5-diazolyl, oxa-3,4-diazolyl, thia-2,3-diazolyl, thia-2,4-diazolyl, thia-2,5-diazolyl, thia-3,4-diazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

When the heteroaryl is substituted with a hydroxyl group, the compounds may exist in various tautomeric form. One non limiting example of tautomerisation is the following:

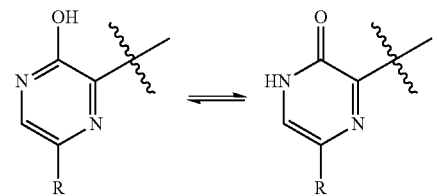

As used herein, the term "aryl" refers to an aromatic hydrocarbon group having 6-20 carbon atoms in the ring portion. Typically, aryl is monocyclic, bicyclic or tricyclic aryl having 6-20 carbon atoms. Non-limiting examples include phenyl, naphthyl. In a preferred embodiment, aryl is phenyl.

Various embodiments of the invention are described herein. It will be recognized that features specified in each embodiment may be combined with other specified features to provide further embodiments of the present invention.

In embodiment 1, the invention provides a compound of the formula (I), or a pharmaceutically acceptable salt thereof, as described above.

In embodiment 2, the invention provides a compound of the formula (I), or a pharmaceutically acceptable salt thereof, according to embodiment 1, wherein $R^4$ is selected from the group consisting of pyrimidinyl, pyrazinyl, triazolyl, triazinyl, pyridinyl, pyridine oxide, pyrimidine oxide, pyrazine oxide, quinolinyl, quinazolinyl, quinoxalinyl, indazolyl, pyrazolopyrimidinyl, pyridopyrazinyl, triazolopyridazinyl, benzooxazolyl, oxadiazolyl, tetrazolyl, thiadiazolyl, oxazolyl, and thiazolyl, each of which is optionally substituted with one or more $R^3$ substituents;

each $R^3$ is independently selected from $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)OC$_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein R$^a$ and R$^b$ are independently H, $C_{1-6}$alkyl, $C_{3-7}$cycloalkyl, $C_{3-7}$cycloalkyl-$C_{1-6}$alkyl or halo $C_{1-6}$alkyl;

wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, C3-7cycloalkoxy, NH$_2$, $C_{1-6}$alkyl, $C_{1-6}$alkoxy, haloC$_{1-6}$alkoxy, hydroxyC1-6alkyl, —S—$C_{1-6}$alkyl; —S-(haloC$_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl; and wherein $R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;

wherein phenyl, heterocyclyl and $C_{3-7}$cycloakyl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl.

In embodiment 3, the invention provides a compound of Formula (I) according to embodiment 1 or 2, or a pharmaceutically acceptable salt thereof, wherein $R^4$ is selected from

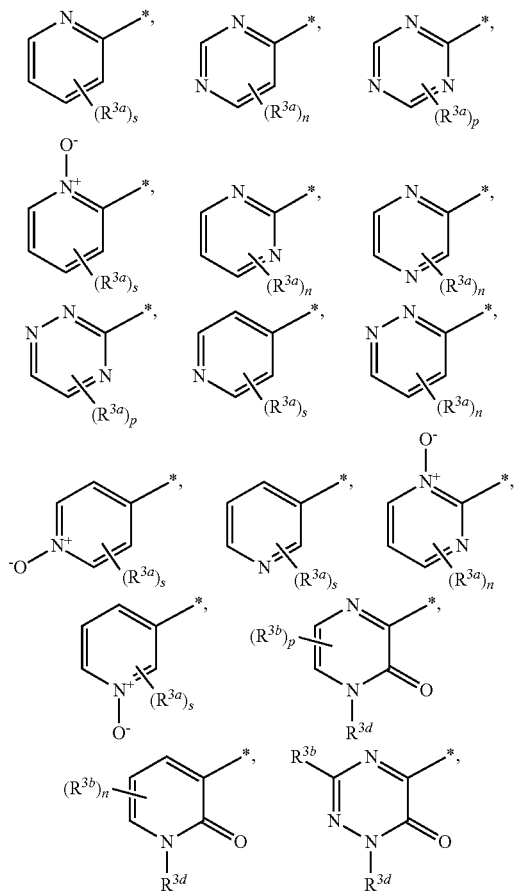

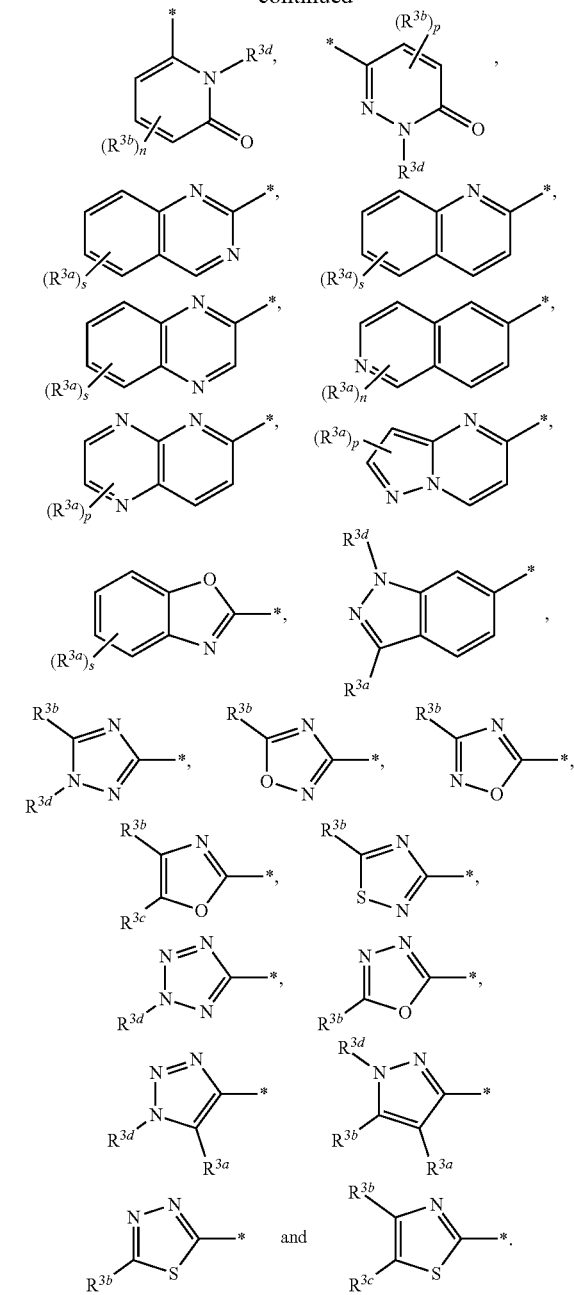

wherein the * depicts the point of attachment to the nitrogen of the spiropiperidinyl moiety; and wherein n is an integer between 1 and 3; p is 1 or 2, s is an integer between 1 and 4; and $R^{3a}$, $R^{3b}$ and $R^{3c}$ are independently selected from the group consisting of H, $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)OC$_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein R$^a$ and R$^b$ are independently H, $C_{1-6}$alkyl, $C_{3-7}$cycloalkyl, $C_{3-7}$cycloalkyl-$C_{1-6}$alkyl or halo $C_{1-6}$alkyl;

wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, $C_{3-7}$cycloalkoxy, $NH_2$, $C_{1-6}$alkyl, $C_{1-6}$alkoxy, halo$C_{1-6}$ alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;

$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;

wherein phenyl, heterocyclyl and $C_{3-7}$cycloakyl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl; and wherein $R^{3d}$ is selected from H, $C_{6-10}$aryl, $C_{1-6}$alkyl, halo$C_{1-6}$ alkyl, $C_{3-6}$cycloalkyl, 5- or 6-membered heteroaryl; and wherein said aryl, cycloalkyl, heteroaryl are further optionally substituted with one or more substituents independently selected from $C_{3-6}$cycloalkyl, $C_{1-6}$alkyl, $C_{1-6}$ alkoxy, halo$C_{1-6}$alkoxy, halo and halo$C_{1-6}$alkyl; or a pharmaceutically acceptable salt thereof.

In embodiment 4, the invention pertains to a compound according to any one of embodiments 1 to 3, wherein the compound has Formula (II):

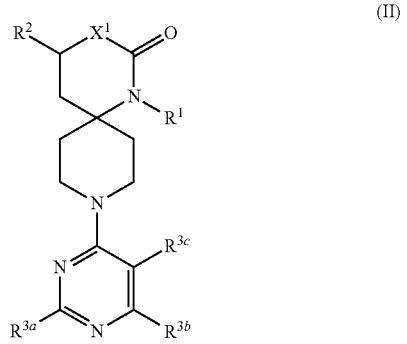

(II)

wherein $R^{3a}$, $R^{3b}$ and $R^{3c}$ are independently selected from the group consisting of H, $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)NH_2, and NR$^a$R$^b$, wherein R$^a$ and R$^b$ are independently H, $C_{1-6}$alkyl, $C_{3-7}$cycloalkyl, $C_{3-7}$cycloalkyl-$C_{1-6}$alkyl or halo $C_{1-6}$ alkyl;

wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, $C_{3-7}$cycloalkoxy, $NH_2$, $C_{1-6}$alkyl, $C_{1-6}$alkoxy, halo$C_{1-6}$ alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;

$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;

wherein phenyl, heterocyclyl and $C_{3-7}$cycloakyl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl; or a pharmaceutically acceptable salt thereof.

In a particular aspect of this embodiment, at least one of $R^{3a}$, $R^{3b}$ and $R^{3c}$ is not hydrogen.

In embodiment 5, the invention relates to compound of Formula (II), or a pharmaceutically acceptable salt thereof, wherein $R^{3a}$ is H; $NH_2$ or hydroxy$C_{1-3}$alkyl;

$R^{3b}$ is selected from the group consisting of halo, $C_{1-6}$alkyl, halo$C_{1-6}$alkyl, $C_{3-7}$cycloalkyl, $OR^5$, 4-10 membered heterocyclyl, 5- to 10-membered heteroaryl, phenyl, and wherein said heterocyclyl, heteroaryl, phenyl and cycloalkyl is further optionally substituted with one or more substituents independently selected from $C_{1-6}$alkyl, $C_{1-6}$alkoxy, halo$C_{1-6}$ alkoxy, halo and halo$C_{1-6}$alkyl; wherein $R^5$ is $C_{1-6}$alkyl, halo$C_{1-6}$alkyl, $C_{3-7}$cycloalkyl, phenyl, benzyl, 4-10 membered heterocyclyl, 5-10 membered heteroaryl;

wherein phenyl, heterocyclyl or $C_{3-7}$cycloakyl is optionally substituted by one or more substituents independently selected from $C_{1-6}$alkyl, halo$C_{1-6}$alkyl, $C_{1-6}$alkoxy, halo; and $R^{3c}$ is H or halo.

In another aspect of embodiment 5, the invention relates to compound of Formula (II), or a pharmaceutically acceptable salt thereof, wherein $R^{4a}$ is H or $NH_2$, —$CH_2OH$;

$R^{3b}$ is selected from the group consisting of halo, $C_{1-6}$alkyl, halo$C_{1-6}$alkyl, $C_{3-7}$cycloalkyl, $OR^5$, a 4-10 membered heterocyclyl selected from:

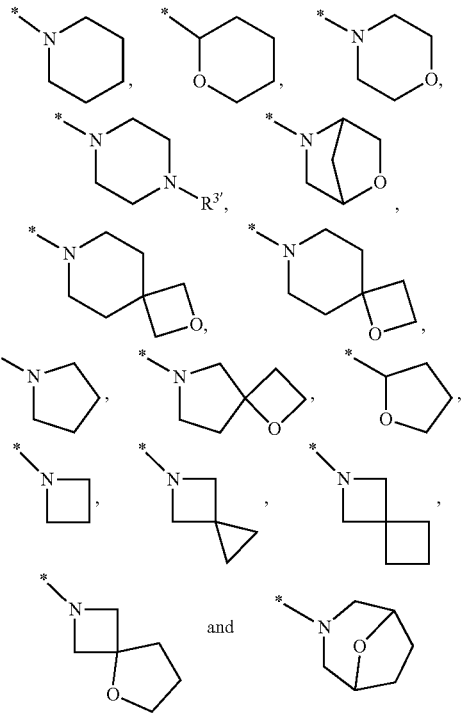

wherein $R^3$ is H, $C_{1-6}$alkyl or halo$C_{1-6}$alkyl;

or $R^{3b}$ is a 5- to 10-membered heteroaryl selected from:

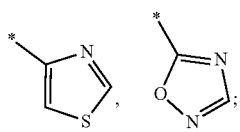

or $R^{3b}$ is a phenyl;

wherein said above heterocyclyl, heteroaryl, phenyl and cycloalkyl are further optionally substituted with one or more substituents independently selected from $C_{1-6}$alkyl, $C_{1-6}$ alkoxy, halo$C_{1-6}$alkoxy, halo and halo$C_{1-6}$ alkyl;

$R^5$ is $C_{1-6}$alkyl, halo$C_{1-6}$alkyl, $C_{3-7}$cycloalkyl, phenyl, benzyl, a 4-10 membered heterocyclyl selected from:

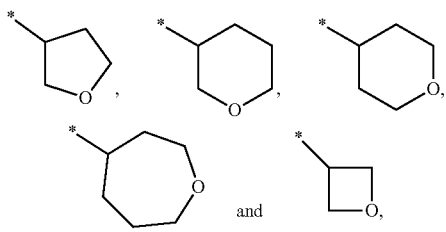

or $R^5$ is a phenyl, a benzyl or a pyridinyl;

wherein cycloalkyl, heterocyclyl, phenyl, benzyl and pyridinyl are optionally substituted with one or more substituents independently selected from halo, $C_{1-6}$alkyl, halo$C_{1-6}$alkyl and $C_{3-7}$alkoxy; and and $R^{4c}$ is H or halo.

In embodiment 6, the invention relates to a compound according to any one of embodiments 1 to 3, wherein the compound has Formula (III):

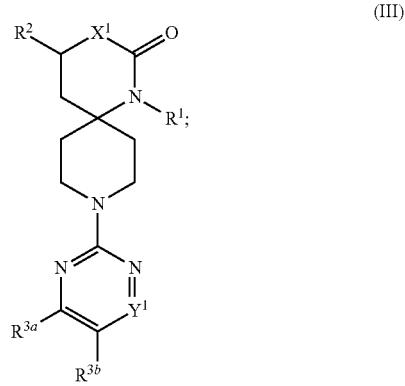

wherein wherein $Y^1$ is N or $CR^{3c}$; and wherein $R^{3a}$, $R^{3b}$ and $R^{3c}$ are independently selected from the group consisting of H, $C_{6-10}$aryl, benzyl, $C_{1-6}$alkyl, $C_{3-7}$cycloalkoxy, hydroxy$C_{1-6}$alkyl, $C_{1-6}$ alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and $NR^aR^b$, wherein $R^a$ and $R^b$ are independently H, $C_{1-6}$alkyl, $C_{3-7}$cycloalkyl, $C_{3-7}$cycloalkyl-$C_{1-6}$ alkyl or halo $C_{1-6}$alkyl;

wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, $C_{3-7}$cycloalkoxy, NH$_2$, $C_{1-6}$alkyl, $C_{1-6}$alkoxy, halo$C_{1-6}$ alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;

$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;

wherein phenyl, heterocyclyl and $C_{3-7}$cycloakyl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl; or a pharmaceutically acceptable salt thereof.

In a particular aspect of this embodiment, at least one of $R^{3a}$, $R^{3b}$ and $R^{3c}$ is not hydrogen.

In one particular aspect of embodiment 6; the invention relates to compound of Formula (III), or a pharmaceutically acceptable salt thereof, wherein $R^{3a}$, $R^{3b}$ and $R^{3c}$ are independently selected from H, $C_{6-10}$aryl, $C_{3-6}$cycloalkoxy, halo$C_{1-6}$alkyl, halo$C_{1-6}$alkoxy, OH, $C_{3-6}$cycloalkyl, 5- or 6-membered heteroaryl, a 5-10 membered heterocyclyl and $NR^aR^b$, wherein $R^a$ and $R^b$ are independently H, $C_{1-6}$alkyl, $C_{3-6}$cycloalkyl, $C_{3-7}$cycloalkyl-$C_{1-6}$alky or halo$C_{1-6}$alkyl or a; and wherein said aryl, heterocyclyl, heteroaryl, $C_{3-6}$cycloalkyl, $C_{3-6}$cycloalkoxy are further optionally substituted with one or more substituents independently selected from $C_{3-6}$cycloalkyl, $C_{1-6}$alkyl, $C_{1-6}$alkoxy, halo$C_{1-6}$ alkoxy, halo and halo$C_{1-6}$alkyl; or a pharmaceutically acceptable salt thereof. In a particular aspect of this embodiment, when $Y^1$ is $CR^{3c}$; at least one of $R^{3a}$, $R^{3b}$ and $R^{3c}$ is not hydrogen. In yet another aspect of this embodiment, when $Y^1$ is N, at least one of $R^{3a}$, and $R^{3b}$ is not hydrogen.

In another aspect of embodiment 6, the invention relates to compound of Formula (III), or a pharmaceutically acceptable salt thereof, wherein $Y^1$ is $CR^{3c}$; $R^{3b}$ and $R^{3c}$ are H; $R^{3a}$ is selected from the group consisting of H, halo, halo$C_{1-6}$ alkyl, $C_{3-6}$cycloalkyl, halo$C_{1-6}$alkoxy, a 5-10 membered heterocyclyl, $NR^aR^b$, wherein $R^a$ and $R^b$ are independently H, $C_{1-6}$alkyl, $C_{3-6}$cycloalkyl, $C_{3-7}$cycloalkyl-$C_{1-6}$alkyl or halo$C_{1-6}$alkyl; and wherein said cycloalkyl, heterocyclyl are further optionally substituted with one or more substituents independently selected from $C_{1-6}$alkyl, $C_{1-6}$alkoxy, halo$C_{1-6}$ alkoxy, halo and halo$C_{1-6}$alkyl.

In another aspect of the embodiment 6, the invention pertains to a compound according to any one of the subembodiments 6, according to Formula (III), or a pharmaceutically acceptable salt thereof, wherein $Y^1$ is $CR^{3c}$.

In another aspect of the embodiment 6, the invention pertains to a compound according to any one of the subembodiments 6, according to Formula (III), or a pharmaceutically acceptable salt thereof, wherein $Y^1$ is N.

In embodiment 7, the invention pertains to a compound according to any one of embodiments 1 to 3, wherein the compound has Formula (IV), or a pharmaceutically acceptable salt thereof;

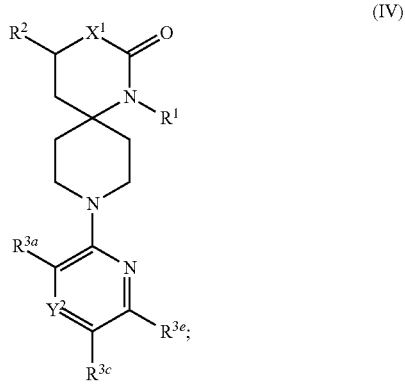

(IV)

and wherein
$R^1$ is as defined in Formula I,
$Y^2$ is N or $CR^{3b}$; and wherein
$R^{3a}$, $R^{3b}$, $R^{3c}$ and $R^{3e}$ are independently selected from H, $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$ alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein $R^a$ and $R^b$ are independently H, $C_{1-6}$alkyl, $C_{3-7}$cycloalkyl, $C_{3-7}$cycloalkyl-$C_{1-6}$alkyl or halo$C_{1-6}$alkyl;
wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, $C_{3-7}$cycloalkoxy, NH$_2$, $C_{1-6}$alkyl, $C_{1-6}$alkoxy, halo$C_{1-6}$alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;
$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;
wherein phenyl, heterocyclyl and $C_{3-7}$cycloakyl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or halo$C_{1-6}$alkyl; or a pharmaceutically acceptable salt thereof.

In one aspect of embodiment 7, the invention relates to a compound according to Formula (IV) or a pharmaceutically acceptable salt thereof, wherein $R^{3a}$, $R^{3b}$, $R^{3c}$ and $R^{3e}$ are independently selected from H, $C_{6-10}$aryl, $C_{3-6}$cycloalkoxy, halo$C_{1-6}$alkyl, halo$C_{1-6}$alkoxy, OH, $C_{3-6}$cycloalkyl, 5- or 6-membered heteroaryl, a 5-10 membered heterocyclyl and NR$^a$R$^b$, wherein $R^a$ and $R^b$ are independently H, $C_{1-6}$alkyl, $C_{3-6}$cycloalkyl, $C_{3-7}$cycloalkyl-$C_{1-6}$ alkyl or halo$C_{1-6}$alkyl; and
wherein said aryl, heterocyclyl, heteroaryl, $C_{3-6}$cycloalkyl, $C_{3-6}$cycloalkyl-$C_{1-6}$alkyl, $C_{3-6}$cycloalkoxy are further optionally substituted with one or more substituents independently selected from $C_{3-6}$cycloalkyl, $C_{1-6}$alkyl, $C_{1-6}$alkoxy, halo$C_{1-6}$alkoxy, halo and halo$C_{1-6}$alkyl; or a pharmaceutically acceptable salt thereof. In a particular aspect of this embodiment, when $Y^2$ is $CR^{3b}$; at least one of $R^{3a}$, $R^{3b}$, $R^{3c}$ and $R^{3e}$ is not hydrogen. In yet another aspect of this embodiment, when $Y^2$ is N, at least one of $R^{3a}$, $R^{3c}$ and $R^{3d}$ is not hydrogen. Preferably the pyridine or pyrazine ring is substituted at the $R^{3b}$ position. (i.e. meta position).

In one aspect of embodiment 7, and subembodiments of embodiment 6, the invention relates to a compound according to Formula (IV), or a pharmaceutically acceptable salt thereof, wherein $Y^2$ is $CR^{3b}$.

In another aspect of embodiment 7, and subembodiments of embodiment 6, the invention relates to a compound according to Formula (IV), or a pharmaceutically acceptable salt thereof, wherein $Y^2$ is N.

In embodiment 8, the invention pertains to a compound according to any one of embodiments 1 to 3, wherein the compound has Formula (V)

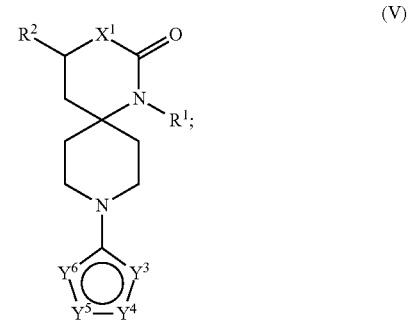

(V)

wherein
$Y^3$ is N, NR$^{3d}$ or $CR^{3a}$;
$Y^4$ is N, NR$^{3f}$ or $CR^{3b}$;
$Y^5$ is N, NR$^{3g}$ or $CR^{3c}$;
$Y^6$ is N, NR$^{3h}$ or $CR^{3e}$;
wherein $R^{3a}$, $R^{3b}$, $R^{3c}$, $R^{3e}$ are independently from H, $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein $R^a$ and $R^b$ are independently H, $C_{1-6}$alkyl, $C_{3-7}$cycloalkyl, $C_{3-7}$cycloalkyl-$C_{1-6}$alkyl or halo$C_{1-6}$alkyl;
wherein said aryl, heterocyclyl, heteroaryl, $C_{3-7}$cycloalkyl, $C_{3-7}$cycloakenyl, $C_{3-7}$cycloalkoxy are further optionally substituted with one or more substituents independently selected from OH, CN, $C_{3-7}$cycloalkyl, C3-7cycloalkoxy, NH$_2$, $C_{1-6}$alkyl, $C_{1-6}$alkoxy, halo$C_{1-6}$alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$ alkyl, phenyl optionally further substituted with halo; and heteroaryl optionally substituted with halo, $C_{1-6}$alkyl, halo$C_{1-6}$alkyl or $C_{3-7}$cycloalkyl;
$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;
wherein phenyl, heterocyclyl and $C_{3-7}$cycloakryl, $C_{3-7}$cycloalkyl$C_{1-6}$alkyl, $C_{3-7}$cycloalkyl$C_{1-6}$alkenyl is optionally substituted by one or more substituents selected from $C_{1-6}$alkyl, $C_{1-6}$ alkoxy, halo, phenyl optionally further substituted with halo; heterocyclyl optionally further substituted with $C_{1-6}$alkyl or haloC$_{1-6}$alkyl;

wherein $R^{3d}$, $R^{3f}$, $R^{3g}$, $R^{3h}$ are independently selected from H, $C_{6-10}$aryl, $C_{1-6}$alkyl, haloC$_{1-6}$ alkyl, $C_{3-6}$cycloalkyl, 5- or 6-membered heteroaryl;

and wherein said aryl, heteroaryl, $C_{3-6}$cycloalkyl are further optionally substituted with one or more substituents independently selected from $C_{3-6}$cycloalkyl, $C_{1-6}$alkyl, $C_{1-6}$alkoxy, haloC$_{1-6}$alkoxy, halo and haloC$_{1-6}$alkyl; or a pharmaceutically acceptable salt thereof.

The inner circle in the 5 membered ring shown in formula (V) means that the ring is an aromatic ring, and hence the members $Y^3$, $Y^4$, $Y^5$ and/or $Y^6$ have to be selected accordingly not to violate aromaticity.

In embodiment 9, the invention pertains to a compound according to embodiment 8; or a pharmaceutically acceptable salt thereof, wherein the moiety

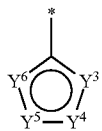

is selected from the following:

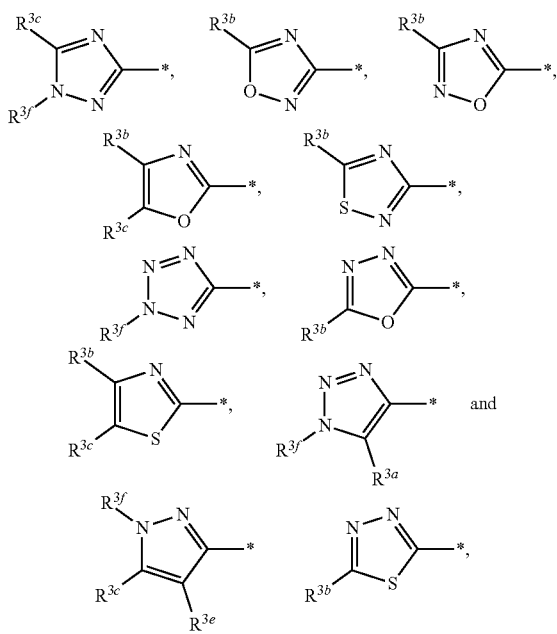

wherein the * depicts the point of attachment to the nitrogen of the spiropiperidinyl moiety and $R^{3a}$, $R^{3b}$, $R^{3c}$, $R^{4e}$ and $R^{4f}$ are as defined in embodiment 8 and * depicts the point of attachment to the nitrogen of the spiropiperidinyl moiety.

In some aspect of embodiment 9, $R^{3a}$ is H; $R^{3b}$ or $R^{3c}$ is selected from phenyl optionally substituted with one or more halo; $C_{1-6}$alkyl; CN, haloC$_{1-6}$alkyl; $C_{3-6}$cycloalkyl, a 5-10 membered heterocyclyl; and NR$^a$R$^b$, wherein R$^a$ and R$^b$ are independently H, $C_{1-6}$alkyl, $C_{3-6}$cycloalkyl or haloC$_{1-6}$alkyl; wherein heterocyclyl is optionally substituted with haloC$_{1-6}$ alkyl or $C_{1-6}$alkyl; and $R^{3f}$ is phenyl optionally substituted with one or more halo.

In embodiment 10, the invention relates to a compound of any of the previous embodiment and sub-embodiments (e.g. a compound according to any one of the formulae (I) to (V)), or a pharmaceutically acceptable salt thereof, wherein $R^1$ is phenyl optionally substituted with one or two substituents independently selected from F and Cl.

In one aspect of embodiment 10, the invention relates to a compound according to embodiment 10, or a pharmaceutically acceptable salt thereof wherein $R^1$ is selected from:

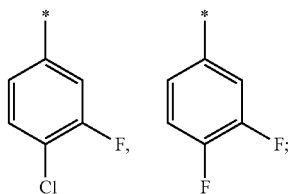

wherein * depicts the point of attachment of the phenyl to the lactam nitrogen of the spiropiperidinyl moiety.

In embodiment 11, the invention relates to a compound of any of the previous embodiment and sub-embodiments wherein $X^1$ is CH$_2$ and $R^2$ is F or H, or a pharmaceutically acceptable salt thereof. In one aspect of embodiment 11, $R^2$ is H. In another aspect of embodiment 11, $R^2$ is F; or a pharmaceutically acceptable salt thereof.

In embodiment 12, the invention relates to a compound of any of the previous embodiment and sub-embodiments wherein $X^1$ is O and $R^2$ is H, or a pharmaceutically acceptable salt thereof.

In embodiment 13, the invention relates to a compound of formula (I), according to embodiment 1, wherein the compound is selected from:

1-(4-chloro-3-fluorophenyl)-9-(1-(4-fluorophenyl)-1H-1,2,4-triazol-3-yl)-1,9-diazaspiro[5.5]undecan-2-one;

1-(4-chloro-3-fluorophenyl)-9-(6-(trifluoromethyl)benzo[d]oxazol-2-yl)-1,9-diazaspiro[5.5]undecan-2-one;

1-(4-chloro-3-fluorophenyl)-9-(2-(trifluoromethyl)pyrazolo[1,5-a]pyrimidin-5-yl)-1,9-diazaspiro[5.5]undecan-2-one;

1-(3,4-difluorophenyl)-9-(6-(2,2,2-trifluoroethoxy)pyrimidin-4-yl)-1,9-diazaspiro[5.5]undecan-2-one;

1-(4-chloro-3-fluorophenyl)-9-(6-(2,2,2-trifluoroethoxy)pyrimidin-4-yl)-1,9-diazaspiro[5.5]undecan-2-one;

1-(4-chloro-3-fluorophenyl)-9-(6-(2,2-difluoroethoxy)pyrimidin-4-yl)-1,9-diazaspiro[5.5]undecan-2-one;

1-(4-chloro-3-fluorophenyl)-9-(5-fluoro-6-(pyrrolidin-1-yl)pyrimidin-4-yl)-1,9-diazaspiro[5.5]undecan-2-one;

1-(4-chloro-3-fluorophenyl)-9-(5-fluoro-6-(3-(trifluoromethyl)azetidin-1-yl)pyrimidin-4-yl)-1,9-diazaspiro[5.5]undecan-2-one;

1-(4-chloro-3-fluorophenyl)-9-(4-(pyrrolidin-1-yl)-1,3,5-triazin-2-yl)-1,9-diazaspiro[5.5]undecan-2-one;

1-(4-chloro-3-fluorophenyl)-9-(4-(2,2,2-trifluoroethoxy)pyridin-2-yl)-1,9-diazaspiro[5.5]undecan-2-one;

2-(1-(4-chloro-3-fluorophenyl)-2-oxo-1,9-diazaspiro[5.5]undecan-9-yl)-4-(4-fluorophenyl)pyridine 1-oxide;

9-(2-(5-azaspiro[2.3]hexan-5-yl)pyrimidin-4-yl)-1-(4-chloro-3-fluorophenyl)-1,9-diazaspiro[5.5]undecan-2-one;

9-(4-(5-azaspiro[2.3]hexan-5-yl)pyrimidin-2-yl)-1-(4-chloro-3-fluorophenyl)-1,9-diazaspiro[5.5]undecan-2-one;

1-(4-chloro-3-fluorophenyl)-9-(2-(3,3-dimethylazetidin-1-yl)pyrimidin-4-yl)-1,9-diazaspiro[5.5]undecan-2-one;

1-(4-chloro-3-fluorophenyl)-9-(5-(((1R,2R/1S,2S)-2-(trifluoromethyl)cyclopropyl)-1,2,4-oxadiazol-3-yl)-1,9-diazaspiro[5.5]undecan-2-one;

1-(4-chloro-3-fluorophenyl)-9-(5-(3-(trifluoromethyl)bicyclo[1.1.1]pentan-1-yl)-1,2,4-oxadiazol-3-yl)-1,9-diazaspiro[5.5]undecan-2-one;

1-(4-chloro-3-fluorophenyl)-9-(6-hydroxy-3-(pyrrolidin-1-yl)-1,2,4-triazin-5-yl)-1,9-diazaspiro[5.5]undecan-2-one;

1-(4-chloro-3-fluorophenyl)-9-(6-(4-fluorophenyl)-4-methyl-3-oxo-3,4-dihydropyrazin-2-yl)-1,9-diazaspiro[5.5]undecan-2-one;

1-(4-chloro-3-fluorophenyl)-9-(5-cyclopentyl-1,2,4-triazin-3-yl)-1,9-diazaspiro[5.5]undecan-2-one;

1-(4-chlorophenyl)-9-(6-(4-fluorophenyl)pyridin-2-yl)-1,9-diazaspiro[5.5]undecan-2-one  1-(4-chloro-3-fluorophenyl)-9-(4-(trifluoromethyl)pyrimidin-2-yl)-1,9-diazaspiro[5.5]undecan-2-one;

1-(4-chloro-3-fluorophenyl)-9-(7-(trifluoromethyl)quinazolin-2-yl)-1,9-diazaspiro[5.5]undecan-2-one;

1-(4-chloro-3-fluorophenyl)-9-(5-(4-fluorophenyl)oxazol-2-yl)-1,9-diazaspiro[5.5]undecan-2-one;

1-(4-chloro-3-fluorophenyl)-9-(2-phenyl-2H-tetrazol-5-yl)-1,9-diazaspiro[5.5]undecan-2-one;

1-(4-chloro-3-fluorophenyl)-9-(5-(3,3-difluoropyrrolidin-1-yl)-1,2,4-thiadiazol-3-yl)-1,9-diazaspiro[5.5]undecan-2-one;

1-(4-chloro-3-fluorophenyl)-9-(3-(4-fluorophenyl)-1H-1,2,4-triazol-5-yl)-1,9-diazaspiro[5.5]undecan-2-one;

1-(4-chloro-3-fluorophenyl)-9-(5-cyclohexyloxazol-2-yl)-1,9-diazaspiro[5.5]undecan-2-one;

1-(4-chloro-3-fluorophenyl)-9-(5-(3-(trifluoromethyl)azetidin-1-yl)-1,2,4-thiadiazol-3-yl)-1,9-diazaspiro[5.5]undecan-2-one;

1-(4-chloro-3-fluorophenyl)-9-(5-(pyrrolidin-1-yl)-1,2,4-thiadiazol-3-yl)-1,9-diazaspiro[5.5]undecan-2-one;

1-(4-chloro-3-fluorophenyl)-9-(5-phenyl-1,3,4-oxadiazol-2-yl)-1,9-diazaspiro[5.5]undecan-2-one;

1-(4-chloro-3-fluorophenyl)-9-(1-(4-fluorophenyl)-1H-1,2,3-triazol-4-yl)-1,9-diazaspiro[5.5]undecan-2-one;

1-(4-chloro-3-fluorophenyl)-9-(1-(4-fluorophenyl)-1H-pyrazol-3-yl)-1,9-diazaspiro[5.5]undecan-2-one;

1-(4-chloro-3-fluorophenyl)-9-(2-(4-fluorophenyl)-2H-1,2,3-triazol-4-yl)-1,9-diazaspiro[5.5]undecan-2-one;

1-(4-chlorophenyl)-9-(6-(4-fluorophenyl)pyridin-2-yl)-1,9-diazaspiro[5.5]undecan-2-one;

2-(1-(4-chloro-3-fluorophenyl)-2-oxo-1,9-diazaspiro[5.5]undecan-9-yl)-4-(4-fluorophenyl)pyridine 1-oxide;

4-(3-chlorophenoxy)-2-(1-(3,4-difluorophenyl)-2-oxo-1,9-diazaspiro[5.5]undecan-9-yl)pyridine 1-oxide;

9-(2-(5-azaspiro[2.3]hexan-5-yl)pyrimidin-4-yl)-1-(4-chloro-3-fluorophenyl)-1,9-diazaspiro[5.5]undecan-2-one;

9-(4-(5-azaspiro[2.3]hexan-5-yl)pyrimidin-2-yl)-1-(4-chloro-3-fluorophenyl)-1,9-diazaspiro[5.5]undecan-2-one;

1-(4-chloro-3-fluorophenyl)-9-(5-fluoro-6-(pyrrolidin-1-yl)pyrimidin-4-yl)-1,9-diazaspiro[5.5]undecan-2-one;

1-(4-chloro-3-fluorophenyl)-9-(5-fluoro-6-(3-(trifluoromethyl)azetidin-1-yl)pyrimidin-4-yl)-1,9-diazaspiro[5.5]undecan-2-one;

1-(4-chloro-3-fluorophenyl)-9-(4-(pyrrolidin-1-yl)-1,3,5-triazin-2-yl)-1,9-diazaspiro[5.5]undecan-2-one;

9-(4-(4-amino-4-(trifluoromethyl)piperidin-1-yl)pyrimidin-2-yl)-1-(3,4-difluorophenyl)-1,9-diazaspiro[5.5]undecan-2-one;

1-(3,4-difluorophenyl)-9-(4-(4-hydroxy-4-(trifluoromethyl)piperidin-1-yl)-1,3,5-triazin-2-yl)-1,9-diazaspiro[5.5]undecan-2-one;

9-(2-amino-5-fluoro-6-(4-hydroxy-4-(trifluoromethyl)piperidin-1-yl)pyrimidin-4-yl)-1-(3,4-difluorophenyl)-1,9-diazaspiro[5.5]undecan-2-one;

1-(3,4-difluorophenyl)-9-(6-(4-hydroxy-4-(trifluoromethyl)piperidin-1-yl)pyridazin-4-yl)-1,9-diazaspiro[5.5]undecan-2-one;

9-(6-amino-2-(3-hydroxy-3-methylazetidin-1-yl)pyrimidin-4-yl)-1-(3,4-difluorophenyl)-1,9-diazaspiro[5.5]undecan-2-one;

1-(4-chloro-3-fluorophenyl)-9-(6-(3,3,4,4-tetrafluoropyrrolidin-1-yl)pyrimidin-4-yl)-1,9-diazaspiro[5.5]undecan-2-one;

9-(6-(1,4-oxazepan-4-yl)pyrimidin-4-yl)-1-(3,4-difluorophenyl)-1,9-diazaspiro[5.5]undecan-2-one;

rac-9-(2-amino-6-((1R,4R)-2-oxa-5-azabicyclo[2.2.1]heptan-5-yl)pyrimidin-4-yl)-1-(3,4-difluorophenyl)-1,9-diazaspiro[5.5]undecan-2-one;

1-(3,4-difluorophenyl)-9-(6-(4-(trifluoromethyl)-1H-pyrazol-1-yl)pyrimidin-4-yl)-1,9-diazaspiro[5.5]undecan-2-one;

1-(3,4-difluorophenyl)-9-(2-methyl-6-(1H-pyrazol-1-yl)pyrimidin-4-yl)-1,9-diazaspiro[5.5]undecan-2-one;

4-(1-(3,4-difluorophenyl)-2-oxo-1,9-diazaspiro[5.5]undecan-9-yl)-6-(1H-pyrazol-1-yl)pyrimidine-2-carbonitrile;

1-(3,4-difluorophenyl)-9-(2-methoxy-6-(1H-pyrazol-1-yl)pyrimidin-4-yl)-1,9-diazaspiro[5.5]undecan-2-one;

9-(6-(1H-pyrazol-1-yl)-2-(trifluoromethyl)pyrimidin-4-yl)-1-(3,4-difluorophenyl)-1,9-diazaspiro[5.5]undecan-2-one;

1-(3,4-difluorophenyl)-9-(2-morpholino-6-(1H-pyrazol-1-yl)pyrimidin-4-yl)-1,9-diazaspiro[5.5]undecan-2-one;

1-(3,4-difluorophenyl)-9-(2-(dimethylamino)-6-(1H-pyrazol-1-yl)pyrimidin-4-yl)-1,9-diazaspiro[5.5]undecan-2-one;

9-(6-(1H-1,2,4-triazol-1-yl)pyrimidin-4-yl)-1-(3,4-difluorophenyl)-1,9-diazaspiro[5.5]undecan-2-one;

9-(6-(4-chloro-1H-pyrazol-1-yl)pyrimidin-4-yl)-1-(3,4-difluorophenyl)-1,9-diazaspiro[5.5]undecan-2-one;

9-(6-(4-fluoro-1H-pyrazol-1-yl)pyrimidin-4-yl)-1-(3,4-difluorophenyl)-1,9-diazaspiro[5.5]undecan-2-one;

1-(3,4-difluorophenyl)-9-(6-(3-(trifluoromethyl)-1H-pyrazol-1-yl)pyrimidin-4-yl)-1,9-diazaspiro[5.5]undecan-2-one;

1-(3,4-difluorophenyl)-9-(6-(4-(trifluoromethyl)-1H-imidazol-1-yl)pyrimidin-4-yl)-1,9-diazaspiro[5.5]undecan-2-one;

9-(2-amino-5-fluoro-6-(1H-pyrazol-1-yl)pyrimidin-4-yl)-1-(3,4-difluorophenyl)-1,9-diazaspiro[5.5]undecan-2-one;

9-(4-amino-6-(4-fluoro-1H-pyrazol-1-yl)-1,3,5-triazin-2-yl)-1-(3,4-difluorophenyl)-1,9-diazaspiro[5.5]undecan-2-one;

1-(3,4-difluorophenyl)-9-(6-(oxetan-3-yloxy)-2-(trifluoromethyl)pyrimidin-4-yl)-1,9-diazaspiro[5.5]undecan-2-one;

1-(3,4-difluorophenyl)-9-(6-(oxazol-2-yl)pyrimidin-4-yl)-1,9-diazaspiro[5.5]undecan-2-one;

9-(6-amino-2-(pyridin-2-yl)pyrimidin-4-yl)-1-(3,4-difluorophenyl)-1,9-diazaspiro[5.5]undecan-2-one;

9-(2-amino-6-(4-(trifluoromethyl)-1H-pyrazol-1-yl)pyrimidin-4-yl)-1-(3,4-difluorophenyl)-1,9-diazaspiro[5.5]undecan-2-one;

1-(3,4-difluorophenyl)-9-(2-(2-hydroxypropan-2-yl)-6-(4-(trifluoromethyl)-1H-pyrazol-1-yl)pyrimidin-4-yl)1,9-diazaspiro[5.5]undecane-2-one;

Synthesis 1-(3,4-difluorophenyl)-9-(2-(hydroxymethyl)-6-(4-(trifluoromethyl)-1H-pyrazol-1-yl)pyrimidin-4-yl)1,9-diazaspiro[5.5]undecane-2-one;

rac-1-(3,4-difluorophenyl)-9-(2-(1-hydroxymethyl)-6-(4-(trifluoromethyl)-1H-pyrazol-1-yl)pyrimidin-4-yl)1,9-diazaspiro[5.5]undecane-2-one;

4-(1-(3,4-difluorophenyl)-2-oxo-1,9-diazaspiro[5.5]undecane-9-yl-6-(4-(trifluoromethyl)-1H-pyrazol-1-yl)pyrimidin-2-carboxamide;

9-(2-chloro-6-(4-(trifluoromethyl)-1H-pyrazol-1-yl)pyrimidin-4-yl)-1-(3,4-difluorophenyl)-1,9-diazaspiro[5.5]undecan-2-one;

(R)-9-(2-chloro-6-((tetrahydrofuran-3-yl)oxy)pyrimidin-4-yl)-1-(3,4-difluorophenyl)-1,9-diazaspiro[5.5]undecan-2-one;

(S)-9-(2-chloro-6-((tetrahydrofuran-3-yl)oxy)pyrimidin-4-yl)-1-(3,4-difluorophenyl)-1,9-diazaspiro[5.5]undecan-2-one;

(R)-9-(4-chloro-6-((tetrahydrofuran-3-yl)oxy)pyrimidin-2-yl)-1-(3,4-difluorophenyl)-1,9-diazaspiro[5.5]undecan-2-one;

1-(3,4-difluorophenyl)-9-(6-(4-fluoro-1H-pyrazol-1-yl)-2-morpholinopyrimidin-4-yl)-1,9-diazaspiro[5.5]undecan-2-one;

9-(2-amino-6-(4,4-difluorocyclohex-1-en-1-yl)pyrimidin-4-yl)-1-(3,4-difluorophenyl)-1,9-diazaspiro[5.5]undecan-2-one;

9-(2-amino-6-(4-fluorophenyl-4-yl)pyrimidin-4-yl)-1-(3,4-difluorophenyl)-1,9-diazaspiro[5.5]undecane-2-one;

9-(2-amino-6-(trifluoromethyl)pyrimidin-4-yl)-1-(3,4-difluorophenyl)-1,9-diazaspiro[5.5]undecan-2-one;

9-(2-amino-6-(perfluoroethyl)pyrimidin-4-yl)-1-(3,4-difluorophenyl)-1,9-diazaspiro[5.5]undecane-2-one;

9-(2-amino-6-(1,1,2,2-tetrafluoroethyl)pyrimidin-4-yl)-1-(3,4-difluorophenyl)-1,9-diazaspiro[5.5]undecan-2-one;

1-(3,4-difluorophenyl)-9-(2-(hydroxynethyl)-6-(perfluoroethyl)pyrimidin-4-yl)-1,9-diazaspiro[5.5]undecane-2-one;

1-(3,4-difluorophenyl)-9-(2-(2-hydroxypropan-2-yl)-6-(trifluoromethyl)pyrimidin-4-yl)-1,9-diazaspiro[5.5]undecan-2-one;

1-(4-chloro-3-fluorophenyl)-9-(4-(2,2,2-trifluoroethoxy)pyridin-2-yl)-1,9-diazaspiro[5.5]undecan-2-one;

1-(4-chloro-3-fluorophenyl)-9-(6-(2,2,2-trifluoroethoxy)pyrimidin-4-yl)-1,9-diazaspiro[5.5]undecan-2-one;

1-(4-chloro-3-fluorophenyl)-9-(6-(2,2-difluoroethoxy)pyrimidin-4-yl)-1,9-diazaspiro[5.5]undecan-2-one;

1-(3,4-difluorophenyl)-9-(4-propoxypyrimidin-2-yl)-1,9-diazaspiro[5.5]undecan-2-one;

rac-1-(3,4-difluorophenyl)-9-(6-(((1,1,1-trifluoropropan-2-yl)oxy)pyrimidin-4-yl)-1,9-diazaspiro[5.5]undecan-2-one;

1-(3,4-difluorophenyl)-9-(6-((tetrahydro-2H-pyran-4-yl)oxy)pyrimidin-4-yl)-1,9-diazaspiro[5.5]undecan-2-one;

9-(2-chloro-6-(2,2,2-trifluoroethoxy)pyrimidin-4-yl)-1-(3,4-difluorophenyl)-1,9-diazaspiro[5.5]undecan-2-one;

(S)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one;

(R)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one;

(R)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one;

(S)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one;

9-(2-amino-6-(3,3-difluorocyclobutoxy)pyrimidin-4-yl)-1-(3,4-difluorophenyl)-1,9-diazaspiro[5.5]undecan-2-one;

9-(2-amino-6-(2,2,2-trifluoroethoxy)pyrimidin-4-yl)-1-(3,4-difluorophenyl)-1,9-diazaspiro[5.5]undecan-2-one;

9-(2-amino-6-(2,2,2-trifluoroethoxy-1,1-d2)pyrimidin-4-yl)-1-(3,4-difluorophenyl)-1,9-diazaspiro[5.5]undecan-2-one;

9-(2-amino-6-isopropoxypyrimidin-4-yl)-1-(3,4-difluorophenyl)-1,9-diazaspiro[5.5]undecan-2-one;

9-(2-amino-6-(2-hydroxyethoxy)pyrimidin-4-yl)-1-(3,4-difluorophenyl)-1,9-diazaspiro[5.5]undecan-2-one;

rac-9-(2-amino-6-((1,1,1-trifluoropropan-2-yl)oxy)pyrimidin-4-yl)-1-(3,4-difluorophenyl)-1,9-diazaspiro[5.5]undecan-2-one;

rac-9-(2-amino-6-(2,2,2-trifluoro-1-(3-methyloxetan-3-yl)ethoxy)pyrimidin-4-yl)-1-(3,4-difluorophenyl)-1,9-diazaspiro[5.5]undecan-2-one;

9-(2-amino-6-(2,2,3,3,3-pentafluoropropoxy)pyrimidin-4-yl)-1-(3,4-difluorophenyl)-1,9-diazaspiro[5.5]undecan-2-one;

rac-9-(2-amino-6-((4,4-difluorotetrahydrofuran-3-yl)oxy)pyrimidin-4-yl)-1-(3,4-difluorophenyl)-1,9-diazaspiro[5.5]undecan-2-one;

rac-9-(2-amino-6-(((3S,4S)-3-fluorotetrahydro-2H-pyran-4-yl)oxy)pyrimidin-4-yl)-1-(3,4-difluorophenyl)-1,9-diazaspiro[5.5]undecan-2-one;

(R)-9-(2-amino-6-((tetrahydro-2H-pyran-3-yl)oxy)pyrimidin-4-yl)-1-(3,4-difluorophenyl)-1,9-diazaspiro[5.5]undecan-2-one;

9-(2-amino-6-((tetrahydro-2H-pyran-4-yl)oxy)pyrimidin-4-yl)-1-(3,4-difluorophenyl)-1,9-diazaspiro[5.5]undecan-2-one;

rac-9-(2-amino-6-(((3R,4R)-4-fluorotetrahydrofuran-3-yl)oxy)pyrimidin-4-yl)-1-(3,4-difluorophenyl)-1,9-diazaspiro[5.5]undecan-2-one;

9-(2-amino-6-((tetrahydro-2H-pyran-4-yl-4-d)oxy)pyrimidin-4-yl)-1-(3,4-difluorophenyl)-1,9-diazaspiro[5.5]undecan-2-one;

rac-9-(2-amino-6-((3-methyltetrahydrofuran-3-yl)oxy)pyrimidin-4-yl)-1-(3,4-difluorophenyl)-1,9-diazaspiro[5.5]undecan-2-one;

rac-9-(2-amino-6-(((3S,4R)-4-fluorotetrahydrofuran-3-yl)oxy)pyrimidin-4-yl)-1-(3,4-difluorophenyl)-1,9-diazaspiro[5.5]undecan-2-one;

1-(3,4-difluorophenyl)-9-(2-(hydroxymethyl)-6-((tetrahydro-2H-pyran-4-yl)oxy)pyrimidin-4-yl)-1,9-diazaspiro[5.5]undecan-2-one;

rac-1-(3,4-difluorophenyl)-9-(6-(((3S,4R)-3-fluorotetrahydro-2H-pyran-4-yl)oxy)-2-(hydroxymethyl)pyrimidin-4-yl)-1,9-diazaspiro[5.5]undecan-2-one;

rac-1-(3,4-difluorophenyl)-9-(6-(((3R,4R)-4-fluorotetrahydrofuran-3-yl)oxy)-2-(hydroxymethyl)pyrimidin-4-yl)-1,9-diazaspiro[5.5]undecan-2-one;

(S)-1-(3,4-difluorophenyl)-9-(2-(hydroxymethyl)-6-((tetrahydrofuran-3-yl)oxy)pyrimidin-4-yl)-1,9-diazaspiro[5.5]undecan-2-one;

(S)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one;

(R)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one;

(R)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one;

(S)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one;

rac ethyl 4-(1-(3,4-difluorophenyl)-2-oxo-1,9-diazaspiro[5.5]undecane-9-yl)-6-(((3S,4S)-4-fluorotetrahydrofuran-3-yl)oxy)pyrimidine-2-carboxylate;

(R)-9-(2-amino-6-((tetrahydrofuran-3-yl)amino)pyrimidin-4-yl)-1-(3,4-difluorophenyl)-1,9-diazaspiro[5.5]undecan-2-one;

(R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

(S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

(S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

(R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

1-(3,4-difluorophenyl)-9-(2-(hydroxymethyl)-6-(4-(trifluoromethyl)-1H-pyrazol-1-yl)pyrimidin-4-yl)-3-oxa-1,9-diazaspiro[5.5]undecan-2-one;

9-(2-amino-6-(4-(trifluoromethyl)-1H-pyrazol-1-yl)pyrimidin-4-yl)-1-(3,4-difluorophenyl)-3-oxa-1,9-diazaspiro[5.5]undecan-2-one;

(R)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

(S)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

(S)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

(R)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

rac-9-(2-amino-6-(perfluoroethyl)pyrimidin-4-yl)-1-(3,4-difluorophenyl)-4-fluoro-1,9-diazaspiro[5.5]undecan-2-one;

rac-1-(3,4-difluorophenyl)-4-fluoro-9-(6-((tetrahydro-2H-pyran-4-yl)oxy)pyrimidin-4-yl)-1,9-diazaspiro[5.5]undecan-2-one;

9-(2-amino-6-(1,1-difluoroethyl)pyrimidin-4-yl)-1-(3,4-difluorophenyl)-1,9-diazaspiro[5.5]undecan-2-one; and 1-(3,4-difluorophenyl)-4-fluoro-9-(6-(2,2,2-trifluoroethoxy)pyrimidin-4-yl)-1,9-diazaspiro[5.5]undecan-2-one; or a pharmaceutically acceptable salt thereof.

In embodiment 14, the invention relates to a compound of Formula I, or a pharmaceutically acceptable salt thereof, wherein the compound is selected from 1-(3,4-difluorophenyl)-9-(6-(2,2,2-trifluoroethoxy)pyrimidin-4-yl)-1,9-diazaspiro[5.5]undecan-2-one;

9-(2-amino-6-(4-(trifluoromethyl)-1H-pyrazol-1-yl)pyrimidin-4-yl)-1-(3,4-difluorophenyl)-1,9-diazaspiro[5.5]undecane-2-one;

(R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

9-(2-amino-6-(1,1-difluoroethyl)pyrimidin-4-yl)-1-(3,4-difluorophenyl)-1,9-diazaspiro[5.5]undecan-2-one; and 9-(2-amino-6-(trifluoromethyl)pyrimidin-4-yl)-1-(3,4-difluorophenyl)-1,9-diazaspiro[5.5]undecan-2-one; or a pharmaceutically acceptable salt thereof.

In another aspect of embodiment 14, the invention relates to a compound of formula (I), according to embodiment 1, wherein the compound is 1-(3,4-difluorophenyl)-9-(6-(2,2,2-trifluoroethoxy)pyrimidin-4-yl)-1,9-diazaspiro[5.5]undecan-2-one, or a pharmaceutically acceptable salt thereof.

In another aspect of embodiment 14, the invention pertains to a compound of formula (I), according to embodiment 1, wherein the compound is 9-(2-amino-6-(4-(trifluoromethyl)-1H-pyrazol-1-yl)pyrimidin-4-yl)-1-(3,4-difluorophenyl)-1,9-diazaspiro[5.5]undecane-2-one; or a pharmaceutically acceptable salt thereof.

In another aspect of embodiment 14, the invention pertains to a compound of formula (I), according to embodiment 1, wherein the compound is (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, or a pharmaceutically acceptable salt thereof.

In another aspect of embodiment 14, the invention pertains to a compound of formula (I), according to embodiment 1, wherein the compound is (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, or a pharmaceutically acceptable salt thereof.

In another aspect of embodiment 14, the invention pertains to a compound of formula (I), according to embodiment 14, wherein the compound is 9-(2-amino-6-(trifluoromethyl)pyrimidin-4-yl)-1-(3,4-difluorophenyl)-1,9-diazaspiro[5.5]undecan-2-one, or a pharmaceutically acceptable salt thereof.

In another aspect of embodiment 14, the invention pertains to a compound of formula (I), according to embodiment 14, wherein the compound is 9-(2-amino-6-(1,1-difluoroethyl)pyrimidin-4-yl)-1-(3,4-difluorophenyl)-1,9-diazaspiro[5.5]undecan-2-one; or a pharmaceutically acceptable salt thereof.

Depending on the choice of the starting materials and procedures, the compounds can be present in the form of one of the possible stereoisomers or as mixtures thereof, for example as pure optical isomers, or as stereoisomer mixtures, such as racemates and diastereoisomer mixtures, depending on the number of asymmetric carbon atoms. The present invention is meant to include all such possible stereoisomers, including racemic mixtures, diasteriomeric mixtures and optically pure forms. Optically active (R)- and (S)-stereoisomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

As used herein, the terms "salt" or "salts" refers to an acid addition or base addition salt of a compound of the invention. "Salts" include in particular "pharmaceutical acceptable salts". The term "pharmaceutically acceptable salts" refers to salts that retain the biological effectiveness and properties of the compounds of this invention and, which typically are not biologically or otherwise undesirable. In many cases, the compounds of the present invention are capable of forming acid and/or base salts by virtue of the presence of amino and/or carboxyl groups or groups similar thereto.

Pharmaceutically acceptable acid addition salts can be formed with inorganic acids and organic acids.

Inorganic acids from which salts can be derived include, for example, hydrochloric acid, hydrobromic acid, sulfuric acid, nitric acid, phosphoric acid, and the like.

Organic acids from which salts can be derived include, for example, acetic acid, propionic acid, glycolic acid, oxalic acid, maleic acid, malonic acid, succinic acid, fumaric acid, tartaric acid, citric acid, benzoic acid, mandelic acid, methanesulfonic acid, ethanesulfonic acid, toluenesulfonic acid, sulfosalicylic acid, and the like.

Pharmaceutically acceptable base addition salts can be formed with inorganic and organic bases.

Inorganic bases from which salts can be derived include, for example, ammonium salts and metals from columns I to XII of the periodic table. In certain embodiments, the salts are derived from sodium, potassium, ammonium, calcium, magnesium, iron, silver, zinc, and copper; particularly suitable salts include ammonium, potassium, sodium, calcium and magnesium salts.

Organic bases from which salts can be derived include, for example, primary, secondary, and tertiary amines, substituted amines including naturally occurring substituted amines, cyclic amines, basic ion exchange resins, and the like. Certain organic amines include isopropylamine, benzathine, cholinate, diethanolamine, diethylamine, lysine, meglumine, piperazine and tromethamine.

In another aspect, the present invention provides compounds of any one of formulae (I) to (V) in acetate, ascorbate, adipate, aspartate, benzoate, besylate, bromide/hydrobromide, bicarbonate/carbonate, bisulfate/sulfate, camphorsulfonate, caprate, chloride/hydrochloride, chlortheophyllonate, citrate, ethandisulfonate, fumarate, gluceptate, gluconate, glucuronate, glutamate, glutarate, glycolate, hippurate, hydroiodide/iodide, isethionate, lactate, lactobionate, laurylsulfate, malate, maleate, malonate, mandelate, mesylate, methylsulphate, mucate, naphthoate, napsylate, nicotinate, nitrate, octadecanoate, oleate, oxalate, palmitate, pamoate, phosphate/hydrogen phosphate/dihydrogen phosphate, polygalacturonate, propionate, sebacate, stearate, succinate, sulfosalicylate, sulfate, tartrate, tosylate trifenatate, trifluoroacetate or xinafoate salt form.

In another aspect, the present invention provides compounds of any one of formulae (I) to (V) in sodium, potassium, ammonium, calcium, magnesium, iron, silver, zinc, copper, isopropylamine, benzathine, cholinate, diethanolamine, diethylamine, lysine, meglumine, piperazine or tromethamine salt form.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Isotopes that can be incorporated into compounds of the invention include, for example, isotopes of hydrogen.

Further, incorporation of certain isotopes, particularly deuterium (i.e., $^2$H or D) may afford certain therapeutic advantages resulting from greater metabolic stability, for example increased in vivo half-life or reduced dosage requirements or an improvement in therapeutic index or tolerability. It is understood that deuterium in this context is regarded as a substituent of a compound of the formula (I). The concentration of deuterium, may be defined by the isotopic enrichment factor. The term "isotopic enrichment factor" as used herein means the ratio between the isotopic abundance and the natural abundance of a specified isotope.

If a substituent in a compound of this invention is denoted as being deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation). It should be understood that the term "isotopic enrichment factor" can be applied to any isotope in the same manner as described for deuterium.

Other examples of isotopes that can be incorporated into compounds of the invention include isotopes of hydrogen, carbon, nitrogen, oxygen, phosphorous, fluorine, and chlorine, such as $^3$H, $^{11}$C, $^{13}$C, $^{14}$C, $^{15}$N, $^{18}$F, $^{31}$P, $^{32}$P, $^{35}$S, $^{36}$Cl, $^{123}$I, $^{124}$I, $^{125}$I respectively. Accordingly it should be understood that the invention includes compounds that incorporate one or more of any of the aforementioned isotopes, including for example, radioactive isotopes, such as $^3$H and $^{14}$C, or those into which non-radioactive isotopes, such as $^2$H and $^{13}$C are present. Such isotopically labelled compounds are useful in metabolic studies (with $^{14}$C), reaction kinetic studies (with, for example $^2$H or $^3$H), detection or imaging techniques, such as positron emission tomography (PET) or single-photon emission computed tomography (SPECT) including drug or substrate tissue distribution assays, or in radioactive treatment of patients. In particular, an $^{18}$F or labeled compound may be particularly desirable for PET or SPECT studies. Isotopically-labeled compounds of formula (I) can generally be prepared by conventional techniques known to those skilled in the art or by processes analogous to those described in the accompanying Examples and Preparations using an appropriate isotopically-labeled reagents in place of the non-labeled reagent previously employed.

Pharmaceutical Composition

As used herein, the term "pharmaceutical composition" refers to a compound of the invention, or a pharmaceutically acceptable salt thereof, together with at least one pharmaceutically acceptable carrier, in a form suitable for oral or parenteral administration.

As used herein, the term "pharmaceutically acceptable carrier" refers to a substance useful in the preparation or use of a pharmaceutical composition and includes, for example, suitable diluents, solvents, dispersion media, surfactants, antioxidants, preservatives, isotonic agents, buffering agents, emulsifiers, absorption delaying agents, salts, drug stabilizers, binders, excipients, disintegration agents, lubricants, wetting agents, sweetening agents, flavoring agents, dyes, and combinations thereof, as would be known to those skilled in the art (see, for example, Remington The Science and Practice of Pharmacy, $22^{nd}$ Ed. Pharmaceutical Press, 2013, pp. 1049-1070).

The term "a therapeutically effective amount" of a compound of the present invention refers to an amount of the compound of the present invention that will elicit the biological or medical response of a subject, for example, reduction or inhibition of an enzyme or a protein activity, or ameliorate symptoms, alleviate conditions, slow or delay disease progression, or prevent a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, or a disorder or a disease (i) mediated by LTC4S, or (ii) associated with LTC4S activity, or (iii) characterized by activity (normal or abnormal) of LTC4S; or (2) reduce or inhibit the activity of LTC4S; or (3) reduce or inhibit the expression of LTC4S. In another non-limiting embodiment, the term "a therapeutically effective amount" refers to the amount of the compound of the present invention that, when administered to a cell, or a tissue, or a non-cellular biological material, or a medium, is effective to at least partially reducing or inhibiting the activity of LTC4S; or at least partially reducing or inhibiting the expression of LTC4S.

As used herein, the term "subject" refers to primates (e.g., humans, male or female), dogs, rabbits, guinea pigs, pigs, rats and mice. In certain embodiments, the subject is a primate. In yet other embodiments, the subject is a human.

As used herein, the term "inhibit", "inhibition" or "inhibiting" refers to the reduction or suppression of a given condition, symptom, or disorder, or disease, or a significant decrease in the baseline activity of a biological activity or process.

As used herein, the term "treat", "treating" or "treatment" of any disease or disorder refers to alleviating or ameliorating the disease or disorder (i.e., slowing or arresting the development of the disease or at least one of the clinical symptoms thereof); or alleviating or ameliorating at least one physical parameter or biomarker associated with the disease or disorder, including those which may not be discernible to the patient.

As used herein, the term "prevent", "preventing" or "prevention" of any disease or disorder refers to the prophylactic treatment of the disease or disorder; or delaying the onset or progression of the disease or disorder As used herein, a subject is "in need of" a treatment if such subject would benefit biologically, medically or in quality of life from such treatment.

As used herein, the term "a," "an," "the" and similar terms used in the context of the present invention (especially in the context of the claims) are to be construed to cover both the singular and plural unless otherwise indicated herein or clearly contradicted by the context.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated double bonds may, if possible, be present in cis-(Z)- or trans-(E)-form.

Accordingly, as used herein a compound of the present invention can be in the form of one of the possible stereoisomers, rotamers, atropisomers, tautomers or mixtures thereof, for example, as substantially pure geometric (cis or trans) stereoisomers, diastereomers, optical isomers (antipodes), racemates or mixtures thereof.

Any resulting mixtures of stereoisomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

Methods of Synthesizing the Spiropiperidinyl Derivatives of the Invention.

Agents of the invention, for example compounds in accordance to the definition of formula (I) wherein X1 is $CH_2$ and $R^2$ is H, may be prepared by a reaction sequence of the reaction schemes 1 and 2 below:

Scheme 1

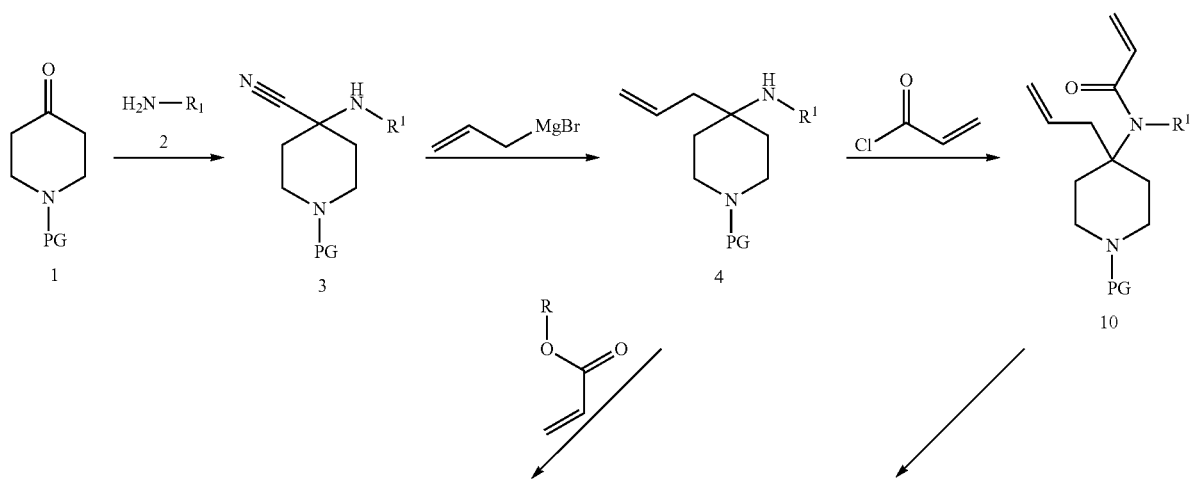

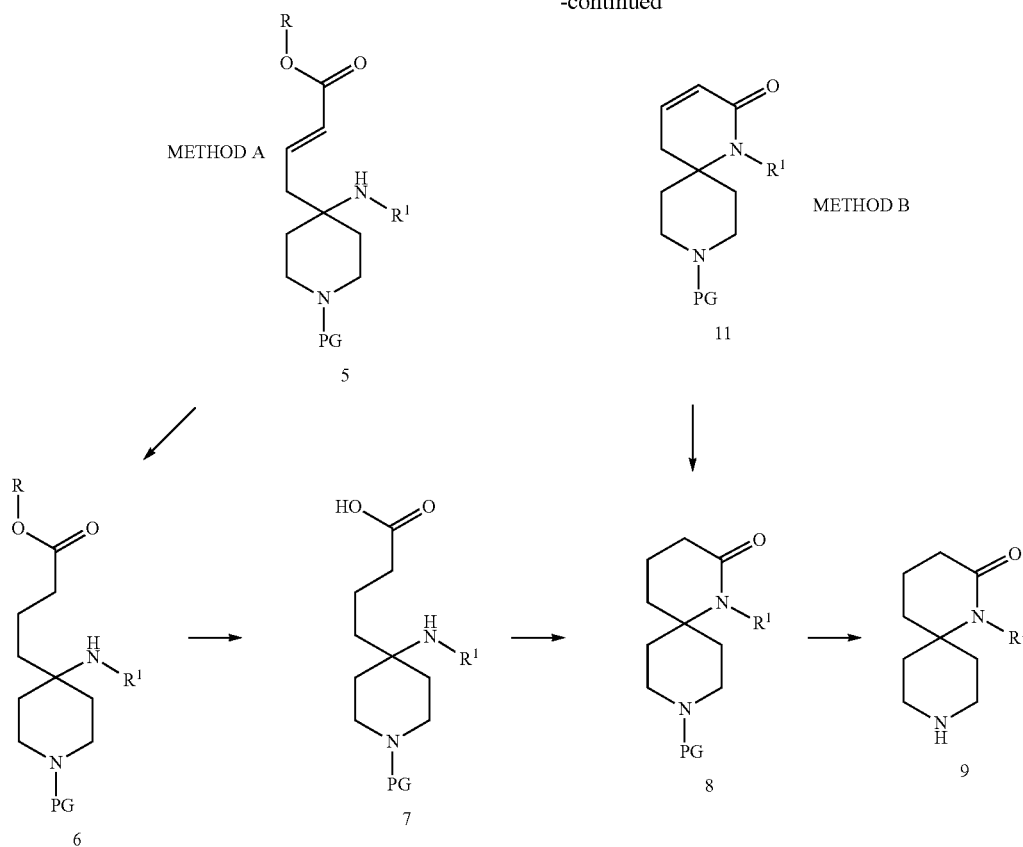

wherein PG is a nitrogen protecting group (e.g., benzyl (Bn), carbobenzyloxy (Cbz), tert-butyloxycarbonyl (BOC) and other well known nitrogen protecting groups), and $R^1$ is as defined in formula I, embodiment 1, and wherein R is an carboxylic acid protecting group, for example a $C_{1-6}$alkyl or benzyl.

In method A, an intermediate 9 is formed by reacting an N-protected piperidinone (1) with an appropriately substituted aniline (2), being typically commercially available, to form intermediate 3, which is reacted with a Grignard reagent (such as allyl magnesium bromide) to form the intermediate 4. A cross-metathesis reaction of 4 with an appropriate acrylate ester provides 5. Hydrogenation of 5 in the presence of a suitable catalyst, such as palladium on carbon or Adams catalyst, produces intermediate 6 which is followed by carboxylic acid deprotection (7) and dehydrative cyclization using a suitable reagent, such as $SOCl_2$. The spirocyclic lactam (8) thus formed can be deprotected to form intermediate 9.

Depending of the selection of protecting groups for the amino group of the piperidine and the carboxylic acid, the deprotection methods must be adapted according to well known methods (such as hydrogenation, acid or basic deprotection methods). For example, methyl or ethyl ester protection for the carboxylic acid may be removed by saponification, and a tert-butyloxycarbonyl (Boc) protecting group for the piperidine nitrogen may be removed by treatment with hydrochloric acid in a suitable solvent, such as dioxane or diethyl ether.

For certain anilines (2) an alternative route can be followed (Method B) wherein N-acylation of intermediate 4 with acroloyl chloride is followed by a ring-closing metathesis reaction using Grubb's II catalyst to provide the unsaturated lactam 11. Intermediate 11 may be saturated under suitable conditions such as hydrogenation, or by conjugate reduction with in situ generated nickel boride. Deprotection of the piperidine nitrogen under suitable conditions as described above provides intermediate 9.

Intermediate 9 may conveniently be reacted with a number of substrates to form the compounds of the invention, such as for example compounds carrying a heteroaromatic ring (Scheme 2).

Scheme 2

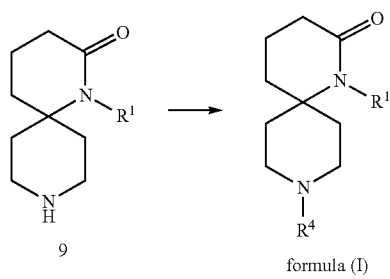

formula (I)

wherein $R^1$ and $R^4$ are as defined in Formula I, embodiment 1.

Compounds of Formula (I) wherein X1 is O and $R^2$ is H are prepared according to Schemes 3 and 4:

Intermediate 17 may conveniently be reacted with a number of substrates to form the compounds of the invention, such as for example compounds carrying a heteroaromatic ring (Scheme 4).

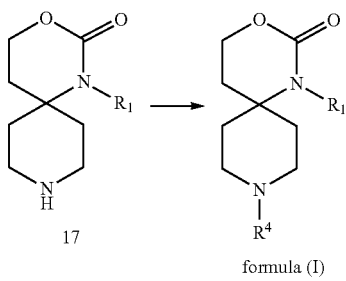

Scheme 4 formula (I)

Compounds of Formula (I) wherein $X^1$ is $CH_2$ and $R^2$ is F can be prepared according to Scheme 5 and 6:

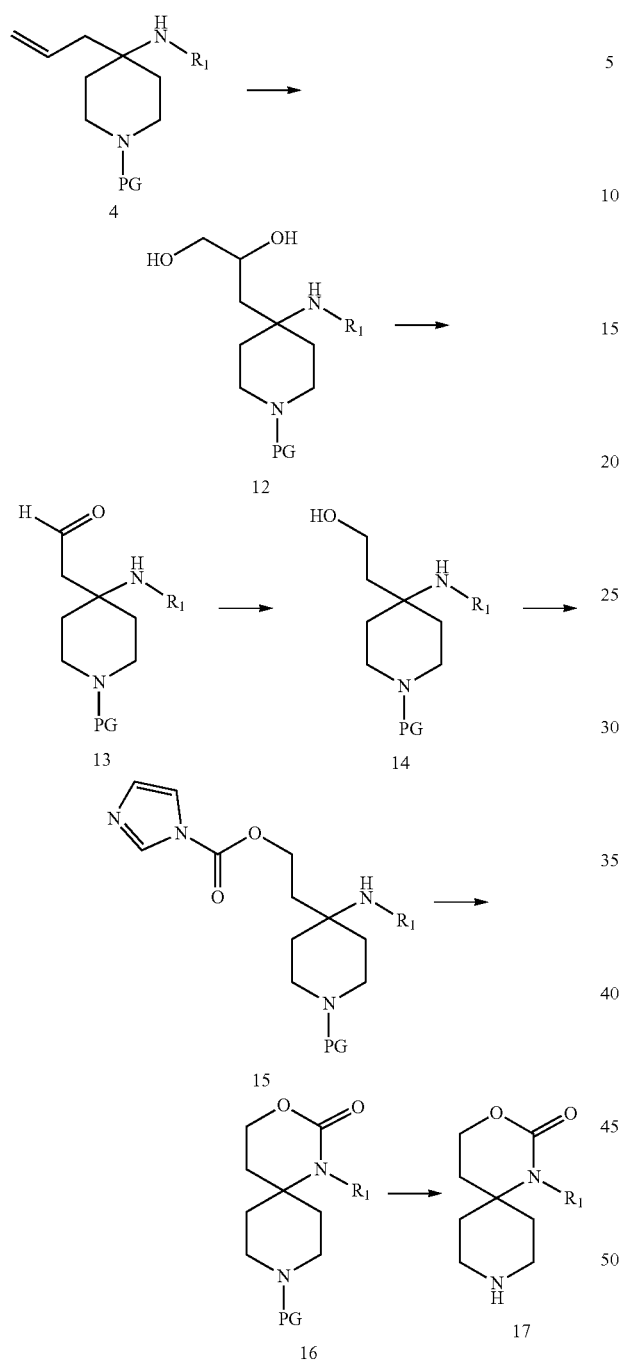

Scheme 3

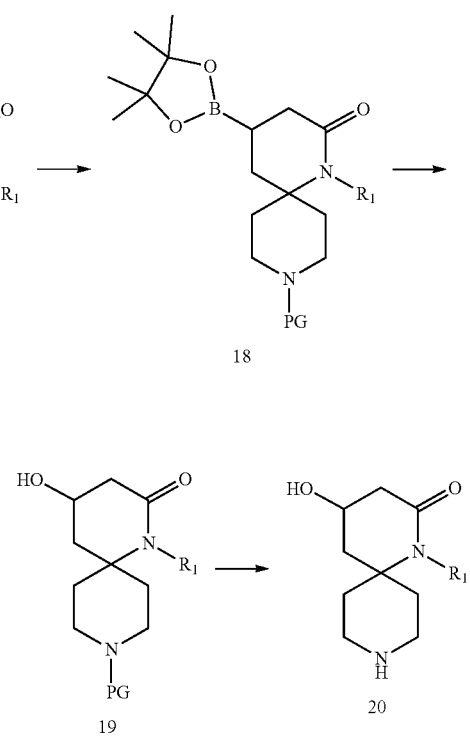

Scheme 5

Dihydroxylation of intermediate 4 followed by oxidative cleavage of the resulting diol using sodium periodate provides the unstable aldehyde 13 which is reduced to the alcohol 14 using sodium borohydride. Cyclization to intermediate 16 is effected in two steps by use of the phosgene equivalent carbonyl diimidazole (CDI) to form the imidazolyl carbamate 15, followed by treatment with pyridine hydrochloride. Intermediate 17 is obtained by deprotection of the piperidine nitrogen under appropriate conditions depending on the nature of the protecting group as described for intermediate 9 in Scheme 1.

A copper catalyzed conjugate borylation of the unsaturated lactam 11 provides the boronate ester 18. Oxidation of the boronate ester under suitable conditions, such as with sodium perborate results in formation of the beta-hydroxy lactam, which followed by piperidine nitrogen deprotection as described above provides the intermediate 20.

Compounds of the invention of formula (I) may be conveniently formed by reaction of intermediate 20 with a number of substrates, such as for example compounds carrying an heteroaromatic ring, followed by deoxyfluorination with DAST or similar reagents (Scheme 6).

Scheme 6.

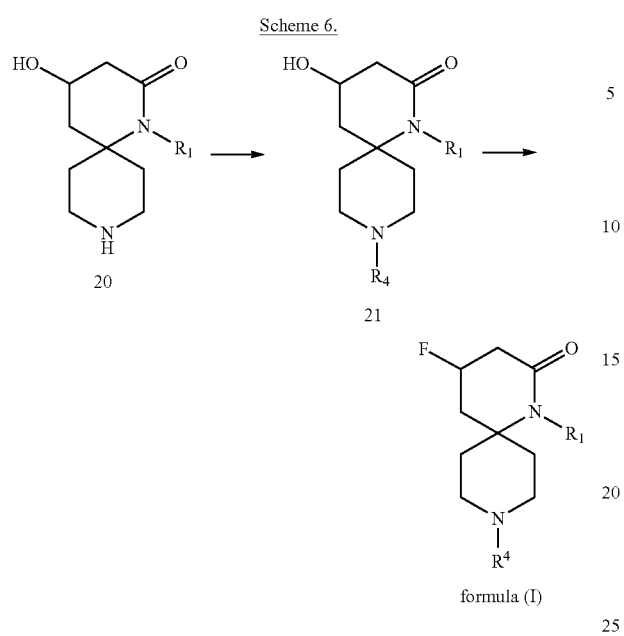

In an additional embodiment, there is provided a compound or salt thereof selected from the group consisting of:

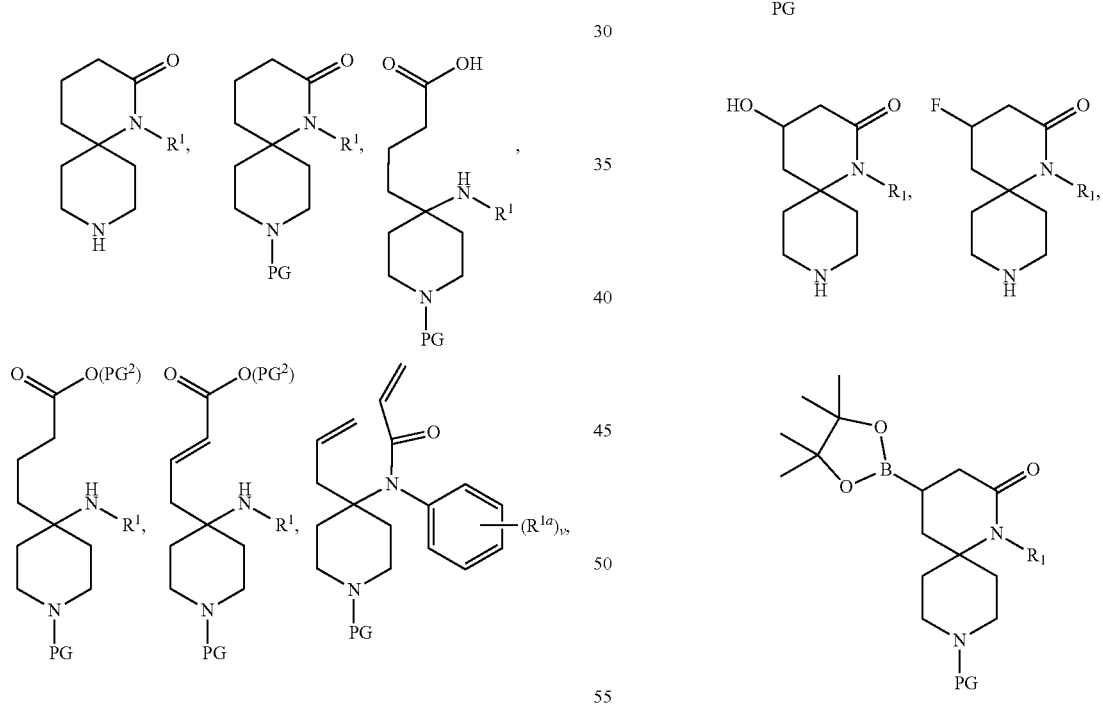

wherein PG is a nitrogen protecting group (e.g. benzyl (Bn), carbobenzyloxy (Cbz), tert-butyloxycarbonyl (BOC) and the like); and $PG^2$ is a carboxylic acid protecting group (for example a $C_{1-6}$alkyl or benzyl; $PG^3$ is carbobenzyloxy (Cbz) or tert-butoxycarbonyl (BOC); each $R^{1a}$ is halo, each $R^{1b}$ is independently selected from F and Cl; v is 1-3, and $R^1$ is phenyl optionally substituted with one, two or three halo substituents.

In yet another embodiment, there is provided a compound or salt thereof selected from the group consisting of:

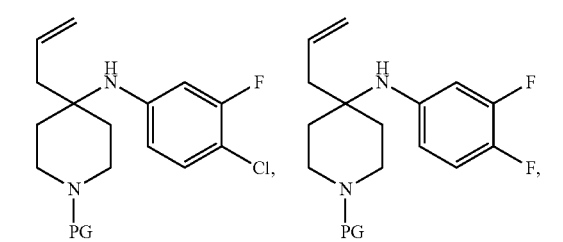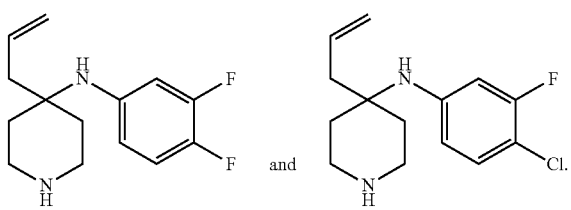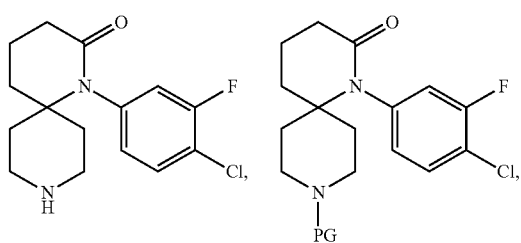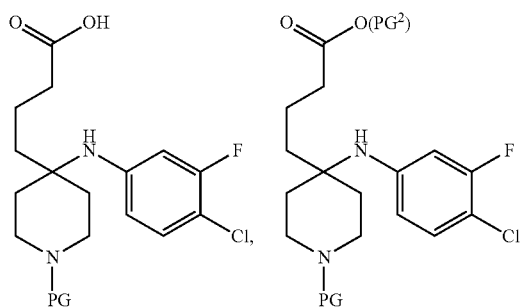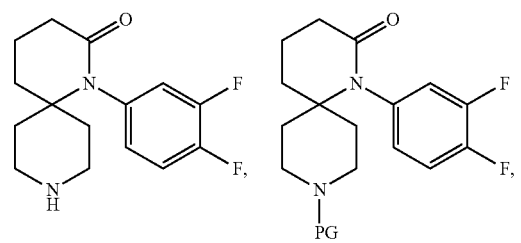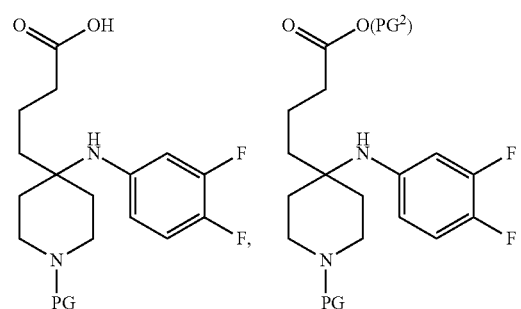
-continued
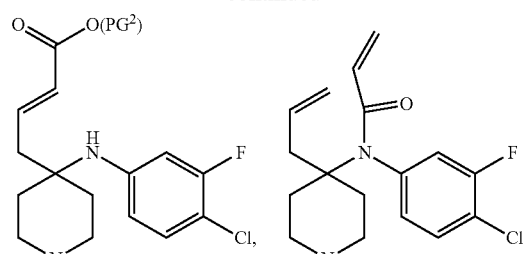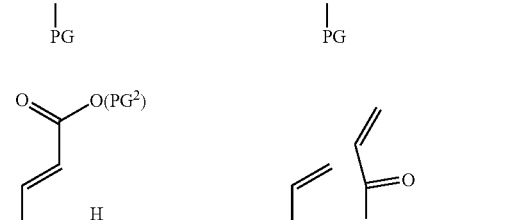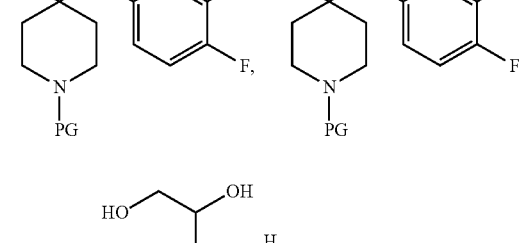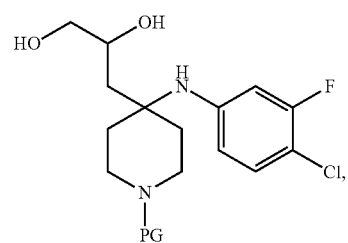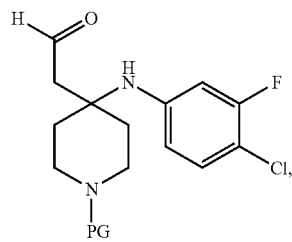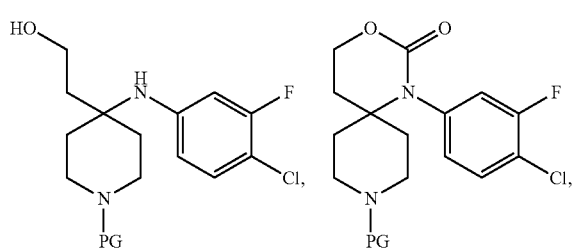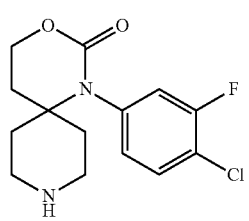

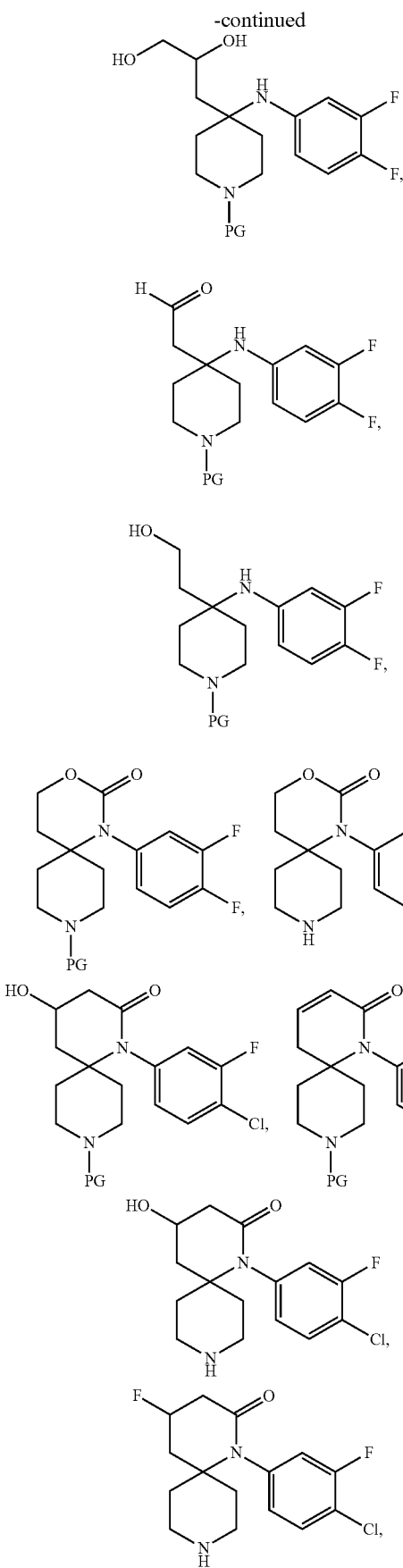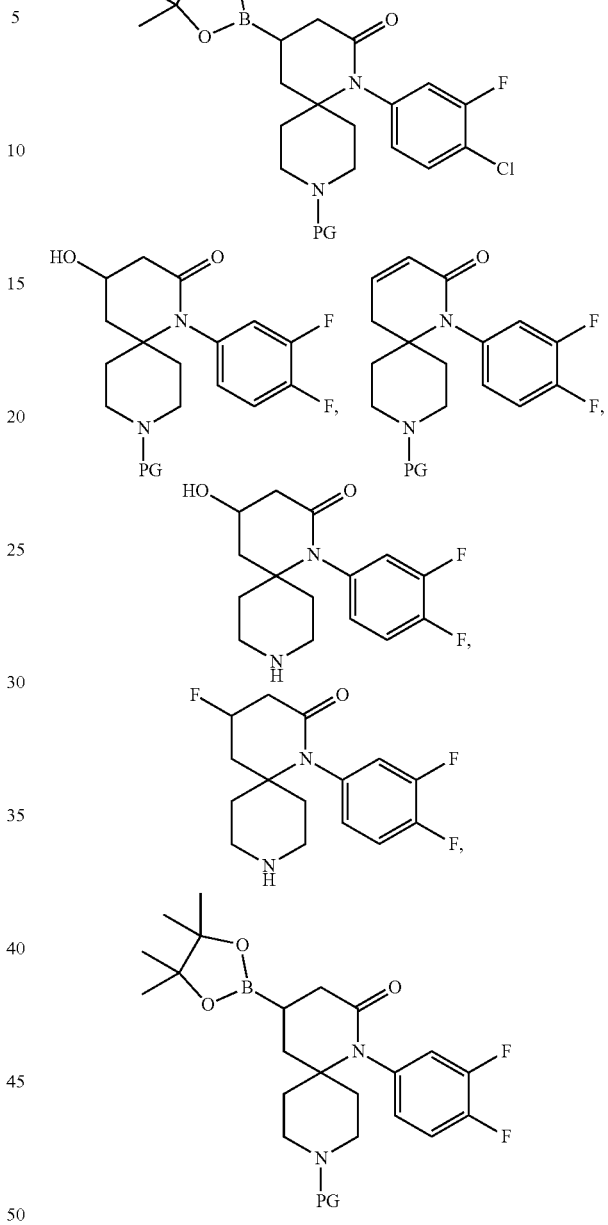

wherein PG and PG² are as defined above.

Compounds of this embodiment are useful in the preparation of compounds of the invention, e.g., compounds of Formula (I) or any one of Formula (II) to (V).

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure material. Compounds of the invention and intermediates can also be converted into each other according to methods generally known to those skilled in the art.

In another aspect, the present invention provides a pharmaceutical composition comprising a compound of the present invention, or a pharmaceutically acceptable salt thereof, and a pharmaceutically acceptable carrier. In a further embodiment, the composition comprises at least two pharmaceutically acceptable carriers, such as those described herein. The pharmaceutical composition can be formulated for particular routes of administration such as oral administration, parenteral administration (e.g. by injection, infusion, transdermal or topical administration), and rectal administration. Topical administration may also pertain to inhalation or intranasal application. The pharmaceutical compositions of the present invention can be made up in a solid form (including, without limitation, capsules, tablets, pills, granules, powders or suppositories), or in a liquid form (including, without limitation, solutions, suspensions or emulsions). Tablets may be either film coated or enteric coated according to methods known in the art. Typically, the pharmaceutical compositions are tablets or gelatin capsules comprising the active ingredient together with one or more of:

a) diluents, e.g., lactose, dextrose, sucrose, mannitol, sorbitol, cellulose and/or glycine;
b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and
e) absorbents, colorants, flavors and sweeteners.

Method of Use of the Invention

The compounds of any one of formulae (I) to (V) in free form or in pharmaceutically acceptable salt form, exhibit valuable pharmacological properties, e.g. LTC4S modulating properties, e.g. as indicated in vitro tests as provided in the next sections, and are therefore indicated for therapy or for use as research chemicals, e.g. as tool compounds.

Compounds of the invention may be useful in the treatment of an indication selected from: respiratory diseases/disorders, inflammation and/or disease/disorders having an inflammatory component, for example allergic disorders, asthma, childhood wheezing, chronic obstructive pulmonary disease, aspirin exacerbated respiratory disease, bronchopulmonary dysplasia, cystic fibrosis, interstitial lung disease (e.g. sarcoidosis, pulmonary fibrosis, scleroderma lung disease, and usual interstitial in pneumonia), ear nose and throat diseases (e.g. sinusitis, rhinitis, nasal polyposis, rhinosinusitis, otitis media, and allergic eosinophilic esophagitis), eye diseases (e.g. conjunctivitis and giant papillary conjunctivitis), skin diseases (e.g. psoriasis, atopic dermatitis, eczema and chronic urticaria), rheumatic diseases (e.g. rheumatoid arthritis, arthrosis, psoriasis arthritis, osteoarthritis, systemic lupus erythematosus, systemic sclerosis), vasculitis (e.g. Henoch-Schonlein purpura, Loffler's syndrome and Kawasaki disease), cardiovascular diseases (e.g. atherosclerosis, cerebrovascular diseases, acute ischemic heart attacks and post-heart attack treatment), gastrointestinal diseases (e.g. eosinophilic diseases in the gastrointestinal system, inflammatory bowel disease, irritable bowel syndrome, colitis, celiaci and gastric haemorrhagia), urologic diseases (e.g. glomerulonephritis, interstitial cystitis, nephritis, nephropathy, nephrotic syndrome, hepatorenal syndrome, and nephrotoxicity), diseases of the central nervous system (e.g. cerebral ischemia, spinal cord injury, migraine, multiple sclerosis, and sleep-disordered breathing), endocrine diseases (e.g. autoimmune thyreoiditis, diabetes-related inflammation), urticaria, anaphylaxis, angioedema, oedema in Kwashiorkor, dysmenorrhoea, burn-induced oxidative injury, multiple trauma, pain (inflammatory and neuropathic), endotoxin shock, sepsis, bacterial infections (e.g. from *Helicobacter pylori, Pseudomonas aerugiosa* or *Shigella dysenteriae*), fungal infections (e.g. vulvovaginal candidasis), viral infections (e.g. hepatitis, meningitis, parainfluenza and respiratory syncytial virus), hypereosinofilic syndrome, and malignancies (e.g. Hodgkin's lymphoma, leukemia (e.g. eosinophil leukemia and chronic myelogenous leukemia), mastocytos, polycytemi vera, and ovarian carcinoma).

Thus, as a further aspect, the present invention provides the use of a compound of formula (I) or any one of Formulae (II) to (V) in therapy. In a further embodiment, the therapy is selected from a disease which may be treated by inhibition on LTC4S. In another embodiment, the disease is selected from the afore-mentioned list, suitably allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably asthma, atopic dermatitis or chronic urticaria.

Thus, as a further aspect, the present invention provides a compound of any one formulae (I) to (V) for use in therapy. In a further embodiment, the therapy is selected from a disease which may be treated by inhibition of LTC4S. In another embodiment, the disease is selected from the afore-mentioned list, suitably allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably asthma, atopic dermatitis or chronic urticaria.

In another aspect, the invention provides a method of treating a disease which is treated by inhibiting LTC4S comprising administration of a therapeutically effective amount of a compound of any one of formulae (I) to (V). In a further embodiment, the disease is selected from the afore-mentioned list, suitably allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably asthma, atopic dermatitis or chronic urticaria.

Thus, as a further aspect, the present invention provides the use of a compound of any one of formulae (I) to (V) for the manufacture of a medicament. In a further embodiment, the medicament is for treatment of a disease which may be treated by inhibition of LTC4S. In another embodiment, the disease is selected from the afore-mentioned list, suitably allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably asthma, atopic dermatitis or chronic urticaria.

In another embodiment of the present invention, there is provided 9-(2-amino-6-(trifluoromethyl)pyrimidin-4-yl)-1-(3,4-difluorophenyl)-1,9-diazaspiro[5.5]undecan-2-one for use in the treatment of a disease selected from the afore-mentioned list, suitably for the treatment of an allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably asthma, atopic dermatitis or chronic urticaria.

In another embodiment of the present invention, there is provided (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one for use in the treatment of a disease selected from the afore-mentioned list, suitably for the treatment of an allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably asthma, atopic dermatitis or chronic urticaria.

In another embodiment of the present invention, there is provided (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one for use in the treatment of a disease selected from the afore-mentioned list, suitably for the treatment of an allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably for the treatment of asthma, atopic dermatitis or chronic urticaria.

In another embodiment of the present invention, there is provided 1-(3,4-difluorophenyl)-9-(6-(2,2,2-trifluoroethoxy)pyrimidin-4-yl)-1,9-diazaspiro[5.5]undecan-2-one for use in the treatment of a disease selected from the afore-mentioned list, or for the treatment of an allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably for the treatment of asthma, atopic dermatitis or chronic urticaria.

In another embodiment of the present invention, there is provided 9-(2-amino-6-(4-(trifluoromethyl)-1H-pyrazol-1-yl)pyrimidin-4-yl)-1-(3,4-difluorophenyl)-1,9-diazaspiro[5.5]undecane-2-one for use in the treatment of the disease is selected from the afore-mentioned list, suitably allergic disorders, asthma, aspirin exacerbated respiratory disease (AERD), COPD, cystic fibrosis, dermatitis, urticaria, rhinitis (allergic rhinitis), nasal polyposis, rhinosinusitis, conjunctivitis, eosinophilic gastrointestinal diseases and inflammatory bowel disease, and more suitably for the treatment of asthma, atopic dermatitis or chronic urticaria.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., aqueous solutions, and in vivo either enterally, parenterally, advantageously intravenously, e.g., as a suspension or in aqueous solution. The dosage in vitro may range between about 10-3 molar and 10-9 molar concentrations. A therapeutically effective amount in vivo may range depending on the route of administration, between about 0.1-500 mg/kg, or between about 1-100 mg/kg.

Combination Product and Combination Therapy of the Invention:

"Combination" refers to either a fixed combination in one dosage unit form, or a combined administration where a compound of the present invention and a combination partner (e.g. another drug as explained below, also referred to as "therapeutic agent" or "co-agent") may be administered independently at the same time or separately within time intervals, especially where these time intervals allow that the combination partners show a cooperative, e.g. synergistic effect. The single components may be packaged in a kit or separately. One or both of the components (e.g., powders or liquids) may be reconstituted or diluted to a desired dose prior to administration. The terms "co-administration" or "combined administration" or the like as utilized herein are meant to encompass administration of the selected combination partner to a single subject in need thereof (e.g. a patient), and are intended to include treatment regimens in which the agents are not necessarily administered by the same route of administration or at the same time. The term "pharmaceutical combination" as used herein means a product that results from the mixing or combining of more than one therapeutic agent and includes both fixed and non-fixed combinations of the therapeutic agents. The term "fixed combination" means that the therapeutic agents, e.g. a compound of the present invention and a combination partner, are both administered to a patient simultaneously in the form of a single entity or dosage. The term "non-fixed combination" means that the therapeutic agents, e.g. a compound of the present invention and a combination partner, are both administered to a patient as separate entities either simultaneously, concurrently or sequentially with no specific time limits, wherein such administration provides therapeutically effective levels of the two compounds in the body of the patient. The latter also applies to cocktail therapy, e.g. the administration of three or more therapeutic agent.

The term "pharmaceutical combination" as used herein refers to either a fixed combination in one dosage unit form, or non-fixed combination or a kit of parts for the combined administration where two or more therapeutic agents may be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients. Alternatively, such administration encompasses co-administration in multiple, or in separate containers (e.g., tablets, capsules, powders, and liquids) for each active ingredient. Powders and/or liquids may be reconstituted or diluted to a desired dose prior to administration. In addition, such administration also encompasses use of each type of therapeutic agent in a sequential manner, either at approximately the same time or at different times. In either case, the treatment regimen will provide beneficial effects of the drug combination in treating the conditions or disorders described herein.

The compound of the present invention may be administered either simultaneously with, or before or after, one or more other therapeutic agent. The compound of the present invention may be administered separately, by the same or different route of administration, or together in the same pharmaceutical composition as the other agents. A therapeutic agent is, for example, a chemical compound, peptide, antibody, antibody fragment or nucleic acid, which is therapeutically active or enhances the therapeutic activity when administered to a patient in combination with a compound of the invention.

In one embodiment, the invention provides a product comprising a compound of formula (I) and at least one other therapeutic agent as a combined preparation for simultaneous, separate or sequential use in therapy. In one embodiment, the therapy is the treatment of a disease or condition mediated by LTC4S. Products provided as a combined preparation include a composition comprising the compound of any one of formulae (I) to (V) and the other therapeutic agent(s) together in the same pharmaceutical composition, or the compound of any one of formulae (I) to (V) and the other therapeutic agent(s) in separate form, e.g. in the form of a kit.

In one embodiment, the invention provides a pharmaceutical combination comprising a compound of any one of formulae (I) to (V) and another therapeutic agent(s). Optionally, the pharmaceutical combination may comprise a pharmaceutically acceptable carrier, as described above.

In one embodiment, the invention provides a kit comprising two or more separate pharmaceutical compositions, at least one of which contains a compound of any one of formulae (I) to (V). In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent.

Accordingly, the invention provides the use of a compound of any one of formulae (I) to (V) for treating a disease or condition mediated by LTC4S, wherein the medicament is prepared for administration with another therapeutic agent. The invention also provides the use of another therapeutic agent for treating a disease or condition mediated by LTC4S wherein the medicament is administered with a compound of any one of formulas (I) to (V).

The invention also provides a compound of any one of formulae (I) to (V) for use in a method of treating a disease or condition mediated by LTC4S, wherein the compound of formula (I), (II), (III), (IV) or (V) is prepared for administration with another therapeutic agent. The invention also provides another therapeutic agent for use in a method of treating a disease or condition mediated by LTC4S, wherein the other therapeutic agent is prepared for administration with a compound of formula (I), (II), (III), (IV) or (V). The invention also provides a compound of formula (I) for use in a method of treating a disease or condition mediated by LTC4S, wherein the compound of formula (I), (II), (III), (IV), or (V) is administered with another therapeutic agent. The invention also provides another therapeutic agent for use in a method of treating a disease or condition mediated by LTC4S, wherein the other therapeutic agent is administered with a compound of formula (I), (II), (III), (IV) or (V).

The invention also provides the use of a compound of an one of formulae (I) to (V) for treating a disease or condition mediated by LTC4S, wherein the patient has previously (e.g. within 24 hours) been treated with another therapeutic agent. The invention also provides the use of another therapeutic agent for treating a disease or condition mediated by LTC4S, wherein the patient has previously (e.g. within 24 hours) been treated with a compound of formula (I), (II), (III), (IV) or (V).

In one embodiment, the other therapeutic agent is a therapeutic agent useful in the treatment of a respiratory disorder and/or a therapeutic agent that is useful in the treatment of inflammation and disorders with an inflammatory component (anti-inflammatory drugs).

In one embodiment, the other therapeutic agent useful in the combination therapy is selected from steroid; corticosteroids; glucocorticosteroids; non-steroidal glucocorticoid receptor agonists; leukotriene receptor antagonists (LTRAs) including LTB4 antagonists, LTD4 antagonists, Leukotriene A4 hydrolase (LTA4H) inhibitors, Cysteinyl-Leukotriene Receptor antagonists (including Montelukast, Pranlukast, Zafirlukast); a modulator of prostaglandin pathway (e.g. CRTH2/DP2 receptor antagonist); Bruton's tyrosine Kinase inhibitors (BTK inhibitors); PDE4 inhibitors; antihistamines; histamine H4 receptor antagonist; H1 receptor antagonists; beta-adrenergic drugs such as beta (p)-2-adrenoceptor agonists; anticholinergic drugs or and anticholinergic or antimuscarinic agents (e.g. M2 and/or M3 antagonists); nonsteroidal anti-inflammatory drugs ("NSAIDs"); analgesics; inhibitors of 5-lipoxygenase; inhibitors of FLAP (5-lipoxygenase activating protein); COX-2 selective inhibitors and statins.

Suitable steroids are in particular, glucocorticosteroids, such as budesonide, beclamethasone dipropionate, fluticasone propionate, fluticasone furoate, ciclesonide or mometasone furoate; or non-steroidal glucocorticoid receptor agonists, such as velsecorat (AZD7594)

Suitable PDE4 inhibitors include for example roflumilast, aprelimast, crisaborole, lotamilast, ensifentrine (RPL554), and CHF 6001.

Suitable beta (p)-2-adrenoceptor agonists are for example albuterol (salbutamol), metaproterenol, terbutaline, salmeterol, fenoterol, procaterol, and especially, formoterol and pharmaceutically acceptable salts thereof, and compounds (in free or salt or solvate form) of formula (I) of WO 00/75114, which document is incorporated herein by reference, preferably compounds of the Examples thereof, especially a compound of formula

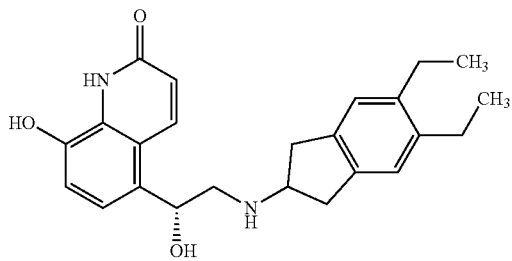 [SMILES: CCc1cc2c(cc1CC)CC(NC[C@H](O)c1ccc(O)c3[nH]c(=O)ccc13)C2]

and pharmaceutically acceptable salts thereof, as well as compounds (in free or salt or solvate form) of formula (I) of WO 04/16601. Further β-2-adrenoreceptor agonists include vilanterol, olodaterol and abediterol.

Suitable bronchodilatory drugs include anticholinergic or antimuscarinic agents, in particular, ipratropium bromide, oxitropium bromide, tiotropium salts, glycopyrromium bromide, umeclidinium bromide and aclidinium bromide, Suitable antihistamine (H1 antagonist) drug substances include cetirizine hydrochloride, clemastine fumarate, promethazine, loratidine, desloratidine, diphenhydramine and fexofenadine hydrochloride.

Suitable β$_2$-agonists for use in the present invention include, but are not limited to, arformoterol, bambuterol, bitolterol, broxaterol, carbuterol, clenbuterol, dopexamine, fenoterol, formoterol, hexoprenaline, ibuterol, Isoetharine, isoprenaline, levosalbutamol, mabuterol, meluadrine, metaproterenol, nolomirole, orciprenaline, pirbuterol, procaterol, reproterol, ritodrine, rimoterol, salbutamol, salmefamol, salmeterol, sibenadet, sotenerot, sulfonterol, terbutaline, tiaramide, tulobuterol, carmoterol, QAB-149 (also known as indacaterol), olodaterol, abediterol and vilanterol and I, and combinations thereof, each of which is optionally in the form of a racemate, enantiomer, diastereomer, or mixtures thereof, and also optionally in the form of a pharmacologically-compatible acid addition salt.

Suitable corticosteroids and glucocorticoids for use in the present invention include, but are not limited to, prednisolone, methylprednisolone, dexamethasone, naflocort, deflazacort, halopredone acetate, budesonide, beclomethasone dipropionate, hydrocortisone, triamcinolone acetonide, fluocinolone acetonide, fluocinonide, clocortolone pivalate, methylprednisolone aceponate, dexamethasone palmitoate, tipredane, hydrocortisone aceponate, prednicarbate, alclometasone dipropionate, halometasone, methylprednisolone suleptanate, mometasone furoate, rimexolone, prednisolone farnesylate, ciclesonide, deprodone propionate, fluticasone propionate, fluticasone furoate, halobetasol propionate, loteprednol etabonate, betamethasone butyrate propionate, flunisolide, prednisone, dexamethasone sodium phosphate, triamcinolone, betamethasone 17-valerate, betamethasone, betamethasone dipropionate, hydrocortisone acetate, hydrocortisone sodium succinate, prednisolone sodium phosphate, hydrocortisone probutate and combinations thereof.

Suitable LTD4 antagonists for use in the present invention include, but are not limited to, tomelukast, ibudilast, pobilukast, pranlukast hydrate, zafirlukast, ritolukast, verlukast, sulukast, cinalukast, iralukast sodium, montelukast sodium, 4-[4-[3-(4-Acetyl-3-hydroxy-2-propylphenoxy)propylsulfonyl] phenyl]-4-oxobutyric acid, [[5-[[3-(4-Acetyl-3-hydroxy-2-propylphenoxy)propyl]thio]-1,3,4-thiadiazol-2-yl] thio]acetic acid, 9-[(4-Acetyl-3-hydroxy-2-n-propylphenoxy)methyl]-3-(1H-tetrazol-5-yl)-4H-pyrido[1,2-a]pyrimidin-4-one, 5-[3-[2-(7-Chloroquinolin-2-yl)vinyl] phenyl]-8-(N,N-dimethylcarbamoyl)-4,6-dithiaoctanoic acid sodium salt; 3-[1-[3-[2-(7-Chloroquinolin-2-yl)vinyl] phenyl]-1-[3-(dimethylamino)-3-oxopropylsulfanyl]methylsulfanyl]propionic acid sodium salt, 6-(2-Cyclohexylethyl)-[1,3,4]thiadiazolo[3,2-a]-1,2,3-triazolo[4,5-d] pyrimidin-9(1H-one, 4-[6-Acetyl-3-[3-(4-acetyl-3-hydroxy-2-propylphenylthio)propoxy]-2-propylphenoxy] butyric acid, (R)-3-Methoxy-4-[1-methyl-5-[N-(2-methyl-4,4,4-trifluorobutyl)carbamoyl] indol-3-ylmethyl]-N-(2-methylphenylsulfonyl)benzamide, (R)-3-[2-Methoxy-4-[N-(2-methylphenylsulfonyl)carbamoyl] benzyl]-1-methyl-N-(4,4,4-trifluoro-2-methylbutyl)indole-5-carboxamide, (+)-4(S)-(4-Carboxyphenylthio)-7-[4-(4-phenoxybutoxy)phenyl]-5(Z)-heptenoic acid, compounds International Application No. PCT/EP03/12581, and combinations thereof.

Suitable NSAIDs for use in the present invention include, but are not limited to, Aceclofenac, acemetacin, acetylsalicylic acid, alclofenac, alminoprofen, amfenac, Ampiroxicam, Antolmetinguacil, Anirolac, antrafenine, azapropazone, benorylate, Bermoprofen, bindarit, bromfenac, bucloxic acid, Bucolom, Bufexamac, Bumadizon, butibufen, Butixirat, Carbasalatcalcium, carprofen, choline magnesium trisalicylate, celecoxib, Cinmetacin, Cinnoxicam, clidanac Clobuzarit Deboxamet, dexibuprofen, Dexketoprofen, diclofenac, diflunisal, droxicam, Eltenac, Enfenaminsaure, Etersalat, etodolac, etofenamate, etoricoxib, Feclobuzon, felbinac, fenbufen, fenclofenac, fenoprofen, fentiazac, Fepradinol, Feprazon, Flobufen, floctafenine, flufenamic acid, flufenisal, Flunoxaprofen, flurbiprofen, Flurbiprofenaxetil, Furofenac, Furprofen, Glucametacin, ibufenac, ibuprofen, Indobufen, indomethacin, Indometacinfarnesil, indoprofen, Isoxepac, Isoxicam, ketoprofen, ketorolac, lobenzarit, Lonazolac, lornoxicam, Loxoprofen, lumiracoxib, meclofenamic, Meclofen, mefenamic acid, meloxicam, mesalazine, Miro Profen, Mofezolac, nabumetone, naproxen, niflumic acid, olsalazine, oxaprozin, Oxipinac, oxyphenbutazone, parecoxib, phenylbutazone, Pelubiprofen, Pimeprofen, Pirazolac, Priroxicam, pirprofen, Pranoprofen, Prifelon, Prinomod, Proglumetacin, Proquazon, Protizininsaure, rofecoxib, Romazarit, salicylamide, salicylic acid, Salmi Stein, Salnacedin, salsalate, sulindac, sudoxicam, suprofen, Talniflumate, tenidap, Tenosal, tenoxicam, tepoxalin, tiaprofenic acid, Taramid, Tilnoprofenarbamel, timegadine, Tinoridin, Tiopinac, tolfenamic acid, tolmetin, Ufenamat, valdecoxib, Ximoprofen, zaltoprofen, Zoliprofen and combinations thereof.

Suitable Leukotriene A4 hydrolase inhibitors include compounds described in WO 2015/092740, WO2014/164658, WO2014/152536, WO2014/152518, WO2014/152229, WO2012/125598, WO2013/012844, WO2014/014874, WO2013/134226, WO2015/009609, WO2015/009611, WO2013/131901.

Of particular interest is a compound described in WO 2015/092740; for example a compound selected from (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl) butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; or pharmaceutically acceptable salt thereof).

Other LTA4H inhibitors of particular interest include Acebilustat, CTX-3397 or a compound disclosed in WO2014/164658 and more specifically compound which is: 4-(((1S,4S)-5-(4-(4-(oxazol-2-yl)phenoxy)benzyl)-2,5-diazabicyclo[2.2.1]heptan-2-yl)methyl)benzoic acid:

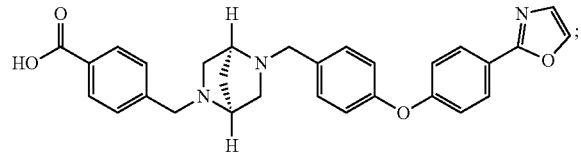 [SMILES: O=C(O)c1ccc(CN2C[C@@H]3C[C@H]2CN3Cc2ccc(Oc3ccc(-c4ncco4)cc3)cc2)cc1]

or a pharmaceutically acceptable salt thereof.

Suitable histamine H4 receptor antagonist include for example a compound described in U.S. Pat. No. 7,943,628; and preferably the compound of example 9 which is $N^4$-(cyclopropylmethyl)-6-[(3R)-3-(methylamino)pyrrolidin-1-yl]pyrimidine-2,4-diamine:

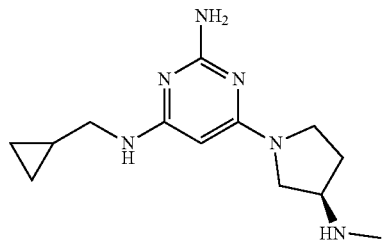 [SMILES: CN[C@@H]1CCN(c2cc(NCC3CC3)nc(N)n2)C1]

or a pharmaceutically acceptable salt thereof, preferably L-titrate salt thereof.

Suitable BTK inhibitors include for example Ibrutinib, Acalabrutinib (ACP-196), Evobrutinib; Fenebrutinib; Tirabrutinib (ONO-4059, GS-4059); Zanubrutinib (BGB-3111), Spebrutinib (CC-292, AVL-292), Poseltinib (HM-71224, LY3337641), Vecabrutinib (SNS-062)BMS-986142; BMS986195; PRN2246; PRN1008, M7583, CT1530, B11B068, AC-0058TA, ARQ-531, TAK-020, TG1701 or a compound described in WO2015/079417, WO2015/083008, WO2015/110923, WO2014/173289, WO2012/021444, WO2013/081016, WO2013/067274, WO2012/170976, WO2011/162515, US2017/119766, WO2016/065226, U.S. Pat. No. 9,688,676, WO2016/201280, WO2017/059702, U.S. Pat. No. 9,630,968, US2014/0256734, WO2017118277, WO2014/039899, WO/16/105531, WO2018/005849, WO2013/185082 or in Journal of Medicinal Chemistry, 2016 59 (19) 9173-9200.

Of particular interest, BTK inhibitors include compound of example 31 described in WO2014/039899, compound of the following structure:

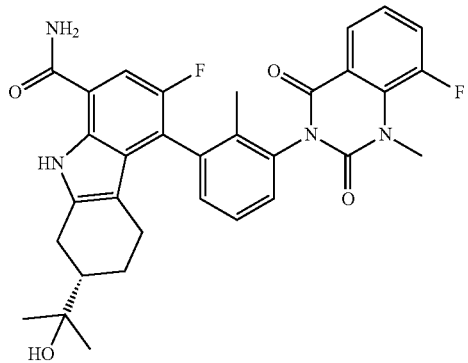 [SMILES: Cc1c(-c2c(F)cc(C(N)=O)c3[nH]c4c(c23)CC[C@H](C(C)(C)O)C4)cccc1-n1c(=O)c2cccc(F)c2n(C)c1=O]

described as compound 14f in Journal of Medicinal Chemistry, 2016, 59 (19), 9173-9200; compound of example 2 described in US2017/119766, compound of example 223 described in WO2016/065226 which is:

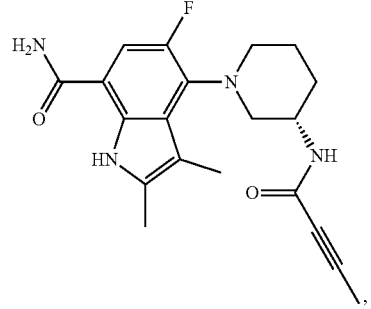 [SMILES: CC#CC(=O)N[C@H]1CCCN(c2c(F)cc(C(N)=O)c3[nH]c(C)c(C)c23)C1]

or compound 1 described in WO2016/201280, compound 1 described in WO2017/059702, or compound 1 described in WO2017/118277; or a pharmaceutically acceptable salt thereof.

Of other particular interest, BTK inhibitors include a compound described in WO2015/079417, for example a compound selected from N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof.

Suitable CRTH2/DP2 receptor antagonists include Fevipiprant, Timapiprant or [8-chloro-3-(4-chlorobenzyl)-4-difluoromethoxy-2-ethylquinolin-5-yloxy]acetic acid L-lysine salt (GB001) or a pharmaceutically acceptable salt thereof.

In a preferred embodiment, the second therapeutic agent is selected from:
1. a modulator of prostaglandin pathway (e.g. CRTH2/DP2 receptor antagonist, for example Fevipiprant);
2. a Leukotriene A4 hydrolase inhibitor (more specifically, a compound described in WO 2015/092740; preferably a compound selected from (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl) butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; or pharmaceutically acceptable salt thereof);

3. a histamine H4 receptor antagonist (for example a compound described in U.S. Pat. No. 7,943,628; and preferably the compound of example 9 which is $N^4$-(cyclopropylmethyl)-6-[(3R)-3-(methylamino)pyrrolidin-1-yl]pyrimidine-2,4-diamine:

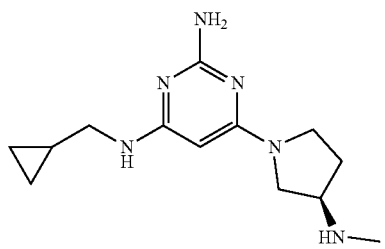 [SMILES: CN[C@@H]1CCN(c2cc(NCC3CC3)nc(N)n2)C1]

or a pharmaceutically acceptable salt thereof, preferably L-titrate salt thereof; and 4. a BTK inhibitor (for example a compound described in WO2015/079417, and preferably a compound selected from N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof.

In one embodiment of the invention, there is provided a product comprising 1-(4-chloro-3-fluorophenyl)-9-(1-(4-fluorophenyl)-1H-1,2,4-triazol-3-yl)-1,9-diazaspiro[5.5]undecan-2-one or a pharmaceutically salt thereof, and a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl) butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof as a combined preparation for simultaneous, separate or sequential use in therapy.

In one embodiment of the invention, there is provided a product comprising 1-(3,4-difluorophenyl)-9-(6-(2,2,2-trifluoroethoxy)pyrimidin-4-yl)-1,9-diazaspiro[5.5]undecan-2-one or a pharmaceutically salt thereof and a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof as a combined preparation for simultaneous, separate or sequential use in therapy.

In one embodiment of the invention, there is provided a product comprising 9-(2-amino-6-(4-(trifluoromethyl)-1H-pyrazol-1-yl)pyrimidin-4-yl)-1-(3,4-difluorophenyl)-1,9-diazaspiro[5.5]undecane-2-one or a pharmaceutically salt thereof and a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof as a combined preparation for simultaneous, separate or sequential use in therapy.

In one embodiment of the invention, there is provided a pharmaceutical composition comprising 9-(2-amino-6-(trifluoromethyl)pyrimidin-4-yl)-1-(3,4-difluorophenyl)-1,9-diazaspiro[5.5]undecan-2-one, or a pharmaceutically salt thereof; a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof, and a pharmaceutically acceptable carrier.

In one embodiment of the invention, there is provided a pharmaceutical composition comprising 9-(2-amino-6-(1,1-difluoroethyl)pyrimidin-4-yl)-1-(3,4-difluorophenyl)-1,9-diazaspiro[5.5]undecan-2-one, or a pharmaceutically salt thereof; a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof, and a pharmaceutically acceptable carrier.

In one embodiment of the invention, there is provided a pharmaceutical composition comprising (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, or (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, or a pharmaceutically salt thereof; a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof, and a pharmaceutically acceptable carrier.

In one embodiment of the invention, there is provided a pharmaceutical composition comprising 9-(2-amino-6-(trifluoromethyl)pyrimidin-4-yl)-1-(3,4-difluorophenyl)-1,9-diazaspiro[5.5]undecan-2-one, or a pharmaceutically salt thereof; a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof, and a pharmaceutically acceptable carrier.

In one embodiment of the invention, there is provided a pharmaceutical composition comprising 1-(3,4-difluorophenyl)-9-(6-(2,2,2-trifluoroethoxy)pyrimidin-4-yl)-1,9-diazaspiro[5.5]undecan-2-one, or a pharmaceutically salt thereof; a second therapeutic agent selected from Fevipiprant, (S)-3-amino-4-(5-(4-((5-chloro-3-fluoropyridin-2-yl)oxy)phenyl)-2H-tetrazol-2-yl)butanoic acid; (S)-3-amino-4-(5-(4-(4-chlorophenoxy)-phenyl)-2H-tetrazol-2-yl)butanoic acid; (R)-3-amino-4-(5-(3-phenethoxyphenyl)-2H-tetrazol-2-yl)butanoic acid; (S)-3-amino-4-(5-(4-(p-tolyloxy)phenyl)-2H-tetrazol-2-yl)butanoic acid; (R)-3-amino-4-(5-(4-butoxyphenyl)-2H-tetrazol-2-yl)butanoic acid; acid; (R)-3-amino-4-(5-(4-phenethoxyphenyl)-2H-tetrazol-2-yl)butanoic acid; (R)-3-amino-4-(5-(4-(4-chlorophenoxy)-phenyl)-2H-tetrazol-2-yl)butanoic acid; $N^4$-(cyclopropylmethyl)-6-[(3R)-3-(methylamino)pyrrolidin-1-yl]pyrimidine-2,4-diamine, N-(3-(5-((1-Acryloylazetidin-3-yl)oxy)-6-aminopyrimidin-4-yl)-5-fluoro-2-methylphenyl)-4-cyclopropyl-2-fluorobenzamide; N-(3-(6-Amino-5-((1-propioloylazetidin-3-yl)oxy)pyrimidin-4-yl)-5-fluoro-2-methylphenyl)-4-cyclopropyl-2-fluorobenzamide; N-(3-(6-Amino-5-(2-(N-methylacrylamido)ethoxy)pyrimidin-4-yl)-5-fluoro-2-methylphenyl)-4-cyclopropyl-2-fluorobenzamide; N-(3-(6-Amino-5-(2-(N-methylpropiolamido)ethoxy)pyrimidin-4-yl)-5-fluoro-2-methylphenyl)-4-cyclopropyl-2-fluorobenzamide; N-(3-(6-Amino-5-(2-(N-methylbut-2-ynamido)ethoxy)pyrimidin-4-yl)-5-fluoro-2-methylphenyl)-4-cyclopropyl-2-fluorobenzamide; N-(3-(6-Amino-5-(2-(N-ethylacrylamido)ethoxy)pyrimidin-4-yl)-5-fluoro-2-methylphenyl)-4-cyclopropyl-2-fluorobenzamide; N-(3-(6-Amino-5-(2-(N-(2-fluoroethyl)acrylamido)ethoxy)pyrimidin-4-yl)-5-fluoro-2-methylphenyl)-4-cyclopropyl-2-fluorobenzamide; (S)—N-(3-(6-Amino-5-(2-(but-2-ynamido)propoxy)pyrimidin-4-yl)-5-fluoro-2-methylphenyl)-4-cyclopropyl-2-fluorobenzamide; (S)—N-(3-(6-Amino-5-(2-(N-methylbut-2-ynamido)propoxy)pyrimidin-4-yl)-5-fluoro-2-methylphenyl)-4-cyclopropyl-2-fluorobenzamide and N-(3-(6-Amino-5-(3-(N-methylacrylamido)propoxy)pyrimidin-4-yl)-5-fluoro-2-methylphenyl)-4-cyclopropyl-2-fluorobenzamide; or a pharmaceutically acceptable salt thereof, and a pharmaceutically acceptable carrier.

Biological Assays and Data

The activity of a compound according to the present invention can be assessed by the following in vitro methods. A compound of formula (I) or a pharmaceutically acceptable salt thereof, exhibit valuable pharmacological properties, e.g. properties susceptible to LTC4S, e.g., as indicated in tests as provided in the next sections and are therefore indicated for therapy related to LTC4S.

A. Human LTC4S Enzymatic Assay:

$LTC_4$ synthase catalyzes the conversion of Leukotriene $A_4$ ($LTA_4$) to Leukotriene $C_4$ ($LTC_4$) in the presence of reduced glutathione (GSH) as a co-substrate. For compound testing, compounds are delivered as 10 mM stock solutions in 90% DMSO in matrix tubes. From this, a 1:3 dilution dose response series is prepared with a starting concentration of 30 μM to 0.1 nM. For the enzymatic assay 97.5 nL of compound/DMSO solution is transferred to each well and 5 μL enzyme solution (assay buffer: 50 mM bis-tris propane pH 7.3, 250 mM NaCl, 10 mM $MgCl_2$, 0.001% MGN3) is added to the wells. The final enzyme concentration in the assay is 0.75 nM. The enzyme compound mixture is incubated at room temperature for 15 minutes prior to the addition of 5 μL substrate solution. As the primary substrate $LTA_4$ is a highly unstable intermediate of the arachidonic acid pathway, $LTA_4$ is substituted for a more stable $LTA_4$ methyl ester form ($LTA_4$-Me) for the purposes of screening. A final substrate concentration of 400 μM GSH and 5 μM $LTA_4$-Me is chosen.

The $LTA_4$-Me is obtained commercially in 2% triethylamine/hexane solvent. As this solvent is incompatible with the HTRF assay it has to be exchanged with DMSO according to following procedure: add 50 μL of 100% DMSO to 50 μL $LTA_4$-Me (3 mM) in a 2 mL Eppendorf tube and mix gently by inverting the tube. The triethylamine/hexane is evaporated under a constant argon flux at room temperature. The DMSO-$LTA_4$-Me (3 mM) is aliquoted and stored at −20° C. for not longer than 4 weeks, as it is not stable in DMSO due to its oxidizing properties.

Upon addition of the substrate, the plate is immediately placed on a shaker for 5 min at room temperature. Immediately after the 5 min incubation 5 μL of $H_2O_2$ solution is added to all wells to stop the reaction. The plate contents are mixed before the addition of detection reagents. The conversion from $LTA_4$-Me and GSH to $LTC_4$-Me is quantified using a $LTC_4$-Me standard curve ranging from 1.5 μM to 0.08 nM. For the detection of the product of the enzymatic reaction $LTC_4$-Me, the Cisbio $LTC_4$-HTRF kit is used as the assay is compatible with the detection of $LTC_4$-Me. 5 μL of diluted $LTC_4$-d2 conjugate (according to manufacturer's protocol) are added to all wells of the assay plate and the contents gently mixed and incubated for 5 minutes at room temperature. Then 5 μL of the diluted $LTC_4$-Eu3+ cryptate (according to manufacturer's protocol) are added to all wells and the contents of the plate gently mixed and incubated 60 min at room temperature before reading the plate on the Spectramax Paradigm (Molecular Devices) using ratiometric analysis (665/616 nM) and the following setup: number of flashes/well of 30, integration time of 0.3 ms, excitation time of 0.05 ms, positioning delay of 0.03 ms, and a ratio multiplicator of 10000. The percent inhibition for each point of an inhibition curve is calculated after data interpolation using the $LTC_4$-Me standard curve, to convert the HTRF signal to the amount of $LTC_4$-Me produced within the $LTC_4S$ catalyzed reaction on each plate. The data is analyzed using parametric curve fitting to determine $IC_{50}$ values of $LTC_4S$ inhibitors. Due to the assay setup, the maximally detectable potency of compounds is at around 2-4 nM. Therefore compounds with a potency that may theoretically result in $IC_{50}$ values lower than 2 nM are measured from diluted stock solutions, usually with 1 µM starting concentration in the assay.

B. Human Whole Blood HTRF Assay $LTC_4$ synthase catalyzes the conversion of Leukotriene $A_4$ ($LTA_4$) to Leukotriene $C_4$ ($LTC_4$) in the presence of reduced glutathione (GSH) as a co-substrate. For testing the inhibition of $LTC_4S$, compounds are prepared for either eight-point or sixteen-point dose response studies in 384-well Labcyte low dead volume (LDV) plates. For eight-point dose response studies, compounds are diluted 1:5 starting at 1 µM concentration in 90% DMSO. For sixteen-point dose response studies, compounds are diluted 1:3.333 starting at 10 µM concentration in 90% DMSO. Compounds are studied in duplicates. Ten wells are filled with 90% DMSO which correspond to the stimulated and unstimulated control wells. On the day before the assay is run, 100 nL from each well, i.e., each compound at each concentration, are printed from the Labcyte LDV plate into each corresponding well on the assay plate (Greiner BioOne #784201) using a Labcyte Echo 650 acoustic liquid handler and stored at 4° C. The morning of the assay, whole blood is collected from three human donors. Donors must be non-smokers and must not have taken NSAIDs within the 48 hours prior to blood collection. The amount of blood collected per donor depends on the amount of compounds to be tested and the dose response format in which they are to be studied (about 8 mL of whole blood for either 22 compounds in 8-point dose response format or 11 compounds in 16-point dose response format). Whole blood from the three donors is diluted 1:3 in RPMI 1640 medium (Gibco #72400-047). 50 µL of diluted blood are then dispensed into each assay plate well with pre-dispensed compounds and DMSO for the stimulated and unstimulated controls using a Thermo Scientific™ Multidrop™ Combi reagent dispenser, and incubated at 37° C. for 4 hours. Calcium ionophore A23187 is used to induce a rapid increase in intracellular levels of $Ca^{2+}$. The $Ca^{2+}$ functions as a universal second messenger in various immune cells, such as T cells, B cells and mast cells, and is used to induce degranulation and release of eicosanoids, including $LTC_4$, by cells contained in the whole blood samples. Shortly before the completion of the 4-hour incubation, 0.5 mg/mL calcium ionophore A23187 is prepared by mixing (for 1 mL) 20 µL of 25 mg/mL calcium ionophore A23187 stock solution (Sigma-Aldrich #C-7522) in 950 µL of warmed-up (37° C.) RPMI 1640 medium and 30 µL of dimethyl sulfoxide (DMSO). All but the unstimulated control wells are subsequently stimulated by dispensing 1 µL of the 0.5 mg/mL calcium ionophore suspension using the Thermo Scientific™ Multidrop™ Combi reagent dispenser. Plates are incubated for 15 minutes at 37° C. Plates are then centrifuged at 300 g for 10 minutes at room temperature to pellet blood cells and stop the reaction. Finally, 25 µL of the resulting supernatants are collected from each well using a Beckman Coulter Biomek $FX^P$ automated liquid handler into empty 384-well plates (Greiner BioOne #781281) for storage. Plates are sealed and stored at −80° C.

In order to measure the amount of $LTC_4$ released by cells in the human blood samples during calcium ionophore stimulation, supernatants are analyzed using the Cisbio $LTC_4$ homogeneous time-resolved FRET (HTRF) kit (Cisbio #64LC4PEH). Supernatants from human whole blood are thawed and diluted by transferring 3.5 µL from each well into high-base, low-volume white plates (Greiner BioOne #784075) already containing 6.5 µL of Diluent #3 solution (Cisbio #62DL3DDD). Ten serially diluted standard curve solutions are also dispensed in duplicate into each plate as instructed in the protocol. Blank controls and cryptate control wells are also prepared. Then, 5 µL of anti-$LTC_4$-d2 working solution are dispensed into all the wells, but the cryptate control wells. Subsequently, 5 µL of anti-$LTC_4$-Eu3+ cryptate working solution are dispensed into all the wells. Plates are then covered with a lid and incubated at room temperature for one hour with gentle orbital shaking (~450 rpm). Time resolved fluorescence at 665 and 620 nm is measured after the incubation using a BMG LABTECH CLARIOstar® (50 flashes per well, integration starting at 60 µs for 400 µs, 12.0 mm focal height). HTRF ratios are calculated for each well by dividing the 665 nm intensity by the 620 nm intensity, and multiplying the resulting ratio by 10,000. $LTC_4$ standard curves are interpolated for each plate and used to convert the HTRF ratio readouts into the amount of $LTC_4$ present in each well (in ng/mL). Parametric curve fitting is used to obtain inhibition curves and $IC_{50}$ values.

TABLE 1

| Example # | human LTC4S $IC_{50}$ (enzymatic assay) | human whole blood HTRF $IC_{50}$ |
|---|---|---|
| 1 | 6 | 13 |
| 2 | 36 | — |
| 3 | 8 | 180 |
| 4 | 7 | 50 |
| 5 | 5 | 10 |
| 6a | 190 | 310 |
| 6b | 44 | — |
| 7 | 76 | 100 |
| 8 | 7 | — |
| 9 | 2 | 48 |
| 10 | — | 5 |
| 11 | — | 6 |
| 12 | — | 2 |
| 13 | — | 36 |
| 14 | — | 1 |
| 15a | — | 1 |
| 15b | — | 180 |
| 16 | — | 16 |
| 17 | — | 9 |
| 18 | — | 2 |
| 19 | — | 3 |
| 20 | 12 | 64 |
| 21 | 4 | 7 |
| 22 | 11 | 530 |
| 23 | 61 | 45 |
| 24 | 33 | 110 |
| 25 | 62 | 170 |
| 26 | 16 | 110 |
| 27 | 25 | 59 |
| 28 | 110 | 450 |
| 29 | 57 | 180 |
| 30 | 13 | 360 |
| 31 | 15 | 120 |
| 32 | 7 | 170 |
| 33 | 24 | 56 |
| 34 | — | 2 |

TABLE 1-continued

| Example # | human LTC4S IC$_{50}$ (enzymatic assay) | human whole blood HTRF IC$_{50}$ |
|---|---|---|
| 35a | 12 | 40 |
| 35b | 3 | — |
| 36 | 6 | 44 |
| 37 | 12 | 120 |
| 38 | 8 | 86 |
| 39 | — | 4 |
| 40 | — | 4 |
| 41 | — | 5 |
| 42 | — | 410 |
| 43 | — | 400 |
| 44 | 13 | — |
| 45 | — | 620 |
| 46 | — | 490 |
| 47 | — | 7 |
| 48 | — | 45 |
| 49 | — | 88 |
| 50 | — | 45 |
| 51 | — | 70 |
| 52 | — | 29 |
| 53 | — | 1140 |
| 54 | — | 300 |
| 55 | — | 6 |
| 56 | — | 17 |
| 57 | — | 850 |
| 58 | — | 560 |
| 59 | — | 640 |
| 60 | — | 680 |
| 61 | — | 29 |
| 62 | — | 410 |
| 63 | — | 430 |
| 64 | — | 2 |
| 65 | — | 1 |
| 66 | — | 1 |
| 67, racemic | — | 2 |
| 68 | — | 120 |
| 69 | — | 35 |
| 70 | — | 110 |
| 71 | — | 580 |
| 72 | — | 760 |
| 73 | — | 68 |
| 74 | — | 4 |
| 75 | — | 4 |
| 76 | — | 57 |
| 77 | — | 31 |
| 78 | — | 24 |
| 79 | — | 56 |
| 80 | — | 24 |
| 81 | 13 | 72 |
| 82 | 12 | 21 |
| 83 | 9 | 9 |
| 84 | 8 | 9 |
| 85 | — | 430 |
| 86, racemic | — | 2 |
| 87 | — | 7 |
| 88 | — | 1370 |
| 89a | — | 1 |
| 89b | — | 5 |
| 90 | — | 4 |
| 91 | — | 3 |
| 92 | — | 5 |
| 93 | — | 10 |
| 94 | — | 830 |
| 95, racemic | — | 2 |
| 96, racemic | — | 3 |
| 97 | — | 3 |
| 98 | — | 3 |
| 99 | — | 4 |
| 100 | — | 2 |
| 101 | — | 5 |
| 102, racemic | — | 9 |
| 103 | — | 8 |
| 104, racemic | — | 5 |
| 105, racemic | — | 6 |
| 106 | — | 69 |
| 107 | — | 6 |
| 108, racemic | — | 22 |
| 109 | — | 15 |
| 110a | — | 3 |
| 110b | — | 5 |
| 111, racemic | — | 17 |
| 112 | — | 67 |
| 113a | — | 15 |
| 113b | — | 36 |
| 114 | — | 7 |
| 115 | — | 28 |
| 116a | — | 13 |
| 116b | — | 33 |
| 117 | — | 18 |
| 118 | — | 8 |
| 119 | — | 29 |
| 120 | — | 32 |

Exemplification of the Invention

The disclosure is further illustrated by the following examples and synthesis schemes, which are not to be construed as limiting this disclosure in scope or spirit to the specific procedures herein described. It is to be understood that the examples are provided to illustrate certain embodiments and that no limitation to the scope of the disclosure is intended thereby. It is to be further understood that resort may be had to various other embodiments, modifications, and equivalents thereof which may suggest themselves to those skilled in the art without departing from the spirit of the present disclosure and/or scope of the appended claims.

Compounds of the present disclosure may be prepared by methods known in the art of organic synthesis. In all of the methods it is understood that protecting groups for sensitive or reactive groups may be employed where necessary in accordance with general principles of chemistry. Protecting groups are manipulated according to standard methods of organic synthesis (T. W. Green and P. G. M. Wuts (1999) Protective Groups in Organic Synthesis, 3rd edition, John Wiley & Sons). These groups are removed at a convenient stage of the compound synthesis using methods that are readily apparent to those skilled in the art.

Unless otherwise noted, reagents and solvents were used as received from commercial suppliers. Proton nuclear magnetic resonance (NMR) spectra are given in ppm (δ) and coupling constants, J, are reported in Hertz. Tetramethylsilane (TMS) was used as an internal standard. Chemical shifts are reported in ppm relative to dimethyl sulfoxide (δ 2.50), methanol (δ 3.31), chloroform (δ 7.26) or other solvent as indicated in NMR spectral data. A small amount of the dry sample (2-5 mg) is dissolved in an appropriate deuterated solvent (1 mL). The chemical names were generated using ChemBioDraw Ultra v12 from CambridgeSoft.

Temperatures are given in degrees Celsius. If not mentioned otherwise, all evaporations are performed under reduced pressure, typically between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art.

Abbreviations Used in the Following Examples and Elsewhere Herein are

2-MeTHF 2-methyltetrahydrofuran
ACN acetonitrile
AcOH acetic acid
Bn or Bzl benzyl
Boc tert-butyloxycarbonyl
$Boc_2O$ di-tert butyl dicarbonate
$B_2Pin_2$ 4,4,4,4,5,5,5,5-Octamethyl-2,2-bi-1,3,2-dioxaborolane, bis(pinacolato)diboron
br broad
brine saturated aqueous NaCl solution
cHex cyclohexane
d doublet
DAST (diethylamino)sulfur trifluoride
DBU 1,8-diazabicyclo(5.4.0)undec-7-ene
DCE dichloroethane
DCM dichloromethane
dd doublet of doublets
DIAD diisopropyl azodicarboxylate
DIBAH diisobutylaluminium hydride
DIPEA diisopropylethylamine
DMAP dimethylaminopyridine
DME 1,2-dimethoxyethane
DMF N,N-dimethyl formamide
DMSO dimethylsulfoxide
DPEPhos bis[(2-diphenylphosphino)phenyl] ether
EDC·HCl N-(3-dimethylaminopropyl)-N-ethylcarbodiimide hydrochloride
$Et_2O$ diethylether
EtOAc ethyl acetate
EtOH ethanol
eq equivalent(s)
equiv. equivalent(s)
Ex example(s)
h hour
HCl hydrochloric acid
HOBt 1-hydroxybenzotriazol
HPLC high performance liquid chromatography
IPA iso-propanol
LC liquid chromatography
LiHMDS lithium bis(trimethylsilyl)amide
m multiplet/milli, depending on the context
mCPBA 3-chloroperoxybenzoic acid
MeCN acetonitrile
MeOH methanol
mg milligram
min minutes
MS mass spectrometry
mL milliliter
mmol millimol
MTBE methyl tert-butyl ether
m/z mass to charge ratio
NMR nuclear magnetic resonance
ppm parts per million
PyBrop bromo-tris-pyrrolidino-phosphonium hexafluorophosphate
q quartet
quint quintet
RT room temperature
RP reversed phase
s singlet
SFC supercritical fluid chromatography
t triplet
TBME tert-butylmethylether
tBu tert-butyl
TEA triethylamine
TFA trifluoroacetic acid
THF tetrahydrofuran
TLC thin layer chromatography
TMSCN trimethylsilylcyanide
$t_R$ retention time
UPLC ultra performance liquid chromatography Analytical Details

NMR:

Measurements were performed on a Bruker Ultrashield™ 400 (400 MHz), Bruker Ultrashield™ 600 (600 MHz), Agilent VNMRS-300 (300 MHz), spectrometer using or not trimethylsilane as an internal standard. Chemical shifts (δ-values) are reported in ppm downfield from tetramethylsilane, spectra splitting pattern are designated as singlet (s), doublet (d), triplet (t), quartet (q), quintet (quint), multiplet, unresolved or overlapping signals (m), broad signal (br). Deuterated solvents are given in parentheses.

LC-MS:

LCMS Method a:
System: Waters Acquity UPLC with Waters SQ detector.
Column: Acquity HSS T3, 2.1×50 mm, 1.8 µm; column temperature: 60° C.
Gradient: from 5 to 98% B in 1.4 min, A=water+0.05% formic acid+3.75 mM ammonium acetate, B=acetonitrile+0.04% formic acid, flow: 1.0 mL/min.

LCMS Method b:
System: Waters Acquity UPLC with Waters SQ detector.
Column: Acquity CSH C18, 2.1×50 mm, 1.7 µm; column temperature: 50° C.
Gradient: from 5 to 98% B in 1.8 min, A=water+0.1% $NH_3$, B=acetonitrile+0.1% $NH_3$, flow: 1.0 mL/min.

LCMS Method c:
System: Waters Acquity UPLC with Waters SQ detector.
Column: Acquity BEH C18, 2.1×50 mm; column temperature: 50° C.
Gradient: from 3 to 98% B in 4.8 min, A=water+0.05% formic acid, B=acetonitrile+0.05% formic acid, flow: 0.6 mL/min.

LCMS Method d:
System: Waters Acquity UPLC with Waters SQ detector.
Column: Acquity BEH C18, 2.1×50 mm, 1.7 µm; column temperature: 40° C.
Gradient: from 3 to 98% B in 2.8 min, A=water+0.1% formic acid, B=acetonitrile+0.1% formic acid, flow: 0.8 mL/min.

LCMS Method e:
System: Waters Acquity UPLC with Waters SQ detector.
Column: Acquity BEH C18, 2.1×30 mm, 1.7 µm; column temperature: 40° C.
Gradient: from 3 to 98% B in 2.8 min, A=water+0.1% formic acid, B=acetonitrile+0.1% formic acid, flow: 1 mL/min.

LCMS Method f:
System: Agilent LC/MSD
Column: Zorbax C18, 4.6×150 mm, 5 µm; column temperature: 40° C.
Gradient: 30% to 70% B in 1 min, 70 to 100% B in 5 min; A=water+0.1% TFA, B=acetonitrile; flow: 1.0 mL/min.

LCMS Method q:
System: Agilent LC/MSD
Column: Kinetex C18 4.6×100 mm, 5 µm; column temperature: 40° C.
Gradient: 0-20% B in 2 min, 20-70% B in 8 min, 70-100% B in 3 min; A=water, B=acetonitrile; flow: 0.75 mL/min.

LCMS Method h:
  System: Waters Acquity UPLC with Waters SQ detector.
  Column: Acquity BEH C18, 2.1×30 mm, 1.7 µm; column temperature: 40° C.
  Gradient: from 2 to 98% B in 1.5 min, A=water+5 mM ammonium hydroxide, B=acetonitrile+5 mM ammonium hydroxide, flow: 1.0 mL/min.
LCMS Method i:
  System: Waters Acquity UPLC with Waters SQ detector
  Column: Acquity BEH C18, 2.1×30 mm, 1.7 µm
  Mobile phases, gradient: A=water+0.05% formic acid, B=methanol+0.04% formic acid; time (min)/% of B: 0.0/2, 0.10/2, 0.50/80, 0.60/95, 0.80/95, 0.90/2, 1.15/2
  Flow rate: 1.0 mL/min
LCMS Method j:
  System: Shimadzu LCMS 2020
  Column: Synergi max-RP 100 Å Mercury, 4.0×30 mm, 2.5 µm; column temperature: 40° C.
  Mobile phases, gradient: A=0.1% HCOOH in water, B=acetonitrile; time (min)/% of B: 0/5, 0.1/5, 0.5/5, 1.0/95, 1.5/95, 2.0/5, 3.0/5
  Flow rate: 2.0 mL/min
  Detection: PDA, 210 nm
LCMS Method k:
  System: Agilent LC/MSD
  Column: Kinetex EVO, 4.6×50 mm, 2.6 µm; column temperature: 40° C.
  Mobile phases, gradient: A=0.1% HCOOH in water, B=acetonitrile; time (min)/% of B: 0.0/20, 0.25/20, 01.0/95.0, 2.5/95, 3.0/20, 4/20
  Flow rate: 1.5 mL/min
  Detection: PDA, 210 nm
LCMS Method l:
  System: Sciex API-2000
  Column: Synergi max-RP 100 Å Mercury, 4.0×30 mm, 2.5 µm; column temperature: 30° C.
  Mobile phases, gradient: A=0.1% HCOOH in water, B=acetonitrile; time (min)/% of B: 0/30, 0.5/30, 1.5/95, 2.4/95, 2.5/30, 3.0/30
  Flow rate: 2.0 mL/min
  Detection: TWC PDA
LCMS Method m:
  System: Agilent 1200-6120
  Column: Poroshell 120 EC-C18, 4.6×50 mm, 2.7 µm; column temperature: 40° C.
  Mobile phases, gradient: A=0.1% formic acid in water, B=0.1% formic acid in acetonitrile; time (min)/% of B: 0/5, 4.0/95, 6.0/95
  Flow rate: 1.2 mL/min
  Detection: PDA, 210 nm
Preparative Methods:
Flash Chromatography System:
  System: Teledyne ISCO, CombiFlash Rf.
  Column: pre-packed RediSep Rf cartridges.
SFC:
  System: Waters Preparative SFC-100-MS system:
  Detection: Waters 2998 Photodiode Array Detector Waters MS Single Quadrupole Detection
  Modifier: Methanol
  ABPR: 120 bar
  Column temperature: 40° C.
  Flow rate: 100 g/min.
Prep HPLC (RP):
  System: Waters Autopurification-MS System
  Detection: Waters 2998 Photodiode Array Detector Waters MS Single Quadrupole Detection
  Column temperature: RT
  Eluent A: water
  Eluent B: acetonitrile, both containing 0.1% TFA or 0.1% NH$_4$OH All reagents, starting materials and intermediates utilized in these examples were available from commercial sources or were readily prepared by methods known to those skilled in the art.

Intermediate A: 1-(3,4-difluorophenyl)-1,9-diazaspiro[5.5]undecane-2-one

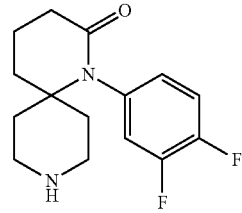 [SMILES: O=C1CCCC2(CCNCC2)N1c1ccc(F)c(F)c1]

Step A: tert-butyl 4-cyano-4-((3,4-difluorophenyl)amino)piperidine-1-carboxylate)

TMSCN (20.2 ml, 151 mmol) was added to solution of tert-butyl 4-oxopiperidine-1-carboxylate (15 g, 75 mmol) and 3,4-difluoroaniline (7.5 mL, 75 mmol) in 10 ml of AcOH. The reaction mixture was stirred at 100° C. for 3 h, partioned between water and DCM and extracted three times. The combined organic extracts were dried over Na$_2$SO$_4$, filtered, and concentrated. The residue was triturated with diethylether and the product was filtered off as a beige solid (19.25 g, 55.9 mmol). $^1$H NMR (400 MHz, DMSO-d$_6$) δ=7.27 (dd, 1H), 6.84 (ddd, 1H), 6.69 (m, 1H), 6.29 (s, 1H), 3.78 (m, 2H), 3.16 (m, 2H), 2.27 (m, 2H), 1.74 (m, 2H), 1.44 (s, 9H) ppm; m/z=382.3 [M+HCO$_2$]$^-$; $t_R$=1.13 min (LCMS method a).

Step B: tert-butyl 4-allyl-4-((3,4-difluorophenyl)amino)piperidine-1-carboxylate Allyl magnesium bromide (1.0 M in diethyl ether, 86 mL, 86 mmol) was added dropwise under argon atmosphere to a stirred solution of tert-butyl 4-cyano-4-((3,4-difluorophenyl)amino)piperidine-1-carboxylate) (19.3 g, 57.1 mmol) in 300 mL of THF cooled to 0° C. The reaction mixture was allowed to reach RT and stirred for 16 h. The mixture was acidified with 2 M aqueous HCl, diluted with DCM, washed with water and brine. The aqueous layers were extracted twice with DCM. The combined organic layers were dried over Na$_2$SO$_4$, filtered, and concentrated. Purification by silica gel chromatography (0-40% MeOH in EtOAc) provided tert-butyl 4-allyl-4-((3,4-difluorophenyl)amino)piperidine-1-carboxylate (7.38 g, 20.5 mmol). $^1$H NMR (400 MHz, DMSO-d$_6$) δ=7.07 (dt, 1H), 6.71 (m, 1H), 6.54 (dt, 1H), 5.7 (m, 1H), 5.34 (s, 1H), 5.01 (m, 2H), 3.59 (m, 2H), 3.09 (m, 2H), 2.43 (m, 2H), 1.87 (m, 2H), 1.42 (m, 2H), 1.40 (s, 9H) ppm; m/z=353.2 [M+H]$^+$; $t_R$=1.32 min (LCMS method a).

Step C: tert-butyl (E)-4-((3,4-difluorophenyl)amino)-4-(4-ethoxy-4-oxobut-2-en-1-yl)piperidine-1-carboxylate Ethyl acrylate (2.5 ml, 23.0 mmol) and Hoveyda-Grubbs Catalyst 2nd Generation (656 mg, 1.05 mmol) were added under argon to a solution of tert-butyl 4-allyl-4-((3,4-difluorophenyl) amino)piperidine-1-carboxylate (7.38 g, 20.9 mmol) in 200 mL of toluene. The reaction mixture was stirred for 16 h at 110° C., cooled to RT, absorbed on Isolute and evaporated to dryness. Purification by silica gel chromatography (0-45% EtOAc in cyclohexane) provided tert-butyl (E)-4-((3,4-difluorophenyl)amino)-4-(4-ethoxy-4-oxobut-2-en-1-yl)piperidine-1-carboxylate (5.00 g, 11.2 mmol). $^1$H NMR (400 MHz, DMSO-$d_6$) δ=7.09 (dd, 1H), 6.76 (m, 2H), 6.56 (m, 1H), 5.86 (d, 1H), 5.50 (s, 1H), 4.07 (q, 2H), 3.59 (m, 2H), 3.08 (m, 2H), 2.64 (d, 2H), 1.88 (m, 2H), 1.48 (m, 2H), 1.40 (s, 9H), 1.20 (t, 3H) ppm; m/z=425.3 [M+H]$^+$; $t_R$=1.28 min (83%, trans), 1.30 min (14%, cis) (LCMS method a).

Step D: tert-butyl 4-((3,4-difluorophenyl)amino)-4-(4-ethoxy-4-oxobutyl)piperidine-1-carboxylate PtO$_2$ (1.34 g, 0.589 mmol) was added under an argon atmosphere to a solution of tert-butyl (E)-4-((3,4-difluorophenyl)amino)-4-(4-ethoxy-4-oxobut-2-en-1-yl)piperidine-1-carboxylate (5.0 g, 11.78 mmol) in 75 mL of MeOH. The reaction mixture was evacuated and ventilated three times with H$_2$. The reaction mixture was then stirred for another 1 h at RT. Additional PtO$_2$ (1.337 g, 0.589 mmol) was added and the reaction mixture stirred for another hour at 40° C. Then the reaction mixture was flushed with argon and filtered over Hyflo® filter aid. The filtrate was absorbed on Isolute® and evaporated to dryness. Purification by silica gel chromatography (0-40% EtOAc in cyclohexane) provided tert-butyl 4-((3,4-difluorophenyl)amino)-4-(4-ethoxy-4-oxobutyl)piperidine-1-carboxylate (4.42 g, 9.84 mmol). $^1$H NMR (400 MHz, DMSO-$d_6$) δ=7.06 (dd, 1H), 6.66 (m, 1H), 6.49 (m, 1H), 5.34 (s, 1H), 4.07 and 4.00 (q, 2H), 3.57 (m, 2H), 3.06 (m, 2H), 2.21 (t, 2H), 1.89 (m, 2H), 1.64 (m, 2H), 1.4-1.5 (m, 4H), 1.40 (s, 9H), 1.20 and 1.15 (t, 3H) ppm; m/z=427.4 [M+H]$^+$; $t_R$=1.29 min (UPLC-MS method a).

Step E: 4-(1-(tert-butoxycarbonyl)-4-((3,4-difluorophenyl)amino)piperidin-4-yl)butanoic acid LiOH (496 mg, 20.71 mmol) was added to a solution of tert-butyl 4-((3,4-difluorophenyl) amino)-4-(4-ethoxy-4-oxobutyl)piperidine-1-carboxylate (4.42 g, 10.35 mmol) in 40 mL of THF/water (1:1) and the reaction mixture stirred for 16 h at 55° C. The reaction mixture was acidified with citric acid and diluted with DCM. The aqueous layer was extracted three times with DCM. The combined organic extracts were dried with Na$_2$SO$_4$, filtered, and concentrated. The resulting solid was dried under vacuum. The crude 4-(1-(tert-butoxycarbonyl)-4-((3,4-difluorophenyl)amino)piperidin-4-yl)butanoic acid (3.81 g, 9.08 mmol) was used in the next step without further purification. $^1$H NMR (400 MHz, DMSO-$d_6$) δ=11.89 (br s, 1H), 7.06 (m, 1H), 6.67 (m, 1H), 6.50 (m, 1H), 5.33 (s, 1H), 3.58 (m, 2H), 3.07 (m, 2H), 2.13 (t, 2H), 1.89 (m, 2H), 1.77 (m, 2H), 1.63 (m, 2H), 1.41 (m, 2H), 1.40 (s, 9H) ppm; m/z=399.4 [M+H]$^+$; $t_R$=1.13 min (LCMS method a).

Step F: tert-butyl 1-(3,4-difluorophenyl)-2-oxo-1,9-diazaspiro[5.5]undecan-9-carboxylate To a solution of 4-(1-(tert-butoxycarbonyl)-4-((3,4-difluorophenyl)amino)piperidin-4-yl)butanoic acid (3.81 g, 9.56 mmol) in 100 mL of dry EtOAc was added SOCl$_2$ (2.4 mL, 33.5 mmol) and the reaction mixture stirred for 2 h at RT. The reaction mixture was treated with water and extracted three times with ethyl acetate. The combined organic layers were dried over Na$_2$SO$_4$, filtered and concentrated. Purification by reverse phase column chromatography (RP C18, 10-100% MeOH in water) provided tert-butyl 1-(3,4-difluorophenyl)-2-oxo-1,9-diazaspiro[5.5]undecan-9-carboxylate (3.64 g, 9.57 mmol); m/z=381.2 [M+H]$^+$; $t_R$=1.00 min (LCMS method a).

Step G: 1-(3,4-difluorophenyl)-1,9-diazaspiro[5.5]undecan-2-one

To a solution of tert-butyl 1-(3,4-difluorophenyl)-2-oxo-1,9-diazaspiro[5.5]undecane-9-carboxylate (3.64 g, 9.57 mmol) in dioxane (25 mL) was added HCl (4 M in dioxane, 25 mL). The reaction mixture was stirred for 2 h at RT. The solid was collected by filtration and washed with dioxane. The HCl salt was solubilized in water and DCM. The pH was adjusted to ~10 by addition of 2 M Na$_2$CO$_3$ solution. The aqueous layer was back extracted three time with DCM. The combined organic extracts were dried over Na$_2$CO$_3$, filtered, and concentrated to provide 1-(3,4-difluorophenyl)-1,9-diazaspiro[5.5]undecan-2-one (3.00 g, 9.00 mmol). $^1$H NMR (400 MHz, DMSO-$d_6$) δ=7.46 (dd, 1H), 7.20 (m, 1H), 6.90 (m, 1H), 2.74 (m, 2H), 2.62 (m, 2H), 2.38 (t, 2H), 2.03 (m, 2H), 1.62-1.81 (m, 4H), 1.46 (m, 2H) ppm, NH not observed; m/z=281.2 [M+H]$^+$; $t_R$=0.49 min (LCMS method a).

Intermediate B: 1-(4-chloro-3-fluorophenyl)-1,9-diazaspiro[5.5]undecan-2-one

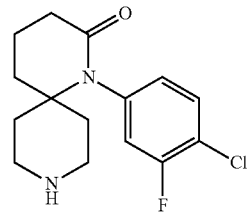 [SMILES: O=C1CCCC2(CCNCC2)N1c1ccc(Cl)c(F)c1]

Step A: tert-butyl 4-((4-chloro-3-fluorophenyl) amino)-4-cyanopiperidine-1-carboxylate)

TMSCN (5.97 g, 60.2 mmol) was added to a solution of tert-butyl 4-oxopiperidine-1-carboxylate (10 g, 50 mmol) and 4-chloro-3-fluoroaniline (8.77 g, 60.2 mmol) in 100 mL of acetic acid. The resulting reaction mixture was stirred for 23 h at RT. Then the mixture was cooled to 0° C. and concentrated ammonium hydroxide solution was added until a pH of 12 was reached. The precipitate was washed with water and dried under vacuum to provide tert-butyl 4-((4-chloro-3-fluorophenyl)amino)-4-cyanopiperidine-1-carboxylate) (16.23 g, 45.0 mmol). $^1$H NMR (400 MHz, DMSO-$d_6$) δ=7.35 (dd, 1H), 6.80 (d, 1H), 6.71 (d, 1H), 6.61 (s, 1H), 3.77 (m, 2H), 3.18 (m, 2H), 2.31 (m, 2H), 1.77 (m, 2H), 1.41 (s, 9H) ppm; m/z=398.3 [M+H]$^+$; $t_R$=1.22 min (LCMS method a).

Step B: tert-butyl 4-allyl-4-((4-chloro-3-fluorophenyl)amino)piperidine-1-carboxylate Tert-butyl 4-((4-chloro-3-fluorophenyl)amino)-4-cyanopiperidine-1-carboxylate) (12 g, 33.9 mmol) was dissolved in 125 mL of dry THF and cooled to 0° C. under argon.

Allymagnesium bromide (1.0 M solution in diethylether, 51 mL, 51 mmol) was added dropwise at 0° C. The reaction mixture was stirred for 2 h at 0° C., then allowed to warm to RT. The reaction mixture was quenched with saturated aqueous NH$_4$Cl and extracted three times with ethyl acetate. The organic extracts were dried over Na$_2$SO$_4$, filtered, and concentrated. Purification by silica gel chromatography (0-10% EtOAc in cyclohexane) provided tert-butyl 4-allyl-4-((4-chloro-3-fluorophenyl)amino)piperidine-1-carboxylate (7.76 g, 19.8 mmol). $^1$H NMR (400 MHz, DMSO-d$_6$) δ=7.15 (dd, 1H), 6.69 (d, 1H), 6.60 (d, 1H), 5.67 (s, 1H), 5.63-5.73 (m, 1H), 4.97-5.04 (m, 2H), 4.01 (m, 1H), 3.59 (m, 2H), 3.30 (m, 1H), 2.46 (m, 2H), 1.88-1.91 (m, 2H), 1.43-1.50 (m, 2H), 1.39 (s, 9H) ppm; m/z=369.4 [M+H]$^+$; t$_R$=1.4 min (LCMS method a).

Step C: tert-butyl 4-allyl-4-(N-(4-chloro-3-fluorophenyl)acrylamido)piperidine-1-carboxylate A solution of tert-butyl 4-allyl-4-((4-chloro-3-fluorophenyl)amino)piperidine-1-carboxylate (8.54 g, 23.2 mmol) and acryloyl chloride (5.6 mL, 70 mmol) in 200 mL of toluene was heated to reflux for 1 h. Triethylamine (16.1 mL, 116 mmol) was added and the mixture was refluxed for 4 h. After cooling to RT, the mixture was diluted with water and extracted twice with DCM. The organic extracts were dried over Na$_2$SO$_4$, filtered, and concentrated. Purification by silica gel chromatography (0-60% EtOAc in cyclohexane) provided tert-butyl 4-allyl-4-(N-(4-chloro-3-fluorophenyl)acrylamido)piperidine-1-carboxylate (5.86 g, 13.6 mmol). $^1$H NMR (400 MHz, DMSO-d$_6$) δ=7.67 (t, 1H), 7.38 (dd, 1H), 7.17-7.07 (m, 1H), 6.05 (dd, 1H), 6.02-5.84 (m, 1H), 5.67 (dd, 1H), 5.42 (dd, 1H), 5.26-5.07 (m, 2H), 3.66 (d, 2H), 3.31 (s, 3H), 3.05 (t, 1H), 2.09 (s, 2H), 1.98 (s, 1H), 1.49-1.36 (m, 1H), 1.36 (s, 9H) ppm; m/z=423.4 [M+H]$^+$; t$_R$=1.36 min (LCMS method a).

Step D: tert-butyl 1-(4-chloro-3-fluorophenyl)-2-oxo-1,9-diazaspiro[5.5]undec-3-ene-9-carboxylate Grubbs II catalyst (0.859 g, 1.37 mmol) was added to a solution of tert-butyl 4-allyl-4-(N-(4-chloro-3-fluorophenyl)acrylamido)piperidine-1-carboxylate (5.8 g, 14 mmol) in 20 mL of toluene under argon. The solution was heated to 110° C. and stirred for 4 h. The reaction mixture was cooled to RT, adsorbed onto silica gel, and evaporated to dryness. Purification by silica gel chromatography (0-100% EtOAc in cyclohexane) provided tert-butyl 1-(4-chloro-3-fluorophenyl)-2-oxo-1,9-diazaspiro[5.5]undec-3-ene-9-carboxylate (2.90 g, 6.98 mmol). $^1$H NMR (400 MHz, DMSO-d$_6$) δ=7.64 (dd, 1H), 7.33 (d, 1H), 7.06 (d, 1H), 6.73 (d, 1H), 5.98 (d, 1H), 2.8-3.3 (m, 4H), 1.86 (m, 2H), 1.33 (s, 9H), 1.40-1.16 (m, 4H) ppm; m/z=395.4 [M+H]$^+$; t$_R$=1.09 min (LCMS method a).

Step E: tert-butyl 1-(4-chloro-3-fluorophenyl)-2-oxo-1,9-diazaspiro[5.5]undecane-9-carboxylate tert-Butyl 1-(4-chloro-3-fluorophenyl)-2-oxo-1,9-diazaspiro[5.5]undec-3-ene-9-carboxylate (2.9 g, 7.34 mmol) was dissolved in 25 mL of MeOH and cooled to 0° C. NiCl$_2$·6 H$_2$O (0.476 g, 3.67 mmol) was added and the resulting reaction mixture was stirred for 10 min. NaBH$_4$ (0.556 g, 14.7 mmol) was added slowly and the mixture was stirred at 0° C. for 2 hr. The reaction mixture was evaporated under reduced pressure. The crude product was dissolved in ethyl acetate, washed with brine and dried over Na$_2$SO$_4$.

Removal of solvent under reduced pressure yielded the crude tert-butyl 1-(4-chloro-3-fluorophenyl)-2-oxo-1,9-diazaspiro[5.5]undecane-9-carboxylate (2.54 g, 6.27 mmol) which was used in the next step without further purification. $^1$H NMR (400 MHz, DMSO-d$_6$) δ=7.62 (dd, 1H), 7.23 (d, 1H), 6.96 (d, 1H), 3.76 (m, 2H), 2.87 (m, 2H), 2.41 (t, 2H), 2.04 (m, 2H), 1.79 (m, 4H), 1.42 (m, 2H), 1.30 (s, 9H) ppm; m/z=397.4 [M+H]$^+$; t$_R$=1.08 min (LCMS method a).

Step F: 1-(4-chloro-3-fluorophenyl)-1,9-diazaspiro[5.5]undecane-2-one

Trifluoroacetic acid (3.88 mL, 50.4 mmol) was added under argon to a solution of tert-butyl 1-(4-chloro-3-fluorophenyl)-2-oxo-1,9-diazaspiro[5.5]undecane-9-carboxylate (2.00 g, 5.04 mmol) in DCM (20 mL) cooled to 0° C. The reaction mixture was allowed to warm up to RT and stir for 2 h. The reaction mixture was quenched with saturated aqueous NaHCO$_3$ and was extracted three times with DCM. The combined organic extracts were dried over Na$_2$SO$_4$, filtered, and concentrated. The resulting solid was triturated with diethyl ether, isolated by filtration, and dried under vacuum to provide 1-(4-chloro-3-fluorophenyl)-1,9-diazaspiro[5.5]undecane-2-one (1.32 g, 4.36 mmol). $^1$H NMR (400 MHz, DMSO-d$_6$) δ=8.59 (br, 1H), 7.98 (br, 1H), 7.67 (dd, 1H), 7.29 (dd, 1H), 6.99 (dd, 1H), 2.95-3.20 (m, 4H), 2.40 (t, 2H), 2.07 (m, 2H), 1.93 (m, 2H), 1.74-1.83 (m, 4H) ppm; m/z=297.3 [M+H]$^+$; t$_R$=0.39 min (LCMS method a).

Intermediate C: Synthesis of 1-(4-chlorophenyl)-1,9-diazaspiro[5.5]undecan-2-one

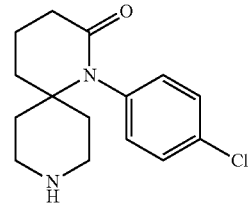 [SMILES: O=C1CCCC2(CCNCC2)N1c1ccc(Cl)cc1]

The title compound was synthesized analogously to Intermediate B starting with 4-chloroaniline. $^1$H NMR (600 MHz, DMSO-d$_6$) δ=8.5 (br, 1H), 7.89 (br, 1H), 7.51 (d, 2H), 7.11 (d, 2H), 3.13 (m, 2H), 3.00 (m, 2H), 2.41-2.37 (m, 2H), 2.11-2.05 (m, 2H), 1.95-1.88 (m, 2H), 1.83-1.76 (m, 2H), 1.72 (m, 2H) ppm; m/z=279.2 [M+H]$^+$; t$_R$=0.38 min (LCMS method a).

Intermediate D: 1-(3,4-difluorophenyl)-4-hydroxy-1,9-diazaspiro[5.5]undecan-2-one

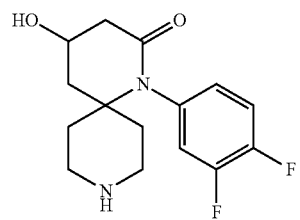

Step A: tert-butyl 4-allyl-4-(N-(3,4-difluorophenyl) acrylamido)piperidine-1-carboxylate DIEA (193 g, 1490 mmol) was added to a solution of tert-butyl 4-allyl-4-((3,4-difluorophenyl)amino)piperidine-1-carboxylate (105 g, 298 mmol) in DCM (1.0 L) cooled to 0° C. under an atmosphere of nitrogen. The mixture was stirred at 25° C. for 1 h. Acryloyl chloride (135 g, 1490 mmol) was added to the solution and the reaction was stirred at 25° C. for 11 h. The reaction was poured into water (1.0 L), then the mixture was extracted with DCM (500 mL×3). The combined organic layers were washed with brine (1.0 L), dried over $Na_2SO_4$, filtered, and concentrated under reduced pressure. Silica gel chromatography (10:1 petroleum ether:EtOAc) provided tert-butyl 4-allyl-4-(N-(3,4-difluorophenyl)acrylamido)piperidine-1-carboxylate (80.1 g, 197 mmol) as a white solid. $^1$H NMR (400 MHz, DMSO-$d_6$) δ=7.55-7.44 (m, 1H), 7.44-7.35 (m, 1H), 7.13-7.03 (m, 1H), 6.09-5.99 (m, 1H), 5.98-5.84 (m, 1H), 5.71-5.59 (m, 1H), 5.44-5.34 (m, 1H), 5.24-5.16 (m, 1H), 5.15-5.06 (m, 1H), 3.80-3.53 (m, 2H), 3.14-2.80 (m, 4H), 2.18-1.87 (m, 2H), 1.52-1.37 (m, 2H), 1.37-1.31 (m, 9H).

Step B: tert-butyl 1-(3,4-difluorophenyl)-2-oxo-1,9-diazaspiro[5.5]undec-3-ene-9-carboxylate To a solution of tert-butyl 4-allyl-4-(N-(3,4-difluorophenyl)acrylamido)piperidine-1-carboxylate (50 g, 123 mmol) in toluene (500 mL) was added Grubbs-II (7.70 g, 12.3 mmol) at 25° C. The mixture was stirred at 120° C. for 12 hrs under $N_2$. The solution was cooled to RT, concentrated under reduced pressure, and the residue purified by silica chromatography (15-100% EtOAc in petroleum ether) to provide tert-butyl 1-(3,4-difluorophenyl)-2-oxo-1,9-diazaspiro[5.5]undec-3-ene-9-carboxylate (35 g, 93 mmol) as grey solid. $^1$H NMR (400 MHz, DMSO-$d_6$) δ=7.52-7.41 (m, 1H), 7.39-7.29 (m, 1H), 7.07-6.96 (m, 1H), 6.76-6.64 (m, 1H), 6.02-5.90 (m, 1H), 3.90-3.65 (m, 2H), 3.01-2.79 (m, 2H), 2.78-2.73 (m, 2H), 1.90-1.79 (m, 2H), 1.39-1.25 (m, 11H); m/z=379.1 [M+H]$^+$

Step C: tert-butyl 1-(3,4-difluorophenyl)-2-oxo-4-(4,4,5,5-tetramethyl-1,3,2-dioxaborolan-2-yl)-1,9-diazaspiro[5.5]undecane-9-carboxylate $B_2Pin$ (7.4 g, 29 mmol) in THF (50 mL) was added dropwise to a stirred solution of CuCl (130 mg, 1.32 mmol), NaOt-Bu (7.60 g, 79.2 mmol) and DPEPhos (7.12 g, 13.2 mmol) in THF (50 mL), under an atmosphere of nitrogen. 1-(3,4-Difluorophenyl)-2-oxo-1,9-diazaspiro[5.5]undec-3-ene-9-carboxylate (10 g, 26.4 mmol) in MeOH (30 mL) followed by THF (20 mL) was added. The reaction mixture was heated at 80° C. for 12 h. LCMS analysis indicated complete conversion of the starting material to the pinacol boronate ester (m/z=507.2 [M+H]$^+$). The reaction was filtered, and the filtrate was directly used in the next step.

Step D: tert-butyl 1-(3,4-difluorophenyl)-4-hydroxy-2-oxo-1,9-diazaspiro[5.5]undecane-9-carboxylate To a solution of $NaBO_3 \cdot 4H_2O$ (11.7 g, 52.8 mmol) in $H_2O$ (120 mL) was added the THF solution of tert-butyl 1-(3,4-difluorophenyl)-2-oxo-4-(4,4,5,5-tetramethyl-1,3,2-dioxaborolan-2-yl)-1,9-diazaspiro[5.5]undecane-9-carboxylate from Step C. The reaction mixture was then heated at 25° C. for 12 h. The mixture was poured into water (100 mL), and extracted with DCM (3×100 mL). The combined organic extracts were washed with brine (200 mL), dried over $Na_2SO_4$, filtered, and concentrated under reduced pressure. Purification by silica gel chromatography (DMC/MeOH=1:0 to 10:1) provided tert-butyl 1-(3,4-difluorophenyl)-4-hydroxy-2-oxo-1,9-diazaspiro[5.5]undecane-9-carboxylate (6.0 g, 15 mmol) as white solid.

Step E: 1-(3,4-difluorophenyl)-4-hydroxy-1,9-diazaspiro[5.5]undecan-2-one

HCl in dioxane (4.0 M, 50 mL) was added to a stirred solution of tert-butyl 1-(3,4-difluorophenyl)-4-hydroxy-2-oxo-1,9-diazaspiro[5.5]undecane-9-carboxylate (10.0 g, 25.2 mmol) in dioxane (50 mL). The reaction mixture was then heated at 25° C. for 6 h. The reaction was concentrated under reduced pressure and the residue was slurried in MTBE (100 mL) at 25° C. for 1 h. The solids were isolated by filtration providing 1-(3,4-difluorophenyl)-4-hydroxy-1,9-diazaspiro[5.5]undecan-2-one, hydrochloride salt (8.0 g, 24 mmol), as a white solid. $^1$H NMR (400 MHz, DMSO-$d_6$) δ=9.13-8.81 (m, 1H), 8.41-8.11 (m, 1H), 7.62-7.42 (m, 1H), 7.37-7.20 (m, 1H), 7.04-6.83 (m, 1H), 4.13-4.06 (m, 1H), 3.22-3.09 (m, 2H), 3.07-2.90 (m, 2H), 2.76-2.63 (m, 1H), 2.49-2.45 (m, 1H), 2.38-2.26 (m, 1H), 2.01-1.65 (m, 5H); m/z=297.1 [M+H]$^+$

Intermediate E: 1-(3,4-difluorophenyl)-3-oxa-1,9-diazaspiro[5.5]undecan-2-one

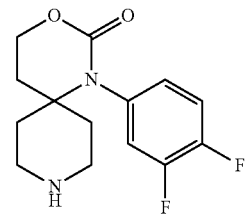 [SMILES: O=C1OCCC2(CCNCC2)N1c1ccc(F)c(F)c1]

Step A: tert-butyl 4-((3,4-difluorophenyl)amino)-4-(2,3-dihydroxypropyl)piperidine-1-carboxylate A solution of N-methylmorpholine N-oxide (8.043 g, 68.75 mmol) in water (20 mL) was added to a stirred solution of tert-butyl 4-allyl-4-((3,4-difluorophenyl) amino) piperidine-1-carboxylate (11 g, 31 mmol) in THF (35 mL) at −7° C. under an atmosphere of argon. A solution of $OsO_4$ (1.56 mmol) in t-BuOH (24 mL) was added dropwise to the reaction mixture at −9° C. The mixture was then allowed to stir at −9° C. for 12 hours after which time sodium bisulphite solution was added to quench the reaction. The solution was extracted with EtOAc, the organic layer was washed with brine solution, dried over $Na_2SO_4$, filtered, and concentrated to a brown sticky solid (12.2 g, 31.6 mmol). This crude material was taken for the next step without purification. m/z=387.15 [M+H]$^+$

Step B: tert-butyl 4-((3,4-difluorophenyl)amino)-4-(2-oxoethyl)piperidine-1-carboxylate A solution of $NaIO_4$ (2.64 g, 12.4 mmol) in water (20 mL) was added to a stirred solution of tert-butyl 4-((3,4-difluorophenyl)amino)-4-(2,3-dihydroxypropyl)piperidine-1-carboxylate (4.0 g, 10 mmol) in MeOH (20 mL). The reaction mixture was stirred at RT for 2 h under an argon atmosphere. The mixture was diluted with water, extracted with EtOAc, washed with brine, dried over Na₂SO₄ and concentrated under reduced pressure to provide the crude product as a brown sticky solid (3.17 g, 8.94 mmol). The crude was taken directly to the next step without further purification.

Step C: tert-butyl 4-((3,4-difluorophenyl)amino)-4-(2-hydroxyethyl)piperidine-1-carboxylate Sodium borohydride (0.20 g, 5.4 mmol) was added to a stirred solution of tert-butyl 4-((3,4-difluorophenyl)amino)-4-(2-oxoethyl)piperidine-1-carboxylate (1.6 g, 4.5 mmol) in MeOH (10 mL) at 0° C. The reaction mixture was stirred at RT for 12 h under an argon atmosphere. The reaction mixture was diluted with water, extracted with EtOAc, washed with brine, dried over Na₂SO₄, filtered, and concentrated under reduced pressure to provide the crude tert-butyl 4-((3,4-difluorophenyl)amino)-4-(2-hydroxyethyl)piperidine-1-carboxylate as brown sticky mass (1.14 g, 3.20 mmol). The crude product was taken for the next step without further purification. m/z=357.15 [M+H]⁺

Step D: tert-butyl 4-(2-((1H-imidazole-1-carbonyl)oxy)ethyl)-4-((3,4-difluorophenyl)amino)piperidine-1-carboxylate 1,1'-Carbonyldiimidazole (1.04 g, 6.40 mmol) was added to a stirred solution of tert-butyl 4-((3,4-difluorophenyl)amino)-4-(2-hydroxyethyl)piperidine-1-carboxylate (1.14 g, 3.20 mmol) in DCM (10 mL) at RT. The reaction mixture was stirred at RT for 12 h under an argon atmosphere. The reaction was diluted with water, extracted with DCM, dried over Na₂SO₄, filtered, and concentrated under reduced pressure to provide the crude tert-butyl 4-(2-((1H-imidazole-1-carbonyl)oxy)ethyl)-4-((3,4-difluorophenyl)amino)piperidine-1-carboxylate as a brown sticky solid (1.31 g, 2.91 mmol). The crude product was taken directly to the next step without purification. m/z=451.20 [M+H]⁺

Step E: tert-butyl 1-(3,4-difluorophenyl)-2-oxo-3-oxa-1,9-diazaspiro[5.5]undecane-9-carboxylate Pyridine hydrochloride (1.00 g, 8.65 mmol) was added to a stirred solution of tert-butyl 4-(2-((1H-imidazole-1-carbonyl)oxy)ethyl)-4-((3,4-difluorophenyl)amino)piperidine-1-carboxylate (1.29 g, 2.88 mmol) in MeCN (10 mL) at RT. The reaction mixture was stirred at RT for 24 h under an argon atmosphere. The mixture was diluted with water, extracted with EtOAc, washed with brine, dried over Na₂SO₄, filtered, and concentrated under reduced pressure to provide the crude of tert-butyl 1-(3,4-difluorophenyl)-2-oxo-3-oxa-1,9-diazaspiro[5.5]undecane-9-carboxylate as sticky brown solid (1.07 g, 2.80 mmol). The crude was taken for the next step without further purification. m/z=383.1 [M+H]⁺

Step F: 1-(3,4-difluorophenyl)-3-oxa-1,9-diazaspiro[5.5]undecan-2-one

HCl in dioxane (4.0 M, 6.0 mL) was added to tert-butyl 1-(3,4-difluorophenyl)-2-oxo-3-oxa-1,9-diazaspiro[5.5]undecane-9-carboxylate (0.600 g, 1.57 mmol) at 0° C. The reaction mixture was stirred at RT for 2 hours under an argon atmosphere. The mixture was concentrated under reduced pressure. The solid was isolated by filtration, washing with diethyl ether to provide the title compound (hydrochloride salt) as a pale brown solid (0.350 g, 1.24 mmol). ¹H NMR (400 MHz, DMSO-d₆) δ 8.83 (s, 1H), 8.16 (s, 1H), 7.54 (dt, J=10.9, 9.0 Hz, 1H), 7.46 (ddd, J=11.6, 7.4, 2.5 Hz, 1H), 7.11 (ddt, J=8.4, 3.9, 2.0 Hz, 1H), 4.44-4.26 (m, 2H), 3.17 (d, J=13.2 Hz, 2H), 3.08-2.91 (m, 2H), 2.31 (t, J=5.5 Hz, 2H), 2.09-1.94 (m, 2H), 1.77 (td, J=13.8, 4.5 Hz, 2H); m/z=283.1 [M+H]⁺; t_R=1.32 min (LCMS method m)

Example 1: 1-(4-chloro-3-fluorophenyl)-9-(1-(4-fluorophenyl)-1H-1,2,4-triazol-3-yl)-1,9-diazaspiro[5.5]undecan-2-one

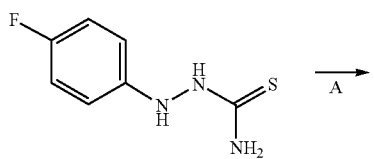

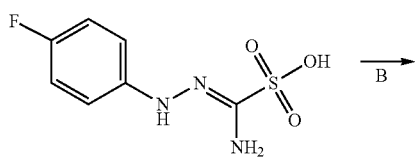

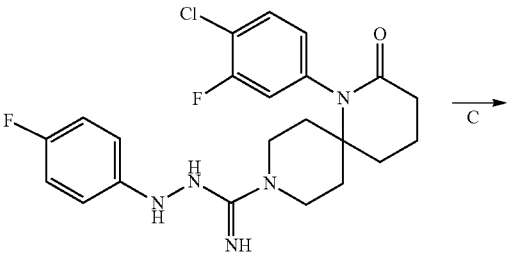

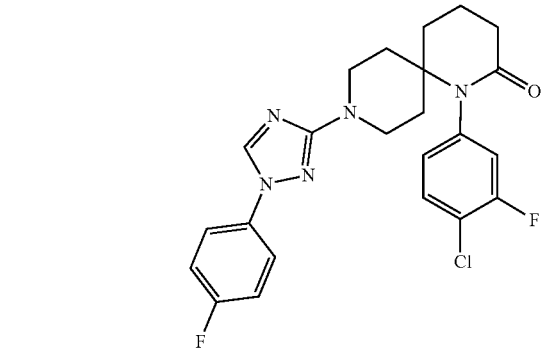

Step A: (E)-amino(2-(4-fluorophenyl)hydrazono)methanesulfonic acid

A mixture of 2-(4-fluorophenyl)1-hydrazinecarbothiomide (2.5 g, 14 mmol), Na$_2$MoO$_4$·2H$_2$O (163 mg, 0.675 mmol) and NaCl (316 mg, 5.40 mmol) in 7 mL of water was cooled to 0° C. A 30% solution of hydrogen peroxide (6.9 mL, 68 mmol) was added dropwise to the cooled suspension. During the addition of the first half, the temperature was kept below 7° C. Then the reaction became exothermic and the temperature reached 76° C. while being cooled with ice bath. Once the addition was completed, the suspension was stirred under ice bath cooling for 1.5 h. The suspension was filtered and the solid was washed with 10-15 mL cold brine to afford a beige solid (1.76 g) which was used in the next step without further purification. m/z=493.3 [M+H]$^+$; t$_R$=0.38 min (LCMS method a).

Step B: 1-(4-chloro-3-fluorophenyl)-N'-(4-fluorophenyl)-2-oxo-1,9-diazaspiro[5.5]undecane-9-carboximidhydrazide A mixture of 1-(4-chloro-3-fluorophenyl)-1,9-diazaspiro[5.5]undecane-2-one (Intermediate B, 1.95 g, 6.58 mmol), (E)-amino(2-(4-fluorophenyl)hydrazono)-methanesulfonic acid (1.76 g, 7.56 mmol) and pyridine (1.17 mL, 14.5 mmol) in 9 mL of acetonitrile was stirred for 1 h at 120° C. under microwave irradiation. The reaction mixture was concentrated and used in the next step without further purification. m/z=448.2 [M+H]$^+$; t$_R$=0.67 min (LCMS method a).

Step C: 1-(4-chloro-3-fluorophenyl)-9-(1-(4-fluorophenyl)-1H-1,2,4-triazol-3-yl)-1,9-diazaspiro[5.5]undecan-2-one 1-(4-chloro-3-fluorophenyl)-N'-(4-fluorophenyl)-2-oxo-1,9-diazaspiro[5.5]undecane-9-carboximidhydrazide (2.95 g, 6.58 mmol) and trimethyl orthoformate (1.5 mL, 6.58 mmol) were heated for 24 h at 90° C. under microwave irradiation. The reaction mixture was filtered through a short silica pad, eluted by 20% MeOH in DCM and evaporated. Purification by silica gel chromatography (0-10% MeOH in DCM) provided the title compound (140 mg, 0.291 mmol). $^1$H NMR (400 MHz, DMSO-d$_6$) δ=8.85 (s, 1H), 7.74 (m, 2H), 7.60 (dd, 1H), 7.34 (dd, 2H), 7.24 (dd, 1H), 6.98 (d, 1H), 3.85-3.88 (m, 2H), 2.99 (t, 2H), 2.42 (m, 2H), 2.09 (m, 2H) 1.85-1.88 (m, 4H), 1.64 (td, 2H) ppm. m/z=458.1 [M+H]$^+$; t$_R$=1.06 min (LCMS method a).

Example 2: 1-(4-chloro-3-fluorophenyl)-9-(6-(trifluoromethyl)benzo[d]oxazol-2-yl)-1,9-diazaspiro[5.5]undecan-2-one

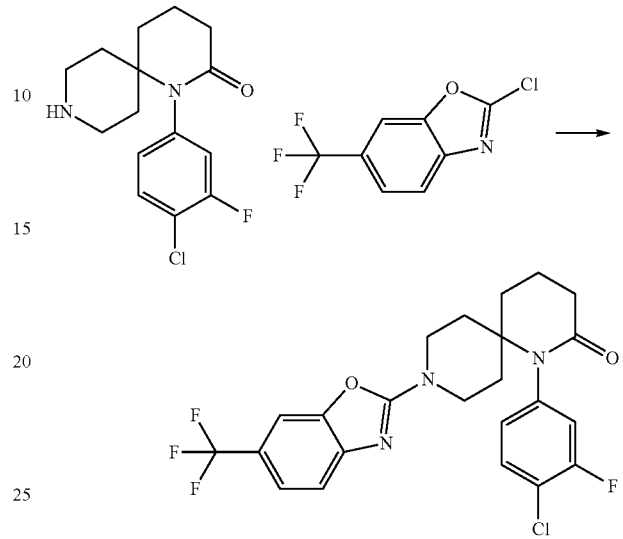

1-(4-chloro-3-fluorophenyl)-1,9-diazaspiro[5.5]undecane-2-one (Intermediate B, 80 mg, 0.27 mmol), 2-chloro-6-(trifluoromethyl)benzo[d]oxazole (60 mg, 0.27 mmol) and triethylamine (0.11 mL, 0.81 mmol) were dissolved in 1.5 mL of EtOH and stirred for 30 min at 160° C. under microwave irradiation. The reaction mixture was concentrated and purification by silica gel chromatography (0-20% MeOH in EtOAc) provided the title compound (49 mg, 0.097 mmol). $^1$H NMR (400 MHz, DMSO-d$_6$) δ=7.73 (d, 1H), 7.59 (dd, 1H), 7.49 (dd, 1H), 7.36 (d, 1H), 7.24 (dd, 1H), 6.96 (dd, 1H), 4.04 (m, 2H), 3.36 (m, 2H) 2.45 (m, 2H), 2.15 (m, 2H), 1.95 (br d, 2H), 1.82-1.91 (m, 2H), 1.66 (m, 2H) ppm; m/z=482.2 [M+H]$^+$; t$_R$=1.22 min (LCMS method a).

By employing similar methods as described for the preparation of Example 2, using appropriate commercially available chloroheterocycles and Intermediate B, the following compounds were prepared:

| Ex | Structure and Name | MS, m/z [M + H]$^+$; t$_R$, method | $^1$H NMR |
|---|---|---|---|
| 3 | 1-(4-chloro-3-fluorophenyl)-9-(4-(trifluoromethyl)pyrimidin-2-yl)-1,9-diazaspiro[5.5]undecan-2-one | 443.2; 1.19 min, LCMS method a | $^1$H NMR (400 MHz, DMSO-d$_6$) δ = 8.59 (d, 1H), 7.56 (t, 1H), 7.20 (d, 1H), 6.93 (m, 2H), 4.50 (m, 2H), 3.07 (t, 2H), 2.45 (t, 2H), 2.16 (m, 2H), 1.86-1.93 (m, 4H), 1.49-1.56 (dt, 2H) ppm. |

| Ex | Structure and Name | MS, m/z [M + H]+; $t_R$, method | 1H NMR |
|---|---|---|---|
| 4 | 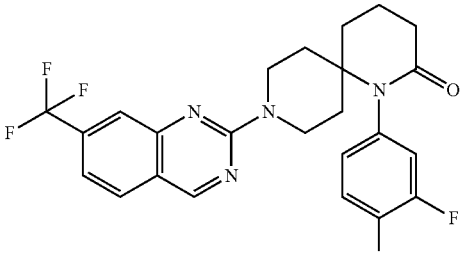<br>1-(4-chloro-3-fluorophenyl)-9-(7-(trifluoromethyl)quinazolin-2-yl)-1,9-diazaspiro[5.5]undecan-2-one | 493.3; 1.31 min, LCMS method a | 1H NMR (400 MHz, DMSO-$d_6$) δ = 9.22 (s, 1H), 7.97 (d, 1H), 7.65 (s, 1H), 7.53 (dd, 1H), 7.41 (dd, 1H), 7.22 (dd, 1H), 6.95 (d, 1H), 4.74 (m, 2H), 3.12 (t, 2H), 2.46 (t, 2H), 2.2 (m, 2H), 1.89-1.99 (m, 4H), 1.56 (m, 2H) ppm. |

Example 5: 1-(4-chloro-3-fluorophenyl)-9-(2-(trifluoromethyl)pyrazolo[1,5-a]pyrimidin-5-yl)-1,9-diazaspiro[5.5]undecan-2-one

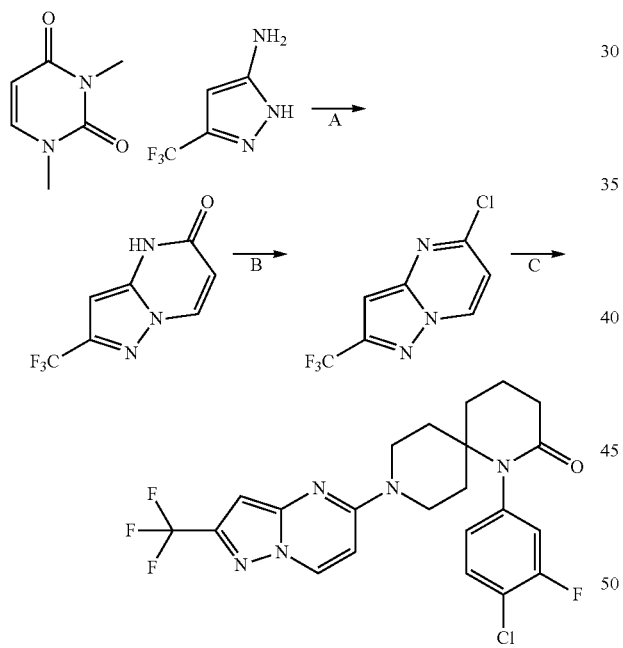

Step A: 2-(trifluoromethyl)pyrazolo[1,5-a]pyrimidin-5(4H)-one 1,3-dimethyluracil (1.855 g, 13.24 mmol) and sodium ethoxide (21% solution in EtOH, 13.6 mL, 36.4 mmol) were added to a solution of 3-(trifluoromethyl)-1H-pyrazol-5-amine (1.00 g, 6.62 mmol) in 30 mL of EtOH. The reaction mixture was stirred for 12 h at 60° C. The mixture was concentrated, diluted with ethyl acetate and washed with 1 M HCl (40 mL) and brine. The organic layer was dried over $Na_2SO_4$, filtered, and concentrated. Purification by silica gel chromatography (20-80% EtOAc in cyclohexane, then 0-20% MeOH in EtOAc) provided 2-(trifluoromethyl)pyrazolo[1,5-a]pyrimidin-5(4H)-one (188 mg, 0.463 mmol). 1H NMR (400 MHz, DMSO-$d_6$) δ=12.47 (br s, 1H), 8.59 (d, J=8 Hz, 1H), 6.33-6.11 (m, 2H) ppm; m/z=202.1 [M−H]−, $t_R$=0.65 min (LCMS method a).

Step B: 5-chloro-2-(trifluoromethyl)pyrazolo[1,5-a]pyrimidine

A mixture of $POCl_3$ (5.0 mL, 54 mmol) and 2-(trifluoromethyl)pyrazolo[1,5-a]pyrimidin-5(4H)-one (188 mg, 0.463 mmol) was stirred for 1 h at 80° C. The mixture was cooled to RT and concentrated. Purification by silica gel chromatography (0-50% EtOAc in cyclohexane) provided 5-chloro-2-(trifluoromethyl)pyrazolo[1,5-a]pyrimidine (98 mg, 0.44 mmol). 1H NMR (600 MHz, DMSO-$d_6$) δ=9.34 (dd, 1H), 7.43 (d, 1H), 7.31 (s, 1H) ppm; $t_R$=1.03 min (LCMS method a).

Step C: 1-(4-chloro-3-fluorophenyl)-9-(2-(trifluoromethyl)pyrazolo[1,5-a]pyrimidin-5-yl)-1,9-diazaspiro[5.5]undecan-2-one 5-chloro-2-(trifluoromethyl)pyrazolo[1,5-a]pyrimidine (95 mg, 0.43 mmol) and TEA (0.16 mL, 1.1 mmol) were added to a solution of 1-(4-chloro-3-fluorophenyl)-1,9-diazaspiro[5.5]undecane-2-one (Intermediate B, 85 mg, 0.29 mmol) in 4 mL of EtOH. The reaction mixture was heated for 2 h at 150° C. under microwave irradiation, evaporated, diluted with EtOAc and washed with saturated aqueous $NaHCO_3$ and brine. The combined organic layers were dried over $Na_2SO_4$, filtered, and concentrated. Purification by SFC (Princeton 4-ethylpyridine, 30×250, 5 μm; 15-25% MeOH in $CO_2$, 10 min) provided the title compound (122 mg, 0.248 mmol). 1H NMR (600 MHz, DMSO-$d_6$) δ=8.69 (dd, 1H), 7.58 (dd, 1H), 7.24 (dd, 1H), 6.96 (dd, 1H), 6.89 (d, 1H), 6.40 (s, 1H), 4.31 (m, 2H), 3.09 (t, 2H), 2.43 (t, 2H), 2.15 (m, 2H), 1.92 (m, 2H), 1.86 (m, 2H), 1.55 (m, 2H) ppm; m/z=482.3 [M+H]+; $t_R$=1.14 min (LCMS method a).

Example 6a: 1-(4-chloro-3-fluorophenyl)-9-(5-((1R,2R)-2-(trifluoromethyl)cyclopropyl)-1,2,4-oxadiazol-3-yl)-1,9-diazaspiro[5.5]undecan-2-one, or 1-(4-chloro-3-fluorophenyl)-9-(5-((1S,2S)-2-(trifluoromethyl)cyclopropyl)-1,2,4-oxadiazol-3-yl)-1,9-diazaspiro[5.5]undecan-2-one, and Example 6b: 1-(4-chloro-3-fluorophenyl)-9-(5-((1S,2S)-2-(trifluoromethyl)cyclopropyl)-1,2,4-oxadiazol-3-yl)-1,9-diazaspiro[5.5]undecan-2-one, or 1-(4-chloro-3-fluorophenyl)-9-(5-((1R,2R)-2-(trifluoromethyl)cyclopropyl)-1,2,4-oxadiazol-3-yl)-1,9-diazaspiro[5.5]undecan-2-one

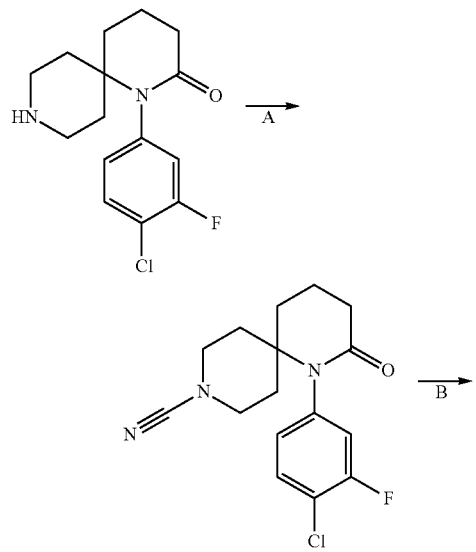

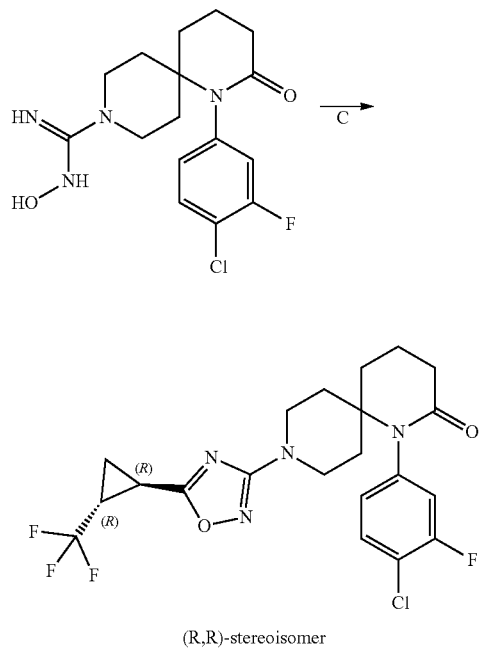

(R,R)-stereoisomer

-continued

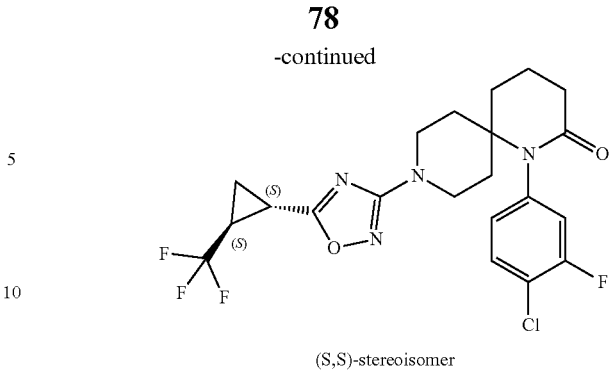

(S,S)-stereoisomer

Step A: 1-(4-chloro-3-fluorophenyl)-2-oxo-1,9-diazaspiro[5.5]undecane-9-carbonitrile Cyanogen bromide (3.0 M in DCM, 1.12 mL, 3.37 mmol) was added dropwise to a solution of 1-(4-chloro-3-fluorophenyl)-1,9-diazaspiro[5.5]undecane-2-one (Intermediate B, 1.00 g, 3.37 mmol) and DIPEA (0.589 mL, 3.37 mmol) in 35 mL of DCM. The reaction mixture was stirred for 1 h at RT. Brine was added to the reaction mixture. The organic layer was separated, dried over $Na_2SO_4$, filtered, and concentrated. The crude product was used in the next step without further purification. m/z=322.2 $[M+H]^+$; $t_R$=0.77 min (LCMS method a).

Step B: 1-(4-chloro-3-fluorophenyl)-N-hydroxy-2-oxo-1,9-diazaspiro[5.5]undecane-9-carboximidamide Hydroxylamine (50% in water, 0.89 mL, 15 mmol) was added to a solution of 1-(4-chloro-3-fluorophenyl)-2-oxo-1,9-diazaspiro[5.5]undecane-9-carbonitrile (1.17 g, 3.64 mmol) in 30 mL of EtOH. The reaction mixture was stirred for 1 h at 80° C., concentrated and was used in the next step without purification. m/z=355.3 $[M+H]^+$; $t_R$=0.47 min (LCMS method a).

Step C: 1-(4-chloro-3-fluorophenyl)-9-(5-((1R,2R/1S,2S)-2-(trifluoromethyl)cyclopropyl)-1,2,4-oxadiazol-3-yl)-1,9-diazaspiro[5.5]undecan-2-one HOBt (926 mg, 6.05 mmol), EDC·HCl (1160 mg, 6.05 mmol) and DIPEA (1.2 mL, 7.00 mmol) were added to a solution of racemic (1R,2R)-2-(trifluoromethyl)cyclopropanecarboxylic acid (754 mg, 4.65 mmol) in DMF (30 mL). The reaction mixture was stirred for 10 min at RT. 1-(4-chloro-3-fluorophenyl)-N-hydroxy-2-oxo-1,9-diazaspiro[5.5]undecane-9-carboximidamide (1.23 g, 2.67 mmol) was added and the mixture was stirred for 72 h at RT. The mixture was concentrated, diluted with TBME and washed twice times with water and brine. The organic layer was dried over $Na_2SO_4$, filtered and concentrated. The crude product was purified by silica gel chromatography (0-6% MeOH in EtOAc) to provide rac-1-(4-chloro-3-fluorophenyl)-9-(5-((1R,2R)-2-(trifluoromethyl)cyclopropyl)-1,2,4-oxadiazol-3-yl)-1,9-diazaspiro[5.5]undecan-2-one (794 mg). $^1$H NMR (400 MHz, DMSO-$d_6$) δ=7.61 (dd, 1H), 7.23 (dd, 1H), 6.96 (m, 1H), 3.64 (m, 2H), 3.05 (m, 2H), 2.70 (m, 1H), 2.59 (m, 1H), 2.4 (t, 2H), 2.08 (m, 2H), 1.87-1.78 (m, 4H), 1.58-1.46 (m, 4H) ppm; m/z 473.3 $[M+H]]^+$; $t_R$=1.14 min (LCMS method a). Preparative chiral HPLC (Chiralpak AD-H, 5 μm, 20×250 mm; mobile phase heptane:EtOH:MeOH 70:15:15; flow rate 15 mL/min; 60 min elution)

provided Example 6a (peak 1, 304 mg, $t_R$=40.6 min) and Example 6b (peak 2, 303 mg, $t_R$=50.0 min).

Example 7: 1-(4-chloro-3-fluorophenyl)-9-(5-(3-(trifluoromethyl)bicyclo[1.1.1]pentan-1-yl)-1,2,4-oxadiazol-3-yl)-1,9-diazaspiro[5.5]undecan-2-one

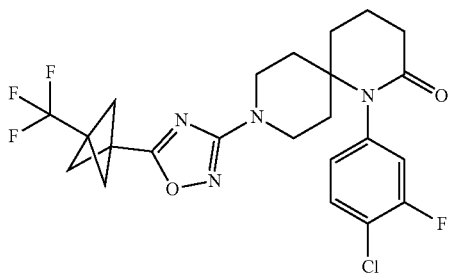 [SMILES: O=C1CCCC2(CCN(c3noc(C45CC(C(F)(F)F)(C4)C5)n3)CC2)N1c1ccc(Cl)c(F)c1]

This compound was synthesized analogously to Examples 6a and 6b using 3-(trifluoromethyl)bicyclo[1.1.1]pentane-1-carboxylic acid. $^1$H NMR (600 MHz, DMSO-d$_6$) δ=7.61 (dd, 1H), 7.23 (dd, 1H), 6.96 (dd, 1H), 3.65 (m, 2H), 3.07 (dd, 2H), 2.41 (m, 8H), 2.08 (m, 2H), 1.86-1.81 (m, 4H), 1.57-1.53 (m, 2H) ppm; m/z=499.2 [M+H]$^+$; $t_R$=1.24 min (LCMS method a).

Example 8: 1-(4-chloro-3-fluorophenyl)-9-(6-hydroxy-3-(pyrrolidin-1-yl)-1,2,4-triazin-5-yl)-1,9-diazaspiro[5.5]undecan-2-one

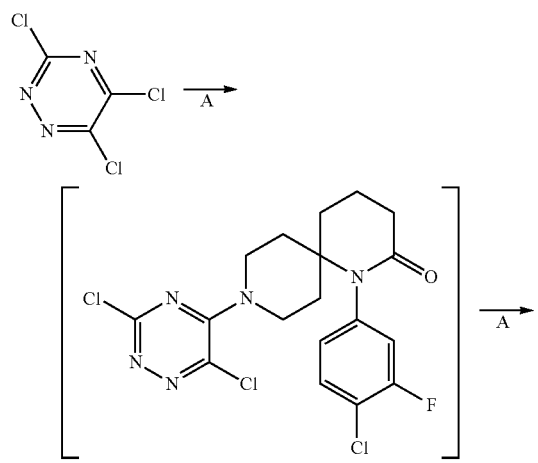

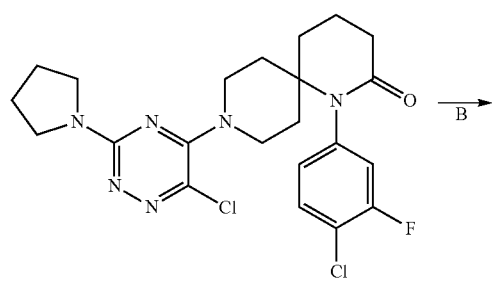

Step A: 9-(6-chloro-3-(pyrrolidin-1-yl)-1,2,4-triazin-5-yl)-1-(4-chloro-3-fluorophenyl)-1,9-diazaspiro[5.5]undecan-2-one A solution of 1-(4-chloro-3-fluorophenyl)-1,9-diazaspiro[5.5]undecane-2-one (Intermediate B, 100 mg, 0.337 mmol) in DMF (0.5 mL) was added dropwise to a solution of trichloro-1,2,4-triazine (93 mg, 0.505 mmol) and TEA (0.094 mL, 0.674 mmol) in DMF (0.5 mL) and cooled to 0° C. The ice bath was taken away and the reaction mixture allowed to reach RT and stir for 20 min. Pyrrolidine (0.28 mL, 3.4 mmol) was added and the reaction mixture stirred for 20 min at RT. The reaction mixture was diluted with EtOAc and washed with water. The organic layer was separated and the remaining aqueous layer was extracted twice with EtOAc. The combined organic layers were dried over Na$_2$SO$_4$, filtered and concentrated. Purification by silica gel chromatography (10-100% EtOAc in cyclohexane) provided 9-(6-chloro-3-(pyrrolidin-1-yl)-1,2,4-triazin-5-yl)-1-(4-chloro-3-fluorophenyl)-1,9-diazaspiro[5.5]undecan-2-one (98 mg, 0.20 mmol) as a yellow powder. $^1$H NMR (400 MHz, DMSO-d$_6$) δ=7.61 (dd, 1H), 7.23 (d, 1H), 6.96 (d, 1H), 4.21 (m, 2H), 3.3-3.5 (m, 4H), 3.12 (t, 2H), 2.43 (t, 2H), 2.13 (m, 2H), 1.8-1.95 (m, 8H), 1.7 (m, 2H) ppm; m/z=479.2 [M+H]$^+$; $t_R$=0.96 min (LCMS method a).

Step B: 1-(4-chloro-3-fluorophenyl)-9-(6-hydroxy-3-(pyrrolidin-1-yl)-1,2,4-triazin-5-yl)-1,9-diazaspiro[5.5]undecan-2-one 9-(6-chloro-3-(pyrrolidin-1-yl)-1,2,4-triazin-5-yl)-1-(4-chloro-3-fluorophenyl)-1,9-diazaspiro[5.5]undecan-2-one (78 mg, 0.163 mmol) was dissolved in a mixture of 2 mL of acetic acid/0.1 mL of water and heated under microwave irradiation for 11 h at 120° C. After evaporation, the residue was dissolved in DCM and treated with triethylamine. The resulting mixture was evaporated and purified by SFC (Reprospher PEI 100 Å, 5 μm, 30×250 mm; 14-18% MeOH in CO$_2$, 10 min). $^1$H NMR (400 MHz, DMSO-d$_6$) δ=11.7 (s, 1H), 7.60 (t, 1H), 7.23 (d, 1H), 6.96 (d, 1H), 5.7 (br, 1H), 4.6 (br, 1H), 3.18 (m, 4H), 3.1 (br, 2H), 2.43 (m, 2H), 2.15 (m, 2H), 1.75-1.95 (m, 8H), 1.6 (m, 2H) ppm; m/z=461.2 [M+H]$^+$; $t_R$=0.90 min (LCMS method a).

Example 9: 1-(4-chloro-3-fluorophenyl)-9-(6-(4-fluorophenyl)-4-methyl-3-oxo-3,4-dihydropyrazin-2-yl)-1,9-diazaspiro[5.5]undecan-2-one

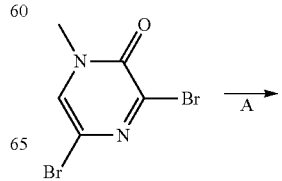

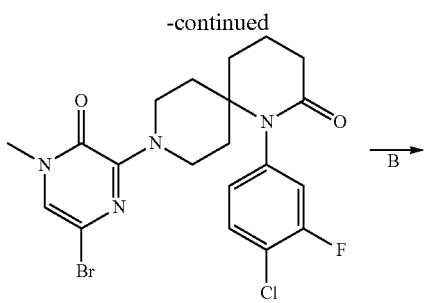

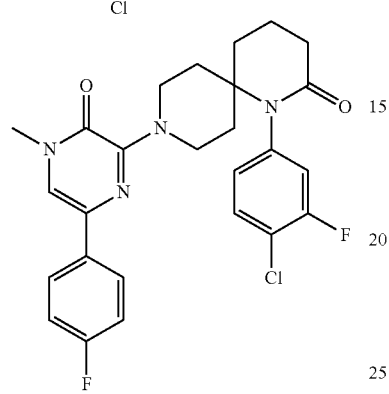

Step A: 9-(6-bromo-4-methyl-3-oxo-3,4-dihydropyrazin-2-yl)-1-(4-chloro-3-fluorophenyl)-1,9-diazaspiro[5.5]undecan-2-one A mixture of 3,5-dibromo-1-methylpyrazin-2(1H)-one (1 g, 3.73 mmol), 1-(4-chloro-3-fluorophenyl)-1,9-diazaspiro[5.5]undecane-2-one (Intermediate B, 1.11 g, 0.373 mmol) and K$_2$CO$_3$ (1.55 g, 11.2 mmol) in DMF (11 mL) here heated under microwave irradiation for 1 h at 160° C. The reaction mixture was filtered and concentrated. Purification by silica gel chromatography (0-10% MeOH in DCM) provided 9-(6-bromo-4-methyl-3-oxo-3,4-dihydropyrazin-2-yl)-1-(4-chloro-3-fluorophenyl)-1,9-diazaspiro[5.5]undecan-2-one (770 mg, 1.51 mmol). $^1$H NMR (400 MHz, DMSO-d$_6$) δ=7.61 (dd, 1H), 7.27 (s, 1H), 7.23 (dd, 1H), 6.97 (m, 1H), 4.55 (m, 2H), 3.28 (s, 3H), 2.94 (t, 2H), 2.42 (t, 2H), 2.11 (m, 2H), 1.64-1.83 (m, 4H), 1.6-1.63 (m, 2H) ppm; m/z=483.0, 485.0 [M+H]$^+$; t$_R$=1.02 min (LCMS method a).

Step B: 1-(4-chloro-3-fluorophenyl)-9-(6-(4-fluorophenyl)-4-methyl-3-oxo-3,4-dihydropyrazin-2-yl)-1,9-diazaspiro[5.5]undecan-2-one A mixture of 9-(6-bromo-4-methyl-3-oxo-3,4-dihydropyrazin-2-yl)-1-(4-chloro-3-fluorophenyl)-1,9-diazaspiro[5.5]undecan-2-one (150 mg, 0.31 mmol), (4-fluorophenyl)boronic acid (45 mg, 0.31 mmol), K$_3$PO$_4$ (132 mg, 0.62 mmol) and PdCl$_2$(dtbpf) (20 mg, 0.031 mmol) in 3:1 dioxane/water (2.7 mL) was heated for 20 min at 90° C. Then the reaction mixture was cooled, diluted with water and extracted with EtOAc. The combined organic layers were dried over Na$_2$SO$_4$, filtered, and concentrated. Purification by silica gel chromatography (0-5% MeOH in DCM) provided 1-(4-chloro-3-fluorophenyl)-9-(6-(4-fluorophenyl)-4-methyl-3-oxo-3,4-dihydropyrazin-2-yl)-1,9-diazaspiro[5.5]undecan-2-one (34 mg, 0.065 mmol). $^1$H NMR (400 MHz, DMSO-d$_6$) δ=7.76-7.78 (m, 2H), 7.72 (s, 1H), 7.59 (t, 1H), 7.18-7.26 (m, 3H), 6.98 (m, 1H), 4.58 (m, 2H), 3.4 (s, 3H), 2.95 (t, 2H), 2.44 (t, 2H), 2.15 (m, 2H), 1.86 (m, 4H), 1.66-1.73 (m, 2H) ppm; m/z=499.1 [M+H]$^+$; t$_R$=1.13 min (LCMS method a).

Example 10: 9-(2-benzyl-3-oxo-6-(2-azaspiro[3.3]heptan-2-yl)-2,3-dihydropyridazin-4-yl)-1-(3,4-difluorophenyl)-1,9-diazaspiro[5.5]undecan-2-one

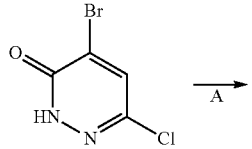

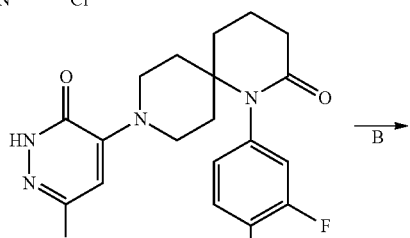

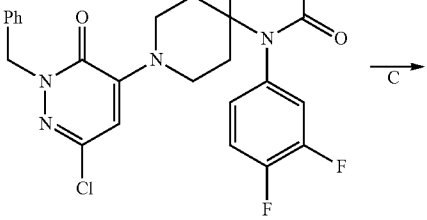

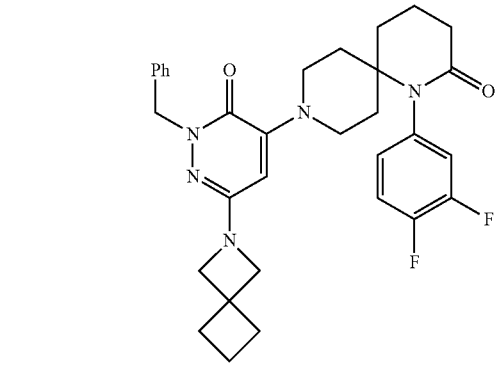

Step A: 9-(6-chloro-3-oxo-2,3-dihydropyridazin-4-yl)-1-(3,4-difluorophenyl)-1,9-diazaspiro[5.5]undecane-2-one A mixture of 1-(3,4-difluorophenyl)-1,9-diazaspiro[5.5]undecane-2-one (Intermediate A, 0.673 g, 2.41 mmol), 4-bromo-6-chloropyridazin-3(2H)-one (0.500 g, 2.41 mmol) and DIPEA (1.3 mL, 7.2 mmol) in DMF (8 mL) were heated at 100° C. for 12 hours. After cooling to RT, water was added and the mixture extracted with EtOAc, washed with brine and dried over Na$_2$SO$_4$. After filtration, concentration under reduced pressure provided the crude 9-(6-chloro-3-oxo-2,3-dihydropyridazin-4-yl)-1-(3,4-difluorophenyl)-1,9-diazaspiro[5.5]undecane-2-one as pale yellow gummy solid (1.355 g) which was taken on without purification. m/z=272 [M+H]$^+$

Step B: 9-(2-benzyl-6-chloro-3-oxo-2,3-dihydro-pyridazin-4-yl)-1-(3,4-difluorophenyl)-1,9-diazaspiro[5.5]undecane-2-one Sodium hydride (0.070 g, 2.94 mmol) and benzyl bromide (0.249 g, 1.47 mmol) were added to a stirred solution of 9-(6-chloro-3-oxo-2,3-dihydropyridazin-4-yl)-1-(3,4-difluorophenyl)-1,9-diazaspiro[5.5]undecane-2-one (0.400 g, 0.980 mmol) in THF (8 mL) cooled to 0° C. The reaction mixture was allowed to warm to RT over five hours. Water was added to the reaction mixture and it was extracted with EtOAc. The extracts were washed with brine, dried over $Na_2SO_4$, filtered, and concentrated under reduced pressure. Purification by silica gel chromatography (60-70% EtOAc: hexane) provided 9-(2-benzyl-6-chloro-3-oxo-2,3-dihydro-pyridazin-4-yl)-1-(3,4-difluorophenyl)-1,9-diazaspiro[5.5]undecane-2-one as a gummy white solid (1.355 g, 2.716 mmol). m/z=499.2 $[M+H]^+$

Step C: 9-(2-benzyl-3-oxo-6-(2-azaspiro[3.3]heptan-2-yl)-(2,3-dihydropyridazin-4-yl)-1-(3,4-difluorophenyl)-1,9-diazaspiro[5.5]undecane-2-one A solution of 9-(2-benzyl-6-chloro-3-oxo-2,3-dihydropyridazin-4-yl)-1-(3,4-difluorophenyl)-1,9-diazaspiro[5.5]undecane-2-one (0.100 g, 0.200 mmol) and 2-azaspiro[3.3]heptane hydrochloride (0.053 g, 0.40 mmol) in dioxane (6 mL) was stirred with argon purging for ten minutes. $Cs_2CO_3$ (0.195 g, 0.600 mmol) was added to the reaction mixture under argon purging followed by the addition of $Pd_2(dba)_3$ (30 mg, 0.040 mmol) and JohnPhos (10 mg, 0.040 mmol). The mixture was heated at 100° C. for 16 h. After cooling to RT, water was added to the reaction mixture and it was extracted with EtOAc, washed with brine, dried over $Na_2SO_4$, filtered, and concentrated under reduced pressure. Purification by silica gel chromatography (60-70% EtOAc: hexane) provided the title compound as a white solid (0.068 g, 0.12 mmol). $^1$H NMR (400 MHz, chloroform-d) δ 7.46-7.34 (m, 2H), 7.24-7.09 (m, 2H), 6.95-6.82 (m, 1H), 6.82-6.69 (m, 1H), 5.64 (s, 1H), 5.09 (s, 2H), 3.9-4.05 (m, 3H), 3.8 (s, 3H), 2.65-2.75 (m, 2H), 2.58-2.61 (m, 2H), 2.14 (t, 3H), 1.98-2.12 (m, 4H), 1.8-1.92 (m, 4H), 1.7-1.78 (m, 3H); m/z=560.3 $[M+H]^+$; $t_R$=1.64 min (LCMS method j)

Example 11: 1-(3,4-difluorophenyl)-9-(6-(4-fluorophenyl)-3-oxo-2,3-dihydropyridazin-4-yl)-1,9-diazaspiro[5.5]undecane-2-one

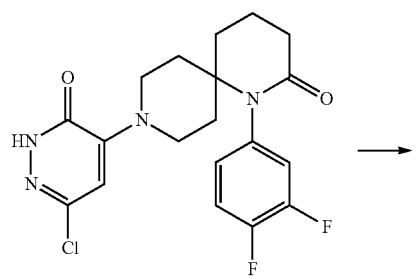

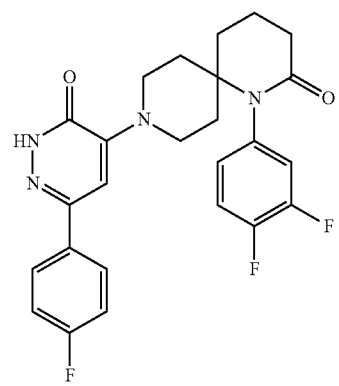

9-(6-chloro-3-oxo-2,3-dihydropyridazin-4-yl)-1-(3,4-difluorophenyl)-1,9-diazaspiro[5.5]undecane-2-one (0.200 g, 0.489 mmol) and 4-fluorophenylboronic acid (0.342 g, 2.45 mmol) were stirred in dioxane (5 mL) and $H_2O$ (2 mL) at RT under argon purging for 10 min. $K_3PO_4$ (0.311 g, 1.47 mmol) was added to the reaction mixture under argon purging followed by the addition of XPhosPd G2 (77 mg, 0.097 mmol). The mixture was refluxed at 110° C. for 48 h. After cooling to RT, water was added to the reaction mixture and it was extracted with EtOAc, washed with brine, dried over $Na_2SO_4$, filtered, and concentrated under reduced pressure. Purification by preparative HPLC (LUNA Phoenomenex, 5 µm, 21.2×250 mm; $H_2O$:MeCN elution) provided the title compound (60 mg, 0.13 mmol) as an off-white solid. $^1$H NMR (400 MHz, chloroform-d) δ 11.19 (s, 1H), 7.68 (dd, 2H), 7.09-7.25 (m, 3H), 6.92 (t, 1H), 6.82 (d, 1H), 6.61 (s, 1H), 4.21 (brs, 2H), 2.91 (t, 2H), 2.62 (t, 2H), 2.10-2.19 (m, 2H), 2.03 (m, 2H), 1.93 (m2H), 1.83 (d, 2H); m/z=469.1 $[M+H]^+$; $t_R$=1.47 min (LCMS method j).

Example 12: 1-(3,4-difluorophenyl)-9-(3-oxo-6-(4-(trifluoromethyl)-1H-pyrazol-1-yl)-2,3-dihydropyridazin-4-yl)-1,9-diazaspiro[5.5]undecane-2-one

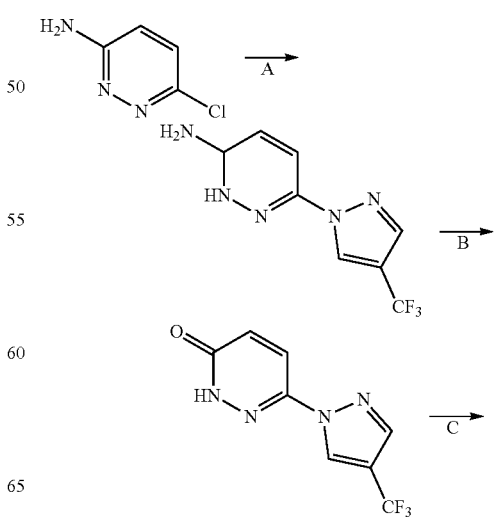

-continued

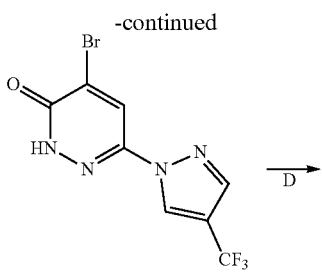

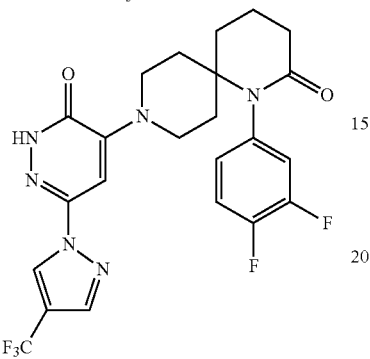

Step A: 6-(4-(trifluoromethyl)-1H-pyrazol-1-yl)-2,3-dihydropyridazine-3-amine

A mixture of 6-chloropyridazin-3-amine (1.0 g, 0.77 mmol), 4-(trifluorophenyl)-1H-pyrazole (0.210 g, 15.4 mmol) and $Cs_2CO_3$ (0.754 g, 2.32 mmol) in dioxane (4 mL) were heated at 120° C. for 12 h. After cooling to RT, water was added to the reaction mixture and it was extracted with EtOAc. The extracts were washed with brine, dried over $Na_2SO_4$, filtered, and concentrated under reduced pressure. Purification by silica gel chromatography (35-40% EtOAC: hexane) provided 6-(4-(trifluoromethyl)-1H-pyrazol-1-yl)-2,3-dihydropyridazine-3-amine (0.400 g, 1.73 mmol). m/z=230.1 $[M+H]^+$ Step B: 6-(4-(trifluoromethyl)-1H-pyrazol-1-yl)pyridazin-3(2H)-one A mixture of 6-(4-(trifluoromethyl)-1H-pyrazol-1-yl)-2,3-dihydropyridazine-3-amine (0.020 g, 0.087 mmol), $NaNO_2$ (0.012 g, 0.471 mmol) and concentrated $H_2SO_4$ (0.5 mL) in AcOH (1 mL) was heated at 80° C. for 16 h. After cooling to RT, water was added to the reaction mixture and it was extracted with EtOAc, washed with brine, dried over $Na_2SO_4$, filtered, and concentrated under reduced pressure. Purification by silica gel chromatography (40-50% EtOAC: hexane) provided 6-(4-(trifluoromethyl)-1H-pyrazol-1-yl)pyridazin-3(2H)-one (0.010 g, 0.43 mmol). m/z=231.0 $[M+H]^+$ Step C: 4-bromo-6-(4-(trifluoromethyl)-1H-pyrazol-1-yl)pyridazin-3(2H)-one A mixture of 6-(4-(trifluoromethyl)-1H-pyrazol-1-yl)pyridazin-3(2H)-one (0.20 g, 0.87 mmol), KOAc (0.640 g, 6.73 mmol) and $Br_2$ (7.0 mL, 7.4 mmol) in AcOH (2 mL) was heated at 80° C. for 24 h. After cooling to RT, water was added to the reaction mixture and it was extracted with EtOAc. The extracts were washed with brine, dried over $Na_2SO_4$, filtered, and concentrated under reduced pressure to provide crude 4-bromo-6-(4-(trifluoromethyl)-1H-pyrazol-1-yl)pyridazin-3(2H)-one (170 mg) which was used in the next step without purification. $^1$H NMR (400 MHz, methanol-$d_4$) b 8.77 (s, 1H), 8.62 (s, 1H), 8.06 (s, 1H). m/z=311.0 $[M+2]^+$.

Step D: 1-(3,4-difluorophenyl)-9-(3-oxo-6-(4-(trifluoromethyl)-1H-pyrazol-1-yl)-2,3-dihydropyridazin-4-yl)-1,9-diazaspiro [5.5]undecane-2-one 1-(3,4-difluorophenyl)-1,9-diazaspiro[5.5]undecane-2-one (Intermediate A, 0.090 g, 0.32 mmol), 4-bromo-6-(4-(trifluoromethyl)-1H-pyrazol-1-yl)-2-pyridazine-3(2H)-one (0.170 g, 0.550 mmol) and DIPEA (0.13 mL, 0.75 mmol) in DMF (3 mL) were refluxed at 80° C. for 12 hours. After cooling to RT, the reaction mixture was diluted with cold water, extracted with EtOAc, washed with brine, and dried over $Na_2SO_4$. After filtration, the filtrate was concentrated under reduced pressure to provide the title compound (85 mg, 0.17 mmol). $^1$H NMR (300 MHz, DMSO-d6) δ 12.8 (s, 1H), 8.88 (s, 1H), 8.22 (s, 1H), 7.46 (m, 1H), 7.29 (m, 1H), 6.9 (m, 2H), 4.16 (d, 2H), 2.96 (t, 2H), 2.41 (m, 2H), 2.04-2.18 (m, 2H), 1.83-1.91 (m, 4H), 1.61-1.76 (m, 2H); m/z=509.15 $[M+H]^+$; $t_R$=1.50 min (LCMS method j)

Example 13: 1-(3,4-difluorophenyl)-9-(3-oxo-6-(2,2,2-trifluoroethoxy)-2,3-dihydropyridazin-4-yl)-1,9-diazaspiro[5.5]undecan-2-one

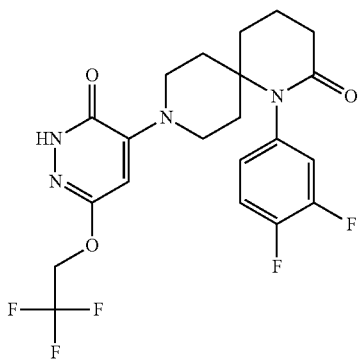 [SMILES: O=C1CCCC2(CCN(c3cc(OCC(F)(F)F)n[nH]c3=O)CC2)N1c1ccc(F)c(F)c1]

This compound was synthesized analogously to Example 12 using 2,2,2-trifluoroethan-1-ol. $^1$H NMR (400 MHz, DMSO-d6) δ 12.1 (s, 1H), 7.41 (m, 1H), 7.22 (m, 1H), 6.92 (m, 1H), 6.15 (s, 1H), 4.62-4.78 (m, 2H), 4.01-4.12 (m, 2H), 2.74-2.88 (m, 2H), 2.41 (t, 2H), 2.07 (brs, 2H), 1.78-1.88 (m, 4H), 1.54-1.7 (m, 2H); m/z=473.4 $[M+H]^+$; $t_R$=0.66 min (LCMS method i)

Example 14: 1-(3,4-difluorophenyl)-9-(2-methyl-3-oxo-6-(4-(trifluoromethyl)-1H-pyrazol-1-yl)-2,3-dihydropyridazin-4-yl)-1,9-diazaspiro[5.5]undecane-2-one

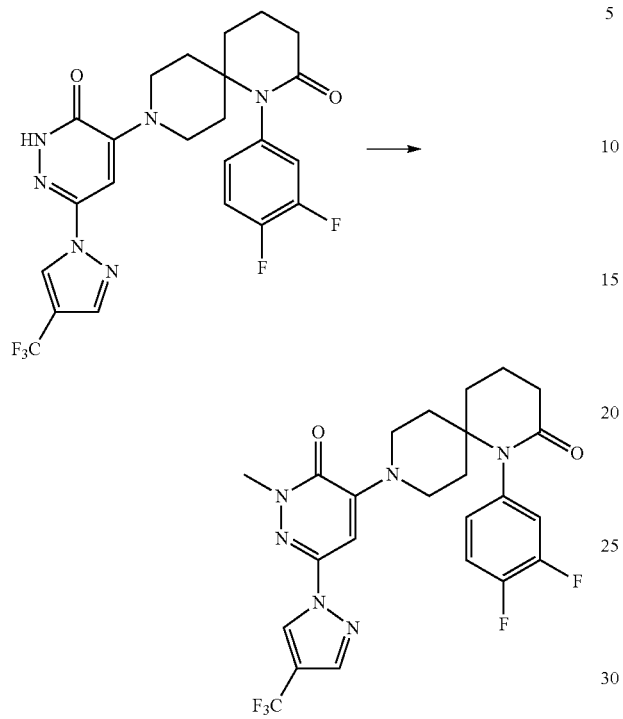

Iodomethane (0.018 g, 0.129 mmol) was added dropwise to a stirred solution of 1-(3,4-difluorophenyl)-9-(3-oxo-6-(4-(trifluoromethyl)-1H-pyrazol-1-yl)-2,3-dihydropyridazin-4-yl)-1,9-diazaspiro[5.5]undecane-2-one (0.040 g, 0.078 mmol) and $Cs_2CO_3$ (0.084 g, 0.259 mmol) in DMF (4 mL) cooled to 0° C. The reaction mixture was allowed to warm to RT over 4 h. Water was added to the reaction mixture and it was extracted with EtOAc, washed with brine, dried over $Na_2SO_4$ and concentrated under reduced pressure to provide the title compound (25 mg, 0.48 mmol). $^1$H NMR (300 MHz, DMSO-$d_6$) δ 8.93 (s, 1H), 8.24 (s, 1H), 7.48 (m, 1H), 7.29 (m, 1H), 6.92-7 (m, 2H), 4.12 (d, 2H), 3.6 (s, 3H), 2.98 (t, 2H), 2.42 (t, 2H), 2.08 (brs, 2H), 1.7-1.92 (m, 4H), 1.68 (t, 2H); m/z=523.3 [M+H]⁺; $t_R$=1.64 min (LCMS method 1).

Example 15a: 1-(3,4-difluorophenyl)-9-(3-oxo-6-((tetrahydro-2H-pyran-4-yl)oxy)-2,3-dihydropyridazin-4-yl)-1,9-diazaspiro[5.5]undecan-2-one and Example 15b: 9-(1-benzyl-6-oxo-3-((tetrahydro-2H-pyran-4-yl)oxy)-1,6-dihydropyridazin-4-yl)-1-(3,4-difluorophenyl)-1,9-diazaspiro[5.5]undecan-2-one

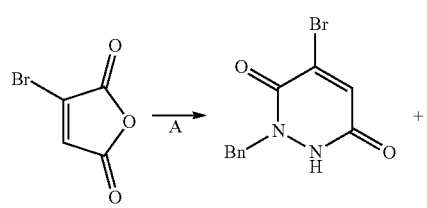

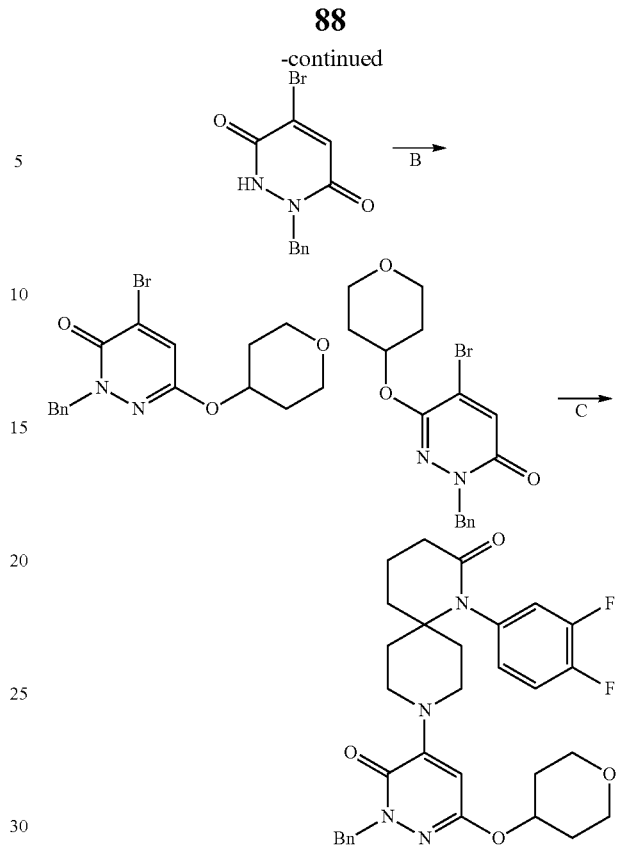

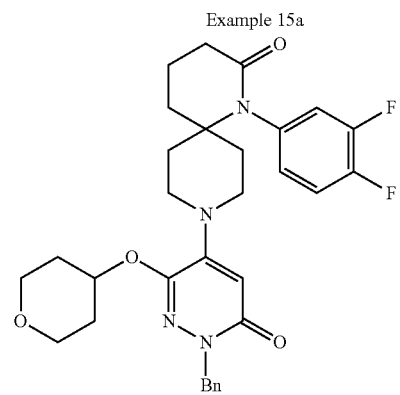

Example 15b

Step A: 1-benzyl-5-bromo-1,2-dihydropyridazine-3,6-dione and 1-benzyl-4-bromo-1,2-dihydropyridazine-3,6-dione A mixture of 3-bromofuran-2,5-dione (5 g, 28.25 mmol) and benzyl hydrazine·2HCl (8.20 g, 42.4 mmol) in water (45 mL) was heated at 100° C. for 16 h. The reaction mixture was cooled to RT and filtered. The clear filtrate was concentrated under reduced pressure to provide a crude mixture of regioisomeric products (4.4 g, crude). m/z=283 [M+2]⁺

Step B: 2-benzyl-4-bromo-6-((tetrahydro-2H-pyran-4-yl)oxy)pyridazin-3(2H)-one and 2-benzyl-5-bromo-6-((tetrahydro-2H-pyran-4-yl)oxy)pyridazin-3(2H)-one A stirred solution of 1-benzyl-5-bromo-1,2-dihydropyridazine-3,6-dione and 1-benzyl-4-bromo-1,2-dihydropyridazine-3,6-dione (2.00 g, 7.14 mmol) in DMF (25 mL) was treated with 4-bromo-tetrahydropyran (1.70 g, 10.3 mmol) and K$_2$CO$_3$ (2.90 g, 20.9 mmol). The reaction mixture was heated at 85° C. for 48 h. After cooling the reaction mixture was diluted with water and extracted with EtOAc twice. The combined organic layers were washed with brine, dried over Na$_2$SO$_4$, filtered and concentrated under reduced pressure to provide the mixture of regioisomeric products as white sticky solid (0.576 g, 1.58 mmol). m/z=367.0 [M+H]$^+$ Step-C: 9-(1-benzyl-6-oxo-3-((tetrahydro-2H-pyran-4-yl)oxy)-1,6-dihydropyridazin-4-yl)-1-(3,4-difluorophenyl)-1,9-diazaspiro[5.5]undecan-2-one and 9-(2-benzyl-3-oxo-6-((tetrahydro-2H-pyran-4-yl)oxy)-2,3-dihydropyridazin-4-yl)-1-(3,4-difluorophenyl)-1,9-diazaspiro[5.5]undecan-2-one A stirred solution of 2-benzyl-4-bromo-6-((tetrahydro-2H-pyran-4-yl)oxy)pyridazin-3(2H)-one and 2-benzyl-5-bromo-6-((tetrahydro-2H-pyran-4-yl)oxy)pyridazin-3(2H)-one (100 mg, 0.273 mmol) in DMF (2 mL) was treated with 1-(3,4-difluorophenyl)-1,9-diazaspiro[5.5]undecan-2-one (Intermediate A, 77 mg, 0.27 mmol) and DIPEA (72 µL, 0.41 mmol). The reaction mixture was heated at 80° C. for 48 h. After cooling to RT, the reaction mixture was diluted with water and extracted with EtOAc twice. The combined organic layers were washed with brine, dried over Na$_2$SO$_4$, filtered, and concentrated under reduced pressure. The crude material was purified by preparative HPLC (YMC, 5 µm, 21.2×150 mm; 0.02% aqueous NH$_4$OH:MeCN elution) to separate the two regioisomeric products:

Example 15a: 9-(2-benzyl-3-oxo-6-((tetrahydro-2H-pyran-4-yl)oxy)-2,3-dihydropyridazin-4-yl)-1-(3,4-difluorophenyl)-1,9-diazaspiro[5.5]undecan-2-one, isolated as a pale yellow solid (115 mg, 0.203 mmol). $^1$H NMR (400 MHz, DMSO-d$_6$) δ 7.3-7.47 (m, 1H), 7.22-7.30 (m, 6H), 6.94-6.96 (m, 1H), 6.08 (s, 1H), 5.03 (s, 2H), 4.72-4.81 (m, 1H), 3.9-4.05 (brs, 2H), 3.74-3.82 (m, 2H), 3.41 (t, 2H), 2.78 (t, 2H), 2.41 (t, 2H), 2.08 (m, 2H), 1.82-1.92 (m, 6H), 1.6-1.71 (m, 2H), 1.48-1.56 (m, 2H); m/z=565.2 [M+H]$^+$; t$_R$=1.71 min (LCMS method 1).

Example 15b: 9-(1-benzyl-6-oxo-3-((tetrahydro-2H-pyran-4-yl)oxy)-1,6-dihydropyridazin-4-yl)-1-(3,4-difluorophenyl)-1,9-diazaspiro[5.5]undecan-2-one: $^1$H NMR (300 MHz, DMSO-d$_6$) δ 7.4-7.48 (m, 1H), 7.2-7.34 (m, 6H), 6.84-6.89 (m, 1H), 5.92 (s, 1H), 4.96 (s, 2H), 4.77-4.84 (m, 1H), 3.52-3.63 (m, 4H), 3.38-3.47 (m, 2H), 2.86 (t, 2H), 2.40 (t, 3H), 2.07 (m, 2H), 1.75-1.9 (m, 5H), 1.58-1.72 (m, 2H), 1.4-1.53 (m, 2H), m/z=565.4 [M+H]$^+$, t$_R$=2.13 min (LCMS method 1);

Example 16: 1-(3,4-difluorophenyl)-9-(3-oxo-6-((tetrahydro-2H-pyran-4-yl)oxy)-2,3-dihydropyridazin-4-yl)-1,9-diazaspiro[5.5]undecan-2-one

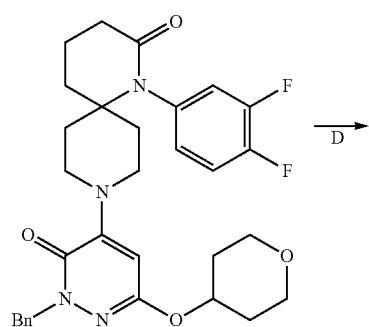

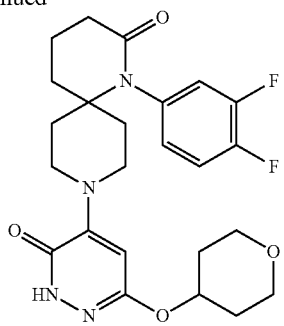

A stirred solution of 9-(2-benzyl-3-oxo-6-((tetrahydro-2H-pyran-4-yl)oxy)-2,3-dihydropyridazin-4-yl)-1-(3,4-difluorophenyl)-1,9-diazaspiro[5.5]undecan-2-one (100 mg, 0.177 mmol) in EtOH (15 mL) was treated with Pd(OH)$_2$ (200 mg) and stirred under an atmosphere of H$_2$ (1 atm) for 48 h. The reaction mixture was flushed with nitrogen, filtered through a bed of celite, and the filtrate concentrated under reduced pressure. Purification by preparative HPLC (LUNA OMEGA C18, 5.0 µm, 21.2×250 mm; water:MeCN elution) afforded the title compound as an off-white solid (40 mg, 0.084 mmol). $^1$H NMR (300 MHz, DMSO-d$_6$) δ 11.84 (s, 1H), 7.4-7.46 (m, 1H), 7.10-7.15 (m, 1H), 6.95-7.0 (m, 1H), 6.02 (s, 1H), 4.70-4.82 (m, 1H), 4.01 (d, 1H), 3.76-3.83 (m, 1H), 3.50-3.38 (m, 2H), 3.29-3.21 (m, 1H), 2.76 (t, 2H), 2.01-2.11 (m, 2H), 1.72-1.98 (m, 8H), 1.52-1.7 (m, 5H); m/z=475.4 [M+H]$^+$; t$_R$=0.45 min (LCMS method 1).

Example 17: 1-(3,4-difluorophenyl)-9-(2-methyl-3-oxo-6-((tetrahydro-2H-pyran-4-yl)oxy)-2,3-dihydropyridazin-4-yl)-1,9-diazaspiro[5.5]undecan-2-one

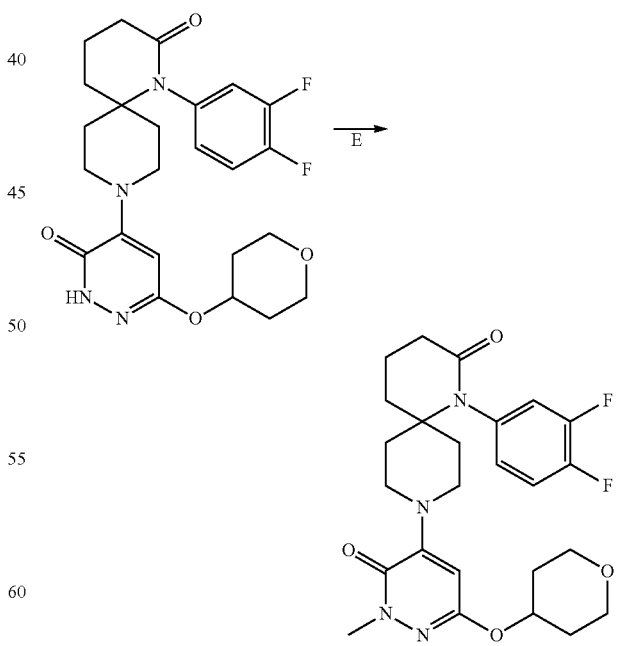

A mixture of 1-(3,4-difluorophenyl)-9-(3-oxo-6-((tetrahydro-2H-pyran-4-yl)oxy)-2,3-dihydropyridazin-4-yl)-1,9-diazaspiro[5.5]undecan-2-one (30 mg, 0.063 mmol), Cs$_2$CO$_3$ (61 mg, 0.19 mmol) and iodomethane (6 µL, 0.096 mmol) in DMF (1 mL) was stirred at RT for 16 h. The reaction mixture was diluted with water and extracted with EtOAc twice. The combined organic layers were washed with brine, dried over $Na_2SO_4$, filtered, and concentrated under reduced pressure. Purification by preparative HPLC (ZORBAX, 5 μm, 21.2×150 mm; water:ACN elution) afforded the title compound (8 mg, 0.016 mmol) as an off-white solid. $^1$H NMR (400 MHz, chloroform-d) δ 7.68 (dd, 1H), 7.10-7.15 (m, 1H), 6.96-7.0 (m, 1H), 6.05 (s, 1H), 4.72-4.84 (m, 1H), 3.92-4.2 (m, 2H), 3.38-3.47 (m, 4H), 2.77 (t, 2H), 2.4 (t, 2H), 2.06 (d, 2H), 1.9-2.0 (m, 2H), 1.8-1.84 (m, 4H), 1.52-1.68 (m, 4H); m/z=489.2 $[M+H]^+$; $t_R$=1.3 min (LCMS method k).

Example 18: 9-(6-(4,4-difluorocyclohex-1-en-1-yl)-3-oxo-3,4-dihydropyrazin-2-yl)-1-(3,4-difluorophenyl)-1,9-diazaspiro[5.5]undecane-2-one

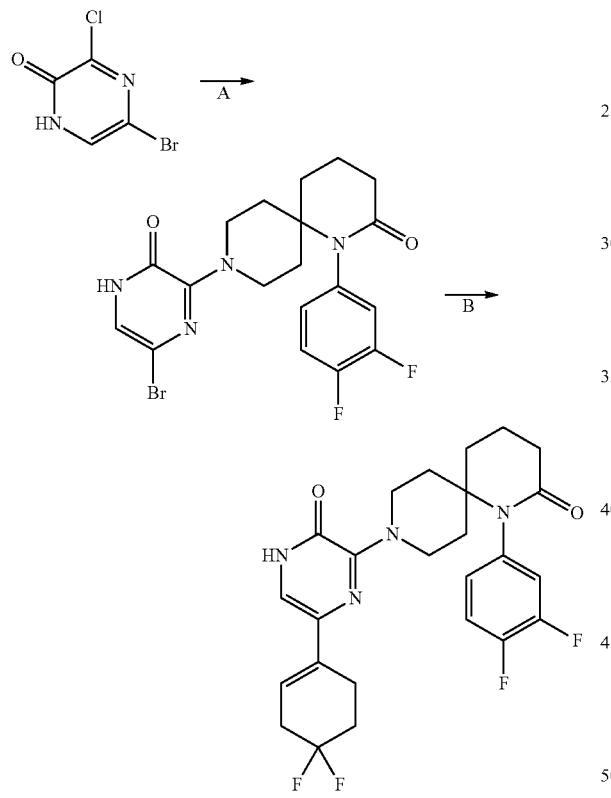

Step A: 9-(6-bromo-3-oxo-3,4-dihydropyrazin-2-yl)-1-(3,4-difluorophenyl)-1,9-diazaspiro[5.5]undecane-2-one 1-(3,4-difluorophenyl)-1,9-diazaspiro[5.5]undecane-2-one (Intermediate A, 0.870 g, 3.10 mmol), 5-bromo-3-chloropyrazin-2(1H)-one (0.650 g, 3.10 mmol) and DIPEA (1.6 mL, 9.3 mmol) in EtOH (10 mL) were heated at 80° C. for 12 h. The reaction mixture was diluted with water and extracted with EtOAc twice. The combined organic layers were washed with brine, dried over $Na_2SO_4$, filtered, and concentrated under reduced pressure. Purification by silica gel chromatography (2-8% MeOH in DCM) provided 9-(6-bromo-3-oxo-3,4-dihydropyrazin-2-yl)-1-(3,4-difluorophenyl)-1,9-diazaspiro[5.5]undecane-2-one as a white solid (0.460 g, 1.01 mmol). m/z=455.05 $[M+H]^+$ Step B: 9-(6-(4,4-difluorocyclohex-1-en-1-yl)-3-oxo-3,4-dihydropyrazin-2-yl)-1-(3,4-difluorophenyl)-1,9-diazaspiro[5.5]undecane-2-one A mixture of 9-(6-bromo-3-oxo-3,4-dihydropyrazin-2-yl)-1-(3,4-difluorophenyl)-1,9-diazaspiro[5.5]undecane-2-one (0.050 g, 0.110 mmol) and 2-(4,4-difluorocyclohex-1-en-1-yl)-4,4,5,5-tetramethyl-1,3,2-dioxaborolane (0.081 g, 0.331 mmol) were stirred in DME (1 mL) and $H_2O$ (0.5 mL) at RT under argon purging for 10 minutes. $K_2CO_3$ (0.046 g, 0.33 mmol) was added to the reaction mixture under argon purging followed by the addition of $Pd(dppf)Cl_2 \cdot DCM$ (0.018 g, 0.022 mmol). The mixture was heated at 100° C. for 16 h. After cooling to RT, the reaction mixture was diluted with water and extracted with EtOAc twice. The extracts were washed with brine, dried over $Na_2SO_4$, filtered, and concentrated under reduced pressure. Purification by preparative HPLC (LUNA C18, 5 μm, 21.2×250 mm; water:ACN elution) provided the title compound (21 mg, 0.043 mmol) as a white solid. $^1$H NMR (400 MHz, DMSO-$d_6$) δ 11.72 (s, 1H), 7.44 (m, 1H), 7.25 (ddd, 1H), 6.93 (m, 1H), 6.75 (s, 1H), 6.24 (s, 1H), 4.50 (d, 2H), 2.85 (m, 2H), 2.67 (m, 2H), 2.41 (m, 4H), 2.09 (m, 4H), 1.91-1.77 (m, 4H), 1.63 (m, 2H). m/z=491.2 $[M+H]^+$; $t_R$=1.49 min (LCMS method j).

Example 19: 9-(6-(4,4-difluorocyclohex-1-en-1-yl)-4-methyl-3-oxo-3,4-dihydropyrazin-2-yl)-1-(3,4-difluorophenyl)-1,9-diazaspiro[5.5]undecane-2-one

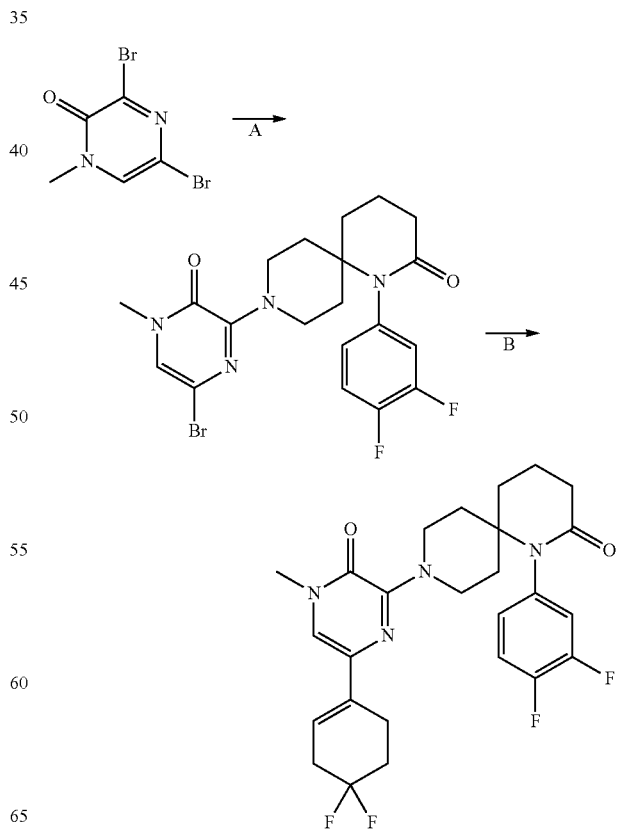

Step A: 9-(6-bromo-4-methyl-3-oxo-3,4-dihydropyrazin-2-yl)-1-(3,4-difluorophenyl)-1,9-diazaspiro[5.5]undecane-2-one A mixture of 1-(3,4-difluorophenyl)-1,9-diazaspiro[5.5]undecane-2-one (Intermediate A, 0.630 g, 2.24 mmol), 3,5-dibromo-1-methylpyrazin-2(1H)-one (0.600 g, 2.24 mmol) and DIPEA (1.2 mL, 6.7 mmol) in EtOH (8 mL) were heated at 80° C. for 12 h. After cooling to RT, the reaction mixture was diluted with water and extracted with EtOAc twice. The extracts were washed with brine, dried over $Na_2SO_4$, filtered, and concentrated under reduced pressure. Purification by silica gel chromatography (2-7% MeOH in DCM) provided 9-(6-bromo-4-methyl-3-oxo-3,4-dihydropyrazin-2-yl)-1-(3,4-difluorophenyl)-1,9-diazaspiro[5.5]undecane-2-one as a light brown solid (0.770 g, 1.65 mmol). m/z=469.05 [M+2]$^+$

Step B: 9-(6-(4,4-difluorocyclohex-1-en-1-yl)-4-methyl-3-oxo-3,4-dihydropyrazin-2-yl)-1-(3,4-difluorophenyl)-1,9-diazaspiro[5.5]undecane-2-one 9-(6-bromo-4-methyl-3-oxo-3,4-dihydropyrazin-2-yl)-1-(3,4-difluorophenyl)-1,9-diazaspiro[5.5]undecane-2-one (0.310 g, 0.660 mmol) and 2-(4,4-difluorocyclohex-1-en-1-yl)-4,4,5,5-tetramethyl-1,3,2-dioxaborolane (0.200 g, 0.820 mmol) were stirred in DME (2.5 mL) and water (1 mL) at RT under argon purging for 10 min. $K_2CO_3$ (0.177 g, 1.28 mmol) was added to the reaction mixture under argon purging followed by the addition of Pd(dppf)Cl$_2$·DCM (0.070 g, 0.086 mmol). The mixture was heated at 100° C. for 16 h. After cooling to RT, the reaction mixture was diluted with water and extracted with EtOAc twice. The combined extracts were washed with brine, dried over $Na_2SO_4$, filtered, and concentrated under reduced pressure. Purification by preparative HPLC (Waters ATLANTIS C18, 5 μm, 21.2×250 mm; water/(1:1 ACN/MeOH) elution) provided the title compound (0.118 g, 0.233 mmol) as a brown solid. $^1$H NMR (400 MHz, DMSO-d$_6$) δ 7.42-7.47 (m, 1H), 7.2-7.28 (m, 1H), 7.16 (s, 1H), 6.88-6.92 (m, 1H), 6.2 (m, 1H), 4.46 (d, 2H), 3.32 (s, 3H), 2.88 (t, 2H), 2.68 (t, 2H), 2.49-2.51 (m, 1H), 2.39-2.43 (m, 4H), 2.07-2.18 (m, 4H), 1.81-1.84 (m, 3H), 1.58-1.68 (m, 2H); m/z=505.2 [M+H]$^+$; $t_R$=1.59 min (LCMS method k).

Example 20: 1-(4-chloro-3-fluorophenyl)-9-(5-cyclopentyl-1,2,4-triazin-3-yl)-1,9-diazaspiro[5.5]undecan-2-one

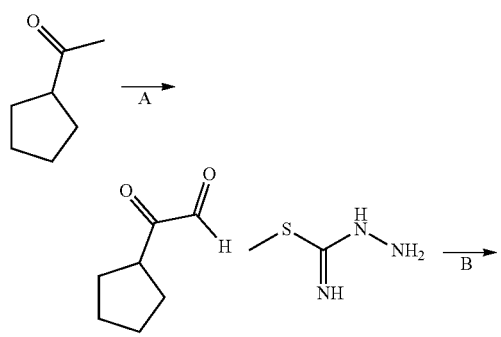

Step A: 2-cyclopentyl-2-oxoacetaldehyde

A mixture of 1-cyclopentylethanone (236 mg, 2.10 mmol) and selenium dioxide (244 mg, 2.20 mmol) in 1 mL of dioxane and 0.1 mL of water was stirred overnight at 80° C. The dark-brown reaction mixture was filtered over cotton wool and washed with 4 mL of water. The filtrate was used without further purification in the next step.

Step B: 5-cyclopentyl-3-(methylthio)-1,2,4-triazine

Sodium bicarbonate (168 mg, 2.00 mmol) was added to the reaction mixture of the previous step. The white suspension was cooled to 0-5° C. and a solution of methyl hydrazinecarbimidothioate hydroiodide (373 mg, 1.60 mmol) in 2 mL of water was added. The reaction mixture was stirred for 2 h at 0-5° C. and then diluted with DCM and water. The organic layers were dried over $Na_2SO_4$, filtered, and concentrated. The crude product was adsorbed onto silica gel and purified by silica gel chromatography (0-50% EtOAc in cyclohexane). m/z=196.2 [M+H]$^+$; $t_R$=1.02 min (LCMS method a).

Step C: 1-(4-chloro-3-fluorophenyl)-9-(5-cyclopentyl-1,2,4-triazin-3-yl)-1,9-diazaspiro[5.5]undecan-2-one

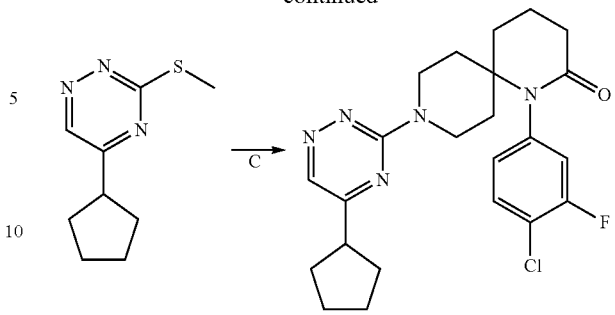

MCPBA (134 mg, 0.584 mmol) was added to a solution of 5-cyclopentyl-3-(methylthio)-1,2,4-triazine (100 mg, 0.486 mmol) DMF (1 mL) cooled to 0° C. The reaction mixture was allowed to warm to RT and was stirred for 1.5 h. Triethylamine (340 μL, 2.43 mmol) and 1-(4-chloro-3-fluorophenyl)-1,9-diazaspiro[5.5]undecan-2-one (Intermediate B, 144 mg, 0.486 mmol) were added and the mixture was stirred at RT for two days. The solution was quenched with ice water, extracted with DCM, and the extracts were concentrated. The crude product was adsorbed onto silica gel and purified by silica gel chromatography (0-50% EtOAc in cyclohexane) followed by SFC (Princeton 4-ethylpyridine 100 Å, 30×250 mm, 5 μm; 9-14% MeOH in $CO_2$, 10 min) to provide the title compound (28 mg, 0.060 mmol). $^1$H NMR (400 MHz, DMSO-d$_6$) δ=8.54 (s, 1H), 7.58 (dd, 1H), 7.23 (d, 1H), 6.96 (d, 1H), 4.54 (m, 1H), 4.08 (m, 2H), 3.18 (m, 4H), 3.05 (m, 3H), 2.45 (t, 2H), 2.18 (m, 2H), 1.9 (m, 4H), 1.5-1.7 (m, 5H) ppm; m/z=444.2 [M+H]$^+$; $t_R$=1.16 min (LCMS method a).

Example 21: 1-(4-chloro-3-fluorophenyl)-9-(5-(4-fluorophenyl)oxazol-2-yl)-1,9-diazaspiro[5.5]undecan-2-one

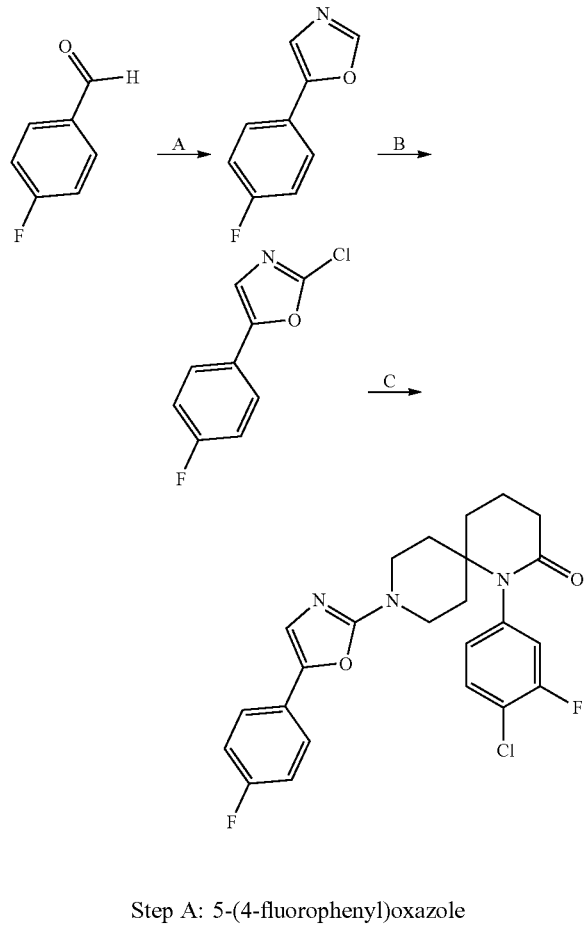

Step A: 5-(4-fluorophenyl)oxazole

Tosylmethylisocyanate (787 mg, 3.95 mmol) and $K_2CO_3$ (655 mg, 4.74 mmol) were added to a solution of 4-fluorobenzaldehyde (0.425 mL, 3.95 mmol) in 20 mL of MeOH. The reaction mixture was stirred for 3 h at 80° C., then 16 h at RT. The reaction mixture was concentrated, diluted with water and extracted three times with ethyl acetate. The organic extracts were dried over $Na_2SO_4$, filtered, and concentrated. Purification by silica gel chromatography (10-60% EtOAc in cyclohexane) provided 5-(4-fluorophenyl)oxazole (539 mg, 3.14 mmol). $^1$H NMR (600 MHz, DMSO-$d_6$) δ=8.45 (s, 1H), 7.78 (m, 2H), 7.68 (s, 1H), 7.34 (m, 2H) ppm; m/z=164.1 [M+H]$^+$; $t_R$=0.88 min (LCMS method d).

Step B: 2-chloro-5-(4-fluorophenyl)oxazole

LiHMDS (1.0 M in THF, 1.53 mL, 1.53 mmol) was added dropwise to a solution of 5-(4-fluorophenyl)oxazole (200 mg, 1.23 mmol) in 10 mL of THF cool to −78° C. The reaction mixture was stirred for 30 min at −78° C. This solution was then added dropwise to a suspension of hexachloroethane (580 mg, 2.45 mmol) in 5 mL of THF at −78° C. The reaction mixture was allowed to warm up to RT and was further stirred at this temperature for 12 h. The mixture was quenched with saturated aqueous $NH_4Cl$ and extracted twice with EtOAc. The combined extracts were dried over $Na_2SO_4$, filtered, and concentrated. The crude product was purified by silica gel chromatography (50-100% DCM in cyclohexane) to provide 2-chloro-5-(4-fluorophenyl)oxazole (61 mg, 0.31 mmol). $^1$H NMR (600 MHz, DMSO-$d_6$) δ=7.78 (s, 1H), 7.75 (m, 2H), 7.36 (m, 2H) ppm; m/z=molecular ion not detected; $t_R$=1.09 min (LCMS method a).

Step C: 1-(4-chloro-3-fluorophenyl)-9-(5-(4-fluorophenyl)oxazol-2-yl)-1,9-diazaspiro[5.5]undecan-2-one A mixture of 2-chloro-5-(4-fluorophenyl)oxazole (57 mg, 0.288 mmol), triethylamine (0.11 mL, 0.81 mmol) and 1-(4-chloro-3-fluorophenyl)-1,9-diazaspiro[5.5]undecan-2-one (Intermediate B, 80 mg, 0.27 mmol) in 4 mL of EtOH was stirred for 3 h at 160° C. After cooling to RT the reaction was concentrated, diluted with ethyl acetate, and washed with brine. The organic layer was dried over $Na_2SO_4$, filtered, and concentrated. Purification by SFC (Princeton 2-ethylpyridine 100 Å, 5 μm, 30×250 mm; 13-18% MeOH in $CO_2$, 13 min) provided the title compound (76 mg, 0.17 mmol) as a white solid. $^1$H NMR (400 MHz, DMSO-$d_6$) δ=7.61 (dd, 1H), 7.54 (dd, 2H), 7.27 (dd, 1H), 7.24 (s, 1H), 7.22 (dd, 2H), 6.98 (dd, 1H), 4.89 (m, 2H), 3.17 (m, 2H), 2.43 (t, 2H), 2.11 (m, 2H), 1.88 (m, 2H), 1.84 (m, 2H), 1.61 (m, 2H) ppm; m/z=458.3 [M+H]$^+$; $t_R$=1.12 min (LCMS method a).

Example 22: 1-(4-chloro-3-fluorophenyl)-9-(2-phenyl-2H-tetrazol-5-yl)-1,9-diazaspiro[5.5]undecan-2-one

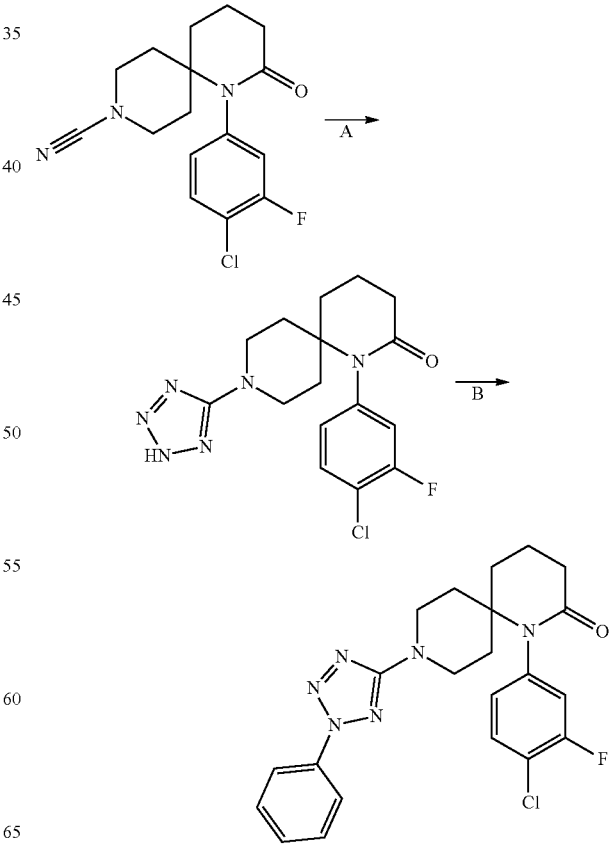

Step A: 1-(4-chloro-3-fluorophenyl)-9-(1H-tetrazol-5-yl)-1,9-diazaspiro[5.5]undecan-2-one A mixture of sodium azide (515 mg, 7.92 mmol), triethylamine hydrochloride (1.09 g, 7.92 mmol) and 1-(4-chloro-3-fluorophenyl)-2-oxo-1,9-diazaspiro[5.5]undecane-9-carbonitrile (850 mg, 2.64 mmol) in 10 mL of DMF was heated under microwave irradiation for 2 h at 130° C. The reaction mixture was filtered, diluted with EtOAc and the pH was adjusted to 5 by addition of 4 N HCl. The aqueous layer was extracted twice with EtOAc. The combined organic extracts were dried over $Na_2SO_4$, filtered and concentrated. Purification by silica gel chromatography (0-30% MeOH in DCM) provided 1-(4-chloro-3-fluorophenyl)-9-(1H-tetrazol-5-yl)-1,9-diazaspiro[5.5]undecan-2-one. $^1$H NMR (400 MHz, DMSO-$d_6$) δ=14.95 (br s, 1H), 7.60 (dd, 1H), 7.26 (d, 1H), 6.98 (dd, 1H), 3.67 (m, 2H), 3.17 (t, 2H), 2.43 (t, 2H), 2.09 (m, 2H), 1.8-1.88 (m, 4H), 1.62 (m, 2H) ppm; m/z=365.2 [M+H]$^+$; $t_R$=0.65 min (LCMS method a).

Step C: 1-(4-chloro-3-fluorophenyl)-9-(2-phenyl-2H-tetrazol-5-yl)-1,9-diazaspiro[5.5]undecan-2-one $K_2CO_3$ (62.5 mg, 0.452 mmol), [Cu(OH)(TMEDA)]$_2$Cl$_2$ (23 mg, 0.049 mmol) and phenyl boronic acid (158 mg, 1.23 mmol) were added under argon to a solution of 1-(4-chloro-3-fluorophenyl)-9-(1H-tetrazol-5-yl)-1,9-diazaspiro[5.5]undecan-2-one (Intermediate B, 150 mg, 0.411 mmol) in 3 mL of DCM. The resulting mixture was momentarily placed under vacuum before adding an O$_2$ balloon and stirred at RT for 48 h. The reaction mixture was filtered through celite and concentrated. Purification by silica gel chromatography (0-5% MeOH in DCM) provided the title compound (32 mg, 0.070 mmol). $^1$H NMR (400 MHz, DMSO-$d_6$) δ=7.93 (d, 2H), 7.58-7.62 (m, 3H), 7.51 (t, 1H), 7.26 (dd, 1H), 6.98 (d, 1H), 3.90 (m, 2H), 3.17-3.19 (m, 2H), 2.45 (t, 2H), 2.13 (m, 2H), 1.86-1.95 (m, 4H), 1.6-1.75 (m, 2H) ppm; m/z=441.2 [M+H]$^+$; $t_R$=1.19 min (LCMS method a).

Example 23: 1-(4-chloro-3-fluorophenyl)-9-(5-(3,3-difluoropyrrolidin-1-yl)-1,2,4-thiadiazol-3-yl)-1,9-diazaspiro[5.5]undecan-2-one

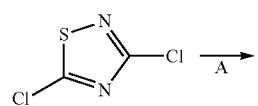

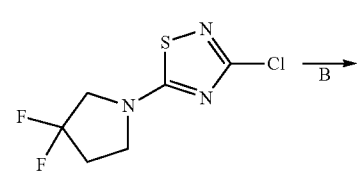

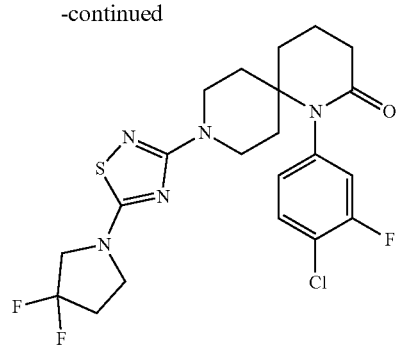

Step A: 3-chloro-5-(3,3-difluoropyrrolidin-1-yl)-1,2,4-thiadiazole

A mixture of 3,5-dichloro-1,2,4-thiadiazole (150 mg, 0.968 mmol), 3,3-difluoropyrrolidine hydrochloride (167 mg, 1.16 mmol) and triethylamine (0.67 mL, 4.8 mmol) in EtOH (1.5 mL) was stirred for 1 h at RT. The reaction was diluted with EtOAc and washed with water. The organic layer was dried over $Na_2SO_4$, filtered, and evaporated. Purification by silica gel chromatography (0-15% EtOAc in cyclohexane) provided 3-chloro-5-(3,3-difluoropyrrolidin-1-yl)-1,2,4-thiadiazole (165 mg, 0.731 mmol) as a white crystalline solid. $^1$H NMR (400 MHz, DMSO-$d_6$) δ=3.95 (t, 2H), 3.70 (m, 2H), 2.6-2.7 (m, 2H) ppm; m/z=226.0 [M+H]$^+$; $t_R$=0.84 min (LCMS method a).

Step B: 1-(4-chloro-3-fluorophenyl)-9-(5-(3,3-difluoropyrrolidin-1-yl)-1,2,4-thiadiazol-3-yl)-1,9-diazaspiro[5.5]undecan-2-one A solution of 1-(4-chloro-3-fluorophenyl)-1,9-diazaspiro[5.5]undecan-2-one (Intermediate B, 100 mg, 0.337 mmol), 3-chloro-5-(3,3-difluoropyrrolidin-1-yl)-1,2,4-thiadiazole (114 mg, 0.505 mmol) and triethylamine (0.14 mL, 1.0 mmol) in DMF (1.5 mL) was heated under microwave irradiation for 3 h at 160° C. After cooling to RT, the reaction mixture was diluted with EtOAc and washed with water. The organic layer was dried over $Na_2SO_4$, filtered, and concentrated. Purification by SFC (Waters Atlantis HILIC silica, 30×250 mm, 5 μm, 11-16% MeOH in CO$_2$, 10 min) provided the title compound (29 mg, 0.059 mmol). $^1$H NMR (400 MHz, DMSO-$d_6$) δ=7.60 (t, 1H), 7.23 (dd, 1H), 6.95 (dd, 1H), 4.05 (m, 2H), 3.8 (m, 2H), 3.55 (t, 2H), 3.0 (m, 2H), 2.55 (m, 2H), 2.45 (t, 2H), 2.1 (m, 2H), 1.8-1.9 (m, 4H), 1.45-1.6 (m, 2H) ppm; m/z=486.2 [M+H]$^+$; $t_R$=1.10 min (LCMS method a).

By employing similar methods as described for the preparation of Example 23, using appropriate starting materials, the following compounds were prepared:

| Ex | Structure and Name | MS, m/z [M + H]+; $t_R$, method | ¹H NMR |
|---|---|---|---|
| 24 | 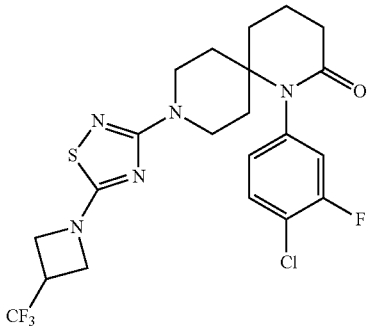 [SMILES: O=C1CCCC2(CCN(c3nsc(N4CC(C(F)(F)F)C4)n3)CC2)N1c1ccc(Cl)c(F)c1]<br>1-(4-chloro-3-fluorophenyl)-9-(5-(3-(trifluoromethyl)azetidin-1-yl)-1,2,4-thiadiazol-3-yl)-1,9-diazaspiro[5.5]undecan-2-one | 504.1; 1.14 min, LCMS method a | ¹H NMR (400 MHz, DMSO-d₆) δ = 7.62 (t, 1H), 7.23 (dd, 1H), 6.95 (d, 1H), 4.25 (t, 2H), 4.0-4.1 (m, 4H), 3.8 (m, 1H), 3.01 (m, 2H), 2.43 (t, 2H), 2.10 (m, 2H), 1.80-1.85 (m, 4H), 1.56 (m, 2H) ppm |
| 25 | 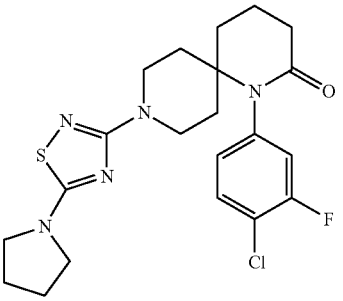 [SMILES: O=C1CCCC2(CCN(c3nsc(N4CCCC4)n3)CC2)N1c1ccc(Cl)c(F)c1]<br>1-(4-chloro-3-fluorophenyl)-9-(5-(pyrrolidin-1-yl)-1,2,4-thiadiazol-3-yl)-1,9-diazaspiro[5.5]undecan-2-one | 450.5; 1.09 min, LCMS method a | ¹H NMR (400 MHz, DMSO-d₆) δ = 7.62 (t, 1H), 7.23 (dd, 1H), 6.95 (d, 1H), 4.09 (m, 2H), 3.25 (m, 4H), 3.00 (m, 2H), 2.45 (t, 2H), 2.10 (m, 2H), 1.93 (m, 4H), 1.8 (m, 4H), 1.51 (m, 2H) ppm |

Example 26: 1-(4-chloro-3-fluorophenyl)-9-(3-(4-fluorophenyl)-1H-1,2,4-triazol-5-yl)-1,9-diazaspiro[5.5]undecan-2-one

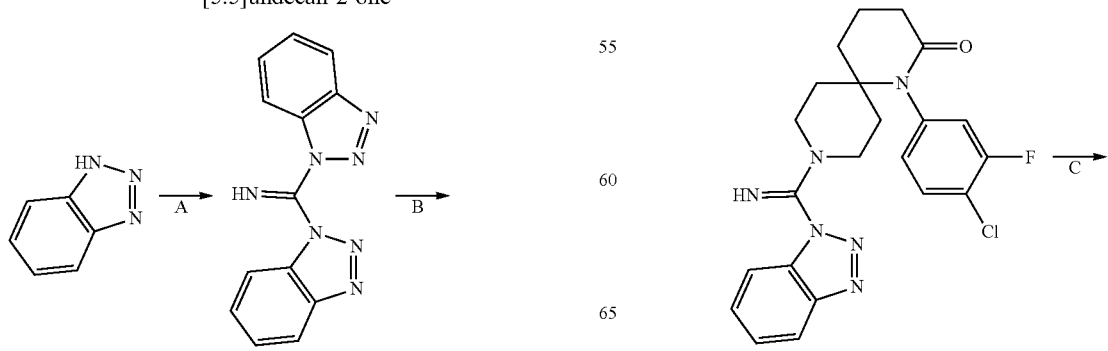

-continued

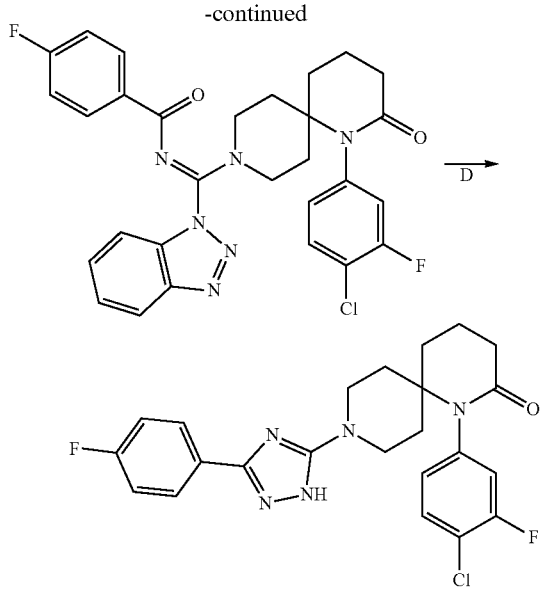

Step A: bis(1H-benzo[d][1,2,3]triazol-1-yl)methanimine

Benzotriazole (5.96 g, 50 mmol) was dissolved in EtOH (100 mL) and stirred at 0° C. A solution of BrCN (2.656 g, 25 mmol) in 10 mL of acetone was added followed by aqueous NaOH (8.0 M, 3.1 mL, 25 mmol). The resulting suspension was stirred for 20 min at 0° C. The white precipitate was filtered off, washed with ice cold EtOH, and dried under reduced pressure to provide crude bis(1H-benzo[d][1,2,3]triazol-1-yl)methanimine. m/z=264.2 [M+H]$^+$; $t_R$=0.92 min (LCMS method a).

Step B: 9-((1H-benzo[d][1,2,3]triazol-1-yl)(imino)methyl)-1-(4-chloro-3-fluorophenyl)-1,9-diazaspiro[5.5]undecan-2-one A suspension of 1-(4-chloro-3-fluorophenyl)-1,9-diazaspiro[5.5]undecan-2-one (Intermediate B, 100 mg, 0.337 mmol) in THF (1 mL) was added dropwise to a suspension of bis(1H-benzo[d][1,2,3]triazol-1-yl)methanimine in dry THF (2.5 mL). The reaction mixture was stirred overnight at RT, diluted with DCM, washed with Na$_2$CO$_3$ solution, dried over Na$_2$SO$_4$, filtered and concentrated. The crude product was used in the next step without further purification. m/z=441.2 [M+H]$^+$; $t_R$=0.65 min (LCMS method a).

Step C: (E)-N-((1H-benzo[d][1,2,3]triazol-1-yl)(1-(4-chloro-3-fluorophenyl)-2-oxo-1,9-diazaspiro[5.5]undecan-9-yl)methylene)-4-fluorobenzamide 4-fluorobenzoyl chloride (37 mg, 0.23 mmol) and TEA (32 μL, 0.23 mmol) were added to a solution of 9-((1H-benzo[d][1,2,3]triazol-1-yl)(imino)methyl)-1-(4-chloro-3-fluorophenyl)-1,9-diazaspiro[5.5]undecan-2-one (170 mg, 0.231 mmol) in DCM (2.5 mL). The resulting mixture was stirred overnight at RT, diluted with DCM and washed with water. The organic layer was dried over Na$_2$SO$_4$, filtered, and concentrated. Purification by silica gel chromatography (0-100% EtOAc in cyclohexane followed by 0-10% MeOH in DCM) provided (E)-N-((1H-benzo[d][1,2,3]triazol-1-yl)(1-(4-chloro-3-fluorophenyl)-2-oxo-1,9-diazaspiro[5.5]undecan-9-yl)methylene)-4-fluorobenzamide (31 mg, 0.05 mmol). m/z=563.3 [M+H]$^+$; $t_R$=1.10 min (LCMS method a).

Step D: 1-(4-chloro-3-fluorophenyl)-9-(3-(4-fluorophenyl)-1H-1,2,4-triazol-5-yl)-1,9-diazaspiro[5.5]undecan-2-one Hydrazine (1.0 M in THF, 0.06 mL, 0.06 mmol) was added to a solution of (E)-N-((1H-benzo[d][1,2,3]triazol-1-yl)(1-(4-chloro-3-fluorophenyl)-2-oxo-1,9-diazaspiro[5.5]undecan-9-yl)methylene)-4-fluorobenzamide (34 mg, 0.06 mmol) in DCM (0.5 mL). After stirring overnight at RT, additional hydrazine (1.0 M in THF, 0.06 mL, 0.06 mmol) was added and stirring was continued for an additional hour. The reaction mixture diluted with DCM, washed with aqueous Na$_2$CO$_3$, dried over Na$_2$SO$_4$, filtered and concentrated. Purification by silica gel chromatography (0-20% MeOH in DCM) provided the title compound. $^1$H NMR (400 MHz, DMSO-d$_6$) δ=12.55 (s, 1H), 7.90 (dd, 2H), 7.60 (t, 1H), 7.24 (m, 3H), 6.98 (d, 1H), 3.75 (m, 2H), 3.0 (m, 2H), 2.43 (t, 2H), 2.10 (m, 2H), 1.85 (m, 4H), 1.63 (m, 2H) ppm; m/z=458.2 [M+H]$^+$; $t_R$=0.96 min (LCMS method a).

Example 27: 1-(4-chloro-3-fluorophenyl)-9-(5-cyclohexyloxazol-2-yl)-1,9-diazaspiro[5.5]undecan-2-one

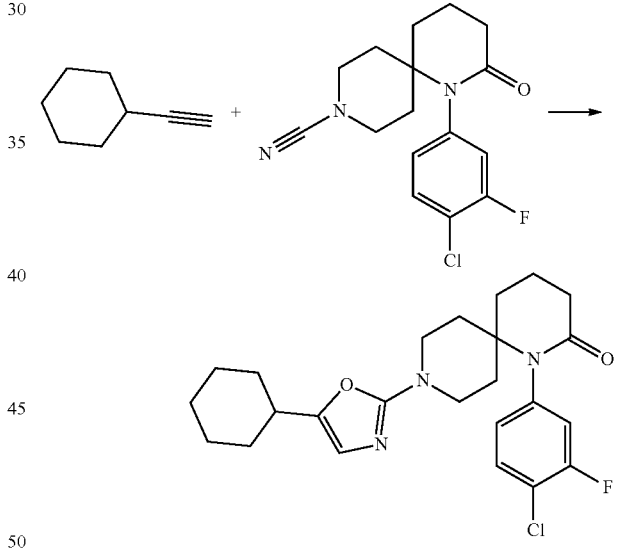

Methanesulfonic acid (0.017 mL, 0.26 mmol) was added to a mixture of 1-(4-chloro-3-fluorophenyl)-2-oxo-1,9-diazaspiro[5.5]undecane-9-carbonitrile (140 mg, 0.435 mmol), 2-picoline N-oxide (47 mg, 0.44 mmol), Ph$_3$PAuNTf$_2$ (2:1 toluene adduct, 17 mg, 0.019 mmol) and ethynylcyclohexane (0.028 mL, 0.218 mmol) in 2 mL of chlorobenzene. The reaction mixture was stirred for 16 h at 60° C. After cooling to RT, the mixture was diluted with DCM and washed with 5% K$_2$CO$_3$ solution and brine. The organic layer was dried over Na$_2$SO$_4$, filtered, and concentrated. Purification by silica gel chromatography (0-10% MeOH in DCM) followed by SFC (Reprospher PEI 100 Å, 5 um, 30×250 mm; 7-17% MeOH in CO$_2$, 10 min) provided the title compound (7 mg, 0.012 mmol). $^1$H NMR (600 MHz, DMSO-d$_6$) δ=7.60 (dd, 1H), 7.23 (dd, 1H), 6.95 (d, 1H), 6.33 (d, 1H), 3.68 (m, 2H), 3.03 (t, 2H), 2.41 (t, 2H), 2.07

(m, 2H), 1.80-1.84 (m, 5H), 1.56-1.67 (m, 6H), 1.15-1.29 (m, 6H) ppm; m/z=446.4 [M+H]⁺; $t_R$=1.23 min (LCMS method a).

Example 28: 1-(4-chloro-3-fluorophenyl)-9-(5-phenyl-1,3,4-oxadiazol-2-yl)-1,9-diazaspiro[5.5]undecan-2-one

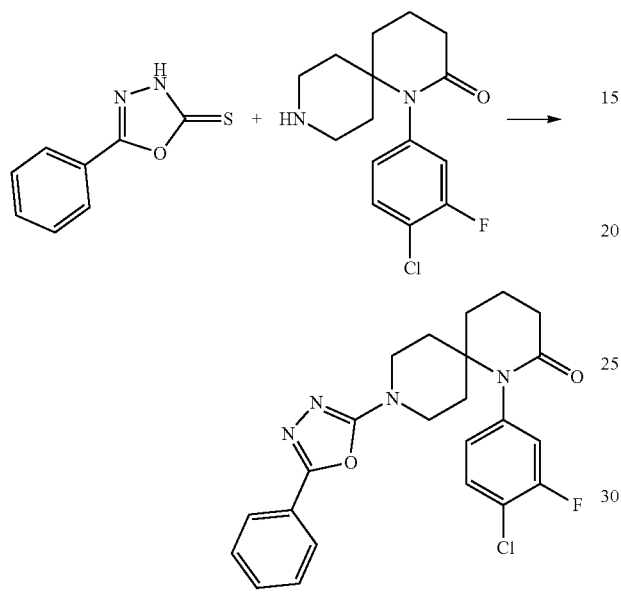

A solution of 5-phenyl-1,3,4-oxadiazole-2-thiol (54 mg, 0.303 mmol) and 1-(4-chloro-3-fluorophenyl)-1,9-diazaspiro[5.5]undecan-2-one (Intermediate B, 90 mg, 0.30 mmol) in EtOH (0.8 mL) was heated under microwave irradiation for 8 h at 160° C. After cooling to RT the reaction mixture was concentrated. Purification by SFC (Reprosphere PEI 100 Å, 30×250, 5 μm, 11-16% MeOH in $CO_2$, 10 min) provided the title compound (33 mg, 0.071 mmol). ¹H NMR (400 MHz, DMSO-d₆) δ=7.82-7.86 (m, 2H), 7.61 (t, 1H), 7.51 (m, 3H), 7.26 (dd, 1H), 6.99 (d, 1H), 3.83 (m, 2H), 3.29 (m, 2H), 2.45 (t, 2H), 2.13 (m, 2H), 1.95 (m, 2H), 1.86 (m, 2H), 1.68 (m, 2H) ppm; m/z=441.2 [M+H]⁺; $t_R$=0.99 min (LCMS method a).

Example 29: 1-(4-chloro-3-fluorophenyl)-9-(1-(4-fluorophenyl)-1H-1,2,3-triazol-4-yl)-1,9-diazaspiro[5.5]undecan-2-one

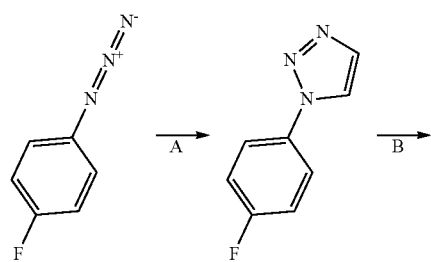

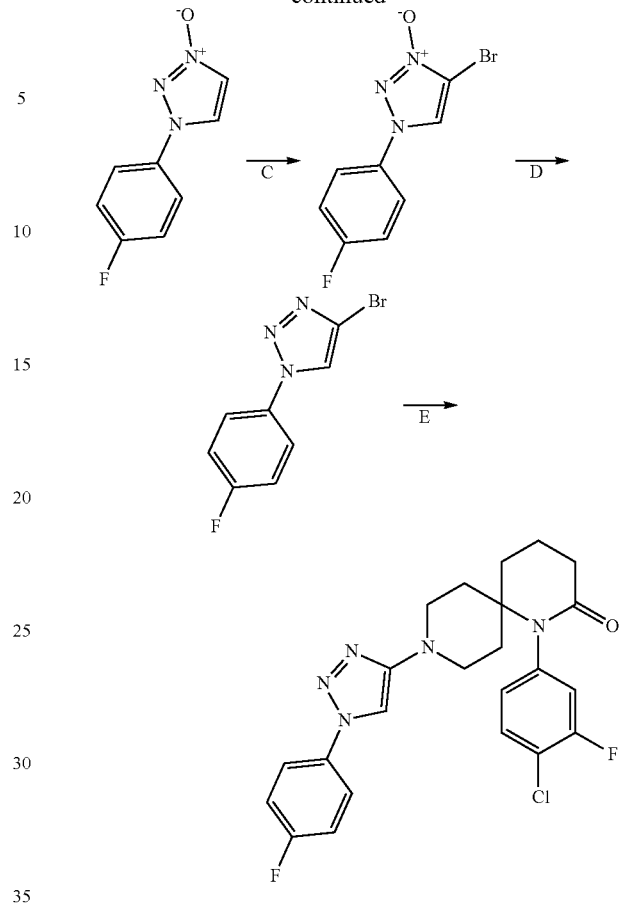

Step A: 1-(4-fluorophenyl)-1H-1,2,3-triazole

Propiolic acid (0.20 mL, 3.3 mmol), sodium ascorbate (174 mg, 0.875 mmol), DBU (0.17 mL, 1.1 mmol) and copper(I) iodide (83 mg, 0.44 mmol) were added to a solution of 1-azido-4-fluorobenzene (4.38 mL, 2.19 mmol) in DMF (10 mL). The reaction mixture was stirred for 3 h at 60° C., cooled to RT, diluted with EtOAc and washed with water. The organic layer was dried over $Na_2SO_4$ and concentrated. Purification by silica gel chromatography (20-70% EtOAc in cyclohexane) provided 1-(4-fluorophenyl)-1H-1,2,3-triazole (295 mg, 1.77 mmol) as a yellow solid. ¹H NMR (600 MHz, DMSO-d₆) δ=8.82 (d, 1H), 7.98 (d, 1H), 7.97-7.91 (m, 2H), 7.48-7.45 (m, 2H) ppm; m/z=164.1 [M+H]⁺; $t_R$=0.70 min (LCMS method a).

Step B: 1-(4-fluorophenyl)-1H-1,2,3-triazole 3-oxide

MCPBA (402 mg, 2.33 mmol) was added to a solution of 1-(4-fluorophenyl)-1H-1,2,3-triazole (292 mg, 1.79 mmol) in EtOAc (2 mL). The reaction mixture was stirred for 72 h at RT. The mixture was diluted with DCM and washed with 1 M NaOH. The organic layer was dried over $Na_2SO_4$ and concentrated. Purification by silica gel chromatography (80-100% EtOAc in cyclohexane, followed by 0-20% MeOH in DCM) provided 1-(4-fluorophenyl)-1H-1,2,3-triazole 3-oxide (177 mg, 0.988 mmol) as a white solid. ¹H NMR (600 MHz, DMSO-d₆) δ=8.92 (d, 1H), 7.94 (d, 1H), 7.87-7.80

(m, 2H), 7.50-7.42 (m, 2H) ppm; m/z=180.1 [M+H]$^+$; $t_R$=0.46 min (LCMS method a).

Step C:
4-bromo-1-(4-fluorophenyl)-1H-1,2,3-triazole 3-oxide

Bromine (0.204 mL, 3.95 mmol) was added dropwise to a solution of 1-(4-fluorophenyl)-1H-1,2,3-triazole 3-oxide (177 mg, 0.988 mmol) and Na$_2$CO$_3$ (209 mg, 1.98 mmol) in a mixture of CHCl$_3$ (0.6 mL) and water (0.8 mL) cooled to 0° C. The reaction mixture was stirred for 12 h at RT. A 10% aqueous solution of sodium thiosulfate was added and stirring continued for 30 min at RT. The mixture was extracted three times with DCM. The combined organic layers were washed with brine, dried over Na$_2$SO$_4$ and concentrated. Purification by silica gel chromatography (0-6% MeOH in DCM) provided 4-bromo-1-(4-fluorophenyl)-1H-1,2,3-triazole 3-oxide (204 mg, 0.791 mmol) as a white crystalline solid. $^1$H NMR (600 MHz, DMSO-d$_6$) δ=9.24 (s, 1H), 7.85-7.78 (m, 2H), 7.52-7.43 (m, 2H) ppm. m/z=258.1, 260.1 [M+H]$^+$; $t_R$=0.59 min (LCMS method a).

Step D:
4-bromo-1-(4-fluorophenyl)-1H-1,2,3-triazole

PCl$_3$ (2.00 mL, 22.9 mmol) was added to 4-bromo-1-(4-fluorophenyl)-1H-1,2,3-triazole 3-oxide (200 mg, 0.775 mmol) and the reaction mixture was stirred for 1 h at 80° C. The mixture was quenched with water and extracted twice with DCM. The combined organic layers were dried over Na$_2$SO$_4$ and concentrated. The crude 4-bromo-1-(4-fluorophenyl)-1H-1,2,3-triazole obtained (177 mg) was used in the next step without further purification. $^1$H NMR (600 MHz, DMSO-d$_6$) δ=9.12 (s, 1H), 7.98-7.92 (m, 2H), 7.54-7.45 (m, 2H) ppm; m/z=242.1, 244.1 [M+H]$^+$; $t_R$=0.94 min (LCMS method a).

Step E: 1-(4-chloro-3-fluorophenyl)-9-(1-(4-fluorophenyl)-1H-1,2,3-triazol-4-yl)-1,9-diazaspiro[5.5]undecan-2-one 4-bromo-1-(4-fluorophenyl)-1H-1,2,3-triazole (80 mg, 0.329 mmol), BrettPhos Precat G1 (22.42 mg, 0.025 mmol) and sodium tert-butoxide (60.7 mg, 0.632 mmol) were added to a solution of 1-(4-chloro-3-fluorophenyl)-1,9-diazaspiro[5.5]undecan-2-one (Intermediate B, 75 mg, 0.253 mmol) in dioxane (3 mL). The reaction mixture was heated under microwave irradiation for 2 h at 120° C., cooled to RT, evaporated, diluted with EtOAc and washed with saturated aqueous NaHCO$_3$ solution. The organic layer was dried over Na$_2$SO$_4$ and concentrated. Purification by SFC (Princeton 4-ethylpyridine 60 Å, 30×250 mm, 5 μm, 5-25% MeOH in CO$_2$, 17 min) provided the title compound (8 mg, 0.02 mmol) as a white solid. $^1$H NMR (600 MHz, DMSO-d$_6$) δ=8.11 (s, 1H), 7.87-7.81 (m, 2H), 7.62 (dd, 1H), 7.42 (dd, 2H), 7.27 (dd, 1H), 7.00 (m, 1H), 3.55 (m, 2H), 2.87 (m, 2H), 2.43 (t, 2H), 2.08 (m, 2H), 1.90-1.82 (m, 4H), 1.72 (m, 2H) ppm; m/z=458.1 [M+H]$^+$; $t_R$=1.05 min (LCMS method a).

Example 30: 1-(4-chloro-3-fluorophenyl)-9-(1-(4-fluorophenyl)-1H-pyrazol-3-yl)-1,9-diazaspiro[5.5]undecan-2-one

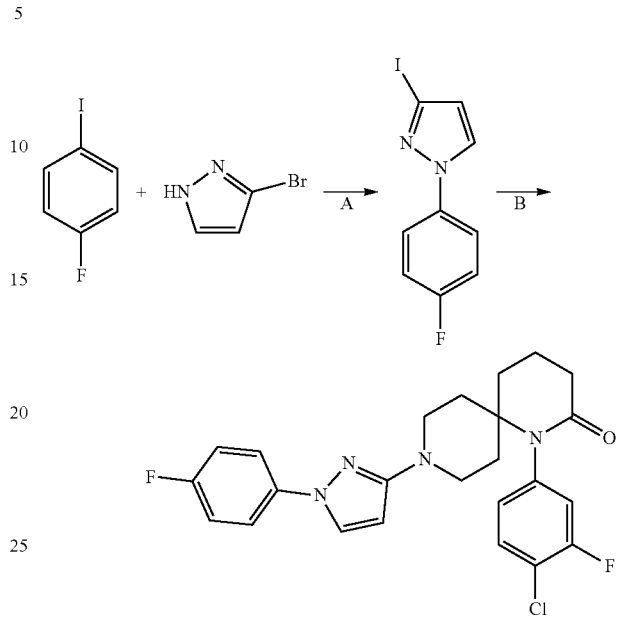

Step A: 1-(4-fluorophenyl)-3-iodo-1H-pyrazole

1-Fluoro-4-iodobenzene (0.476 mL, 4.08 mmol), CuI (13 mg, 0.068 mmol), trans-N,N'-Dimethylcyclohexane-1,2-diamine (0.043 mL, 0.27 mmol) and K$_2$CO$_3$ (564 mg, 4.08 mmol) were added to a solution of 3-bromo-1H-pyrazole (200 mg, 1.36 mmol) in toluene (12 mL). The reaction mixture was stirred for 72 h at 100° C., cooled to RT, concentrated, diluted with EtOAc and washed with brine. The organic layer was dried over Na$_2$SO$_4$ and concentrated. Purification by silica gel chromatography (0-20% EtOAc in cyclohexane) provided 1-(4-fluorophenyl)-3-iodo-1H-pyrazole (204 mg, 0.673 mmol) as a pale yellow solid. $^1$H NMR (600 MHz, DMSO-d$_6$) δ=8.40 (d, 1H), 7.83 (m, 2H), 7.35 (m, 2H), 6.78 (d, 1H) ppm; m/z=289.1 [M+H]$^+$; $t_R$=1.13 min (LCMS method a).

Step B: 1-(4-chloro-3-fluorophenyl)-9-(1-(4-fluorophenyl)-1H-pyrazol-3-yl)-1,9-diazaspiro[5.5]undecan-2-one 1-(4-Fluorophenyl)-3-iodo-1H-pyrazole (93 mg, 0.323 mmol), BrettPhos Precat G1 (24 mg, 0.027 mmol) and sodium tert-butoxide (78 mg, 0.81 mmol) were added to a solution of 1-(4-chloro-3-fluorophenyl)-1,9-diazaspiro[5.5]undecan-2-one (Intermediate B, 80 mg, 0.27 mmol) in dioxane (4 mL). The reaction mixture was heated under microwave irradiation for 12 h at 100° C., cooled to RT, concentrated, diluted with EtOAc and washed with brine. The organic layer was dried over Na$_2$SO$_4$ and concentrated. Purification by SFC (Reprospher PEI, 30×205 mm, 5 μm, 10-15% MeOH in CO$_2$, 10 min) provided the title compound (39 mg, 0.083 mmol) as a white solid. $^1$H NMR (400 MHz, DMSO-d$_6$) δ=8.21 (s, 1H), 7.67 (m, 2H), 7.61 (m, 1H), 7.24 (m, 3H), 6.98 (m, 1H), 6.01 (s, 1H), 3.60 (m, 2H), 2.85 (t, 2H), 2.42 (m, 2H), 2.07 (m, 2H), 1.85 (m, 4H), 1.67 (m, 2H) ppm; m/z=457.4 [M+H]$^+$; $t_R$=1.21 min (LCMS method a).

Example 31: 1-(4-chloro-3-fluorophenyl)-9-(2-(4-fluorophenyl)-2H-1,2,3-triazol-4-yl)-1,9-diazaspiro[5.5]undecan-2-one

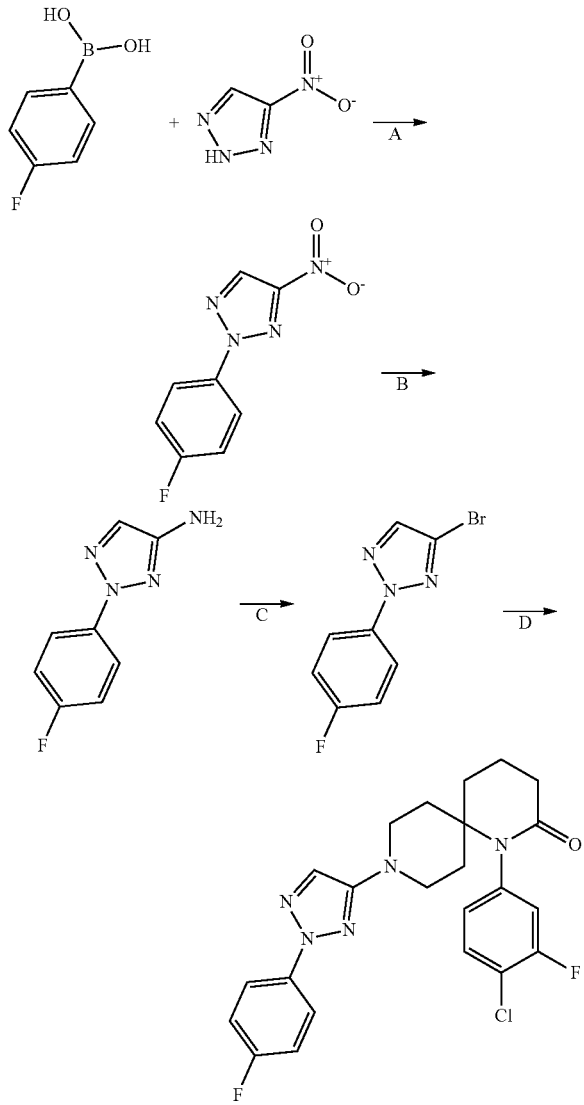

Step A: 2-(4-fluorophenyl)-4-nitro-2H-1,2,3-triazole (4-Fluorophenyl)boronic acid (6.13 g, 43.8 mmol), copper-(II)-acetate (5.97 g, 32.9 mmol) and pyridine (3.6 mL, 44 mmol) were added to a solution of 4-nitro-2H-1,2,3-triazole (2.50 g, 21.9 mmol) in DCE (70 mL). The reaction mixture was stirred for 12 h at RT, filtered over a bed of celite, diluted with DCM and washed with water, NaHCO₃ solution and brine. The organic layer was dried over Na₂SO₄ and concentrated. Purification by silica gel chromatography (0-30% EtOAc in cyclohexane) provided 2-(4-fluorophenyl)-4-nitro-2H-1,2,3-triazole (930 mg, 4.47 mmol) as a white solid. m/z=molecular ion not detected; $t_R$=1.05 min (LCMS method a).

Step B: 2-(4-fluorophenyl)-2H-1,2,3-triazol-4-amine

Acetic acid (2.6 mL, 45 mmol) and iron (1.25 g, 22.3 mmol) were added to a solution of 2-(4-fluorophenyl)-4-nitro-2H-1,2,3-triazole (930 mg, 4.47 mmol) in THF (30 mL). The reaction mixture was stirred for 12 h at 80° C. Additional AcOH (2.56 mL, 44.7 mmol) and iron (500 mg, 8.95 mmol) were added and the mixture was stirred for 3 h at 80° C. The mixture was filtered over a bed of celite, diluted with EtOAc and washed with saturated NaHCO₃ solution and brine. The organic layer was dried over Na₂SO₄ and concentrated. Purification by silica gel chromatography (0-56% EtOAc in cyclohexane) provided 2-(4-fluorophenyl)-2H-1,2,3-triazol-4-amine (690 mg, 3.37 mmol) as a white solid. ¹H NMR (600 MHz, DMSO-$d_6$) δ=7.80 (m, 2H), 7.32 (m, 2H), 7.25 (s, 1H), 5.52 (br s, 2H) ppm; m/z=179.1 [M+H]⁺; $t_R$=0.80 min (LCMS method a).

Step C: 4-bromo-2-(4-fluorophenyl)-2H-1,2,3-triazole

A solution of 2-(4-fluorophenyl)-2H-1,2,3-triazol-4-amine (300 mg, 1.68 mmol) in 7 mL of acetonitrile was added dropwise to a solution of copper-(II)-bromide (451 mg, 2.02 mmol) and tert-butyl nitrite (0.36 mL, 2.7 mmol) in acetonitrile (7 mL). The reaction mixture was stirred for 2 h at RT, diluted with EtOAc and washed with brine. The organic layer was dried over Na₂SO₄ and concentrated. Purification by silica gel chromatography (0-24% EtOAc in cyclohexane) provided 4-bromo-2-(4-fluorophenyl)-2H-1,2,3-triazole (330 mg, 1.27 mmol). ¹H NMR (600 MHz, DMSO-$d_6$) δ=8.35 (s, 1H), 8.01 (m, 2H), 7.43 (m, 2H) ppm; $t_R$=0.80 min (LCMS method a)

Step D: 1-(4-chloro-3-fluorophenyl)-9-(2-(4-fluorophenyl)-2H-1,2,3-triazol-4-yl)-1,9-diazaspiro[5.5]undecan-2-one 4-Bromo-2-(4-fluorophenyl)-2H-1,2,3-triazole (73.4 mg, 0.303 mmol), BrettPhos Precat G1 (29.9 mg, 0.034 mmol) and sodium tert-butoxide (81 mg, 0.842 mmol) were added to a solution of 1-(4-chloro-3-fluorophenyl)-1,9-diazaspiro[5.5]undecan-2-one (Intermediate B, 100 mg, 0.337 mmol) in dioxane (3 mL). The reaction mixture was heated under microwave irradiation for 3 h at 120° C., cooled to RT, concentrated, diluted with EtOAc and washed with saturated NaHCO₃ solution and brine. The organic layer was dried over Na₂SO₄ and concentrated. Purification by silica gel chromatography (50-100% EtOAc in cyclohexane, followed by 0-5% MeOH in EtOAc), then SFC (Reprosil NH2, 5 μm, 30×250 mm; 18-23% MeOH in CO₂, 10 min) provided the title compound (8 mg, 0.02 mmol) as a white solid. ¹H NMR (600 MHz, DMSO-$d_6$) δ=7.83 (dd, 2H), 7.61 (m, 2H), 7.32 (dd, 2H), 7.27 (dd, 1H), 6.99 (d, 1H), 3.62 (m, 2H), 2.98 (m, 2H), 2.43 (t, 2H), 2.09 (m, 2H), 1.82-1.88 (m, 4H), 1.66-1.72 (m, 2H) ppm; m/z=458.3 [M+H]⁺; $t_R$=1.27 min (LCMS method a).

Example 32: 1-(4-chlorophenyl)-9-(6-(4-fluorophenyl)pyridin-2-yl)-1,9-diazaspiro[5.5]undecan-2-one

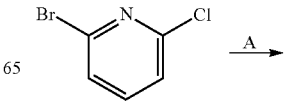

-continued

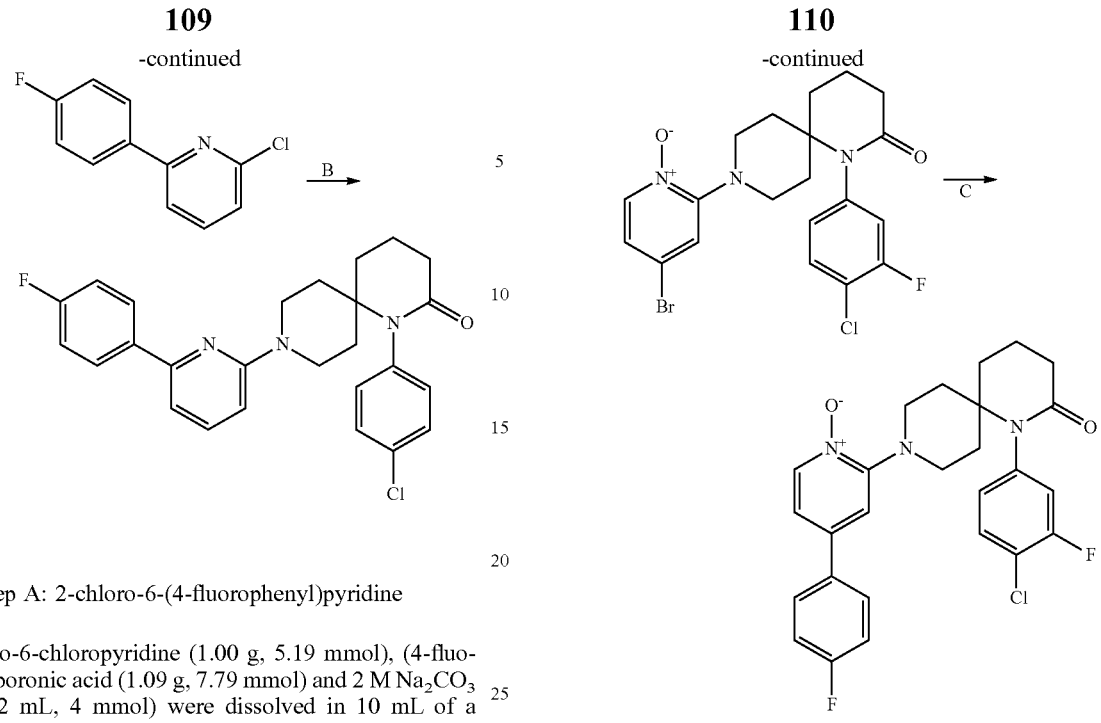

Step A: 2-chloro-6-(4-fluorophenyl)pyridine

2-Bromo-6-chloropyridine (1.00 g, 5.19 mmol), (4-fluorophenyl)boronic acid (1.09 g, 7.79 mmol) and 2 M $Na_2CO_3$ solution (2 mL, 4 mmol) were dissolved in 10 mL of a mixture of toluene and EtOH and purged with argon for 30 min. Then $Pd(PPh_3)_4$ (300 mg, 0.25 mmol) was added and the reaction mixture was stirred for 12 h at 100° C. After cooling to RT, the reaction mixture was concentrated. Purification by silica gel chromatography (1-2% EtOAc in petroleum ether) provided 2-chloro-6-(4-fluorophenyl)pyridine. m/z=184.1 $[M+H]^+$, $t_R$=2.23 min (LCMS method a)

Step B: 1-(4-chlorophenyl)-9-(6-(4-fluorophenyl)pyridin-2-yl)-1,9-diazaspiro[5.5]undecan-2-one 2-chloro-6-(4-fluorophenyl)pyridine (50 mg, 0.241 mmol), 1-(4-chlorophenyl)-1,9-diazaspiro[5.5]undecan-2-one (Intermediate C, 99 mg, 0.27 mmol) and NaOtBu (35 mg, 0.36 mmol) were dissolved in 10 mL of a mixture of toluene and EtOH and purged with argon for 30 min. Then $Pd_2(dba)_3$ (12 mg, 0.012 mmol) and Dave-phos (10 mg, 0.024 mmol) were added and the reaction mixture was stirred for 16 h at 100° C. The reaction mixture was cooled to RT and concentrated. Purification by preparative HPLC provided the title compound (14 mg, 0.030 mmol) as a white solid. $^1$H NMR (400 MHz, DMSO-$d_6$) δ=8.03 (dd, 2H), 7.55 (dd, 1H), 7.42 (d, 2H), 7.25 (dd, 2H), 7.14 (d, 1H), 7.09 (d, 2H), 6.70 (d, 1H), 4.25 (m, 2H), 2.95 (br t, 2H), 2.44 (t, 2H), 2.13 (m, 2H), 1.85-1.90 (m, 4H), 1.57-1.64 (dt, 2H) ppm; m/z=450.2 $[M+H]^+$; $t_R$=2.38 min (LCMS method d)

Example 33: 2-(1-(4-chloro-3-fluorophenyl)-2-oxo-1,9-diazaspiro[5.5]undecan-9-yl)-4-(4-fluorophenyl)pyridine 1-oxide

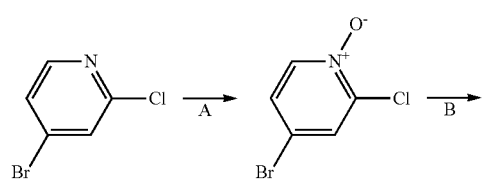

Step A: 4-bromo-2-chloropyridine 1-oxide

MCPBA (1.569 g, 9.09 mmol) was added portionwise to a solution of 4-bromo-2-chloropyridine (0.50 g, 2.6 mmol) in DCM (24 mL). The reaction mixture was stirred overnight at 50° C., cooled to RT, diluted with EtOAc and washed with water, saturated aqueous sodium bisulfite solution, and $NaHCO_3$ solution. The organic layer was dried over $Na_2SO_4$, filtered, and concentrated. Purification by silica gel chromatography (50-75% EtOAc in cyclohexane) followed by SFC (Reprosphere PEI 100 Å, 5 µm, 30×250 mm; 2-7% MeOH in $CO_2$, 10 min) provided 4-bromo-2-chloropyridine 1-oxide (78 mg, 0.37 mmol). $^1$H NMR (400 MHz, DMSO-$d_6$) δ=8.36 (d, 1H), 8.19 (d, 1H), 7.66 (dd, 1H) ppm; m/z=208.0, 210.0, 212.0 $[M+H]^+$; $t_R$=0.45 min (LCMS method a)

Step B: 4-bromo-2-(1-(4-chloro-3-fluorophenyl)-2-oxo-1,9-diazaspiro[5.5]undecan-9-yl)pyridine 1-oxide 1-(4-Chloro-3-fluorophenyl)-1,9-diazaspiro[5.5]undecan-2-one (Intermediate B, 111 mg, 0.374 mmol) and $NaHCO_3$ (29 mg, 0.34 mmol) were added to a solution of 4-bromo-2-chloropyridine 1-oxide (65 mg, 0.31 mmol) in 1 mL of tert-amyl alcohol. The reaction mixture was refluxed overnight at 110° C. After cooling to RT the mixture was diluted with EtOAc and washed with water. The combined organic layers were dried over $Na_2SO_4$, filtered, and concentrated. The crude product was purified by silica gel chromatography (0-10% EtOAc in cyclohexane). $^1$H NMR (400 MHz, DMSO-$d_6$) δ=7.99 (d, 1H), 7.65 (dd, 1H), 7.29 (d, 1H), 7.14-7.16 (m, 2H), 7.01 (d, 1H), 3.76 (m, 2H), 2.84 (br t, 2H), 2.43 (t, 2H), 2.10-2.18 (m, 2H), 1.8-1.9 (m, 4H), 1.7 (m, 2H) ppm; m/z=468.2, 470.2 $[M+H]^+$; $t_R$=0.80 min (LCMS method a).

Step C: 2-(1-(4-chloro-3-fluorophenyl)-2-oxo-1,9-diazaspiro[5.5]undecan-9-yl)-4-(4-fluorophenyl)pyridine 1-oxide K$_3$PO$_4$ (160 mg, 0.755 mmol) and PdCl$_2$(dtbpf) (16 mg, 0.025 mmol) were added to a solution of 4-bromo-2-(1-(4-chloro-3-fluorophenyl)-2-oxo-1,9-diazaspiro[5.5]undecan-9-yl)pyridine 1-oxide (118 mg, 0.250 mmol) and 4-fluorophenylboronic acid pinacol ester (56 mg, 0.25 mmol) in 1.3 mL of dioxane and 0.43 mL of water. The reaction mixture was heated under microwave irradiation for 45 min at 110° C. After cooling to RT, the mixture was concentrated. Purification by silica gel chromatography (0-7% MeOH in DCM) provided the title compound (52 mg, 0.11 mmol). $^1$H NMR (400 MHz, DMSO-d$_6$) δ=8.12 (d, 1H), 7.83 (d, 1H), 7.82 (d, 1H), 7.66 (t, 1H), 7.2-7.35 (m, 5H), 7.03 (d, 1H), 3.84 (m, 2H), 2.87 (br t, 2H), 2.43 (t, 2H), 2.15 (m, 2H), 1.8-1.9 (m, 4H), 1.7-1.8 (m, 2H) ppm; m/z=484.3 [M+H]$^+$; t$_R$=0.92 min (LCMS method a).

Example 34: 4-(3-chlorophenoxy)-2-(1-(3,4-difluorophenyl)-2-oxo-1,9-diazaspiro[5.5]undecan-9-yl)pyridine 1-oxide

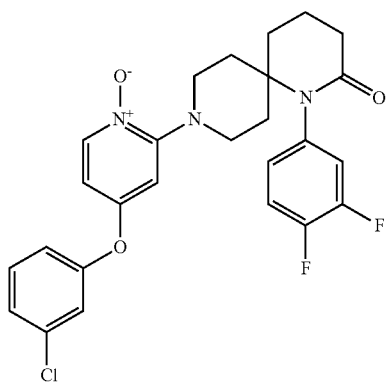 [SMILES: O=C1CCCC2(CCN(c3cc(Oc4cccc(Cl)c4)cc[n+]3[O-])CC2)N1c1ccc(F)c(F)c1]

The title compound was synthesized analogously to Example 33 starting with 2-chloro-4-(3-chlorophenoxy)pyridine. $^1$H NMR (300 MHz, DMSO-d6) δ 8.02 (d, 1H), 7.56-7.41 (m, 2H), 7.35-7.21 (m, 3H), 7.07-7.10 (m, 1H), 6.95-6.98 (m, 1H), 6.66 (d, 1H), 6.57 (dd, 1H), 3.83 (d, 2H), 2.77 (t, 2H), 2.41 (t, 2H), 2.02-2.12 (m, 2H), 1.62-1.86 (m, 6H); m/z=500.2 [M+H]$^+$; t$_R$=1.34 min (LCMS method 1)

Example 35a: 9-(2-(5-azaspiro[2.3]hexan-5-yl)pyrimidin-4-yl)-1-(4-chloro-3-fluorophenyl)-1,9-diazaspiro[5.5]undecan-2-one and Example 35b: 9-(4-(5-azaspiro[2.3]hexan-5-yl)pyrimidin-2-yl)-1-(4-chloro-3-fluorophenyl)-1,9-diazaspiro[5.5]undecan-2-one

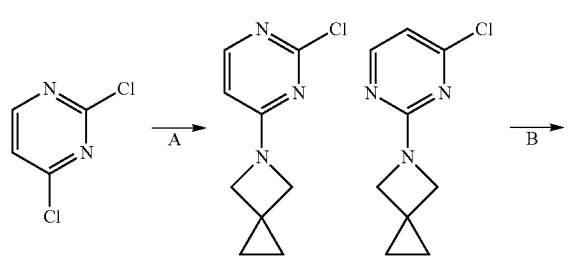

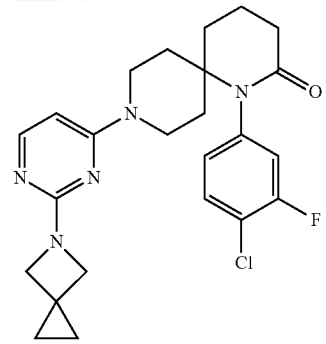

Example 35a

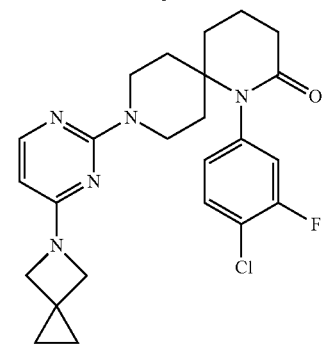

Example 35b

Step A: 2-chloro-4-(5-azaspiro[2.3]hexan-5-yl)pyrimidine and 5-(4-chloropyrimidin-2-yl)-5-azaspiro[2.3]hexane A mixture of 2,4-dichloropyrimidine (96 mg, 0.52 mmol), 5-azaspiro[2.3]hexane (60 mg, 0.47 mmol) and triethylamine (65 µL, 0.47 mmol) in DMF (1.5 mL) was stirred for 18 h at RT. Silica gel chromatography (ethyl acetate) provided a mixture of 5-(2-chloropyrimidin-4-yl)-5-azaspiro[2.3]hexane and 5-(4-chloropyrimidin-2-yl)-5-azaspiro[2.3]hexane which were used directly in the next step. m/z=195.9.

Step B: 9-(2-(5-azaspiro[2.3]hexan-5-yl)pyrimidin-4-yl)-1-(4-chloro-3-fluorophenyl)-1,9-diazaspiro[5.5]undecan-2-one and 9-(4-(5-azaspiro[2.3]hexan-5-yl)pyrimidin-2-yl)-1-(4-chloro-3-fluorophenyl)-1,9-diazaspiro[5.5]undecan-2-one The mixture 5-(2-chloropyrimidin-4-yl)-5-azaspiro[2.3]hexane and 5-(4-chloropyrimidin-2-yl)-5-azaspiro[2.3]hexane from step A, 1-(4-chloro-3-fluorophenyl)-1,9-diazaspiro[5.5]undecan-2-one (Intermediate B, 111 mg, 0.375 mmol) and triethylamine (0.16 mL, 1.1 mmol) in 1 mL of EtOH was stirred in a microwave oven for 1 h at 160° C. The reaction mixture was concentrated and the crude products were purified by silica gel chromatography (0-15% MeOH in DCM) followed by preparative HPLC (XBridge Phenyl OBD, 5 µm, 30×100 mm; mobile phase A: 0.1% NH4OH, mobile phase B: ACN; 30 mL/min; 28-58% ACN over 15 min) to provide the regioisomeric products:

Example 35a: 9-(2-(5-azaspiro[2.3]hexan-5-yl)pyrimidin-4-yl)-1-(4-chloro-3-fluorophenyl)-1,9-diazaspiro[5.5]undecan-2-one. $^1$H NMR (400 MHz, methanol-d$_4$) b ppm 7.73 (d, J=6.36 Hz, 1H) 7.51 (t, J=8.38 Hz, 1H) 7.07 (dd, J=9.90, 2.20 Hz, 1H) 6.93 (dt, J=8.44, 1.04 Hz, 1H) 6.01 (d, J=6.36 Hz, 1H) 4.30 (br d, J=12.35 Hz, 2H) 4.04 (s, 4H) 3.01 (br t, J=12.41 Hz, 2H) 2.57 (t, J=6.79 Hz, 2H) 2.24 (br s, 2H) 1.86-2.02 (m, 4H) 1.62-1.75 (m, 2H) 0.66 (s, 4H); m/z=456.2 [M+H]⁺; $t_R$=0.77 min (LCMS method a).

Example 35b: 9-(4-(5-azaspiro[2.3]hexan-5-yl)pyrimidin-2-yl)-1-(4-chloro-3-fluorophenyl)-1,9-diazaspiro[5.5]undecan-2-one. ¹H NMR (400 MHz, methanol-d₄) b ppm 7.73 (d, J=5.87 Hz, 1H) 7.49 (t, J=8.15 Hz, 1H) 7.06 (dd, J=9.90, 2.20 Hz, 1H) 6.91 (d, J=8.68 Hz, 1H) 5.63 (d, J=5.99 Hz, 1H) 4.41-4.55 (m, 2H) 3.96-4.09 (m, 4H) 2.90-3.00 (m, 2H) 2.57 (t, J=6.79 Hz, 2H) 2.16-2.28 (m, 2H) 1.81-2.04 (m, 4H) 1.67 (td, J=12.65, 4.40 Hz, 2H) 0.63-0.71 (m, 4H); m/z=456.3 [M+H]⁺; $t_R$=0.81 min (LCMS method a).

By employing similar methods as described for the preparation of Examples 35a and 35b using appropriate spirocyclic piperidine intermediates and commerically available amines for Step A, the following compounds were prepared:

| Ex | Structure and Name | MS, m/z [M + H]⁺; $t_R$, method | ¹H NMR |
|---|---|---|---|
| 36 | 1-(4-chloro-3-fluorophenyl)-9-(5-fluoro-6-(pyrrolidin-1-yl)pyrimidin-4-yl)-1,9-diazaspiro[5.5]undecan-2-one | 462.1; 1.12 min, LCMS method a | ¹H NMR (400 MHz, DMSO-d₆) δ = 7.78 (d, 1H), 7.6 (t, 1H), 7.23 (dd, 1H), 6.96 (dd, 1H), 3.95 (m, 2H), 3.5 (m, 4H), 3.05 (m, 2H), 2.43 (t, 2H), 2.13 (m, 2H), 1.82 (m, 8H) 1.6 (m, 2H). ppm |
| 37 | 1-(4-chloro-3-fluorophenyl)-9-(5-fluoro-6-(3-(trifluoromethyl)azetidin-1-yl)pyrimidin-4-yl)-1,9-diazaspiro[5.5]undecan-2-one | 516.2; 1.12 min, LCMS method a | ¹H NMR (400 MHz, DMSO-d₆) δ = 7.82 (d, 1H), 7.6 (t, 1H), 7.22 (dd, 1H), 6.96 (dd, 1H), 4.31 (m, 2H), 4.0-4.1 (m, 4H), 3.7 (m, 1H), 3.08 (m, 2H), 2.43 (t, 2H), 2.13 (m, 2H), 1.82 (m, 4H), 1.5-1.6 (m, 2H). ppm |
| 38 | 1-(4-chloro-3-fluorophenyl)-9-(4- | 445.2; 0.97 min, LCMS method a | ¹H NMR (400 MHz, DMSO-d₆) δ = 8.01 (s, 1H), 7.58 (t, 1H), 7.22 (d, 1H), 6.95 (d, 1H), 4.56 (m, 2H), 3.38 (m, 4H), 2.94 (br t, 2H), 2.43 (t, 2H), 2.14 (m, 2H), 1.84-1.87 (m, 8H) 1.42 (m, 2H) ppm |

| Ex | Structure and Name | MS, m/z [M + H]+; t$_R$, method | $^1$H NMR |
|---|---|---|---|
| | (pyrrolidin-1-yl)-1,3,5-triazin-2-yl)-1,9-diazaspiro[5.5]undecan-2-one | | |
| 39 | 9-(4-(4-amino-4-(trifluoromethyl)piperidin-1-yl)pyrimidin-2-yl)-1-(3,4-difluorophenyl)-1,9-diazaspiro[5.5]undecan-2-one | 525.3; 0.48 min, LCMS method i | $^1$H NMR (400 MHz, DMSO-d6) δ 7.79 (d, 1H), 7.41 (m, 1H), 7.30-7.15 (m, 1H), 6.91 (d, 1H), 6.05 (d, 1H), 4.47 (d, 2H), 4.13 (brs, 2H), 3.12 (dt, 2H), 2.87 (t, 2H), 2.42 (t, 2H), 2.05-2.11 (m, 4H), 1.79-1.88 (m, 3H), 1.4-1.52 (m, 4H) ppm |
| 40 | 1-(3,4-difluorophenyl)-9-(4-(4-hydroxy-4-(trifluoromethyl)piperidin-1-yl)-1,3,5-triazin-2-yl)-1,9-diazaspiro[5.5]undecan-2-one | 527.4; 0.65 min, LCMS method i | $^1$H NMR (300 MHz, DMSO-d6) δ 8.06 (s, 1H), 7.41 (m, 1H), 7.22 (m, 1H), 6.91 (d, 1H), 4.42-4.62 (m, 4H), 3.12-2.78 (m, 3H), 2.42 (t, 2H), 2.20-2.02 (m, 2H), 1.92-1.79 (m, 4H), 1.62-1.75 (m, 4H), 1.32-1.54 (m, 4H). |
| 41 | | 559.4; 0.58 min, LCMS method i | $^1$H NMR (300 MHz, DMSO-d6) δ 7.44 (m, 1H), 7.23 (m, 1H), 6.91 (d, 1H), 5.99 (s, 1H), 5.70 (s, 2H), 3.82-4.0 (m, 4H), 2.91-3.07 (m, 4H), 2.41 (t, 2H), 2.09 (m, 2H), 1.75-1.88 (m, 4H), 1.51-1.62 (m, 6H). |

| Ex | Structure and Name | MS, m/z [M + H]+; tR, method | 1H NMR |
|---|---|---|---|
|  | 9-(2-amino-5-fluoro-6-(4-hydroxy-4-(trifluoromethyl)piperidin-1-yl)pyrimidin-4-yl)-1-(3,4-difluorophenyl)-1,9-diazaspiro[5.5]undecan-2-one | | |
| 42 | 1-(3,4-difluorophenyl)-9-(6-(4-hydroxy-4-(trifluoromethyl)piperidin-1-yl)pyridazin-4-yl)-1,9-diazaspiro[5.5]undecan-2-one | 526.3; 1.28 min, LCMS method j | 1H NMR (chloroform-d, 300 MHz) δ 8.3 (s, 1H), 7.25-7.1 (m, 1H), 6.94-6.9 (m, 1H), 6.8 (m, 1H), 4.26-4.23 (m, 2H), 3.70 (d, 2H), 3.25 (t, 2H), 2.99 (t, 2H), 2.62 (t, 2H), 2.1 (br, 2H), 1.98-1.88 (m, 4H), 1.79-1.7 (m, 4H), 1.32-1.25 (m, 2H). |
| 43 | 9-(6-amino-2-(3-hydroxy-3-methylazetidin-1-yl)pyrimidin-4-yl)-1-(3,4-difluorophenyl)-1,9-diazaspiro[5.5]undecan-2-one | 459.3; 0.48 min, LCMS method i | 1H NMR (DMSO-d6, 300 MHz) δ 7.5-7.38 (m, 1H), 7.3-7.18 (m, 1H), 6.92 (br, 1H), 5.63 (brs, 2H), 5.5 (s, 1H), 4.81 (s, 1H), 4.09 (d, 2H), 3.64 (s, 4H), 2.79 (t, 2H), 2.41 (m, 2H), 2.08 (br, 2H), 1.81-1.77 (m, 4H), 1.5-1.35 (m, 4H) |
| 44 |  | 516.1; 0.66 min, LCMS method i | 1H NMR (400 MHz, DMSO-d6) δ ppm 8.06 (s, 1 H) 7.59 (t, J = 8.44 Hz, 1 H) 7.24 (dd, J = 10.27, 2.08 Hz, 1 H) 6.96 (d, J = 8.65 Hz, 1 H) 5.70-5.76 (m, 1 H) 4.25 (br d, J = 12.59 Hz, 2 H) 4.09 (br t, J = 15.16 Hz, 4 H) 2.94 (br t, J = 12.47 Hz, 2 H) 2.39-2.47 (m, 2 H) 1.93-2.19 (m, 2 H) 1.82-1.92 (m, 4 H) 1.48 (td, J = 12.84, 4.28 Hz, 2 H) |

| Ex | Structure and Name | MS, m/z [M + H]+; $t_R$, method | 1H NMR |
|---|---|---|---|
| 45 | 1-(4-chloro-3-fluorophenyl)-9-(6-(3,3,4,4-tetrafluoropyrrolidin-1-yl)pyrimidin-4-yl)-1,9-diazaspiro[5.5]undecan-2-one | | |
| | 9-(6-(1,4-oxazepan-4-yl)pyrimidin-4-yl)-1-(3,4-difluorophenyl)-1,9-diazaspiro[5.5]undecan-2-one | 458.4; 0.47 min, LCMS method i | 1H NMR (400 MHz, DMSO-d6) δ 7.97 (s, 1H), 7.42 (dt, J = 10.9, 8.8 Hz, 1H), 7.31-7.13 (m, 1H), 6.92 (dq, J = 6.5, 2.3 Hz, 1H), 5.66 (s, 1H), 4.20 (d, J = 13.4 Hz, 2H), 3.64 (t, J = 9.5 Hz, 6H), 3.57-3.46 (m, 2H), 2.96-2.79 (m, 2H), 2.42 (t, J = 6.7 Hz, 2H), 2.11 (s, 2H), 1.81 (td, J = 12.3, 5.6 Hz, 6H), 1.50 (dd, J = 14.4, 9.9 Hz, 2H). |
| 46 | rac-9-(2-amino-6-((1R,4R)-2-oxa-5-azabicyclo[2.2.1]heptan-5-yl)pyrimidin-4-yl)-1-(3,4-difluorophenyl)-1,9-diazaspiro[5.5]undecan-2-one | 471.3; 0.44 min, LCMS method i | 1H NMR (DMSO-d6, 300 MHz) δ 7.47-7.38 (m, 1H), 7.28-7.2 (m, 1H), 6.94-6.88 (m, 1H), 5.55 (br, 2H), 4.95 (br, 1H), 4.73 (br, 1H), 4.57 (s, 1H), 4.12 (d, 2H), 3.7-3.52 (m, 2H), 3.25 (s, 1H), 3.17-3.09 (m, 1H), 2.78 (t, 2H), 2.41 (t, 2H), 2.07 (br, 2H), 1.9-1.75 (m, 5H), 1.5-1.38 (m, 2H). |

Example 47: 1-(3,4-difluorophenyl)-9-(6-(4-(trifluoromethyl)-1H-pyrazol-1-yl)pyrimidin-4-yl)-1,9-diazaspiro[5.5]undecan-2-one

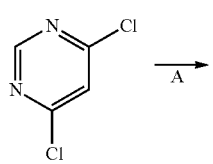

-continued

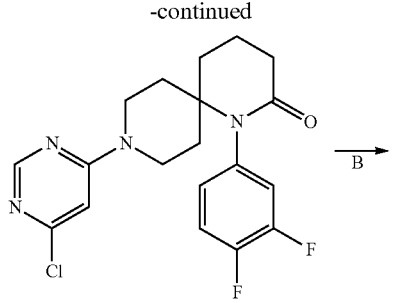

121

-continued

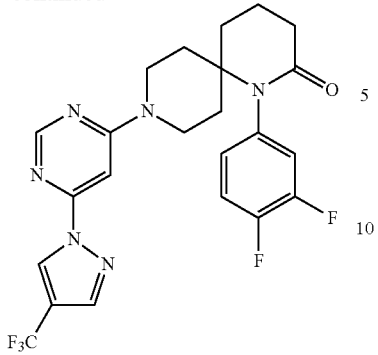

Step A: (9-(6-chloropyrimidin-4-yl)-1-(3,4-difluorophenyl)-1,9-diazaspiro[5.5]undecan-2-one A solution of 4,6-dichloropyrimidine (0.188 g, 1.26 mmol) and 1-(3,4-difluorophenyl-1,9-diazaspiro[5.5]undecane-2-one hydrochloride (Intermediate A, 0.564, 1.26 mmol) in EtOH (2 mL) was treated with TEA (0.642 g, 1.50 mmol) and the reaction mixture was stirred at RT for 2 h. The mixture was concentrated and the residue partitioned between water and EtOAc. The organic layer was dried over Na$_2$SO$_4$, filtered and concentrated to provide (9-(6-chloropyrimidin-4-yl)-1-(3,4-difluorophenyl)-1,9-diazaspiro[5.5]undecan-2-one (0.410 g, crude) as a white solid. m/z=393.1 [M+H]$^+$; t$_R$=1.43 min (LCMS method j)

Step B: 1-(3,4-difluorophenyl)-9-(6-(4-(trifluoromethyl)-1H-pyrazol-1-yl)pyrimidin-4-yl)-1,9-diazaspiro[5.5]undecan-2-one A mixture of (9-(6-chloropyrimidin-4-yl)-1-(3,4-difluorophenyl)-1,9-diazaspiro[5.5]undecan-2-one (0.10 g, 0.25 mmol), 4-trifluoromethylpyrazole (0.041 g mmol, 0.30 mmol) and Cs$_2$CO$_3$ (0.165 g, 0.5 mmol) in DMF (1 mL) was heated at 120° C. for 12 h. The mixture was cooled to RT, partitioned between water and EtOAc. The organic layer was dried over Na$_2$SO$_4$ and concentrated under reduced pressure. Purification by preparative HPLC (Waters Xbridge, 5 µm, 21.2×150 mm; water/ACN elution) provided the title compound (24 mg, 0.048 mmol) as an off-white solid. $^1$H NMR (400 MHz, methanol-d$_4$) b 8.92 (s, 1H), 8.36 (s, 1H), 8.02 (s, 1H), 7.24-7.31 (m, 1H), 7.16 (s, 1H), 7.08-7.14 (m 1H), 6.92 (d, 1H), 4.40 (brs, 2H), 3.16 (t, 2H), 2.58 (t, 2H), 2.27 (brs, 2H), 1.96-2.02 (m, 4H), 1.68-1.81 (m, 2H); m/z=493.2 [M+H]$^+$; t$_R$=1.25 min (LCMS method j)

By employing similar methods as described for the preparation of Example 47, using appropriate starting materials, the following compounds were prepared:

| Ex | Structure and Name | MS, m/z [M + H]$^+$; t$_R$, method | $^1$H NMR |
|---|---|---|---|
| 48 | 1-(3,4-difluorophenyl)-9-(2-methyl-6-(1H-pyrazol-1-yl)pyrimidin-4-yl)-1,9-diazaspiro[5.5]undecan-2-one | 439.2; 1.53 min, LCMS method g | $^1$H NMR (400 MHz, DMSO-d6) δ 8.50 (s, 1H), 7.80 (s, 1H), 7.42 (m, 1H), 7.25 (m, 1H), 6.91 (d, 1H), 6.87 (s, 1H), 6.53 (s, 1H), 4.30 (brs, 2H), 3.06 (t, 3H), 2.40 (m, 3H), 2.15 (brs, 2H), 1.8-1.95 (m, 4H), 1.53 (t, 2H). |
| 49 | 4-(1-(3,4-difluorophenyl)-2-oxo-1,9-diazaspiro[5.5]undecan-9-yl)-6-(1H-pyrazol-1-yl)pyrimidine-2-carbonitrile | 450.2; 4.50 min, LCMS method f | $^1$H NMR (300 MHz, DMSO-d6) δ 8.52 (d, 1H), 7.89 (s, 1H), 7.42 (m, 1H), 7.30-7.17 (m, 1H), 7.72 (s, 1H), 6.60 (dd, 1H), 3.41 (m, 2H), 3.30-3.07 (brs, 2H), 2.45 (t, 2H), 2.12-2.2 (m, 2H), 1.8-1.98 (m, 4H), 1.5-1.62 9 (m, 2H) |

Example 50: 1-(3,4-difluorophenyl)-9-(2-methoxy-6-(1H-pyrazol-1-yl)pyrimidin-4-yl)-1,9-diazaspiro[5.5]undecan-2-one

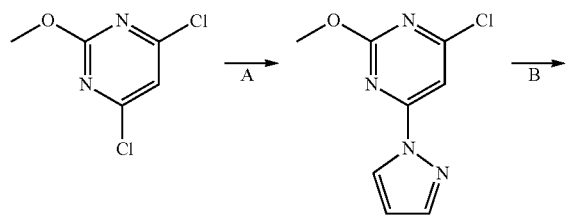

Step A.
4-chloro-2-methoxy-6-(1H-pyrazol-1-yl)pyrimidine

A mixture of cesium carbonate (71.8 mg, 0.220 mmol), 1H-pyrazole (15 mg, 0.22 mmol) and 4,6-dichloro-2-methoxypyrimidine (39 mg, 0.22 mmol) in DMF (0.9 mL) was stirred at RT for two hours. LCMS analysis indicates complete conversion to 4-chloro-2-methoxy-6-(1H-pyrazol-1-yl)pyrimidine which was not isolated. m/z=211.1 [M+H]$^+$; $t_R$=0.93 min (LCMS method e)

Step B. 1-(3,4-difluorophenyl)-9-(2-methoxy-6-(1H-pyrazol-1-yl)pyrimidin-4-yl)-1,9-diazaspiro[5.5]undecan-2-one To the reaction mixture in Step A was added 1-(3,4-difluorophenyl-1,9-diazaspiro[5.5]undecane-2-one (Intermediate A, 62 mg, 0.22 mmol), DIEA (0.13 mL, 0.74 mmol). The mixture was heated at 50° C. overnight. After cooling to RT, the mixture was partitioned between 2:1 EtOAc/heptane, washed with water (5×), brine, dried over sodium sulfate and concentrated. Purification by silica gel chromatography (0-100% MeOH in EtOAc), followed by reverse phase chromatography (RediSep® Rf Gold® Reversed Phase C18 50 g column, 0-100% ACN in water) provided the title compound (30 mg, 0.065 mmol) as a white solid. $^1$H NMR (400 MHz, DMSO-d6) δ 8.49 (dd, J=2.7, 0.7 Hz, 1H), 7.81 (dd, J=1.6, 0.7 Hz, 1H), 7.42 (dt, J=10.7, 8.9 Hz, 1H), 7.25 (ddd, J=11.5, 7.4, 2.4 Hz, 1H), 6.93 (dtd, J=7.0, 2.5, 1.3 Hz, 1H), 6.73 (s, 1H), 6.54 (dd, J=2.7, 1.6 Hz, 1H), 4.14 (d, J=100.0 Hz, 2H), 3.83 (s, 3H), 3.09 (t, J=13.1 Hz, 2H), 2.44 (t, J=6.7 Hz, 2H), 2.15 (s, 2H), 1.98-1.80 (m, 4H), 1.65-1.46 (m, 2H); m/z=455.3 [M+H]$^+$; $t_R$=1.01 min (LCMS method e).

By employing similar methods as described for the preparation of Example 50, using appropriate starting materials, the following compounds were prepared:

| Ex | Structure and Name | MS, m/z [M + H]$^+$; $t_R$, method | $^1$H NMR |
|---|---|---|---|
| 51 | 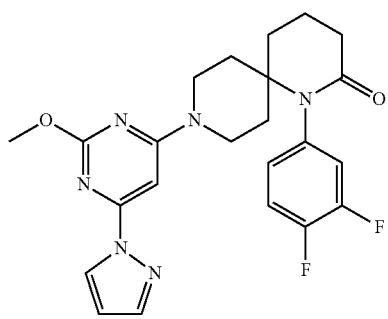<br>9-(6-(1H-pyrazol-1-yl)-2-(trifluoromethyl)pyrimidin-4-yl)-1-(3,4-difluorophenyl)-1,9-diazaspiro[5.5]undecan-2-one | 493.2; 1.19 min, LCMS method e | $^1$H NMR (400 MHz, DMSO-d6) δ 8.50 (dd, J = 2.7, 0.7 Hz, 1H), 7.89 (dd, J = 1.6, 0.7 Hz, 1H), 7.42 (dt, J = 10.7, 8.9 Hz, 1H), 7.25 (ddd, J = 11.6, 7.4, 2.4 Hz, 1H), 7.18 (s, 1H), 6.94 (ddd, J = 8.7, 3.8, 1.8 Hz, 1H), 6.60 (dd, J = 2.7, 1.6 Hz, 1H), 4.96-3.72 (m, 2H), 3.18 (s, 2H), 2.44 (t, J = 6.7 Hz, 2H), 2.16 (d, J = 7.7 Hz, 2H), 2.01-1.91 (m, 2H), 1.86 (p, J = 6.6 Hz, 2H), 1.72-1.50 (m, 2H). |

-continued

| Ex | Structure and Name | MS, m/z [M + H]+; $t_R$, method | 1H NMR |
|---|---|---|---|
| 52 | 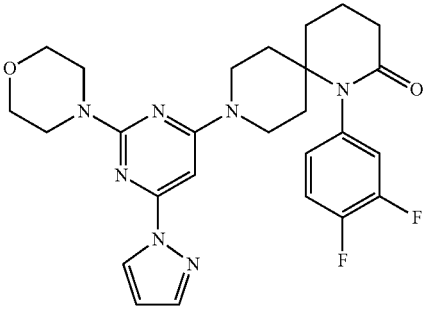 [SMILES: O=C1CCCC2(CCN(c3cc(-n4cccn4)nc(N4CCOCC4)n3)CC2)N1c1ccc(F)c(F)c1]<br>1-(3,4-difluorophenyl)-9-(2-morpholino-6-(1H-pyrazol-1-yl)pyrimidin-4-yl)-1,9-diazaspiro[5.5]undecan-2-one | 510.4; 1.08 min, LCMS method e | 1H NMR (400 MHz, DMSO-d6) δ 8.54 (dd, J = 2.6, 0.7 Hz, 1H), 7.75 (dd, J = 1.6, 0.7 Hz, 1H), 7.42 (dt, J = 10.6, 8.9 Hz, 1H), 7.24 (ddd, J = 11.6, 7.4, 2.4 Hz, 1H), 6.93 (ddd, J = 9.6, 4.5, 2.4 Hz, 1H), 6.49 (dd, J = 2.6, 1.6 Hz, 1H), 6.43 (s, 1H), 4.23 (s, 2H), 3.71-3.58 (m, 8H), 3.02 (t, J = 13.1 Hz, 2H), 2.43 (t, J = 6.7 Hz, 2H), 2.13 (s, 2H), 1.99-1.75 (m, 4H), 1.62-1.45 (m, 2H). |
| 53 | 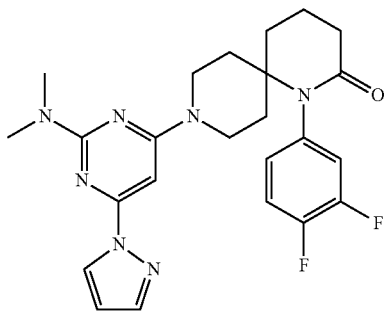 [SMILES: CN(C)c1nc(N2CCC3(CCCC(=O)N3c3ccc(F)c(F)c3)CC2)cc(-n2cccn2)n1]<br>1-(3,4-difluorophenyl)-9-(2-(dimethylamino)-6-(1H-pyrazol-1-yl)pyrimidin-4-yl)-1,9-diazaspiro[5.5]undecan-2-one | 468.4; 1.18 min, LCMS method e | 1H NMR (400 MHz, DMSO-d6) δ 8.52 (dd, J = 2.6, 0.8 Hz, 1H), 7.74 (dd, J = 1.6, 0.7 Hz, 1H), 7.42 (dt, J = 10.7, 8.9 Hz, 1H), 7.24 (ddd, J = 11.6, 7.4, 2.4 Hz, 1H), 6.99-6.88 (m, 1H), 6.49 (dd, J = 2.6, 1.6 Hz, 1H), 6.37 (s, 1H), 4.24 (S, 2H), 3.07 (S, 6H), 3.00 (d, J = 13.1 Hz, 2H), 2.43 (t, J = 6.7 Hz, 2H), 2.14 (s, 2H), 1.96-1.75 (m, 4H), 1.54 (d, J = 13.8 Hz, 2H). |
| 54 | 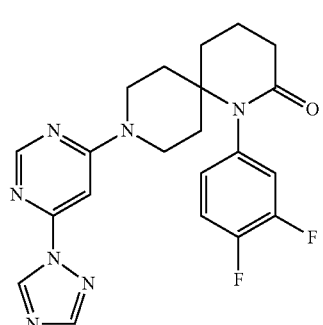<br>9-(6-(1H-1,2,4-triazol-1-yl)pyrimidin-4-yl)-1-(3,4-difluorophenyl)-1,9-diazaspiro[5.5]undecan-2-one | 426.2; 0.80 min, LCMS method e | 1H NMR (400 MHz, DMSO-d6) δ 9.31 (s, 1H), 8.43 (d, J = 0.9 Hz, 1H), 8.31 (s, 1H), 7.42 (dt, J = 10.7, 8.9 Hz, 1H), 7.25 (ddd, J = 11.6, 7.5, 2.5 Hz, 1H), 7.00 (d, J = 1.1 Hz, 1H), 6.93 (ddt, J = 8.6, 3.9, 1.9 Hz, 1H), 4.09 (d, J = 5.3 Hz, 2H), 3.12 (t, J = 13.2 Hz, 2H), 2.44 (t, J = 6.7 Hz, 2H), 2.16 (s, 2H), 2.00-1.78 (m, 4H), 1.67-1.46 (m, 2H). |

| Ex | Structure and Name | MS, m/z [M + H]+; t_R, method | 1H NMR |
|---|---|---|---|
| 55 | 9-(6-(4-chloro-1H-pyrazol-1-yl)pyrimidin-4-yl)-1-(3,4-difluorophenyl)-1,9-diazaspiro[5.5]undecan-2-one | 459.2; 1.15 min, LCMS method e | 1H NMR (400 MHz, DMSO-d6) δ 8.71 (d, J = 0.8 Hz, 1H), 8.38 (d, J = 0.9 Hz, 1H), 7.98 (d, J = 0.8 Hz, 1H), 7.41 (dt, J = 10.7, 8.9 Hz, 1H), 7.24 (ddd, J = 11.6, 7.5, 2.5 Hz, 1H), 7.01 (d, J = 1.0 Hz, 1H), 6.97-6.85 (m, 1H), 3.38 (s, 2H), 3.10 (t, J = 13.1 Hz, 2H), 2.43 (t, J = 6.7 Hz, 2H), 2.15 (s, 2H), 2.00-1.75 (m, 4H), 1.55 (td, J = 12.9, 4.7 Hz, 2H). |
| 56 | 9-(6-(4-fluoro-1H-pyrazol-1-yl)pyrimidin-4-yl)-1-(3,4-difluorophenyl)-1,9-diazaspiro[5.5]undecan-2-one | 443.2; 1.06 min, LCMS method e | 1H NMR (400 MHz, DMSO-d6) δ 8.60 (dd, J = 4.5, 0.9 Hz, 1H), 8.37 (d, J = 0.9 Hz, 1H), 7.96 (dd, J = 4.3, 0.9 Hz, 1H), 7.41 (dt, J = 10.7, 8.9 Hz, 1H), 7.24 (ddd, J = 11.6, 7.5, 2.5 Hz, 1H), 7.01 (d, J = 1.0 Hz, 1H), 6.93 (ddt, J = 8.7, 3.8, 1.6 Hz, 1H), 4.30 (s, 2H), 3.10 (t, J = 13.1 Hz, 2H), 2.43 (t, J = 6.8 Hz, 2H), 2.15 (s, 2H), 1.97- 1.75 (m, 4H), 1.55 (td, J = 13.1, 12.4, 4.3 Hz, 2H). |
| 57 | 1-(3,4-difluorophenyl)-9-(6-(3-(trifluoromethyl)-1H-pyrazol-1-yl)pyrimidin-4-yl)-1,9-diazaspiro[5.5]undecan-2-one | 493.1; 1.60 min, LCMS method f | 1H NMR (400 MHz, methanol-d4) δ 8.65-8.64 (m, 1H), 8.37 (s, 1H), 7.32-7.25 (m, 1H), 7.14-7.08 (m, 2H), 6.93-6.91 (m, 1H), 6.82 (m, 1H), 4.45 (brs, 2H), 3.16 (t, 2H), 2.58 (t, 2H), 2.27 (br, 2H), 2.03-1.96 (m, 4H), 1.82-1.7 (m, 2H). |

-continued

| Ex | Structure and Name | MS, m/z [M + H]+; $t_R$, method | 1H NMR |
|---|---|---|---|
| 58 | 1-(3,4-difluorophenyl)-9-(6-(4-(trifluoromethyl)-1H-imidazol-1-yl)pyrimidin-4-yl)-1,9-diazaspiro[5.5]undecan-2-one | 492.9; 0.65 min, LCMS method i | 1H NMR (400 MHz, chloroform-d) δ 8.44 (s, 1H), 8.32 (s, 1H), 7.92 (s, 1H), 7.21-7.12 (m, 1H), 6.92-6.86 (m, 1H), 6.82-6.74 (m, 1H), 6.35 (s, 1H), 4.45 (brs, 2H), 3.1 (t, 2H), 2.64-2.62 (m, 2H), 2.2-2.17 (m, 2H), 1.99-1.81 (m, 6H). |
| 59 | 9-(2-amino-5-fluoro-6-(1H-pyrazol-1-yl)primidin-4-yl)-1-(3,4-difluorophenyl)-1,9-diazaspiro[5.5]undecan-2-one | 4588.3; 0.58 min, LCMS method i | 1H NMR DMSO-d6, 300 MHz) δ 8.21 (d, 1H), 7.76 (s, 1H), 7.5-7.39 (m, 1H), 7.3-7.2 (m, 1H), 6.96-6.9 (m, 1H), 6.5-6.49 (m, 1H), 6.32 (s, 2H), 4.2 (d, 2H), 3.12 (t, 2H), 2.42 (t, 2H), 2.2-2.1 (m, 2H), 1.89-1.84 (m, 4H), 1.68-1.52 (m, 2H). |
| 60 | 9-(4-amino-6-(4-fluoro-1H-pyrazol-1-yl)-1,3,5-triazin-2-yl)-1-(3,4-difllorophenyl)-1,9-diazaspiro[5.5]undecan-2-one | 459.3; 0.65 min, LCMS method l | 1H NMR (chloroform-d, 300 MHz) δ 8.25 (d, 1H), 7.63 (d, 1H), 7.2-7.12 (m, 1H), 6.9-6.84 (m, 1H), 6.8-6.72 (m, 1H), 5.3 (br, 2H), 4.8 (br, 2H), 3.05-2.9 (m, 2H), 2.62 (t, 2H), 2.2-2.12 (br, 2H), 1.97-1.92 (m, 2H), 1.81-1.7 (m, 4H). |

| Ex | Structure and Name | MS, m/z [M + H]+; tR, method | 1H NMR |
|---|---|---|---|
| 61 | 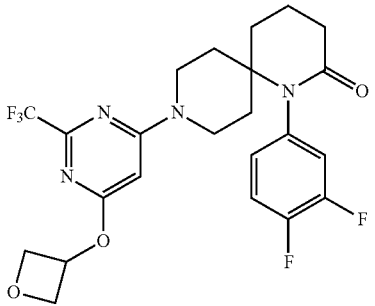 [SMILES: O=C1CCCC2(CCN(c3cc(OC4COC4)nc(C(F)(F)F)n3)CC2)N1c1ccc(F)c(F)c1]

1-(3,4-difluorophenyl)-9-(6-(oxetan-3-yloxy)-2-(trifluoromethyl)pyrimidin-4-yl)-1,9-diazaspiro[5.5]undecan-2-one | 499.3; 1.11 min, LCMS method e | 1H NMR (400 MHz, methanol-d4) δ 7.29 (dt, J = 10.5, 8.8 Hz, 1H), 7.16-7.05 (m, 1H), 6.92 (ddt, J = 8.3, 3.9, 2.0 Hz, 1H), 6.11 (s, 1H), 5.57 (p, J = 5.7 Hz, 1H), 4.92 (t, J = 6.9 Hz, 2H), 4.63 (dd, J = 7.6, 5.1 Hz, 2H), 4.29 (s, 2H), 3.10 (td, J = 13.3, 2.8 Hz, 2H), 2.58 (t, J = 6.8 Hz, 2H), 2.35-2.16 (m, 2H), 1.97 (td, J = 13.3, 7.6 Hz, 4H), 1.73 (s, 2H). |

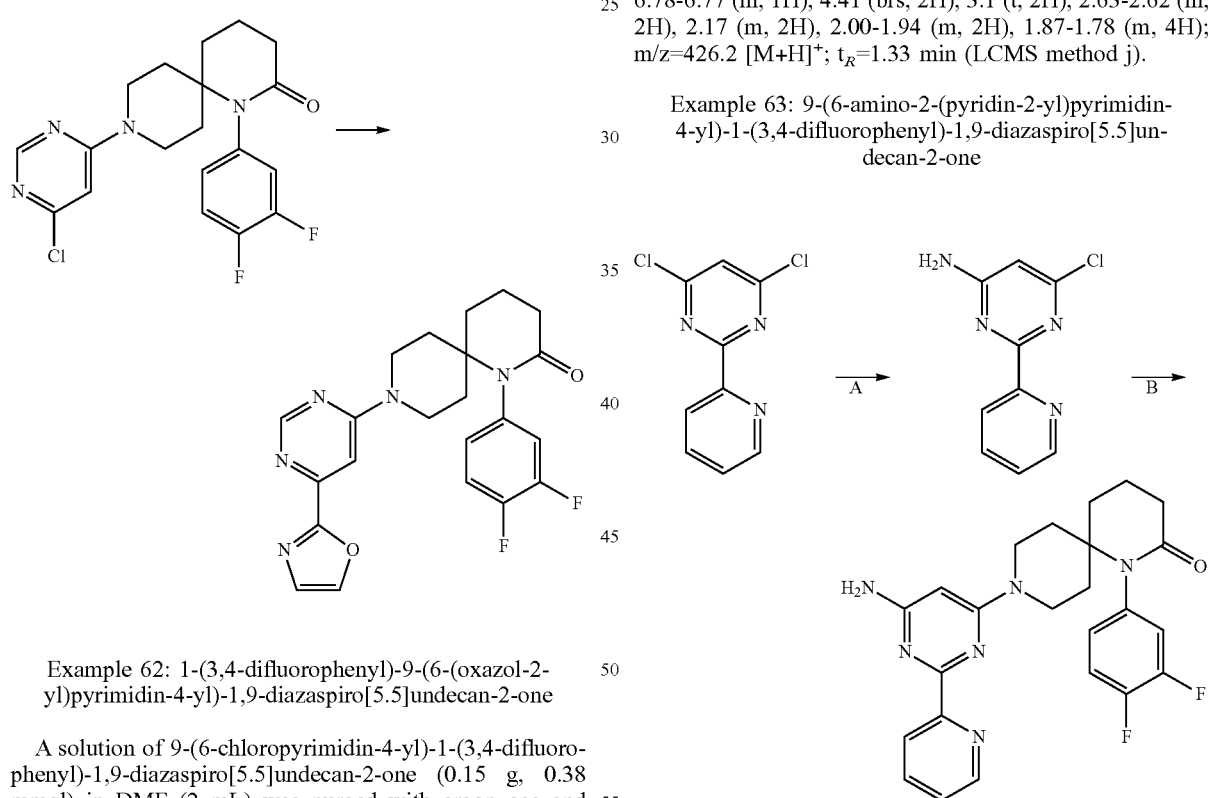

Example 62: 1-(3,4-difluorophenyl)-9-(6-(oxazol-2-yl)pyrimidin-4-yl)-1,9-diazaspiro[5.5]undecan-2-one A solution of 9-(6-chloropyrimidin-4-yl)-1-(3,4-difluorophenyl)-1,9-diazaspiro[5.5]undecan-2-one (0.15 g, 0.38 mmol) in DMF (2 mL) was purged with argon gas and treated with 2-(tributylstannyl)oxazole (0.273 g, 0.76 mmol) and tetrakis triphenylphosphine palladium(0) (0.080 g, 0.11 mmol). The reaction mixture was heated to 100° C. for 16 h. The reaction mixture was cooled to RT, diluted with water, and extracted with EtOAc twice. The combined organic extracts were washed with brine, dried over anhydrous Na2SO4, and concentrated under reduced pressure. Purification by preparative HPLC (LUNA 5.0μ, 21.2×250 mm; 0.1% aqueous HCOOH:ACN elution) provided the title compound (44 mg) as an off-white solid. 1H NMR (chloroform-d, 600 MHz) b 8.64 (s, 1H), 7.81 (s, 1H), 7.29 (m, 1H), 7.25-7.24 (m, 1H), 7.25-7.14 (m, 1H), 6.89-6.88 (m, 1H), 6.78-6.77 (m, 1H), 4.41 (brs, 2H), 3.1 (t, 2H), 2.63-2.62 (m, 2H), 2.17 (m, 2H), 2.00-1.94 (m, 2H), 1.87-1.78 (m, 4H); m/z=426.2 [M+H]+; tR=1.33 min (LCMS method j).

Example 63: 9-(6-amino-2-(pyridin-2-yl)pyrimidin-4-yl)-1-(3,4-difluorophenyl)-1,9-diazaspiro[5.5]undecan-2-one

Step A: 6-chloro-2-(pyridin-2-yl)pyrimidin-4-amine

A suspension of 4,6-dichloro-2-(pyridin-2-yl)pyrimidine (112 mg, 0.495 mmol) in isopropanol (0.5 mL) and ammonium hydroxide (33%, 0.5 mL, 4.24 mmol) was stirred at 50° C. After 3 h, an additional portion of ammonium hydroxide solution (0.25 mL) as added and stirring continued for 3 h. The solution was cooled to RT, diluted with saturated sodium bicarbonate and extracted with DCM. The organic extracts were dried over magnesium sulfate and concentrated to provide 6-chloro-2-(pyridin-2-yl)pyrimidin-4-amine (85 mg, 0.41 mmol) as a tan-colored solid. $^1$H NMR (400 MHz, DMSO-d6) δ 8.68 (ddd, J=4.7, 1.8, 0.9 Hz, 1H), 8.21 (dt, J=8.0, 1.1 Hz, 1H), 7.93 (td, J=7.7, 1.8 Hz, 1H), 7.50 (ddd, J=7.5, 4.7, 1.2 Hz, 1H), 7.40 (s, 2H), 6.48 (s, 1H); m/z=207.1 [M+H]$^+$; $t_R$=0.48 min (LCMS method e).

Step B: 9-(6-amino-2-(pyridin-2-yl)pyrimidin-4-yl)-1-(3,4-difluorophenyl)-1,9-diazaspiro[5.5]undecan-2-one A solution of 1-(3,4-difluorophenyl)-1,9-diazaspiro[5.5]undecane-2-one (Intermediate A, 56 mg, 0.20 mmol), 6-chloro-2-(pyridin-2-yl)pyrimidin-4-amine (41 mg, 0.20 mmol) and DIEA (104 µL, 0.595 mmol) in DMF (0.7 mL) was heated at 100° C. overnight. After cooling to RT, the mixture was diluted with DCM and washed with water, then brine. The organic layer was dried over magnesium sulfate, filtered and concentrated. Purification by silica gel chromatography (0-100% MeOH in EtOAc), followed by reverse phase chromatography (RediSep® Rf Gold® Reversed Phase C18 50 g column, 0-100% ACN in water) provided the title compound (16 mg, 0.034 mmol) as a white solid. $^1$H NMR (400 MHz, DMSO-d6) δ 8.61 (ddd, J=4.8, 1.8, 0.9 Hz, 1H), 8.23-8.08 (m, 1H), 7.83 (td, J=7.7, 1.8 Hz, 1H), 7.51-7.34 (m, 2H), 7.25 (ddd, J=11.5, 7.5, 2.4 Hz, 1H), 7.00-6.88 (m, 1H), 6.32 (s, 2H), 5.56 (s, 1H), 4.18 (s, 2H), 2.95 (t, J=12.9 Hz, 2H), 2.43 (t, J=6.8 Hz, 2H), 2.13 (s, 2H), 1.88 (t, J=9.5 Hz, 4H), 1.55 (t, J=11.1 Hz, 2H); m/z=451.3 [M+H]$^+$; $t_R$=1.29 min (LCMS method e).

Example 64: 9-(2-amino-6-(4-(trifluoromethyl)-1H-pyrazol-1-yl)pyrimidin-4-yl)-1-(3,4-difluorophenyl)-1,9-diazaspiro[5.5]undecane-2-one Step A: 4-Chloro-6-(4-trifluoromethyl)-1H-pyrazol-1-yl)pyrimidin-2-amine A mixture of 4-(trifluoromethyl)-1H-pyrazole (0.183 g, 1.35 mmol), 2-amino-4,6-dichloropyrimidine (0.200 g, 1.23 mmol) and Cs$_2$CO$_3$ (0.799 g, 2.45 mmol) in dioxane (4 mL) were stirred at 100° C. for 12 h. After cooling to RT, the reaction mixture was diluted with water and extracted with EtOAc. The extracts were washed with brine, dried over Na$_2$SO$_4$ and concentrated under reduced pressure to provide 4-chloro-6-(4-trifluoromethyl)-1H pyrazol-1-yl)pyrimidin-2-amine as a white solid. The crude was taken for the next step without purification. m/z=264.0 [M+H]$^+$ Step B: 9-(2-amino-6-(4-(trifluoromethyl)-1H-pyrazol-1-yl)pyrimidin-4-yl)-1-(3,4-difluorophenyl)-1,9-diazaspiro[5.5]undecane-2-one 1-(3,4-difluorophenyl)-1,9-diazaspiro[5.5]undecane-2-one (Intermediate A, 0.150 g, 0.535 mmol), 4-chloro-6-(4-trifluoromethyl)-1H pyrazol-1-yl)pyrimidin-2-amine (0.197 g, 0.749 mmol) and DIPEA (0.28 mL, 1.61 mmol) in EtOH (3 mL) were stirred at 80° C. for 12 h. The reaction was diluted with water and extracted with EtOAc. The extracts were washed with brine, dried over Na$_2$SO$_4$, filtered, and concentrated under reduced pressure. Purification by preparative HPLC (KINETEX EVO C18, 5 µm, 21.2×150 mm; water:ACN elution) provided the title compound (97 mg, 0.19 mmol) as a white solid. $^1$H NMR (400 MHz, DMSO-d6) δ 8.82 (s, 1H), 8.21 (s, 1H), 7.41 (m, 1H), 7.23 (m, 1H), 6.91 (m, 1H), 6.41 (d, 3H), 4.24 (m, 2H), 3.01 (t, 2H), 2.42 (t, 2H), 2.13 (d, 2H), 1.85 (m, 4H), 1.50 (m, 2H); m/z=508.15 [M+H]$^+$; $t_R$=1.50 min (LCMS method j)

Example 65: 1-(3,4-difluorophenyl)-9-(2-(2-hydroxypropan-2-yl)-6-(4-(trifluoromethyl)-1H-pyrazol-1-yl)pyrimidin-4-yl)1,9-diazaspiro[5.5]undecane-2-one

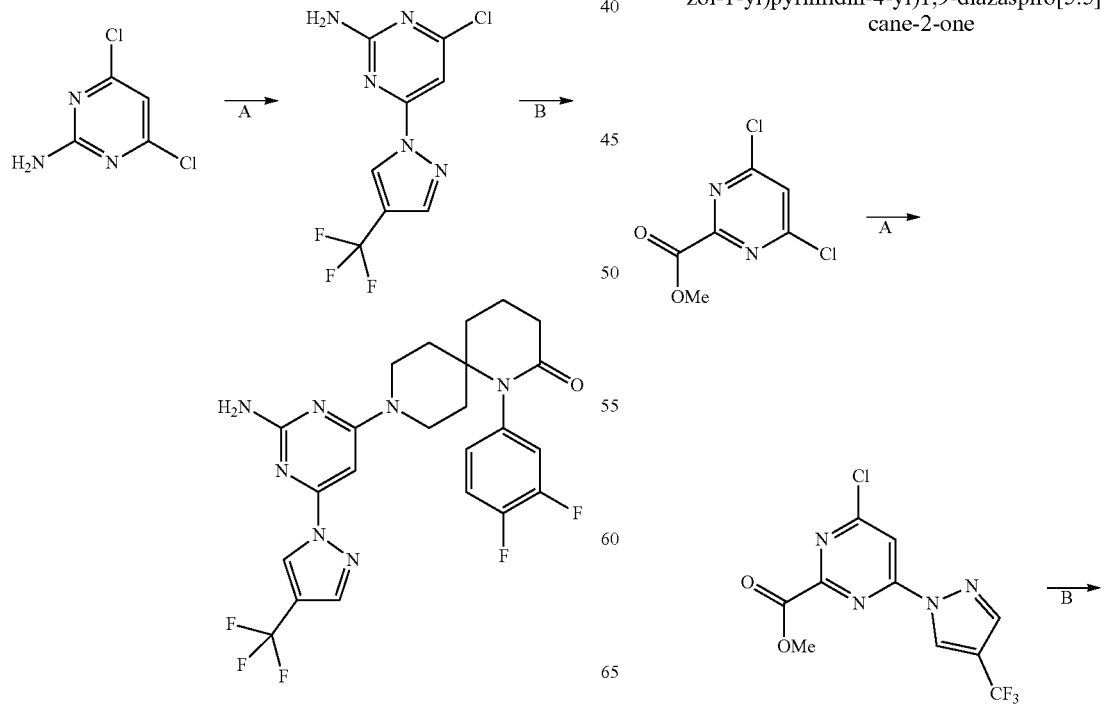

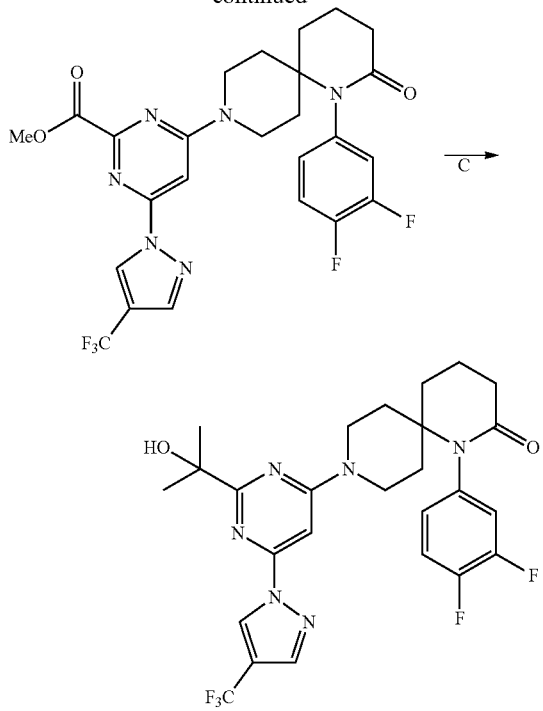

Step A: methyl 4-chloro-6-(4-trifluoromethyl)-1H-pyrazol-1-yl)pyrimidine-2-carboxylate A mixture of methyl 4,6-dichloropyrimidine-2-carboxylate (0.500 g, 2.66 mmol), 4-(trifluoromethyl)-1H-pyrazole (0.360 g, 2.66 mmol) and $Cs_2CO_3$ (1.70 g, 5.31 mmol) in dioxane (5 mL) was stirred at RT for three hours. Water was added to the reaction mixture and it was extracted with EtOAc. The extracts were washed with brine, dried over $Na_2SO_4$, filtered, and concentrated under reduced pressure to provide methyl 4-chloro-6-(4-trifluoromethyl)-1H-pyrazol-1-yl)pyrimidine-2-carboxylate as a white solid (0.550 g). The crude was taken on without further purification.

Step B: methyl 4-(1-(3,4-difluorophenyl)-2-oxo-1,9-diazaspiro[5.5]undecane-9-yl)-6-(4-chloro-(4-(trifluoromethyl)-1H-pyrazol-1-yl)pyrimidine-2-carboxylate A mixture of 1-(3,4-difluorophenyl)-1,9-diazaspiro[5.5]undecane-2-one (Intermediate A, 0.370 g, 1.35 mmol), methyl-4-chloro-6-(4-(trifluoromethyl)-1H-pyrazol-1-yl)pyrimidine-2-carboxylate (0.550 g, 1.79 mmol) and DIPEA (0.700 g, 5.37 mmol) in EtOH (5 mL) were heated at 80° C. for two hours. The mixture was diluted with water and extracted with EtOAc twice. The extracts were washed with brine, dried over $Na_2SO_4$, filtered, and concentrated under reduced pressure to provide methyl 4-(1-(3,4-difluorophenyl)-2-oxo-1,9-diazaspiro[5.5]undecane-9-yl)-6-(4-chloro-(4-(trifluoromethyl)-1H-pyrazol-1-yl)pyrimidine-2-carboxylate (0.350 g, 0.636 mmol) as a white solid. m/z=551.2 $[M+H]^+$

Step C: 1-(3,4-difluorophenyl)-9-(2-(2-hydroxypropan-2-yl)-6-(4-(trifluoromethyl)-1H-pyrazol-1-yl)pyrimidin-4-yl)1,9-diazaspiro[5.5]undecane-2-one Methylmagnesium bromide (3.0 M solution in diethyl ether, 0.034 mL, 0.10 mmol) was added to a stirred solution of methyl 4-(1-(3,4-difluorophenyl)-2-oxo-1,9-diazaspiro[5.5]undecane-9-yl)-6-(4-chloro-(4-(trifluoromethyl)-1H-pyrazol-1-yl)pyrimidine-2-carboxylate (0.050 g, 0.034 mmol) in THF (2 mL) cooled to 0° C. The reaction mixture was then stirred at RT for three hours. The reaction was quenched with aqueous $NH_4Cl$ and extracted with EtOAc. The extracts were washed with brine, dried over $Na_2SO_4$, filtered, and concentrated under reduced pressure. Purification by preparative HPLC (LUNA Phenomenex, 5 μm, 21.2×250 mm; 0.02% $NH_4OH$ in $H_2O$:ACN elution) provided the title compound (3 mg, 0.006 mmol) as a white solid. $^1H$ NMR (300 MHz, methanol-$d_4$) b 9.16 (s, 1H), 8.02 (s, 1H), 7.23-7.28 (m, 1H), 7.07-7.14 (m, 1H), 7.04 (s, 1H), 6.90-6.94 (m, 1H), 4.45 (brs, 2H), 3.16 (t, 2H), 2.58 (t, 2H), 2.19-2.35 (m, 2H), 1.88-2.09 (m, 4H), 1.76 (brs, 2H), 1.51 (s, 6H); m/z=551.2 $[M+H]^+$; $t_R$=1.80 min (LCMS method 1).

Example 66: Synthesis 1-(3,4-difluorophenyl)-9-(2-(hydroxymethyl)-6-(4-(trifluoromethyl)-1H-pyrazol-1-yl)pyrimidin-4-yl)1,9-diazaspiro[5.5]undecane-2-one

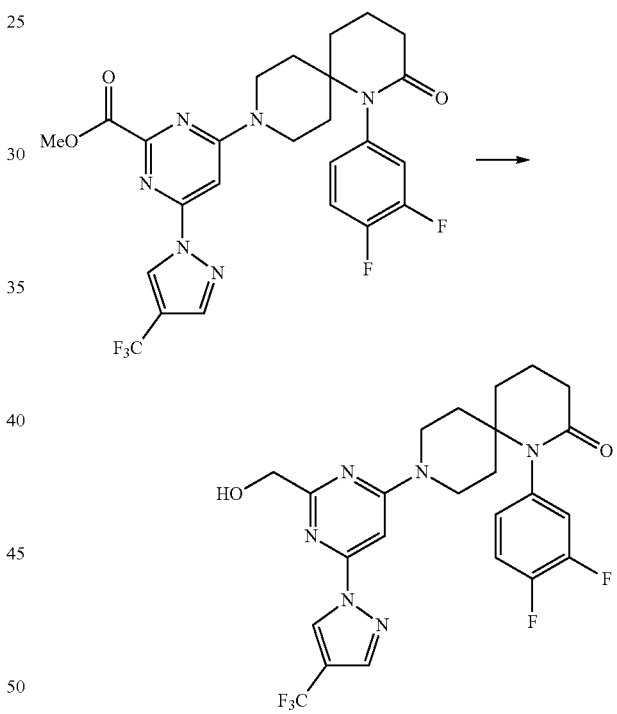

Step A: 1-(3,4-difluorophenyl)-9-(2-(hydroxymethyl)-6-(4-(trifluoromethyl)-1H-pyrazol-1-yl)pyrimidin-4-yl)1,9-diazaspiro[5.5]undecane-2-one To a stirred solution of methyl 4-(1-(3,4-difluorophenyl)-2-oxo-1,9-diazaspiro[5.5]undecane-9-yl)-6-(4-chloro-(4-(trifluoromethyl)-1H-pyrazol-1-yl)pyrimidine-2-carboxylate (1.100 g, 1.998 mmol) in MeOH (15 mL) cooled to 0° C., $NaBH_4$ (0.230 g, 5.99 mmol) was added portionwise. The reaction mixture was stirred at RT for two hours. The reaction was quenched with water and extracted with EtOAc. The extracts were washed with brine, dried over $Na_2SO_4$, filtered, and concentrated under reduced pressure. Washing the resulting solid with pentane provided the title compound (0.950 g, 1.82 mmol) as an off-white solid. ¹H NMR (300 MHz, DMSO-d6) δ 9.30 (s, 1H), 8.30 (s, 1H), 7.42 (m, 1H), 7.25 (m, 1H), 6.9-6.96 (m, 2H), 4.97 (t, 1H), 4.37 (d, 2H), 3.10-3.18 (m, 2H), 2.40-2.45 (m, 2H), 2.1-2.2 (m, 2H), 1.8-1.98 (m, 4H), 1.49-1.6 (m, 2H) (2 aliphatic protons merged with DMSO peak); m/z=523.2 [M+H]⁺; t$_R$=1.64 min (LCMS method 1)

Example 67: rac-1-(3,4-difluorophenyl)-9-(2-(1-hydroxymethyl)-6-(4-(trifluoromethyl)-1H-pyrazol-1-yl)pyrimidin-4-yl)1,9-diazaspiro[5.5]undecane-2-one

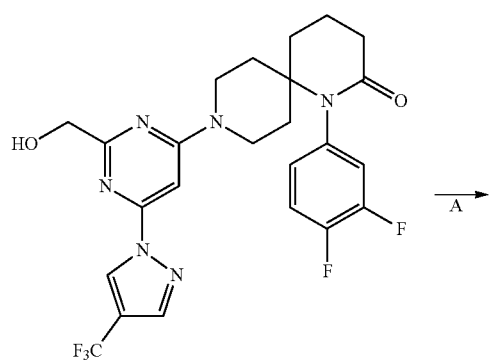

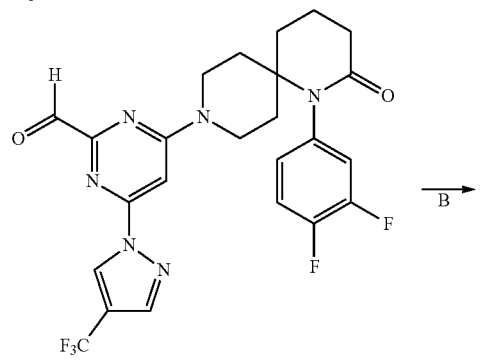

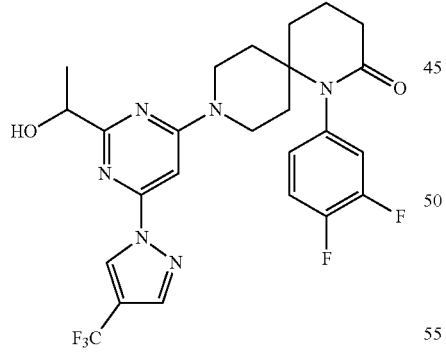

Step A: 4-(1-(3,4-difluorophenyl)-2-oxo-1,9-diazaspiro[5.5]undecane-9-yl)-6-(4-(trifluoromethyl)-1H-pyrazol-1-yl)pyrimidine-2-carbaldehyde MnO₂ (0.230 g, 2.6 mmol) was added to a stirred solution of 1-(3,4-difluorophenyl)-9-(2-(hydroxymethyl)-6-(4-(trifluoromethyl)-1H-pyrazol-1-yl)pyrimidin-4-yl)1,9-diazaspiro[5.5]undecane-2-one (0.020 g, 0.038 mmol) in DCM (5 mL) cooled to 0° C. The reaction mixture was stirred at RT for 12 h. The reaction mixture was poured into water and extracted with EtOAc. The extracts were washed with brine, dried over Na₂SO₄, filtered, and concentrated under reduced pressure to provide crude product as yellow gummy solid (0.025 g) which was taken forward without purification. m/z=523.2 [M+H]⁺

Step B: rac-1-(3,4-difluorophenyl)-9-(2-(1-hydroxymethyl)-6-(4-(trifluoromethyl)-1H-pyrazol-1-yl)pyrimidin-4-yl)1,9-diazaspiro[5.5]undecane-2-one MeMgBr (3.0 M in diethylether, 170 µL, 0.52 mmol) was added to a stirred solution of 4-(1-(3,4-difluorophenyl)-2-oxo-1,9-diazaspiro[5.5]undecane-9-yl)-6-(4-(trifluoromethyl)-1H-pyrazol-1-yl)pyrimidine-2-carbaldehyde (0.080 g, 0.172 mmol) in THF (2 mL) cooled to 0° C. The reaction mixture was stirred at RT for 3 hours. The reaction was quenched with aqueous NH₄Cl and extracted with EtOAc. The extracts were washed with brine, dried over Na₂SO₄, filtered, and concentrated under reduced pressure. Purification by preparative HPLC (LUNA Phenomenex, 5 µm, 21.2×250 mm; 0.02% NH₄OH in H₂O:ACN elution) provided the title compound (2 mg, 0.004 mmol) as an off-white solid. ¹H NMR (300 MHz, methanol-d₄) b 9.13 (s, 1H), 8.02 (s, 1H), 7.28 (m, 1H), 7.11 (m, 1H), 7.04 (s, 1H), 6.92 (m, 1H), 4.65 (q, 1H), 4.46 (s, 2H), 3.15 (m, 2H), 2.58 (t, 2H), 2.27 (d, 2H), 1.98 (dd, 4H), 1.75 (s, 2H), 1.46 (d, 3H); m/z=537.3 [M+H]⁺; t$_R$=1.74 min (LCMS method 1).

Example 68: 4-(1-(3,4-difluorophenyl)-2-oxo-1,9-diazaspiro[5.5]undecane-9-yl)-6-(4-(trifluoromethyl)-1H-pyrazol-1-yl)pyrimidin-2-carboxamide

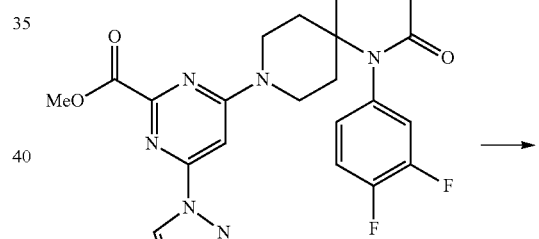

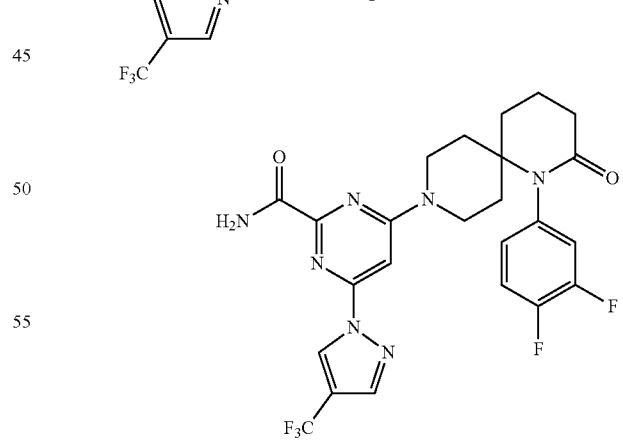

Step A: 4-(1-(3,4-difluorophenyl)-2-oxo-1,9-diazaspiro[5.5]undecane-9-yl)-6-(4-(trifluoromethyl)-1H-pyrazol-1-yl)pyrimidin-2-carboxamide Ammonia (2.0 M in ethanol, 3 mL) was added to methyl 4-(1-(3,4-difluorophenyl)-2-oxo-1,9-diazaspiro[5.5]undecane-9-yl)-6-(4-chloro-(4-(trifluoromethyl)-1H-pyrazol-1-yl)pyrimidine-2-carboxylate (0.085 g, 0.15 mmol) and the mixture heated at 50° C. for 4 hours. The mixture was concentrated under reduced pressure. Purification by preparative HPLC (Waters Xbridge, 5 µm, 21.2×150 mm; 0.02% NH$_3$ in H$_2$O:ACN elution) provided the title compound (0.028 g, 0.052 mmol) as an off-white solid. $^1$H NMR (300 MHz, DMSO-d$_6$) δ 9.58 (s, 1H), 8.50 (s, 1H), 8.32 (s, 1H), 7.74 (s, 1H), 7.41 (m, 1H), 7.2-7.3 (m, 1H), 7.13 (s, 1H), 6.9-6.94 (m, 1H), 3.14 (s, 2H), 2.44 (t, 3H), 2.17 (m, 2H), 2.00-1.86 (m, 4H), 1.56 (t, 2H); m/z=536.4 [M+H]$^+$; t$_R$=1.47 min (LCMS method 1)

Example 69: 9-(2-chloro-6-(4-(trifluoromethyl)-1H-pyrazol-1-yl)pyrimidin-4-yl)-1-(3,4-difluorophenyl)-1,9-diazaspiro[5.5]undecan-2-one

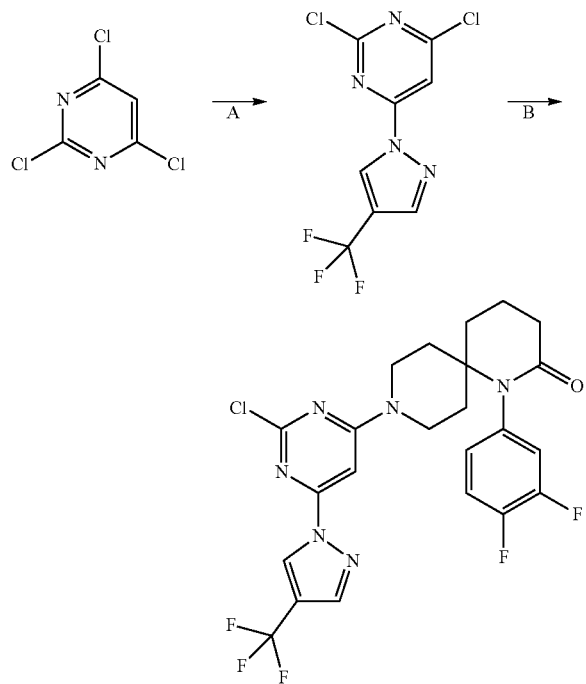

Step-A: 2,4-dichloro-6-(4-(trifluoromethyl)-1H-pyrazol-1-yl)pyrimidine

A mixture of 2,4,6-trichloropyrimidine (0.50 g, 2.7 mmol), 4-(trifluoromethyl)-1H-pyrazole (0.27 g, 2.0 mmol) and Cs$_2$CO$_3$ (1.70 g, 5.45 mmol) in dioxane (5 mL) was stirred at RT for 3 h. The reaction mixture was diluted with water and extracted with EtOAc twice. The extracts were washed with brine, dried over Na$_2$SO$_4$, filtered and concentrated under reduced pressure to provide the crude product (0.20 g) which was used for next step without further purification.

Step-B: 9-(2-chloro-6-(4-(trifluoromethyl)-1H-pyrazol-1-yl)pyrimidin-4-yl)-1-(3,4-difluorophenyl)-1,9-diazaspiro[5.5]undecan-2-one A mixture of 2,4-dichloro-6-(4-(trifluoromethyl)-1H-pyrazol-1-yl)pyrimidine (0.20 g, 0.71 mmol), 1-(3,4-difluorophenyl)-1,9-diazaspiro[5.5]undecan-2-one (Intermediate A, 0.197 g, 0.706 mmol) and DIPEA (0.27 mL, 2.1 mmol) in EtOH (3 mL) was heated at 80° C. for 2 h. The reaction mixture was cooled to RT, diluted with water and extracted with EtOAc twice. The combined extracts were washed with brine, dried over Na$_2$SO$_4$, filtered and concentrated under reduced pressure. Purification by preparative HPLC (YMC-ACTUS TRIART, 5.0 µm, 20×150 mm; 0.02% NH$_4$OH in water:ACN elution) provided the title compound (85 mg, 0.16 mmol). $^1$H NMR (300 MHz, DMSO-d$_6$) δ 9.17 (s, 1H), 8.20 (s, 1H), 7.41 (m, 1H), 7.25 (m, 1H), 6.99-6.83 (m, 2H), 4.82 (s, 1H), 3.96 (s, 1H), 3.10 (brs, 2H), 2.42 (t, 2H), 2.14 (d, 2H), 2.01-1.72 (m, 4H), 1.53 (m, 2H); m/z=527.1 [M+H]$^+$; t$_R$=1.74 min (LCMS method 1).

By employing similar methods as described for the preparation of Example 69, using appropriate starting materials, the following compounds were prepared:

| Ex | Structure and Name | MS, m/z [M+H]$^+$; t$_R$, method | $^1$H NMR |
|---|---|---|---|
| 70 | (R)-9-(2-chloro-6-((tetrahydrofuran-3-yl)oxy)pyrimidin-4-yl)-1-(3,4-difluorophenyl)-1,9- | 479.2; 1.47 min, LCMS method j | $^1$H NMR (400 MHz, DMSO-d$_6$) δ 7.43 (m, 1H), 7.25 (m, 1H), 6.92 (m, 1H), 6.54 (s, 1H), 5.32 (t, 1H), 3.66-3.86 (m, 4H), 3.03 (t, 2H), 3.21-3.13 (m, 1H), 2.42 (t, 2H), 2.25-2.02 (m, 3H), 1.71-1.98 (m, 5H), 1.46-1.52 (m, 2H) |

| Ex | Structure and Name | MS, m/z [M+H]+; $t_R$, method | 1H NMR |
|---|---|---|---|
| | diazaspiro[5.5]undecan-2-one | | |
| 71 | (S)-9-(2-chloro-6-((tetrahydrofuran-3-yl)oxy)pyrimidin-4-yl)-1-(3,4-difluorophenyl)-1,9-diazaspiro[5.5]undecan-2-one | 479.2; 1.47 min, LCMS method j | 1H NMR (DMSO-$d_6$, 300 MHz) δ 7.46-7.38 (m, 1H), 7.24-7.2 (m, 1H), 6.84 (m, 1H), 6.52 (s, 1H), 5.32-5.28 (m, 1H), 4.5-3.62 (m, 6H), 3.0 (br, 2H), 2.42-2.39 (m, 2H), 2.18-2.07 (m, 3H), 1.92-1.74 (m, 5H), 1.52-1.4 (m, 2H). |
| 72 | (R)-9-(4-chloro-6-((tetrahydrofuran-3-yl)oxy)pyrimidin-2-yl)-1-(3,4-difluorophenyl)-1,9-diazaspiro[5.5]undecan-2-one | 479.4; 1.74 min, LCMS method l | 1H NMR (DMSO-$d_6$, 300 MHz) δ 7.44-7.3 (m, 1H), 7.24-7.18 (m, 1H), 6.92-6.88 (m, 1H), 6.08 (s, 1H), 5.4 (m, 1H), 4.42-4.32 (m, 2H), 3.88-3.62 (m, 4H), 3.0 (t, 2H), 2.42-2.40 (m, 3H), 2.25-2.08 (m, 3H), 1.88-1.84 (m, 4H), 1.51-1.4 (m, 2H). |

Example 73: 1-(3,4-difluorophenyl)-9-(6-(4-fluoro-1H-pyrazol-1-yl)-2-morpholinopyrimidin-4-yl)-1,9-diazaspiro[5.5]undecan-2-one

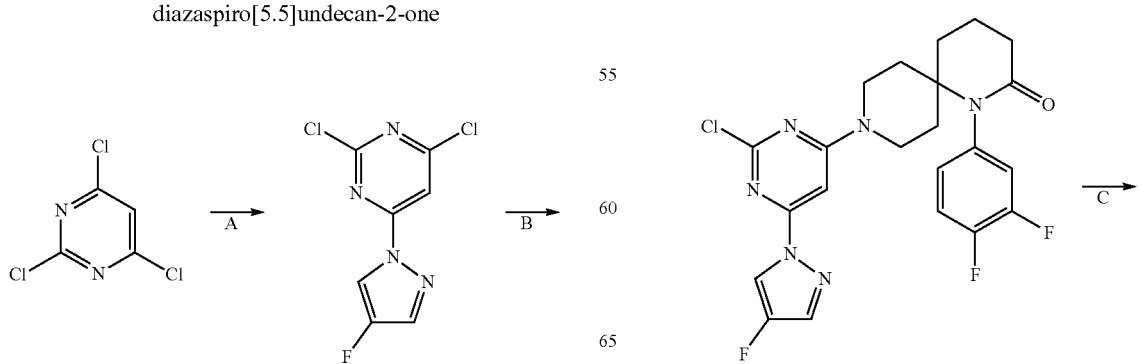

-continued

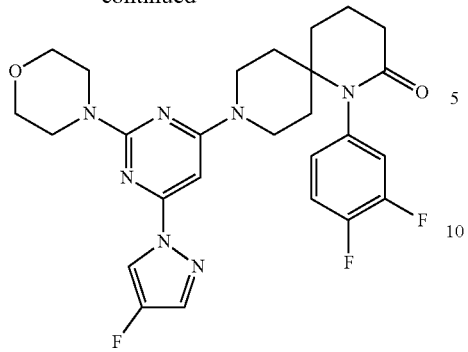

Step A: 2,4-dichloro-6-(4-fluoro-1H-pyrazol-1-yl)pyrimidine

A mixture of 2,4,6-trichloropyrimidine (0.200 g, 1.09 mmol), Cs$_2$CO$_3$ (1.42 g, 2.18 mmol) and 4-fluoro-1H-pyrazole (0.18 g, 2.2 mmol) in dioxane (6 mL) was stirred at RT for 12 h. The reaction mixture was diluted with water and extracted with EtOAc twice. The extracts were washed with brine, dried over Na$_2$SO$_4$, filtered and concentrated under reduced pressure. Purification by preparative TLC eluting with 1:1 EtOAc/hexane provided 2,4-dichloro-6-(4-fluoro-1H-pyrazol-1-yl)pyrimidine as an off-white solid (60 mg, 0.26 mmol); m/z=233.0, [M+H]$^+$

Step B: 9-(2-chloro-6-(4-fluoro-1H-pyrazol-1-yl)pyrimidin-4-yl)-1-(3,4-difluorophenyl)-1,9-diazaspiro[5.5]undecan-2-one A solution of 2,4-dichloro-6-(4-fluoro-1H-pyrazol-1-yl)pyrimidine (60 mg, 0.26 mmol) in EtOH (5 mL) was treated with 1-(3,4-difluorophenyl)-1,9-diazaspiro[5.5]undecan-2-one (Intermediate A, 72 mg, 0.26 mmol) and DIPEA (0.10 mL, 0.77 mmol), and heated at 80° C. for 2 h. The reaction mixture was cooled to RT, diluted with water, and extracted with EtOAc twice. The extracts were washed with brine, dried over Na$_2$SO$_4$, filtered, and concentrated under reduced pressure. The crude solid was washed with pentane to provide 9-(2-chloro-6-(4-fluoro-1H-pyrazol-1-yl)pyrimidin-4-yl)-1-(3,4-difluorophenyl)-1,9-diazaspiro[5.5]undecan-2-one (110 mg, 0.231 mmol) as an off-white solid. m/z=476.9 [M+H]$^+$

Step-C: 1-(3,4-difluorophenyl)-9-(6-(4-fluoro-1H-pyrazol-1-yl)-2-morpholinopyrimidin-4-yl)-1,9-diazaspiro[5.5]undecan-2-one A solution of 9-(2-chloro-6-(4-fluoro-1H-pyrazol-1-yl)pyrimidin-4-yl)-1-(3,4-difluorophenyl)-1,9-diazaspiro[5.5]undecan-2-one (100 mg, 0.209 mmol) in n-butanol (2 mL) was treated with morpholine (91 mg, 1.0 mmol) and DIPEA (80 µL, 0.45 mmol) and the reaction mixture was heated at 120° C. for 12 h. The reaction mixture was cooled to RT, diluted with water, and extracted with EtOAc twice. The extracts were washed with brine solution, dried over Na$_2$SO$_4$, filtered, and concentrated under reduced pressure. The crude solid was washed with pentane to afford the title compound (34 mg, 0.064 mmol) as a brown solid. $^1$H NMR (400 MHz, DMSO-d$_6$) δ 8.60 (dd, 1H), 7.76 (dd, 1H), 7.39-7.45 (m, 1H), 7.1-7.26 (m, 1H), 6.92-6.94 (m, 1H), 5.76 (s, 1H), 4.33 (brs, 2H), 3.63 (m, 4H), 3.53 (m, 4H), 2.96 (t, 2H), 2.43 (t, 2H), 2.14 (brs, 2H), 1.95-1.78 (m, 3H), 1.50 (m, 2H); m/z=528.3 [M+H]$^+$; $t_R$=1.37 min (LCMS method k).

Example 74: 9-(2-amino-6-(4,4-difluorocyclohex-1-en-1-yl)pyrimidin-4-yl)-1-(3,4-difluorophenyl)-1,9-diazaspiro[5.5]undecan-2-one

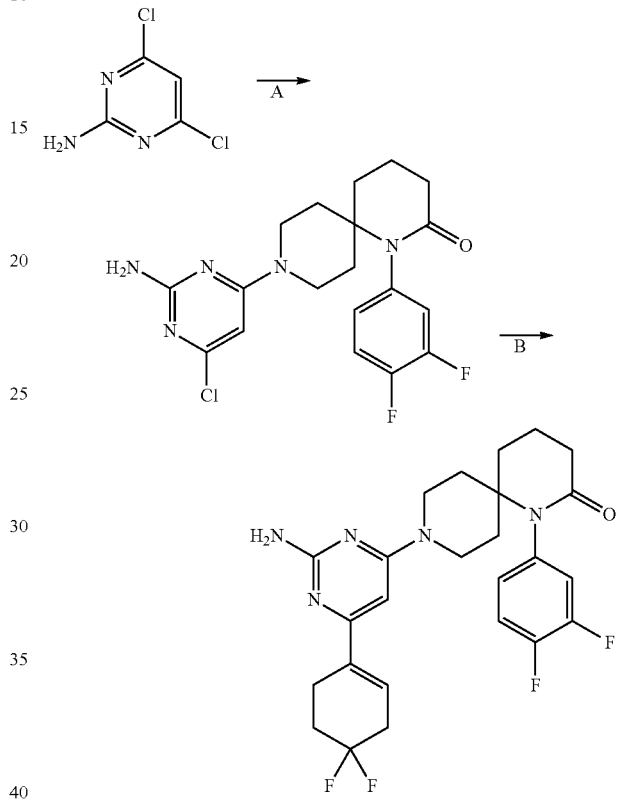

Step A: 9-(2-amino-6-chloropyrimidin-4-yl)-1-(3,4-difluorophenyl)-1,9-diazaspiro[5.5]undecane-2-one A mixture of 1-(3,4-difluorophenyl)-1,9-diazaspiro[5.5]undecane-2-one (Intermediate A, 0.513 g, 1.83 mmol), 2-amino-4,6-dichloropyrimidine (0.300 g, 1.83 mmol) and DIPEA (0.64 mL, 3.7 mmol) in EtOH (7 mL) was heated at 80° C. for 12 hours. After cooling to RT, the mixture was diluted with water and extracted with EtOAc. The extracts were washed with brine, dried over Na$_2$SO$_4$, filtered, and concentrated under reduced pressure. Purification by silica gel chromatography (2-5% MeOH in DCM) provided 9-(2-amino-6-chloropyrimidin-4-yl)-1-(3,4-difluorophenyl)-1,9-diazaspiro[5.5]undecane-2-one (0.520 g, 1.27 mmol) as a white solid. m/z=410.3 [M+2]

Step B: 9-(2-amino-6-(4,4-difuorocyclohex-1-en-1-yl)pyrimidin-4-yl)-1-(3,4-difluorophenyl)-1,9-diazaspiro[5.5]undecan-2-one 9-(2-amino-6-chloropyrimidin-4-yl)-1-(3,4-difluorophenyl)-1,9-diazaspiro[5.5]undecan-2-one (0.300 g, 0.735 mmol) and 2-(4,4-difluorocyclohex-1-en-1-yl))-4,4,5,5-tetramethyl-1,3,2-dioxaborolane (0.540 g, 2.21 mmol) were stirred in DME (6 mL) and H$_2$O (2 mL) at RT with argon purging for 10 min. K₂CO₃ (0.304 g, 2.21 mmol) was added to the reaction mixture under argon purging followed by the addition of Pd(dppf)Cl₂·DCM (0.120 g, 0.147 mmol). The mixture was heated at 100° C. for 16 h. After cooling to RT, water was added to the reaction mixture and it was extracted with EtOAc. The extracts were washed with brine, dried over Na₂SO₄, filtered, and concentrated under reduced pressure. Purification by preparative HPLC (Waters Xbridge, 5 μm, 21.2×150 mm; 0.02% NH₄OH in H₂O:ACN elution) provided the title compound (17 mg, 0.035 mmol) as a white solid. ¹H NMR (300 MHz, chloroform-d) δ 7.17 (m, 1H), 6.72-6.92 (m, 2H), 6.53 (s, 1H), 5.88 (s, 1H), 4.68 (s, 2H), 4.26 (d, 2H), 3.53 (brs, 2H), 2.90-2.96 (m, 2H), 2.59-2.81 (m, 6H), 2.1-2.22 (m, 2H), 1.92-1.96 (m, 2H), 1.74-1.92 (m, 2H); m/z=490.25 [M+H]⁺; $t_R$=1.32 min (LCMS method j)

Example 75: 9-(2-amino-6-(4-fluorophenyl-4-yl)-1-(3,4-difluorophenyl)-1,9-diazaspiro[5.5]undecane-2-one

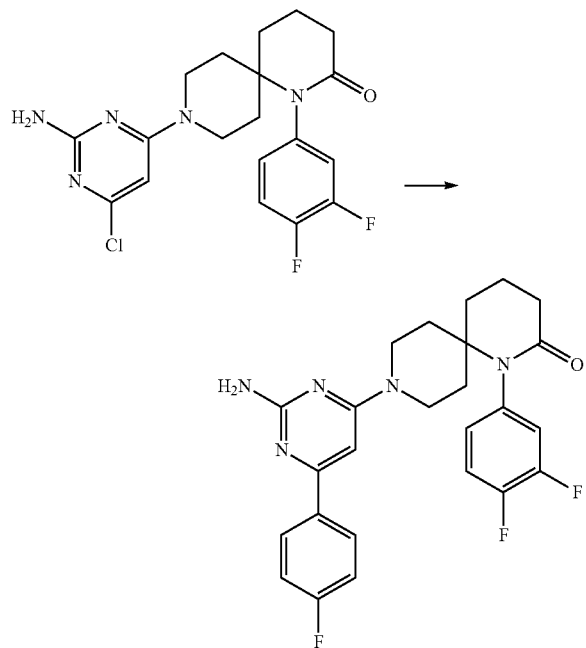

9-(2-amino-6-chloropyrimidin-4-yl)-1-(3,4-difluorophenyl)-1,9-diazaspiro[5.5]undecane-2-one (0.100 g, 0.245 mmol) and 4-fluorophenylboronic acid (0.068 g, 0.49 mmol) were stirred in DME (0.9 mL) and H₂O (2.1 mL) at RT with argon purging for 10 min. K₂CO₃ (0.101 g, 0.735 mmol) was added to the reaction mixture under argon purging followed by the addition of Pd(dppf)Cl₂·DCM (0.035 g, 0.049 mmol). The mixture was heated at 90° C. for 16 h. After cooling to RT, water was added to the reaction mixture and it was extracted with EtOAc. The extracts were washed with brine, dried over Na₂SO₄, filtered, and concentrated under reduced pressure. Purification by preparative HPLC (Gemini, 5 μm, 21.2×250 mm; 0.02% NH₄OH in H₂O:ACN elution) provided the title compound (50 mg, 0.11 mmol) as a white solid. ¹H NMR (400 MHz, DMSO-d₆) δ 8.05 (m, 2H), 7.36-7.48 (m, 1H), 7.21-7.35 (m, 3H), 6.9-6.94 (m, 1H), 6.92-6.49 (s, 1H), 6.05 (s, 2H), 4.3-4.62 (m, 2H), 2.93 (t, 2H), 2.41-2.43 (m, 2H), 2.07-2.15 (m, 2H), 1.79-1.93 (m, 4H), 1.57-1.35 (m, 2H); m/z=468.25 [M+H]⁺; $t_R$=1.30 min (LCMS method j)

Example 76: 9-(2-amino-6-(trifluoromethyl)pyrimidin-4-yl)-1-(3,4-difluorophenyl)-1,9-diazaspiro[5.5]undecan-2-one

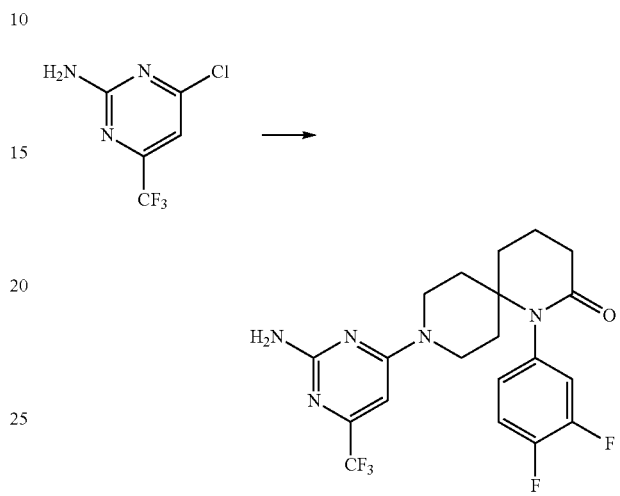

A mixture of 1-(3,4-difluorophenyl)-1,9-diazaspiro[5.5]undecane-2-one (Intermediate A, 50 mg, 0.18 mmol), 4-chloro-6-(trifluoromethyl)pyrimidin-2-amine (49 mg, 0.25 mmol) and cesium carbonate (106 mg, 0.325 mmol) in DMF (0.7 mL) was heated at 50° C. for three hours. The reaction was cooled to RT, diluted with water, extracted with DCM, dried over magnesium sulfate and concentrated. Purification by reverse phase chromatography (RediSep® Rf Gold® Reversed Phase C18 50 g column, 0-100% ACN in water) provided the title compound (55 mg, 0.125 mmol) as a white solid. 1H NMR (400 MHz) δ 7.38-7.22 (m, 1H), 7.17-7.03 (m, 1H), 6.98-6.85 (m, 1H), 6.65 (s, 1H), 4.43 (s, 2H), 3.20 (t, J=13.6 Hz, 2H), 2.58 (t, J=6.9 Hz, 2H), 2.26 (d, J=7.8 Hz, 2H), 2.10-1.89 (m, 4H), 1.75 (s, 2H); m/z=242.3 [M+H]⁺; $t_R$=0.88 min (LCMS method h)

Example 77: 9-(2-amino-6-(perfluoroethyl)pyrimidin-4-yl)-1-(3,4-difluorophenyl)-1,9-diazaspiro[5.5]undecane-2-one

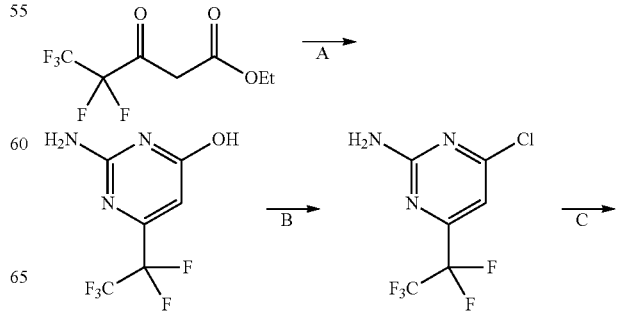

147

-continued

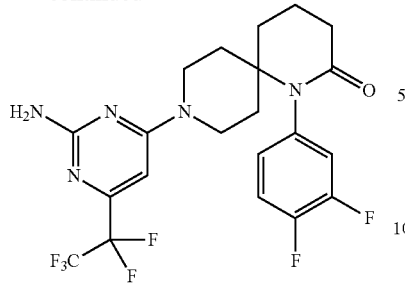

Step A: 2-amino-6-(perfluoroethyl)pyrimidine-4-ol

A mixture of ethyl 4,4,5,5,5-pentafluoro-3-oxopentanoate (3.00 g, 12.8 mmol), guanidine hydrochloride (3.65 g, 38.4 mmol) and NaOMe (1.30 g, 24.0 mmol) in MeOH (10 mL) were stirred at 80° C. for 12 h. Water was added to the reaction mixture and it was extracted with EtOAc. The extracts were washed with brine, dried over $Na_2SO_4$, filtered, and concentrated under reduced pressure to provide 2-amino-6-(perfluoroethyl)pyrimidine-4-ol as gummy brown mass (2.645 g). The crude product was taken further without purification. m/z=230.2 $[M+H]^+$ Step B:
4-chloro-6-(perfluoroethyl)pyrimidine-2-amine A mixture of $POCl_3$ (39 mL, 30 v) and 2-amino-6-(perfluoroethyl)pyrimidine-4-ol (1.30 g, 5.67 mmol) was refluxed at 100° C. for 12 h. After cooling to RT, aqueous $NaHCO_3$ was added and the mixture extracted with EtOAc. The extracts were washed with brine, dried over $Na_2SO_4$, filtered, and concentrated under reduced pressure. Purification by silica gel chromatography (8-12% EtOAc in hexane) provided 4-chloro-6-(perfluoroethyl)pyrimidine-2-amine (0.180 g, 0.728 mmol) as a yellow liquid. m/z=248.1 $[M+H]^+$ Step C: 9-(2-amino-6-(perfluoroethyl)pyrimidin-4-yl)-1-(3,4-difluorophenyl)-1,9-diazaspiro[5.5]undecane-2-one A mixture of 4-chloro-6-(perfluoroethyl)pyrimidine-2-amine (0.180 g, 0.725 mmol), 1-(3,4-difluorophenyl)-1,9-diazaspiro[5.5]undecane-2-one (Intermediate A, 0.163 g, 0.581 mmol) and DIPEA (0.38 mL, 2.2 mmol) in EtOH (5 mL) were stirred at 80° C. for 12 h. Water was added to the reaction mixture and it was extracted with EtOAc. The extracts were washed with brine, dried over $Na_2SO_4$, filtered, and concentrated under reduced pressure. Purification by preparative HPLC (Waters Xbridge, 5 μm, 20×150 mm; 0.02% $NH_4OH$ in $H_2O$:ACN elution) provided the title compound (16 mg, 0.033 mmol) as a white solid. $^1$H NMR (300 MHz, DMSO-$d_6$) δ 7.42 (m, 1H), 7.24 (m, 1H), 6.97-6.84 (m, 1H), 6.55 (s, 2H), 6.33 (s, 1H), 2.97 (m, 2H), 2.42 (t, 4H), 2.12 (m, 2H), 1.86 (d, 4H), 1.49 (m, 2H); m/z=492.4 $[M+H]^+$; $t_R$=2.12 min (LCMS method 1)

148

Example 78: 9-(2-amino-6-(1,1,2,2-tetrafluoroethyl)pyrimidin-4-yl)-1-(3,4-difluorophenyl)-1,9-diazaspiro[5.5]undecan-2-one

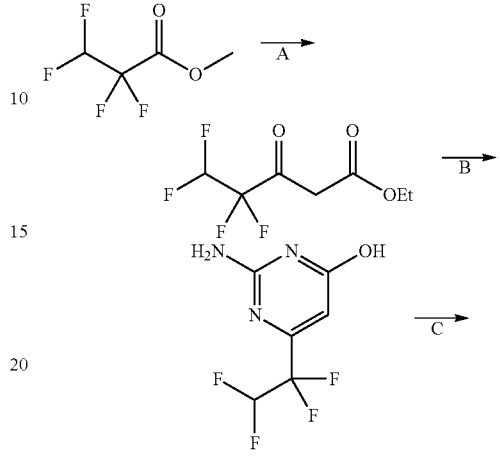

Step A: ethyl 4,4,5,5-tetrafluoro-3-oxopentanoate

NaH (1.125 g, 46.88 mmol) was added to a stirred solution of methyl 2,2,3,3-tetrafluoropropanoate (2.50 g, 15.6 mmol) in EtOAc (10 mL). The reaction mixture was refluxed at 70° C. for 12 hours. Water was added to the reaction mixture and it was extracted with EtOAc. The extracts were washed with brine, dried over $Na_2SO_4$, filtered, and concentrated under reduced pressure to provide the crude product as yellow liquid (4.361 g). The crude was taken on to the next step without purification. m/z=215.1 $[M+H]^+$ Step B:
2-amino-6-(1,1,2,2-tetrafluoroethyl)pyrimidin-4-ol A mixture of ethyl 4,4,5,5-tetrafluoro-3-oxopentanoate (2.00 g, 9.24 mmol), guanidine hydrochloride (2.638 g, 27.77 mmol) and NaOMe (0.749 g, 13.9 mmol) in MeOH (20 mL) were stirred at 80° C. for 12 h. Water was added to the reaction mixture and it was extracted with EtOAc. The extracts were washed with brine, dried over $Na_2SO_4$, filtered, and concentrated under reduced pressure. Washing the resulting solids with pentane and EtOAc provided 2-amino-6-(1,1,2,2-tetrafluoroethyl)pyrimidin-4-ol (0.728 g, 3.45 mmol) as a yellow solid. m/z=212.05 $[M+H]^+$ Step C: 9-(2-amino-6-(1,1,2,2-tetrafluoroethyl)pyrimidin-4-yl)-1-(3,4-difluorophenyl)-1,9-diazaspiro[5.5]undecan-2-one A mixture of 2-amino-6-(1,1,2,2-tetrafluoroethyl)pyrimidin-4-ol (0.200 g, 0.947 mmol), 1-(3,4-difluorophenyl)-1,9- diazaspiro[5.5]undecane-2-one (Intermediate A, 0.265 g, 0.947 mmol), PyBrop (0.485 g, 1.04 mmol) and TEA (0.40 mL, 2.8 mmol) in MeCN (4 mL) were heated at 80° C. for 24 h. Water was added to the reaction mixture and it was extracted with EtOAc. The extracts were washed with brine, dried over $Na_2SO_4$, filtered, and concentrated under reduced pressure. Purification by silica gel chromatography (EtOAc elution) provided the title compound as a pale yellow solid (0.231 g, 0.489 mmol). $^1$H NMR (400 MHz, DMSO-$d_6$) δ 7.41 (m, 1H), 7.23 (m, 1H), 6.90-6.92 (m, 1H), 6.42-6.7 (m, 3H), 6.27 (s, 1H), 4.25 (brs, 2H), 2.97 (t, 2H), 2.42 (t, 2H), 2.19-2.05 (m, 2H), 1.93-1.75 (m, 4H), 1.58-1.38 (m, 2H); m/z=474.2 [M+H]$^+$; $t_R$=1.28 min (LCMS method j)

Example 79: 1-(3,4-difluorophenyl)-9-(2-(hydroxynethyl)-6-(perfluoroethyl)pyrimidin-4-yl)-1,9-diazaspiro[5.5]undecane-2-one

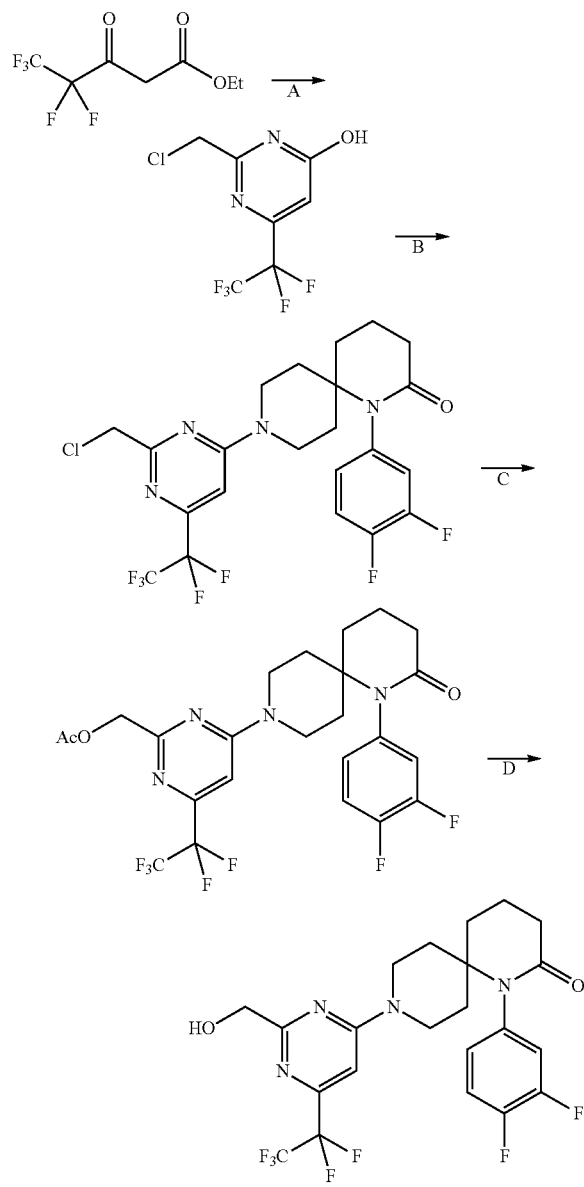

Step A:
2-(Chloromethyl)-6-(perfluoroethyl)pyrimidine-4-ol

A mixture of ethyl 4,4,5,5,5-pentafluoro-3-oxopentanoate (5.0 g, 21 mmol), 2-chloroacetimidamide hydrochloride (5.89 g, 45.7 mmol) and NaOMe (1.73 g, 32.0 mmol) in MeOH (20 mL) were stirred at 80° C. for 12 h. Water was added to the reaction mixture and it was extracted with EtOAc. The extracts were washed with brine, dried over $Na_2SO_4$, filtered, and concentrated under reduced pressure. Purification by silica gel chromatography (35-40% EtOAc in hexane) provided 2-(chloromethyl)-6-(perfluoroethyl)pyrimidine-4-ol as an orange solid (0.254 g, 0.977 mmol). m/z=260.95, [M+H]$^+$ Step B: 9-(2-(chloromethyl)-6-(perfluoroethyl)pyrimidin-4-yl)-1-(3,4-difluorophenyl)-1,9-diazaspiro[5.5]undecane-2-one A mixture of 2-(chloromethyl)-6-(perfluoroethyl)pyrimidine-4-ol (0.100 g, 0.381 mmol), 1-(3,4-difluorophenyl)-1,9-diazaspiro[5.5]undecane-2-one (Intermediate A, 0.106 g, 0.381 mmol), PyBrop (0.266 g, 0.571 mmol) and TEA (0.16 mL, 1.1 mmol) in dioxane (5 mL) was stirred at RT for 12 h. Water was added to the reaction mixture and it was extracted with EtOAc. The extracts were washed with brine, dried over $Na_2SO_4$, filtered, and concentrated under reduced pressure. Purification by preparative TLC by eluting with EtOAc provided 9-(2-(chloromethyl)-6-(perfluoroethyl)pyrimidin-4-yl)-1-(3,4-difluorophenyl)-1,9-diazaspiro[5.5]undecane-2-one as a yellow solid (0.091 g, 1.91 mmol). m/z=525.1 [M+H]$^+$ Step C: (4-(1-(3,4-difluorophenyl)-2-oxo-1,9-diazaspiro[5.5]undecane-9-yl)-6-(perfluoroethyl)pyrimidin-2-yl)methylacetate KOAc (0.044 g, 0.458 mmol) was added to a stirred solution of 9-(2-(chloromethyl)-6-(perfluoroethyl)pyrimidin-4-yl)-1-(3,4-difluorophenyl)-1,9-diazaspiro[5.5]undecane-2-one (0.080 g, 0.152 mmol) in DMF (4 mL). The reaction mixture was allowed to stir at RT for 12 h. Cold water was added to the reaction mixture and it was extracted with EtOAc. The extracts were washed with brine, dried over $Na_2SO_4$, filtered, and concentrated under reduced pressure to provide (4-(1-(3,4-difluorophenyl)-2-oxo-1,9-diazaspiro[5.5]undecane-9-yl)-6-(perfluoroethyl)pyrimidin-2-yl)methylacetate (0.045 g, 0.082 mmol) as a sticky yellow solid which was taken to the next step without purification. m/z=549.1 [M+H]$^+$; $t_R$=1.55 min (LCMS method j).

Step D: 1-(3,4-difluorophenyl)-9-(2-(hydroxynethyl)-6-(perfluoroethyl)pyrimidin-4-yl)-1,9-diazaspiro[5.5]undecane-2-one NaOMe (6 mg, 0.116 mmol) was added to a stirred solution of (4-(1-(3,4-difluorophenyl)-2-oxo-1,9-diazaspiro[5.5]undecane-9-yl)-6-(perfluoroethyl)pyrimidin-2-yl)methylacetate (0.080 g, 0.15 mmol) in MeOH (4 mL). The reaction mixture was allowed to stir at RT for 12 h. Water was added to the reaction mixture and it was extracted with EtOAc. The extracts were washed with brine, dried over $Na_2SO_4$, filtered, and concentrated under reduced pressure. Purification by preparative TLC by eluting with EtOAc provided the title compound (19 mg, 0.038 mmol) as an off-white solid. $^1$H NMR (300 MHz, DMSO-$d_6$) δ 7.40 (m, 1H), 7.24 (m, 1H), 7.02 (s, 1H), 6.89-6.92 (m, 1H), 5.02 (t, 1H), 4.33 (d, 2H), 3.06 (brs, 2H), 2.41 (t, 2H), 2.10 (d, 2H), 1.97-1.74 (m, 4H), 1.4-1.58 (m, 2H); m/z=507.1 [M+H]$^+$; $t_R$=1.48 min (LCMS method j).

Example 80: 1-(3,4-difluorophenyl)-9-(2-(2-hydroxypropan-2-yl)-6-(trifluoromethyl)pyrimidin-4-yl)-1,9-diazaspiro[5.5]undecan-2-one

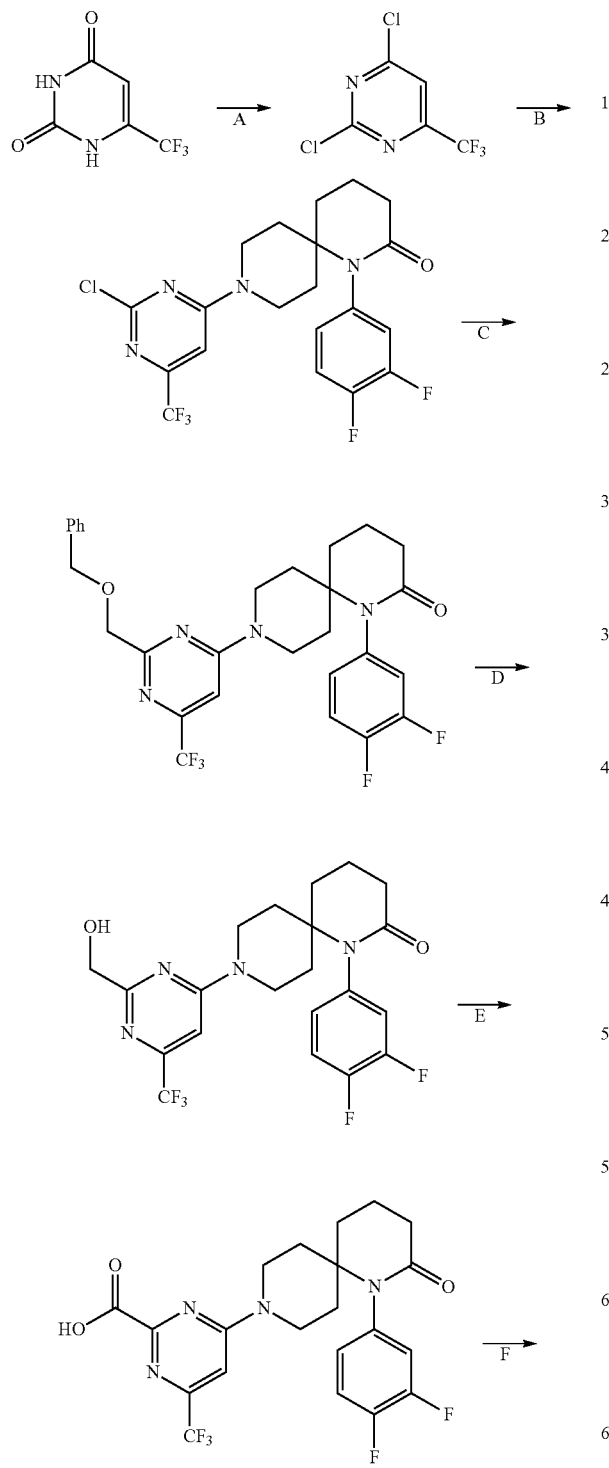

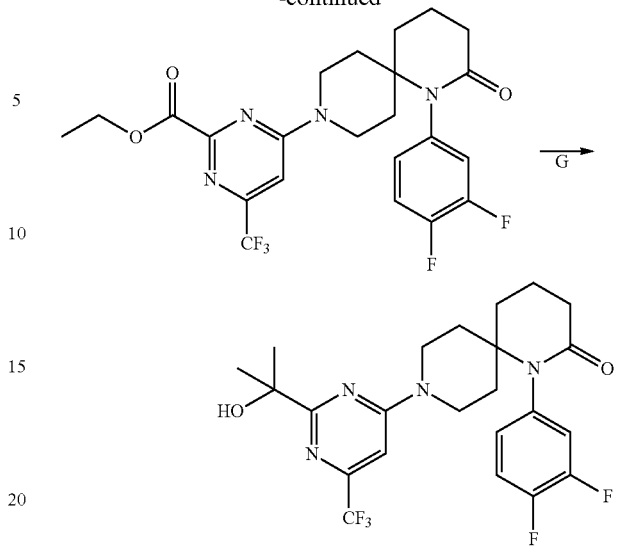

Step A: 2,4-dichloro-6-(trifluoromethyl)pyrimidine

A mixture of 6-(trifluoromethyl)pyrimidine-2,4(1H,3H)-dione (5.00 g, 27.7 mmol), N,N-dimethylaniline (0.260 g, 25.0 mmol) and POCl$_3$ (15.7 g, 103 mmol) in MeCN (25 mL) was heated at 80° C. for 6 h. After cooling to RT, the reaction mixture was concentrated under reduced pressure, diluted with water and extracted with EtOAc twice. The combined organic layers were dried over Na$_2$SO$_4$, filtered, and concentrated under reduced pressure to provide crude 2,4-dichloro-6-(trifluoromethyl)pyrimidine as brown oil (6.0 g) which was used for the next step without further purification.

Step B: 9-(2-chloro-6-(trifluoromethyl)pyrimidin-4-yl)-1-(3,4-difluorophenyl)-1,9-diazaspiro[5.5]undecan-2-one A mixture of 1-(3,4-difluorophenyl)-1,9-diazaspiro[5.5]undecan-2-one (Intermediate A, 1.50 g, 5.35 mmol), 2,4-dichloro-6-(trifluoromethyl)pyrimidine (1.16 g, 5.35 mmol) and DIPEA (2.8 mL, 16 mmol) in EtOH (20 mL) was heated at 80° C. for 16 h. After cooling to RT, the reaction mixture was diluted with water and extracted twice with EtOAc. The organic layers were combined, washed with brine, dried over Na$_2$SO$_4$, filtered, and concentrated under reduced pressure. Purification by silica gel chromatography (4-12% in MeOH in DCM) provided 9-(2-chloro-6-(trifluoromethyl)pyrimidin-4-yl)-1-(3,4-difluorophenyl)-1,9-diazaspiro[5.5]undecan-2-one as an off-white solid (1.37 g). m/z=461.00 [M+H]$^+$

Step C: 9-(2-((benzyloxy)methyl)-6-(trifluoromethyl)pyrimidin-4-yl)-1-(3,4-difluorophenyl)-1,9-diazaspiro[5.5]undecan-2-one To a stirred solution of 9-(2-chloro-6-(trifluoromethyl)pyrimidin-4-yl)-1-(3,4-difluorophenyl)-1,9-diazaspiro[5.5]undecan-2-one (0.65 g, 1.4 mmol) in dioxane (4 mL) and water (4 mL) was added potassium benzyloxymethyltrifluoroborate (0.97 g, 4.2 mmol) and Cs$_2$CO$_3$ (1.4 g, 4.2 mmol). The reaction mixture was purged with argon for 5 min. CataCXium-A® (0.10 g, 0.28 mmol) and Pd(OAc)$_2$ (0.032 g, 0.14 mmol) was added and the argon purging continued for 5 min. The reaction mixture was heated at 120° C. for 18 h. The reaction mixture was cooled to RT, diluted with water and extracted with EtOAc twice. The combined organic layers were washed with brine, dried over Na$_2$SO$_4$, filtered, and concentrated under reduced pressure. Purification by silica gel chromatography (12-65% EtOAc in hexane) provided 9-(2-((benzyloxy)methyl)-6-(trifluoromethyl)pyrimidin-4-yl)-1-(3,4-difluorophenyl)-1,9-diazaspiro[5.5]undecan-2-one (1.36 g). m/z=547.2 [M+H]$^+$ Step D: 1-(3,4-difluorophenyl)-9-(2-(hydroxymethyl)-6-(trifluoromethyl)pyrimidin-4-yl)-1,9-diazaspiro[5.5]undecan-2-one A mixture of 9-(2-((benzyloxy)methyl)-6-(trifluoromethyl)pyrimidin-4-yl)-1-(3,4-difluorophenyl)-1,9-diazaspiro[5.5]undecan-2-one (1.36 g) and Pd(OH)$_2$ (2.72 g) in EtOH (40 mL) was placed under at atmosphere of hydrogen (1 atm, balloon) for 18 h. The reaction mixture was purged with nitrogen, filtered through a celite bed, washed with EtOAc and the clear filtrate was concentrated under reduced pressure. Purification by silica gel chromatography (4-12% MeOH in DCM) provided 1-(3,4-difluorophenyl)-9-(2-(hydroxymethyl)-6-(trifluoromethyl)pyrimidin-4-yl)-1,9-diazaspiro[5.5]undecan-2-one as an off-white solid (0.61 g, 1.1 mmol). m/z=547.1 [M+H]$^+$ Step E: 4-(1-(3,4-difluorophenyl)-2-oxo-1,9-diazaspiro[5.5]undecan-9-yl)-6-(trifluoromethyl)pyrimidine-2-carboxylic acid Jones reagent (1.8 mL) was added to a stirred solution of 1-(3,4-difluorophenyl)-9-(2-(hydroxymethyl)-6-(trifluoromethyl)pyrimidin-4-yl)-1,9-diazaspiro[5.5]undecan-2-one (0.33 g, 0.72 mmol) in acetone (7 mL). The reaction mixture was stirred at RT for 2 h followed by addition of isopropanol (1.5 mL). The reaction mixture was diluted with water and extracted with EtOAc twice. The combined organic extracts were washed with brine, dried over Na$_2$SO$_4$, filtered, and concentrated under reduced pressure to provide crude 4-(1-(3,4-difluorophenyl)-2-oxo-1,9-diazaspiro[5.5]undecan-9-yl)-6-(trifluoromethyl)pyrimidine-2-carboxylic acid (0.230 g, 0.489 mmol) which was used for the next step without purification.

Step F: ethyl 4-(1-(3,4-difluorophenyl)-2-oxo-1,9-diazaspiro[5.5]undecan-9-yl)-6-(trifluoromethyl)pyrimidine-2-carboxylate A mixture of 4-(1-(3,4-difluorophenyl)-2-oxo-1,9-diazaspiro[5.5]undecan-9-yl)-6-(trifluoromethyl)pyrimidine-2-carboxylic acid (0.230 g, 0.489 mmol), Cs$_2$CO$_3$ (0.160 g, 0.489 mmol) and ethyl iodide (0.060 mL, 0.73 mmol) in DMF (6 mL) was stirred at RT for 16 h. The reaction mixture was diluted with water and extracted with EtOAc. The organic extracts were washed with brine, dried over Na$_2$SO$_4$, filtered, and concentrated under reduced pressure to provide ethyl 4-(1-(3,4-difluorophenyl)-2-oxo-1,9-diazaspiro[5.5]undecan-9-yl)-6-(trifluoromethyl)pyrimidine-2-carboxylate as gummy brown liquid. (0.21 g, 0.42 mmol). m/z=499.1 [M+H]$^+$ Step G: 1-(3,4-difluorophenyl)-9-(2-(2-hydroxypropan-2-yl)-6-(trifluoromethyl)pyrimidin-4-yl)-1,9-diazaspiro[5.5]undecan-2-one A stirred solution of ethyl 4-(1-(3,4-difluorophenyl)-2-oxo-1,9-diazaspiro[5.5]undecan-9-yl)-6-(trifluoromethyl)pyrimidine-2-carboxylate (0.21 g, 0.42 mmol) in THF (10 mL) was cooled to 0° C. and treated with MeMgBr (3.0 M in ether, 4 mL, 12 mmol). The reaction temperature was raised to RT and stirring continued for 18 h. The reaction mixture was quenched with saturated aqueous NH$_4$Cl and extracted with EtOAc twice. The combined extracts were washed with brine, dried over Na$_2$SO$_4$, filtered, and concentrated under reduced pressure. Purification by preparative HPLC (LUNA OMEGA, 5.0μ, 21.2×250 mm; water/ACN elution) provided the title compound as an off-white solid (5 mg, 0.010 mmol). $^1$H NMR (400 MHz, DMSO-d$_6$) δ 7.28-7.45 (m, 1H), 7.23-7.27 (m, 1H), 7.03 (s, 1H), 6.93 (d, 1H), 3.07 (brs, 2H), 2.43 (t, 2H), 2.14 (brs, 2H), 1.84-1.93 (m, 4H), 1.5-1.62 (m, 2H), 1.37 (s, 6H). 2 protons obscured by DMSO peak; m/z=485.2 [M+H]$^+$; t$_R$=1.54 min (LCMS method j).

Example 81: 1-(4-chloro-3-fluorophenyl)-9-(4-(2,2,2-trifluoroethoxy)pyridin-2-yl)-1,9-diazaspiro[5.5]undecan-2-one

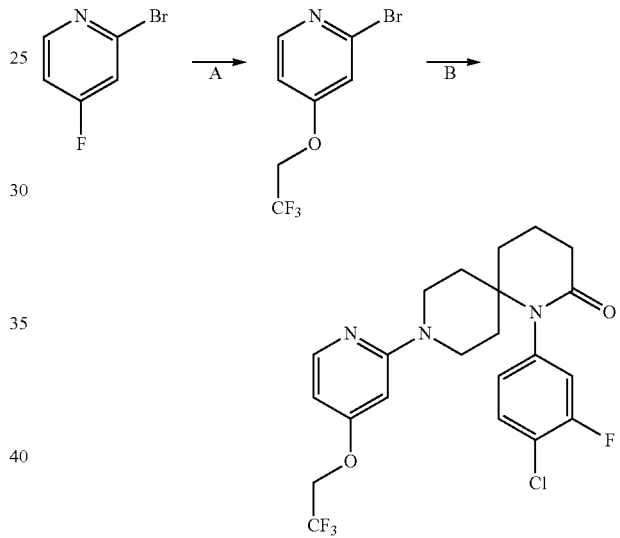

Step A: 2-bromo-4-(2,2,2-trifluoroethoxy)pyridine

A solution of NaOtBu (0.529 g, 5.50 mmol) in DMSO (3 mL) was added dropwise to a solution of 2-bromo-4-fluoropyridine (0.52 mL, 5 mmol) and 2,2,2-trifluoroethanol (0.54 mL, 7.5 mmol) in 1 mL of DMSO. The reaction mixture was stirred for 2 h at RT, quenched with ice water, and extracted with DCM. The combined organic extracts were carefully evaporated (the product is volatile). The crude product was purified by silica gel chromatography (0-50% EtOAc in cyclohexane) providing 2-bromo-4-(2,2,2-trifluoroethoxy)pyridine (1.02 g, 3.78 mmol) as a colorless liquid. $^1$H NMR (400 MHz, DMSO-d$_6$) δ=8.28 (d, 1H), 7.45 (d, 1H), 7.19 (dd, 1H), 4.97 (q, 2H) ppm; m/z=256.1 [M+H]$^+$; t$_R$=0.96 min (LCMS method a).

Step B: 1-(4-chloro-3-fluorophenyl)-9-(4-(2,2,2-trifluoroethoxy)pyridin-2-yl)-1,9-diazaspiro[5.5]undecan-2-one 1-(4-Chloro-3-fluorophenyl)-1,9-diazaspiro[5.5]undecan-2-one (Intermediate A) (119 mg, 0.40 mmol) and NaOtBu (67 mg, 0.70 mmol) were stirred in toluene (3 mL) for 15 min. 2-Bromo-4-(2,2,2-trifluoroethoxy)pyridine (138 mg, 0.540 mmol) and bis(tri-tert-butylphosphine)palladium (0) (10 mg, 0.020 mmol) were added to the white suspension and the mixture was heated for 1 h at 90° C. After cooling to RT the reaction was filtered over celite and the filtrate concentrated. Purification by SFC (Reprosphere PEI 100 Å, 5 μm, 30×250 mm; 6-16% MeOH in $CO_2$ over 10 min) provided the title compound (97 mg, 0.20 mmol) as a white foam. $^1$H NMR (400 MHz, DMSO-$d_6$) δ=7.91 (d, 1H), 7.59 (dd, 1H), 7.24 (dd, 1H), 6.98 (dd, 1H), 6.33 (m, 2H), 4.77 (q, 2H), 4.07-4.18 (m, 2H), 2.89 (m, 2H), 2.44 (t, 2H), 2.12 (m, 2H), 1.84-1.88 (m, 4H) 1.51-1.59 (m, 2H) ppm; m/z=472.4 [M+H]$^+$; $t_R$=0.98 min (LCMS method a).

Example 82: 1-(3,4-difluorophenyl)-9-(6-(2,2,2-trifluoroethoxy)pyrimidin-4-yl)-1,9-diazaspiro[5.5]undecan-2-one

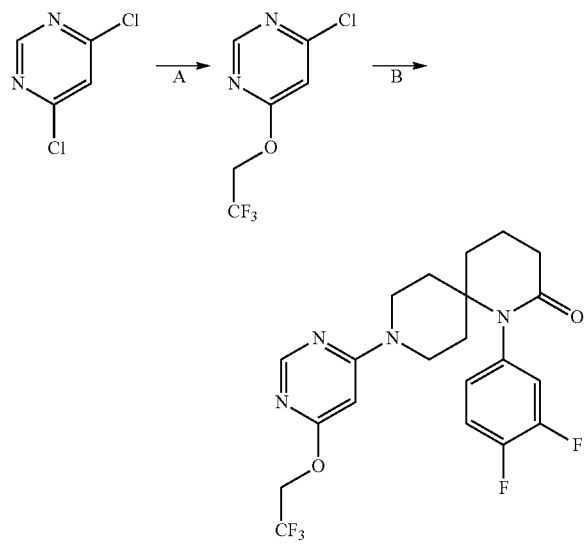

Step A: 4-chloro-6-(2,2,2-trifluoroethoxy)pyrimidine

NaH (60% in mineral oil, 831 mg, 20.8 mmol) was added in portions to a stirred solution of 4,6-dichloropyrimidine (1.769 g, 11.88 mmol) and 2,2,2-trifluoroethanol (1.0 g, 9.9 mmol) in THF (100 mL) at 0° C. The reaction mixture was allowed to warm to RT and stir overnight. The reaction mixture was quenched with saturated $NH_4Cl$ solution, diluted with EtOAc and extracted twice with EtOAc. The combined organic layers were dried over $Na_2SO_4$, filtered, and concentrated. Purification by silica gel chromatography (0-7% EtOAc in cyclohexane) provided 4-chloro-6-(2,2,2-trifluoroethoxy)pyrimidine (1.51 g, 6.75 mmol). $^1$H NMR (400 MHz, DMSO-$d_6$) δ=8.77 (s, 1H), 7.44 (s, 1H), 5.12 (q, 2H) ppm; m/z=213.0 [M+H]$^+$; $t_R$=0.96 min (LCMS method a).

Step B: 1-(3,4-difluorophenyl)-9-(6-(2,2,2-trifluoroethoxy)pyrimidin-4-yl)-1,9-diazaspiro[5.5]undecan-2-one 1-(3,4-difluorophenyl)-1,9-diazaspiro[5.5]undecan-2-one (Intermediate A, 750 mg, 2.68 mmol), 4-chloro-6-(2,2,2-trifluoroethoxy)pyrimidine (1.137 g, 3.75 mmol) and triethylamine (1.12 mL, 8.03 mmol) were dissolved EtOH (10 mL) and heated under microwave irradiation for 30 min at 160° C. After cooling to RT, the reaction mixture was concentrated. Purification by silica gel chromatography (0-10% MeOH in DCM) provided the title compound (667 mg, 2.26 mmol). $^1$H NMR (400 MHz, DMSO-$d_6$) δ=8.20 (s, 1H), 7.41 (m, 1H), 7.23 (m, 1H), 6.87-6.94 (m, 1H), 6.18 (s, 1H), 4.93 (q, 2H), 4.11-4.34 (m, 2H), 2.99 (br t, 2H), 2.42 (t, 2H), 2.12 (m, 2H), 1.80-1.90 (m, 4H) 1.42-1.56 (m, 2H) ppm; m/z=457.2 [M+H]$^+$; $t_R$=1.07 min (LCMS method a).

By employing similar methods as described for the preparation of Example 82, using appropriate starting materials, the following compounds were prepared:

| Ex | Structure and Name | MS, m/z [M + H]$^+$; $t_R$, method | $^1$H NMR |
|---|---|---|---|
| 83 | 1-(4-chloro-3-fluorophenyl)-9-(6-(2,2,2-trifluoroethoxy)pyrimidin-4-yl)-1,9-diazaspiro[5.5]undecan-2-one | 473.3; 1.14 min, LCMS method a | $^1$H NMR (400 MHz, DMSO-$d_6$) δ = 8.21 (s, 1H), 7.59 (dd, 1H), 7.24 (dd, 1H), 6.95 (d, 1H), 6.19 (s, 1H), 4.94 (q, 2H), 4.14-4.32 (m, 2H), 2.99 (brt, 2H), 2.43 (t, 2H), 2.14 (m, 2H), 1.86 (m, 4H) 1.50 (m, 2H). ppm. |

-continued

| Ex | Structure and Name | MS, m/z [M + H]+; $t_R$, method | 1H NMR |
|---|---|---|---|
| 84 | 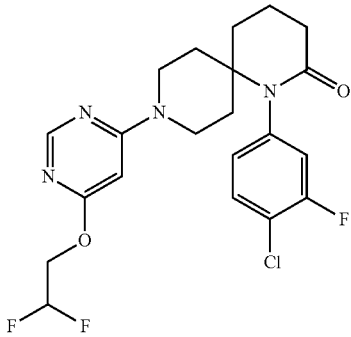 [SMILES: O=C1CCCC2(CCN(c3cc(OCC(F)F)ncn3)CC2)N1c1ccc(Cl)c(F)c1]  1-(4-chloro-3-fluorophenyl)-9-(6-(2,2-difluoroethoxy)pyrimidin-4-yl)-1,9-diazaspiro[5.5]undecan-2-one | 455.2; 1.05 min, LCMS method a | 1H NMR (400 MHz, DMSO-$d_6$) δ = 8.19 (s, 1H), 7.58 (t, 1H), 7.23 (dd, 1H), 6.95 (d, 1H), 6.31 (m, 1H), 6.12 (s, 1H), 4.51 (dt, 2H), 4.48 (m, 2H), 2.98 (br t, 2H), 2.43 (t, 2H), 2.13 (m, 2H), 1.86 (m, 4H) 1.53-1.50 (m, 2H). ppm. |
| 85 | 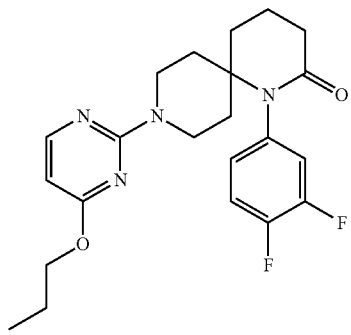 [SMILES: CCCOc1ccnc(N2CCC3(CCCC(=O)N3c3ccc(F)c(F)c3)CC2)n1]  1-(3,4-difluorophenyl)-9-(4-propoxypyrimidin-2-yl)-1,9-diazaspiro[5.5]undecan-2-one | 417.3; 0.68 min, LCMS method i | 1H NMR (400 MHz, DMSO-d6) δ 8.00 (d, J = 5.8 Hz, 1H), 7.42 (dt, J = 10.8, 9.0 Hz, 1H), 7.23 (ddd, J = 11.4, 7.5, 2.5 Hz, 1H), 6.92 (ddd, J = 8.3, 4.2, 2.1 Hz, 1H), 5.98 (d, J = 5.8 Hz, 1H), 4.58-4.41 (m, 2H), 4.15 (t, J = 6.6 Hz, 2H), 2.97 (td, J = 13.3, 2.5 Hz, 2H), 2.43 (t, J = 6.8 Hz, 2H), 2.14 (s, 2H), 1.95-1.77 (m, 4H), 1.66 (h, J = 7.1 Hz, 2H), 1.49 (td, J = 13.5, 4.9 Hz, 2H), 0.91 (t, J = 7.4 Hz, 3H). |

-continued

| Ex | Structure and Name | MS, m/z [M + H]+; $t_R$, method | ¹H NMR |
|---|---|---|---|
| 86 | 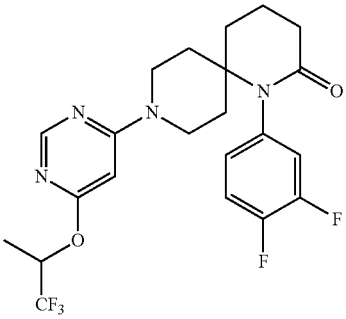 [SMILES: CC(Oc1cc(N2CCC3(CCCC(=O)N3c3ccc(F)c(F)c3)CC2)ncn1)C(F)(F)F]<br>rac-1-(3,4-dfluorophenyl)-9-(6-((1,1,1-trifluoropropan-2-yl)oxy)pyrimidin-4-yl)-1,9-diazaspiro[5.5]undecan-2-one | 471.2; 0.68 min, LCMS method i | ¹H NMR (400 MHz, chloroform-d) δ 8.22 (s, 1H), 7.17 (m, 1H), 6.89 (m, 1H), 6.76-6.78 (m, 1H), 5.81 (s, 1H), 5.73 (m, 1H), 4.22 (t, 2H), 3.05-2.89 (m, 2H), 2.61 (t, 2H), 2.13-2.15 (m, 2H), 1.93-1.98 (m, 2H), 1.85-1.71 (m, 4H), 1.44 (d, 3H). |
| 87 | 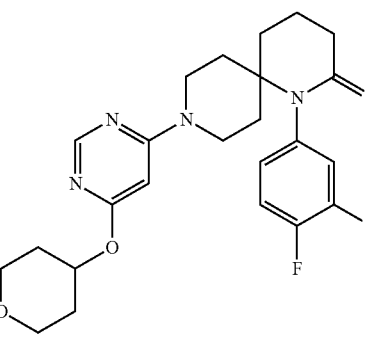<br>1-(3,4-difluorophenyl)-9-(6-((tetrahydro-2H-pyran-4-yl)oxy)pyrimidin-4-yl)-1,9-diazaspiro[5.5]undecan-2-one | 459.4; 1.94 min, LCMS method k | ¹H NMR (400 MHz, methanol-d₄) δ 8.11 (s, 1H), 7.44-7.36 (m, 1H), 7.28-7.2 (m, 1H), 6.92 (m, 1H), 5.98 (s, 1H), 5.28-5.15 (m, 1H), 4.24-4.1 (m, 2H), 3.83-3.79 (m, 2H), 3.43 (t, 2H), 2.93 (t, 2H), 2.41 (t, 2H), 2.12 (br, 2H), 1.98-1.8 (m, 6H), 1.6-1.41 (m, 4H). |
| 88 | 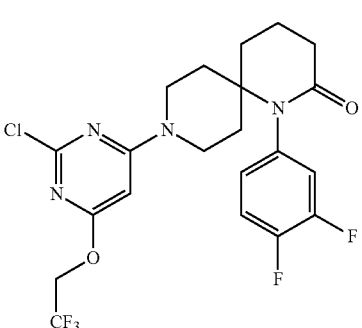<br>9-(2-chloro-6-(2,2,2-trifluoroethoxy)pyrimidin-4-yl)-1-(3,4-difluorophenyl)-1,9-diazaspiro[5.5]undecan-2-one | 491.08; 0.71 min, LCMS method i | 1H NMR (DMSO-d₆, 300 MHz) δ 7.46-7.40 (m, 1H), 7.28-7.2 (m, 1H), 6.93-6.91 (m, 1H), 6.29 (s, 1H), 4.98 (q, 2H), 4.4 (br, 2H), 3.04 (t, 2H), 2.43 (t, 2H), 2.13 (br, 2H), 1.9-1.83 (m, 4H), 1.48 (br, 2H). |

Example 89a: (S)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one or (R)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one, and Example 89b: (R)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one or (S)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one

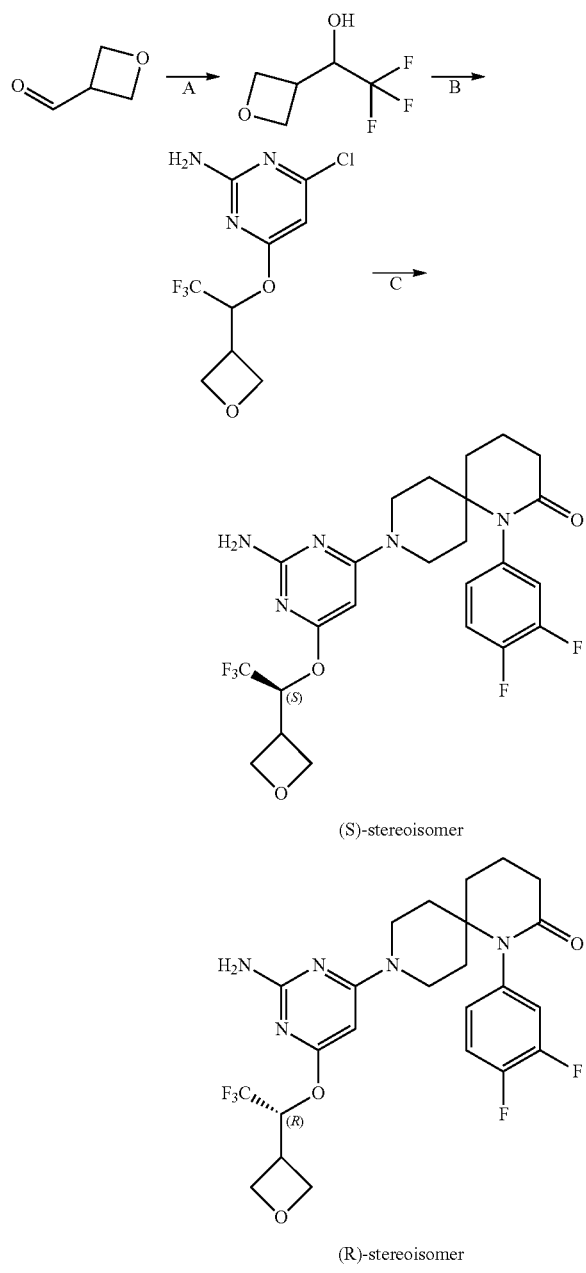

Step A: 2,2,2-trifluoro-1-(oxetan-3-yl)ethan-1-ol

A solution of oxetane-3-carbaldehyde (1.80 g, 20.9 mmol) in THF (8 mL) was cooled to −70° C. and treated with trimethyl(trifluoromethyl)silane (5.94 g, 41.8 mmol) followed by tetrabutylammonium fluoride (5.46 g, 20.9 mmol). The reaction was warmed to RT, and stirred for 3 h. The reaction mixture was diluted with water, and extracted twice with EtOAc. The combined organic layers were washed with brine solution, dried over anhydrous $Na_2SO_4$, filtered, and concentrated under reduced pressure to afford 2,2,2-trifluoro-1-(oxetan-3-yl)ethan-1-ol (2.8 g, crude).

Step B: 4-chloro-6-(2,2,2-trifluoro-1-(oxetan-3-yl)ethoxy)pyrimidin-2-amine

A stirred solution of 4,6-dichloropyrimidin-2-amine (2.20 g, 13.4 mmol) and 2,2,2-trifluoro-1-(oxetan-3-yl)ethan-1-ol (2.72 g, 17.4 mmol) in 1,4-dioxane (10 mL) was treated with $Cs_2CO_3$ (13.11 g, 40.24 mmol). The reaction mixture was heated to 80° C. for 12 h. The reaction mixture was cooled to RT, diluted with water, and extracted twice with EtOAc. The combined organic layers were washed with brine, dried over anhydrous $Na_2SO_4$, filtered, and concentrated under reduced pressure. Purification by silica gel chromatography (1% MeOH in DCM) provided 4-chloro-6-(2,2,2-trifluoro-1-(oxetan-3-yl)ethoxy)pyrimidin-2-amine (2.10 g, 55.2%). m/z=284.0, [M−H]$^+$; $t_R$=1.45 min (LCMS method 1)

Step C: 9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one A stirred solution of 4-chloro-6-(2,2,2-trifluoro-1-(oxetan-3-yl)ethoxy)pyrimidin-2-amine (0.303 g, 1.07 mmol) and 1-(3,4-difluorophenyl)-1,9-diazaspiro[5.5]undecan-2-one (Intermediate A, 0.300 g, 1.07 mmol) was treated with $Cs_2CO_3$ (1.04 g, 3.21 mmol). The reaction mixture was heated to 80° C. for 15 h. The mixture was cooled to RT, diluted with water, and extracted twice with EtOAc. The combined organic layers were washed with brine, dried over anhydrous $Na_2SO_4$, filtered, and concentrated under reduced pressure. Purification by preparative HPLC (GEMINI, 5 µm, 21.2×150 mm; water/ACN elution) provided pure racemic material. $^1$H NMR (300 MHz, DMSO-$d_6$) δ 7.40 (m, 1H), 7.21 (m, 1H), 6.94-6.82 (m, 1H), 6.22 (s, 2H), 6.12 (m, 1H), 5.44 (s, 1H), 4.69-4.47 (m, 3H), 4.35 (t, 1H), 4.13 (brs, 2H), 3.57 (m, 1H), 2.87 (t, 2H), 2.39 (t, 2H), 2.08 (s, 2H), 1.72-1.82 (m, 4H), 1.55-1.34 (m, 2H). m/z=528.1, [M+H]$^+$, $t_R$=1.53 min (LCMS method 1). Chiral SFC (CHIRAL PAK IA, 10 µm, 10×250 mm; mobile phase A: $CO_2$, mobile phase B: IPA; flow rate 15 mL/min; isocratic elution A:B 77:23) provided Example 89a (peak 1, 27 mg; SFC $t_R$=10.23 min) and Example 89b (peak 2, 28 mg; SFC $t_R$=10.94 min).

By employing similar methods as described for the preparation of Examples 89a and 89b, using appropriate starting materials, the following compounds were prepared:

| Ex | Structure and Name | MS, m/z [M + H]$^+$; $t_R$, method | $^1$H NMR |
|---|---|---|---|
| 90 | 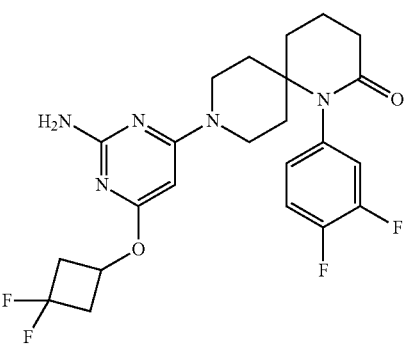 [SMILES: Nc1nc(OC2CC(F)(F)C2)cc(N2CCC3(CCCC(=O)N3c3ccc(F)c(F)c3)CC2)n1]<br>9-(2-amino-6-(3,3-difluorocyclobutoxy)pyrimidin-4-yl)-1-(3,4-difluorophenyl)-1,9-diazaspiro[5.5]undecan-2-one | 480.3; 0.55 min, LCMS method i | $^1$H NMR (400 MHz, DMSO-d$_6$) δ 7.42 (m, 1H), 7.23 (m, 1H), 6.91 (m, 1H), 6.03 (s, 2H), 5.28 (s, 1H), 5.03-4.88 (m, 1H), 4.11 (brs, 2H), 2.97-3.06 (m, 2H), 2.84 (t, 2H), 2.55-2.63 (m, 2H), 2.41 (t, 2H), 2.08 (d, 2H), 1.78-1.85 (m, 4H), 1.43 (t, 2H). |
| 91 | 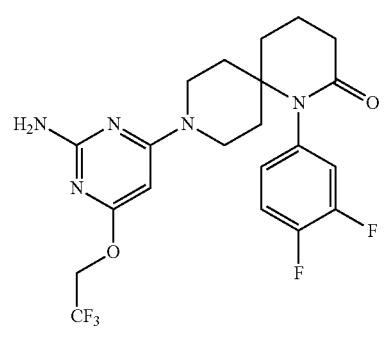<br>9-(2-amino-6-(2,2,2-trifluoroethoxy)pyrimidin-4-yl)-1-(3,4-difluorophenyl)-1,9-diazaspiro[5.5]undecan-2-one | 472.2; 0.61 min, LCMS method i | $^1$H NMR (400 MHz, chloroform-d) δ 7.21 (dtd, J = 10.0, 8.6, 3.4 Hz, 1H), 6.90 (ddd, J = 10.6, 7.1, 2.5 Hz, 1H), 6.80 (dddd, J = 8.4, 4.0, 2.5, 1.7 Hz, 1H), 5.37 (s, 1H), 4.68 (dq, J = 12.9, 8.5 Hz, 2H), 4.16 (dd, J = 28.3, 13.7 Hz, 2H), 3.01 (d, J = 14.5 Hz, 2H), 2.62 (td, J = 6.8, 3.6 Hz, 2H), 2.19-2.10 (m, 2H), 2.01-1.86 (m, 3H), 1.83 (s, 3H). |
| 92 | 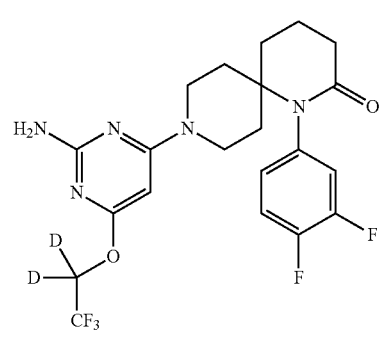 [SMILES: [2H]C([2H])(Oc1cc(N2CCC3(CCCC(=O)N3c3ccc(F)c(F)c3)CC2)nc(N)n1)C(F)(F)F]<br>9-(2-amino-6-(2,2,2-trifluoroethoxy-1,1-d2)pyrimidin-4-yl)-1-(3,4-difluorophenyl)-1,9-diazaspiro[5.5]undecan-2-one | 474.2; 0.59 min, LCMS method i | $^1$H NMR (400 MHz, DMSO-d$_6$) δ 7.42 (m, 1H), 7.23 (m, 1H), 6.91 (m, 1H), 6.18 (s, 2H), 5.40 (s, 1H), 4.1-4.18 (m, 2H), 2.87 (t, 2H), 2.41 (t, 2H), 2.08-2.12 (m, 2H), 1.82 (m, 4H), 1.38-1.5 (m, 2H). |

| Ex | Structure and Name | MS, m/z [M + H]+; $t_R$, method | $^1$H NMR |
|---|---|---|---|
| 93 | 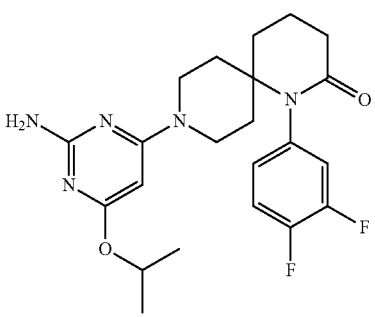<br>9-(2-amino-6-isopropoxypyrimidin-4-yl)-1-(3,4-difluorophenyl)-1,9-diazaspiro[5.5]undecan-2-one | 432.3; 0.49 min, LCMS method i | $^1$H NMR (400 MHz, DMSO-d$_6$) δ 7.42 (m, 1H), 7.23 (m, 1H), 6.91 (m, 1H), 5.92 (s, 2H), 5.18 (s, 1H), 5.12 (h, 1H), 4.18-3.97 (m, 2H), 2.82 (t, 2H), 2.41 (t, 2H), 2.15-2.02 (m, 2H), 1.91-1.75 (m, 4H), 1.4-1.45 (m, 2H), 1.16 (d, 6H). |
| 94 | 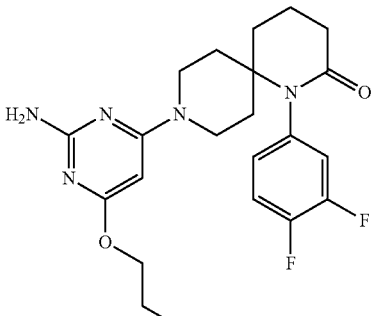<br>9-(2-amino-6-(2-hydroxyethoxy)pyrimidin-4-yl)-1-(3,4-difluorophenyl)-1,9-diazaspiro[5.5]undecan-2-one | 434.1; 0.42 min, LCMS method i | $^1$H NMR (DMSO-d$_6$, 300 MHz) δ 7.42-7.36 (m, 1H), 7.24-7.18 (m, 1H), 6.91-6.88 (m, 1H), 6.17 (br, 2H), 5.3 (s, 1H), 4.7 (br, 1H), 4.18-4.08 (m, 4H), 3.57 (t, 2H), 2.86 (t, 2H), 2.41-2.37 (m, 2H), 2.07 (br, 2H), 1.81-1.77 (m, 4H), 1.46-1.38 (m, 2H). |
| 95 | 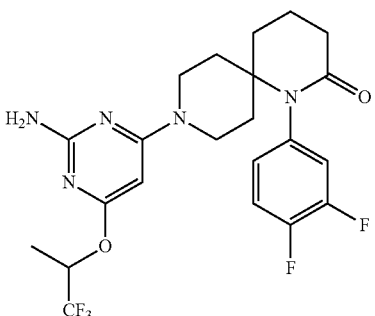<br>rac-9-(2-amino-6-((1,1,1-trifluoropropan-2-yl)oxy)pyrimidn-4-yl)-1-(3,4-difluorophienyl)-1,9-diazaspiro[5.5]undecan-2-one | 486.2; 0.68 min, LCMS method i | $^1$H NMR (600 MHz, chloroform-d) δ 7.16 (m, 1H), 6.87 (m, 1H), 6.76 (d, 1H), 4.80 (s, 2H), 4.69-4.56 (m, 4H), 3.06 (t, 2H), 2.86 (t, 2H), 2.60 (t, 2H), 2.13 (brs, 2H), 1.88-1.98 (m, 4H), 1.80-1.72 (m, 6H). |

| Ex | Structure and Name | MS, m/z [M + H]+; $t_R$, method | 1H NMR |
|---|---|---|---|
| 96 | 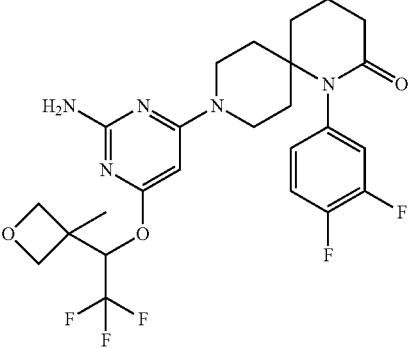 [SMILES: CC1(C(Oc2cc(N3CCC4(CCCC(=O)N4c4ccc(F)c(F)c4)CC3)nc(N)n2)C(F)(F)F)COC1]<br>rac-9-(2-amino-6-(2,2,2-trifluoro-1-(3-methyloxetan-3-yl)ethoxy)pyrimidin-4-yl)-1-(3,4-difluorophenyl)-1,9-diazaspiro[5.5]undecan-2-one | 542.3; 2.05 min, LCMS method k | 1H NMR (400 MHz, DMSO-d6) δ 7.41 (m, 1H), 7.23 (m, 1H), 6.91 (m, 1H), 6.25 (s, 2H), 6.14 (m, 1H), 5.44 (s, 1H), 4.61 (d, 1H), 4.47 (d, 1H), 4.21 (d, 2H), 4.13 (d, 2H), 2.88 (t, 2H), 2.41 (t, 2H), 2.15-2.04 (m, 2H), 1.89-1.76 (m, 3H), 1.46 (s, 4H). |
| 97 | 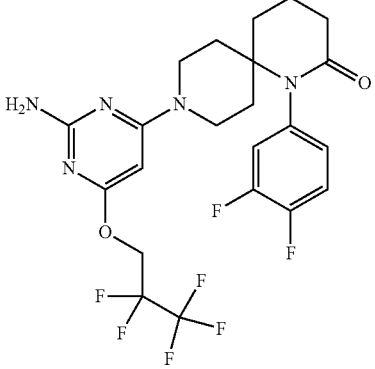<br>9-(2-amino-6-(2,2,3,3,3-pentafluoroprop)oxy)pyrimidin-4-yl)-1-(3,4-difluorophenyl)-1,9-diazaspiro[5.5]undecan-2-one | 522.2; 0.64 min, LCMS method i | 1H NMR (400 MHz, DMSO-d6) δ 7.41 (m, 1H), 7.22 (m, 1H), 6.91 (m, 1H), 6.20 (s, 2H), 5.38 (s, 1H), 4.92 (t, 2H), 4.25-4.00 (m, 2H), 2.88 (t, 2H), 2.41 (t, 2H), 2.18-2.04 (brs, 2H), 1.72-1.9 (m, 4H), 1.36-1.5 (m, 2H). |
| 98 | 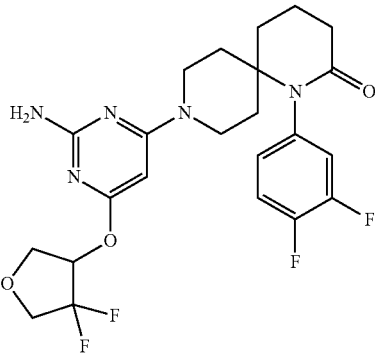 [SMILES: Nc1nc(OC2COCC2(F)F)cc(N2CCC3(CCCC(=O)N3c3ccc(F)c(F)c3)CC2)n1]<br>rac-9-(2-amino-6-((4,4-difluorotetrahydrofuran-3-yl)oxy)pyrimidin-4-yl)-1-(3,4-difluorophenyl)-1,9-diazaspiro[5.5]undecan-2-one | 496.3; 1.16 min, LCMS method k | 1H NMR (300 MHz, DMSO-d6) δ 7.45 (m, 1H), 7.23 (m, 1H), 6.91 (m, 1H), 6.11 (s, 2H), 5.49 (dt, 1H), 5.36 (s, 1H), 4.29 (m, 1H), 4.22-3.69 (m, 4H), 2.87 (t, 2H), 2.47-2.33 (m, 2H), 2.09 (d, 2H), 1.72-1.88 (m, 4H), 1.38-1.5 (m, 2H). |

| Ex | Structure and Name | MS, m/z [M + H]+; $t_R$, method | 1H NMR |
|---|---|---|---|
| 99 | 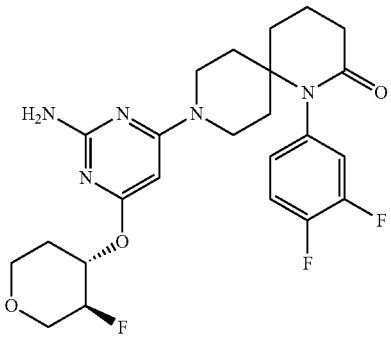 [SMILES: Nc1nc(O[C@H]2CCOC[C@@H]2F)cc(N2CCC3(CCCC(=O)N3c3ccc(F)c(F)c3)CC2)n1]<br>rac-9-(2-amino-6-(((3S,4S)-3-fluorotetrahydro-2H-pyran-4-yl)oxy)pyrimidin-4-yl)-1-(3,4-difluorophenyl)-1,9-diazaspiro[5.5]undecan-2-one | 492.3; 0.51 min, LCMS method i | 1H NMR (400 MHz, DMSO-$d_6$) δ 7.42 (m, 1H), 7.23 (m, 1H), 6.91 (d, 1H), 6.05 (s, 2H), 5.29 (s, 1H), 5.19-5.22 (m, 1H), 4.58 (d, 1H), 4.11 (brs, 2H), 3.82-3.94 (m, 2H), 3.77-3.64 (m, 1H), 3.55-3.42 (m, 2H), 2.85 (t, 2H), 2.41 (t, 2H), 2.15-2.01 (m, 3H), 1.77-1.88 (m, 3H) |
| 100 | 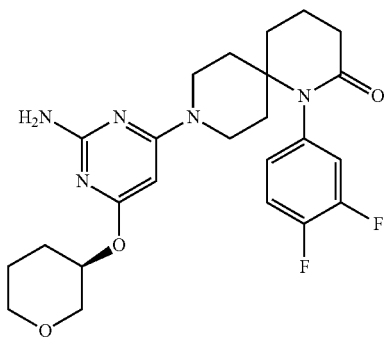 [SMILES: Nc1nc(O[C@@H]2CCCOC2)cc(N2CCC3(CCCC(=O)N3c3ccc(F)c(F)c3)CC2)n1]<br>(R)-9-(2-amino-6-((tetrahydro-2H-pyran-3-yl)oxy)pyrimidin-4-yl)-1-(3,4-difluorophenyl)-1,9-diazaspiro[5.5]undecan-2-one | 474.3; 0.79 min, LCMS method k | 1H NMR (300 MHz, DMSO-$d_6$) δ 7.39 (m, 1H), 7.20 (m, 1H), 6.94-6.81 (m, 1H), 5.96 (s, 2H), 5.21 (s, 1H), 4.8-4.9 (m, 1H), 3.74 (dd, 2H), 3.51-3.62 (m, 1H), 3.35-3.46 (m, 1H), 3.26-3.32 (m, 1H), 2.81 (t, 2H), 2.39 (t, 3H), 1.67-1.88 (m, 8H), 1.32-1.5 (m, 4H). |
| 101 | 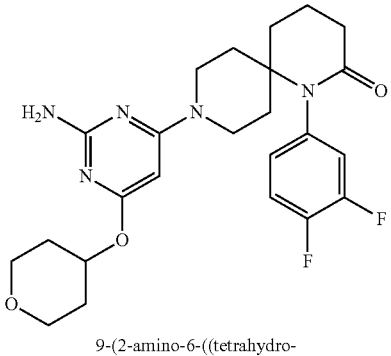<br>9-(2-amino-6-((tetrahydro-2H-pyran-4-yl)oxy)pyrimidin-4-yl)-1-(3,4-difluorophenyl)-1,9-diazaspiro[5.5]undecan-2-one | 474.4; 0.17 min, LCMS method l | 1H NMR (400 MHz, DMSO-$d_6$) δ 7.37 (m, 1H), 7.21 (m, 1H), 6.90 (m, 1H), 5.22 (s, 1H), 4.98-5.03 (m, 1H), 4.09 (d, 2H), 3.75-3.82 (m, 2H), 3.42-3.34 (m, 4H), 2.82 (t, 2H), 2.40 (t, 2H), 2.15-1.99 (m, 2H), 1.93-1.71 (m, 5H), 1.41-1.52 (m, 3H). |

-continued
| Ex | Structure and Name | MS, m/z [M + H]+; $t_R$, method | 1H NMR |
|---|---|---|---|
| 102 | 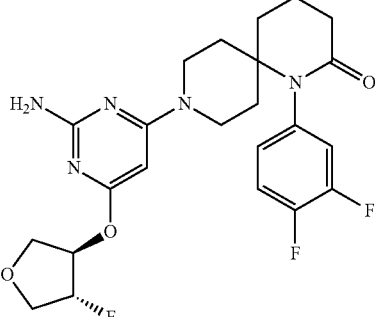<br>rac-9-(2-amino-6-(((3R,4R)-4-fluorotetrahydrofuran-3-yl)oxy)pyrimidin-4-yl)-1-(3,4-difluorophenyl)-1,9-diazaspiro[5.5]undecan-2-one | 478.3; 0.52 min, LCMS method i | 1H NMR (400 MHz, DMSO-$d_6$) δ 7.42 (m, 1H), 7.23 (m, 1H), 6.91 (m, 1H), 6.11 (s, 2H), 5.41 (dd, 2H), 5.28 (m, 1H), 5.14 (d, 1H), 4.02-4.14 (m, 2H), 3.86-3.94 (m, 2H), 3.68-3.72 (m, 1H), 3.62-3.68 (m, 1H), 2.85 (t, 2H), 2.41 (t, 2H), 2.09 (s, 2H), 1.77-1.81 (m, 4H), 1.48-1.52 (d, 2H). |
Example 103: 9-(2-amino-6-((tetrahydro-2H-pyran-4-yl-4-d)oxy)pyrimidin-4-yl)-1-(3,4-difluorophenyl)-1,9-diazaspiro[5.5]undecan-2-one
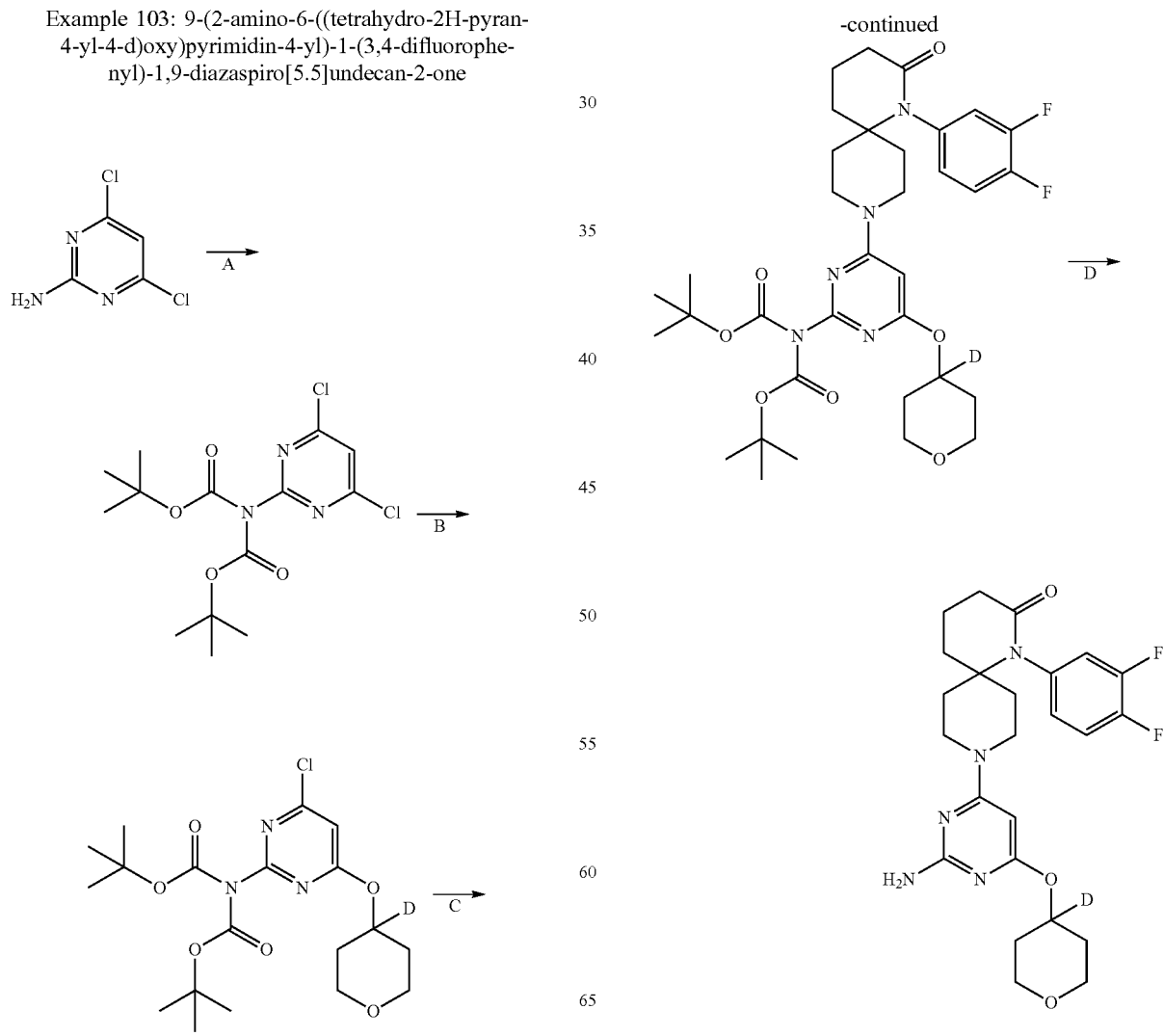

Step A: tert-butyl (tert-butoxycarbonyl)(4,6-dichloropyrimidin-2-yl)carbamate A stirred solution of 4,6-dichloropyrimidin-2-amine (10.00 g, 60.97 mmol) in THF (100 mL), was treated with DMAP (0.744 g, 6.10 mmol) and di-tertbutyl dicarbonate (29.27 g, 134.1 mmol) and stirred at RT for 12 h. The reaction was quenched by addition of ice and it was then extracted with EtOAc. The combined extracts were washed with aqueous NaHCO$_3$, dried over anhydrous Na$_2$SO$_4$, filtered, and concentrated under reduced pressure. Purification by silica gel chromatography (10% EtOAc in hexane) provided tert-butyl (tert-butoxycarbonyl)(4,6-dichloropyrimidin-2-yl)carbamate (16.23 g) as light brown liquid. $^1$H NMR (300 MHz, DMSO-d$_6$) δ 8.01 (s, 1H), 1.4 (s, 18H).

Step B: tert-butyl (tert-butoxycarbonyl)(4-chloro-6-((tetrahydro-2H-pyran-4-yl-4-d)oxy)pyrimidin-2-yl)carbamate A stirred solution of tert-butyl (tert-butoxycarbonyl)(4,6-dichloropyrimidin-2-yl)carbamate (0.500 g, 1.37 mmol) in dioxane (7 mL) was treated with tetrahydro-2H-pyran-4-d-4-ol (0.170 g, 1.65 mmol) and Cs$_2$CO$_3$ (1.342 g, 4.118 mmol). The reaction mixture was stirred at 80° C. for 12 h. The reaction mixture was cooled to RT, diluted with water, and extracted twice with EtOAc. The combined organic extracts were washed with brine, dried over Na$_2$SO$_4$, filtered, and concentrated under reduced pressure. The crude material (0.56 g) was used as such for the next step without any purification. m/z=431.1, [M+H]$^+$; t$_R$=1.68 min (LCMS method j).

Step C: tert-butyl (tert-butoxycarbonyl)(4-(1-(3,4-difluorophenyl)-2-oxo-1,9-diazaspiro[5.5]undecan-9-yl)-6-((tetrahydro-2H-pyran-4-yl-4-d)oxy)pyrimidin-2-yl)carbamate 1-(3,4-difluorophenyl)-1,9-diazaspiro[5.5]undecan-2-one (Intermediate A, 0.300 g, 1.07 mmol) and DIPEA (0.56 mL, 3.2 mmol) were added to a stirred solution of tert-butyl (tert-butoxycarbonyl)(4-chloro-6-((tetrahydro-2H-pyran-4-yl-4-d)oxy)pyrimidin-2-yl)carbamate (0.553 g, 1.28 mmol) in EtOH (7 mL). The reaction mixture was heated to 80° C. for 12 h. The reaction mixture was cooled to RT, diluted with water and extracted twice with EtOAc. The combined organic extracts were washed with brine, dried over Na$_2$SO$_4$, filtered, and concentrated under reduced pressure. The crude material (0.788 g) was used as such for the next step without purification. m/z=675.2, [M+H]$^+$; t$_R$=1.60 min (LCMS method j).

Step-D: 9-(2-amino-6-((tetrahydro-2H-pyran-4-yl-4-d)oxy)pyrimidin-4-yl)-1-(3,4-difluorophenyl)-1,9-diazaspiro[5.5]undecan-2-one A solution of hydrochloric acid (4.0 M in dioxane, 15 mL) was added to a stirred solution of tert-butyl (tert-butoxycarbonyl)(4-(1-(3,4-difluorophenyl)-2-oxo-1,9-diazaspiro[5.5]undecan-9-yl)-6-((tetrahydro-2H-pyran-4-yl-4-d)oxy)pyrimidin-2-yl)carbamate (0.780 g, 1.16 mmol) in dioxane (5 mL). The reaction mixture was stirred at RT for 12 h. The reaction mixture was concentrated under reduced pressure and the residue slurried with saturated aqueous NaHCO$_3$. The mixture was extracted with EtOAc. The combined extracts were washed with brine, dried over anhydrous Na$_2$SO$_4$, filtered, and concentrated under reduced pressure.

Purification by preparative HPLC (LUNA Phenomenex, 5.0 μm, 21.2×250 mm; 0.01% HCOOH in water:ACN elution) provided the title compound as an off-white solid (78 mg). $^1$H NMR (300 MHz, DMSO-d$_6$) δ 8.26 (brs, 2H), 7.42 (m, 1H), 7.23 (m, 1H), 6.91 (m, 1H), 5.23 (s, 1H), 4.11 (d, 2H), 3.80 (dt, 2H), 3.40 (t, 2H), 2.83 (t, 2H), 2.41 (t, 2H), 2.02-2.12 (m, 2H), 1.71-1.9 (m, 6H), 1.35-1.52 (m, 4H); m/z=475.2 [M+H]$^+$; t$_R$=1.31 min (LCMS method j).

Example 104: rac-9-(2-amino-6-((3-methyltetrahydrofuran-3-yl)oxy)pyrimidin-4-yl)-1-(3,4-difluorophenyl)-1,9-diazaspiro[5.5]undecan-2-one

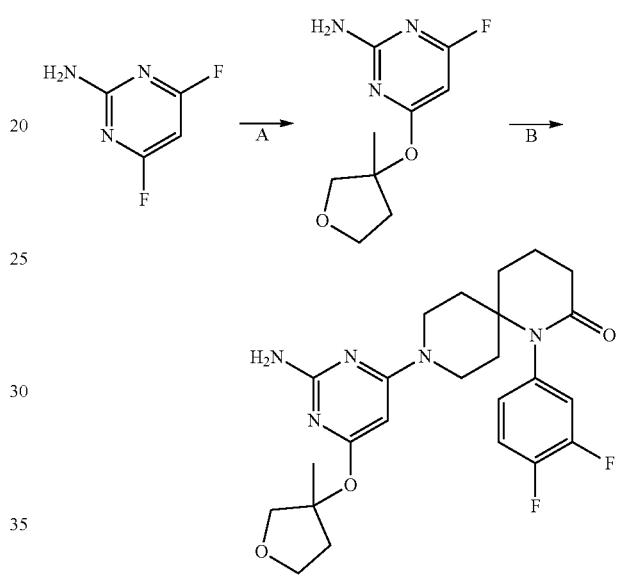

Step-A: 4-fluoro-6-((3-methyltetrahydrofuran-3-yl)oxy)pyrimidin-2-amine

Sodium hydride (0.183 g, 7.63 mmol) was added portionwise to a stirred solution of 3-methyltetrahydrofuran-3-ol (0.311 g, 3.05 mmol) in THF (5 mL) at 0° C., and stirred at the same temperature for 30 minutes. A solution of 4,6-difluoropyrimidine-2-amine (0.200 g, 1.52 mmol) in THF (5 mL) was added and the mixture was stirred at RT for 16 h. Saturated aqueous NH$_4$Cl was added and the mixture was extracted twice with EtOAc. The combined organic extracts were washed with brine, dried over anhydrous Na$_2$SO$_4$, filtered, and concentrated under reduced pressure. Purification by preparative TLC (30% EtOAc in hexane) provided 4-fluoro-6-((3-methyltetrahydrofuran-3-yl)oxy)pyrimidin-2-amine (0.163 g) as an off-white solid. m/z=214.2 [M+H]$^+$; t$_R$=0.41 min (LCMS method 1).

Step-B: 9-(2-amino-6-((3-methyltetrahydrofuran-3-yl)oxy)pyrimidin-4-yl)-1-(3,4-difluorophenyl)-1,9-diazaspiro[5.5]undecan-2-one 1-(3,4-difluorophenyl)-1,9-diazaspiro[5.5]undecan-2-one (Intermediate A, 0.214 mg, 0.764 mmol) and DIPEA (0.40 mL, 2.3 mmol) were added to a stirred solution of 4-fluoro-6-((3-methyltetrahydrofuran-3-yl)oxy)pyrimidin-2-amine (0.163 mg, 0.764 mmol) in EtOH (1 mL) at RT. The reaction mixture was heated at 80° C. for 48 h. The mixture was cooled to RT, diluted with water and extracted twice with EtOAc. The combined organic extracts were washed with brine, dried over anhydrous $Na_2SO_4$, filtered, and concentrated under reduced pressure. The crude product was purified by preparative TLC (10% MeOH in DCM) to provide the title compound (0.125 mg) as an off-white solid. $^1$H NMR (300 MHz, DMSO-$d_6$) δ 7.42 (m, 1H), 7.23 (m, 1H), 6.91 (ddd, 1H), 5.93 (s, 2H), 5.19 (s, 1H), 4.09 (d, 2H), 3.92 (d, 1H), 3.70-3.78 (m, 3H), 2.82 (t, 2H), 2.48-2.27 (m, 4H), 2.05-2.15 (m, 2H), 1.72-1.9 (m, 4H), 1.59 (s, 3H), 1.32-1.5 (m, 2H); m/z=474.3 [M+H]$^+$; $t_R$=0.50 min (LCMS method i).

Example 105: rac-9-(2-amino-6-(((3S,4R)-4-fluorotetrahydrofuran-3-yl)oxy)pyrimidin-4-yl)-1-(3,4-difluorophenyl)-1,9-diazaspiro[5.5]undecan-2-one

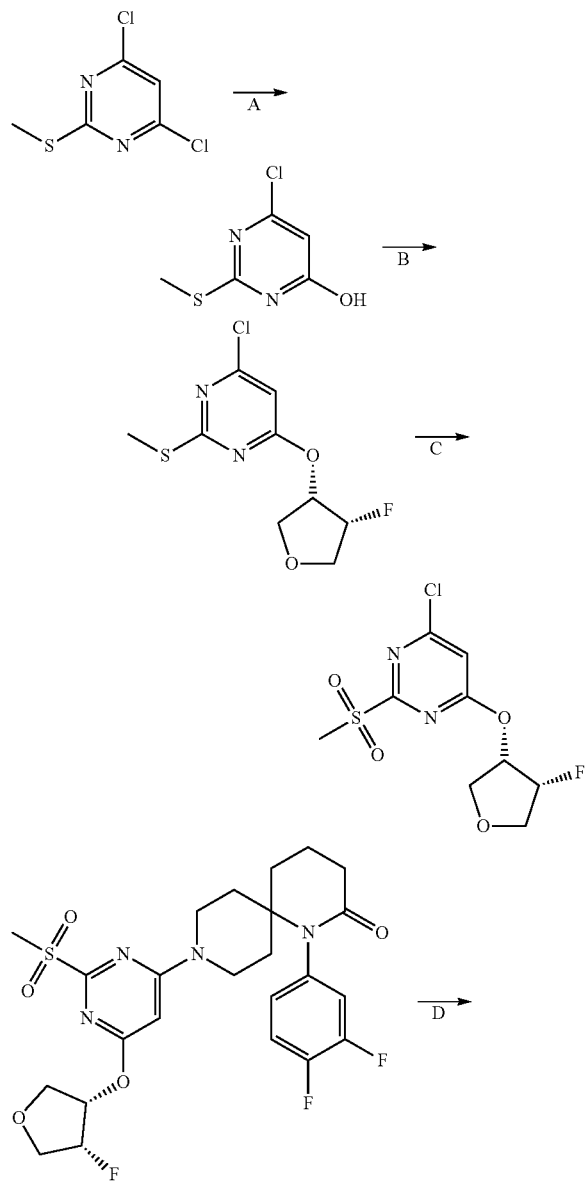

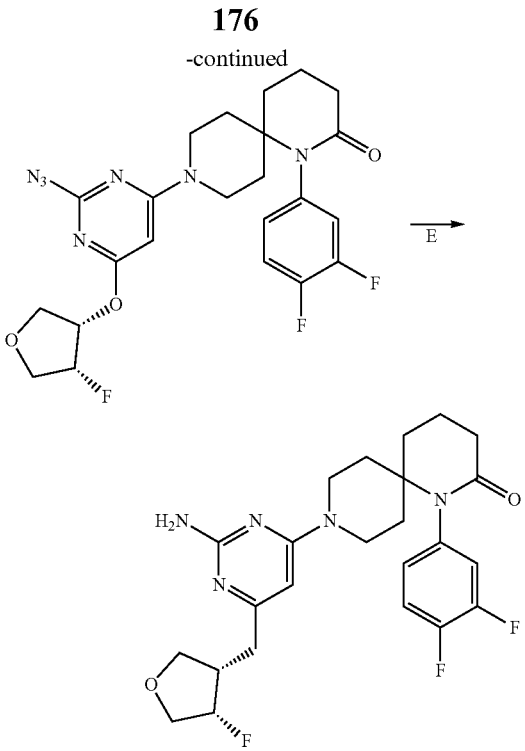

Step A: 6-chloro-2-(methylthio)pyrimidin-4-ol

A stirred solution of 4,6-dichloro-2 (methylthio)pyrimidine (5.0 g, 25.6 mmol) in 2 M NaOH (125 mL) was heated at 120° C. for 5 h. The reaction mixture was cooled to RT and acidified to pH 6 by slow addition of AcOH. The white solid obtained was isolated by filtration and dried under vacuum to provide 6-chloro-2-(methylthio)pyrimidin-4-ol as an off-white solid (4.07 g, crude). $^1$H NMR (300 MHz, DMSO-$d_6$) δ 13.1 (brs, 1H), 6.22 (s, 1H), 2.5 (s, 3H).

Step B: 4-chloro-6-(((3S,4R)-4-fluorotetrahydrofuran-3-yl)oxy)-2-(methylthio)pyrimidine A stirred solution of 6-chloro-2-(methylthio)pyrimidin-4-ol (3.40 g, 32.0 mmol) and triphenyl phosphine (11.6 g, 44.2 mmol) in THF (100 mL) was treated with (3R,4R)-4-fluorotetrahydrofuran-3-ol (2.00 g, 11.3 mmol) and DIAD (7.67 g, 37.9 mmol). The reaction mixture was heated to 80° C. for 12 h. After cooling to RT, the mixture was diluted with pentane and the solvent was decanted. The decanted solvent was concentrated under reduced pressure. Purification by silica gel chromatography (10% EtOAc in hexane) provided 4-chloro-6-(((3S,4R)-4-fluorotetrahydrofuran-3-yl)oxy)-2-(methylthio)pyrimidine as an off-white solid (1.82 g). $^1$H NMR (300 MHz, DMSO-$d_6$) δ 6.96 (s, 1H), 5.59-5.32 (m, 2H), 4.11-4.01 (m, 2H), 3.97-3.78 (m, 2H), 2.53 (s, 3H).

Step C: 4-chloro-6-(((3S,4R)-4-fluorotetrahydrofuran-3-yl)oxy)-2-(methylsulfonyl)pyrimidine A stirred solution of 4-chloro-6-(((3S,4R)-4-fluorotetrahydrofuran-3-yl)oxy)-2-(methylthio)pyrimidine (1.80 g, 6.80 mmol) in THF (30 mL) and water (7 mL) was treated with Oxone® (6.20 g, 20.4 mmol). The reaction mixture was stirred at RT for 3 h, after which time it was diluted with water and extracted twice with EtOAc. The organic extracts were washed with $NaHCO_3$ solution, brine, dried over anhydrous Na$_2$SO$_4$, filtered, and concentrated under reduced pressure. The crude material (1.86 g) was used as such for the next step without any purification. $^1$H NMR (400 MHz, DMSO-d$_6$) δ 7.68 (s, 1H), 5.65-5.41 (m, 2H), 4.14-3.87 (m, 4H), 3.45 (s, 3H).

Step D: 1-(3,4-difluorophenyl)-9-(6-(((3S,4R)-4-fluorotetrahydrofuran-3-yl)oxy)-2-(methylsulfonyl)pyrimidin-4-yl)-1,9-diazaspiro[5.5]undecan-2-one A mixture of 4-chloro-6-(((3S,4R)-4-fluorotetrahydrofuran-3-yl)oxy)-2-(methylsulfonyl)pyrimidine (1.00 g, 3.57 mmol), 1-(3,4-difluorophenyl)-1,9-diazaspiro[5.5]undecan-2-one (Intermediate A, 1.06 g, 3.57 mmol) and DIPEA (1.38 g, 10.7 mmol) in EtOH (8 mL) was heated at 80° C. for 1 h. The reaction mixture was cooled to RT, diluted with water, and extracted twice with EtOAc. The combined extracts were washed with NaHCO$_3$ solution, brine, dried over anhydrous Na$_2$SO$_4$, filtered, and concentrated under reduced pressure to provide 1-(3,4-difluorophenyl)-9-(6-(((3S,4R)-4-fluorotetrahydrofuran-3-yl)oxy)-2-(methylsulfonyl)pyrimidin-4-yl)-1,9-diazaspiro[5.5]undecan-2-one (0.643 g). m/z=541.1 [M+H]$^+$; t$_R$=0.93 min (LCMS method 1).

Step E: 9-(2-azido-6-(((3S,4R)-4-fluorotetrahydrofuran-3-yl)oxy)pyrimidin-4-yl)-1-(3,4-difluorophenyl)-1,9-diazaspiro[5.5]undecan-2-one A mixture of 1-(3,4-difluorophenyl)-9-(6-(((3S,4R)-4-fluorotetrahydrofuran-3-yl)oxy)-2-(methylsulfonyl)pyrimidin-4-yl)-1,9-diazaspiro[5.5]undecan-2-one (0.640 g, 1.18 mmol) and sodium azide (0.900 g, 13.8 mmol) in DMF (15 mL) was heated at 50° C. for 24 h. The reaction mixture was cooled to RT, diluted with water, and extracted twice with EtOAc. The extracts were washed with aqueous NaHCO$_3$, brine, dried over anhydrous Na$_2$SO$_4$, filtered, and concentrated under reduced pressure. The crude material (0.651 g) was used as such for the next step without further purification. m/z=504.4 [M+H]$^+$; t$_R$=2.18 min (LCMS method 1).

Step F: 9-(2-amino-6-(((3S,4R)-4-fluorotetrahydrofuran-3-yl)oxy)pyrimidin-4-yl)-1-(3,4-difluorophenyl)-1,9-diazaspiro[5.5]undecan-2-one A stirred solution of 9-(2-azido-6-(((3S,4R)-4-fluorotetrahydrofuran-3-yl)oxy)pyrimidin-4-yl)-1-(3,4-difluorophenyl)-1,9-diazaspiro[5.5]undecan-2-one (0.651 g, 1.29 mmol) in THF (6 mL) was cooled to −78° C. Trimethyl phosphine (0.108 g, 1.42 mmol) was added and the temperature was gradually raised to RT. The mixture was stirred at RT for 12 h, then heated at 50° C. for 24 h. The reaction mixture was cooled to RT, diluted with water, and extracted twice with EtOAc. The extracts were washed with NaHCO$_3$ solution, brine, dried over anhydrous Na$_2$SO$_4$, filtered, and concentrated under reduced pressure. Purification by preparative HPLC (Acquity XSelect, 5.0 μm, 21.2×250 mm; mobile phase 0.02% NH$_4$OH in water:ACN) provided the title compound (0.356 g) as an off-white solid. $^1$H NMR (300 MHz, chloroform-d) δ 7.17 (m, 1H), 6.88 (m, 1H), 6.77 (m, 1H), 5.34 (m, 2H), 5.17 (m, 1H), 4.56 (s, 2H), 4.22-4.07 (m, 3H), 4.06-3.94 (m, 1H), 3.87-3.76 (m, 2H), 2.8-2.95 (m, 2H), 2.60 (t, 2H), 2.18-2.05 (m, 2H), 1.88-1.95 (m, 2H), 1.7-1.78 (m, 4H); m/z=478.2 [M+H]$^+$, t$_R$=0.50 min (LCMS method i).

Example 106: 1-(3,4-difluorophenyl)-9-(2-(hydroxymethyl)-6-((tetrahydro-2H-pyran-4-yl)oxy)pyrimidin-4-yl)-1,9-diazaspiro[5.5]undecan-2-one

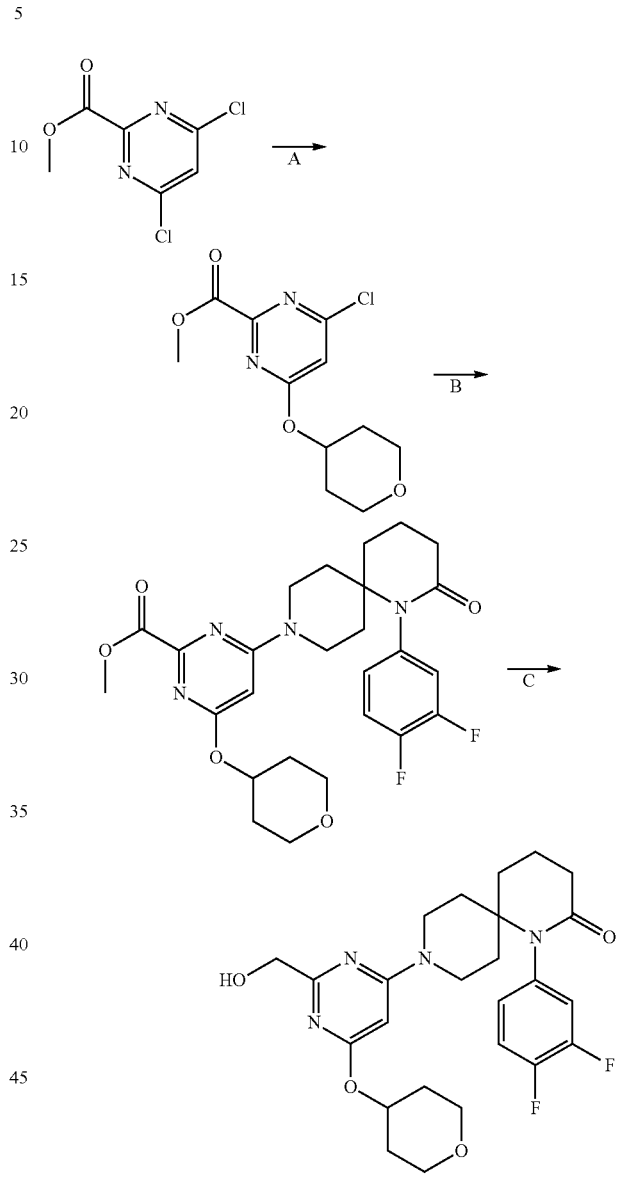

Step A: methyl 4-chloro-6-((tetrahydro-2H-pyran-4-yl)oxy)pyrimidine-2-carboxylate A mixture of methyl 4,6-dichloropyrimidine-2-carboxylate (300 mg, 1.45 mmol), tetrahydro-2H-pyran-4-ol (148 mg, 1.45 mmol) and Cs$_2$CO$_3$ (944 mg, 2.90 mmol) in dioxane (5 mL) was heated to 80° C. for 2 h. The reaction mixture was cooled to RT, diluted with water and extracted twice with EtOAc. The combined organic extracts were washed with brine, dried over anhydrous Na$_2$SO$_4$, filtered, and concentrated under reduced pressure to provide methyl 4-chloro-6-((tetrahydro-2H-pyran-4-yl)oxy)pyrimidine-2-carboxylate (130 mg) which was used without purification.

Step B: methyl 4-(1-(3,4-difluorophenyl)-2-oxo-1,9-diazaspiro[5.5]undecan-9-yl)-6-((tetrahydro-2H-pyran-4-yl)oxy)pyrimidine-2-carboxylate A mixture of methyl 4-chloro-6-((tetrahydro-2H-pyran-4-yl)oxy)pyrimidine-2-carboxylate (130 mg, 0.476 mmol), 1-(3,4-difluorophenyl)-1,9-diazaspiro[5.5]undecan-2-one (Intermediate A, 133 mg, 0.476 mmol) and DIPEA (0.18 mL, 1.4 mmol) in EtOH was heated at 80° C. for 2 h. The reaction mixture was cooled to RT, diluted with water and extracted twice with EtOAc. The combined organic extracts were washed with brine, dried over anhydrous $Na_2SO_4$, filtered, and concentrated under reduced pressure to provide methyl 4-(1-(3,4-difluorophenyl)-2-oxo-1,9-diazaspiro[5.5]undecan-9-yl)-6-((tetrahydro-2H-pyran-4-yl)oxy)pyrimidine-2-carboxylate (120 mg, crude). m/z=517.2 [M+H]$^+$; $t_R$=1.31 min (LCMS method k).

Step-C: 1-(3,4-difluorophenyl)-9-(2-(hydroxymethyl)-6-((tetrahydro-2H-pyran-4-yl)oxy)pyrimidin-4-yl)-1,9-diazaspiro[5.5]undecan-2-one A stirred solution of methyl 4-(1-(3,4-difluorophenyl)-2-oxo-1,9-diazaspiro[5.5]undecan-9-yl)-6-((tetrahydro-2H-pyran-4-yl)oxy)pyrimidine-2-carboxylate (120 mg, 0.232 mmol) in MeOH (5 mL) was treated with sodium borohydride (35 mg, 0.93 mmol) at 0° C. The mixture was stirred at RT for 2 h. The mixture was diluted with water and extracted twice with EtOAc. The combined organic extracts were washed with brine, dried over anhydrous $Na_2SO_4$, filtered, and concentrated under reduced pressure. Purification by preparative HPLC (LUNA C18, 5 μm, 21.2×250 mm; 0.1% HCOOH:MeCN elution) provided the title compound (5 mg). $^1$H NMR (400 MHz, DMSO-$d_6$) δ 7.42 (m, 1H), 7.24 (m, 1H), 6.90-6.92 (m, 1H), 5.84 (s, 1H), 5.11-5.2 (m, 1H), 4.70 (t, 1H), 4.23 (d, 3H), 3.78-3.83 (m, 2H), 3.45 (t, 2H), 2.92 (t, 2H), 2.42 (t, 2H), 2.11 (brs, 2H), 1.83-1.92 (m, 5H), 1.57-1.57 (m, 4H); m/z=489.3 [M+H]$^+$; $t_R$=1.1 min (LCMS method k).

By employing similar methods as described for the preparation of Example 106, using appropriate starting materials, the following compounds were prepared:

| Ex | Structure and Name | MS, m/z [M + H]$^+$; $t_R$, method | $^1$H NMR |
|---|---|---|---|
| 107 | 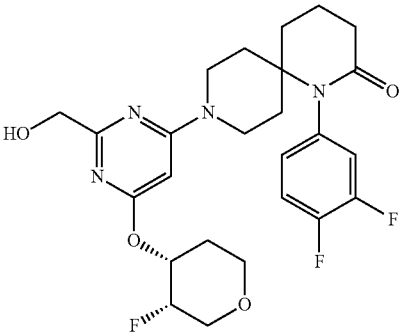 [SMILES: O=C1CCCC2(CCN(c3cc(O[C@@H]4CCOC[C@@H]4F)nc(CO)n3)CC2)N1c1ccc(F)c(F)c1]<br>rac-1-(3,4-difluorophenyl)-9-(6-(((3S,4R)-3-fluorotetrahydro-2H-pyran-4-yl)oxy)-2-(hydroxymethyl)pyrimidin-4-yl)-1,9-diazaspiro[5.5]undecan-2-one | 507.3; 0.57 min, LCMS method i | $^1$H NMR (400 MHz, DMSO-$d_6$) δ 7.42 (m, 1H), 7.25 (m, 1H), 6.92 (d, 1H), 5.92 (s, 1H), 5.25-5.32 (m, 1H), 4.82 (d, 1H), 4.74 (t, 1H), 4.24 (d, 3H), 3.84-3.98 (m, 2H), 3.46-3.65 (m, 2H), 2.94 (t, 2H), 2.42 (t, 2H), 2.11 (brs, 2H), 1.83-1.91 (m, 4H), 1.41-1.52 (m, 2H). |
| 108 | 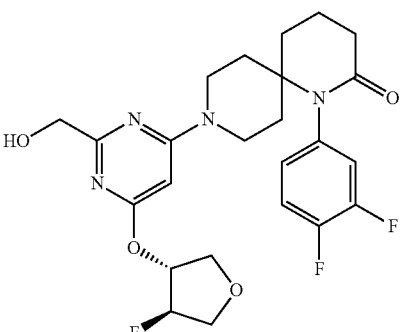<br>rac-1-(3,4-diflurophenyl)-9-(6-(((3R,4R)-4-fluorotetrahydrofuran-3-yl)oxy)-2- | 493.2; 0.58 min, LCMS method i | $^1$H NMR (400 MHz, DMSO-$d_6$) δ 7.42 (m, 1H), 7.24 (m, 1H), 6.92 (d, 1H), 5.92 (s, 1H), 5.52 (d, 1H), 5.25 (d, 1H), 4.78 (t, 1H), 4.26 (d, 2H), 4.13 (dd, 1H), 4.02-3.78 (m, 2H), 3.68 (d, 1H), 2.94 (t, 2H), 2.42 (t, 2H), 2.12 (brs, 2H), 1.80-1.88 (m, 3H), 1.46 (t, 2H). |

| Ex | Structure and Name | MS, m/z [M + H]+; t_R, method | 1H NMR |
|---|---|---|---|
| | (hydroxymethyl)pyrimidin-4-yl)-1,9-diazaspiro[5.5]undecan-2-one | | |
| 109 | 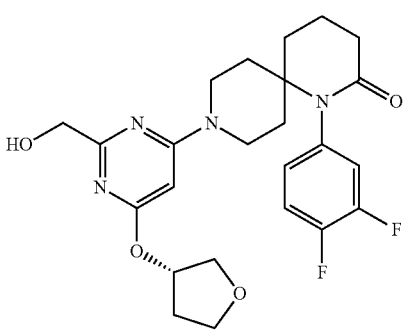 [SMILES: O=C1CCCC2(CCN(c3cc(O[C@H]4CCOC4)nc(CO)n3)CC2)N1c1ccc(F)c(F)c1]<br>(S)-1-(3,4-difluorophenyl)-9-(2-(hydroxymethyl)-6-((tetrahydrofuran-3-yl)oxy)pyrimidin-4-yl)-1,9-diazaspiro[5.5]undecan-2-one | 475.2; 0.55 min, LCMS method i | 1H NMR (300 MHz, methanol-d4) δ 7.27 (m, 1H), 7.05 (m, 1H), 6.95 (m, 1H), 5.78 (s, 1H), 5.52 (m, 1H), 4.38 (s, 2H), 4.3 (m, 2H), 3.82-3.95 (m, 4H), 3.02 (t, 2H), 2.56 (t, 2H), 2.18-2.25 (m, 3H), 1.88-2.01 (m, 5H), 1.7 (brs, 2H). |

Example 110a: (S)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one or (R)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one and Example 110b: (R)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one or (S)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one

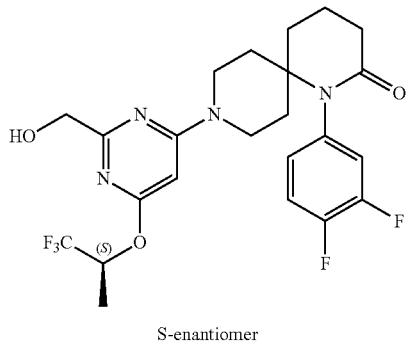

S-enantiomer

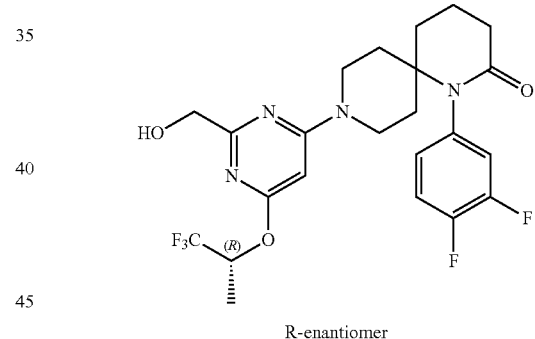

R-enantiomer

Racemic 1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one or (R)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one was synthesized in a manner similar to that employed for Example 106 using rac-1,1,1-trifluoropropan-2-ol. 1H NMR (400 MHz, DMSO-d6) δ 7.42 (m, 1H), 7.24 (m, 1H), 6.98-6.84 (m, 1H), 6.00 (s, 1H), 5.94 (m, 1H), 4.84 (t, 1H), 4.26 (d, 3H), 2.96 (t, 2H), 2.42 (t, 2H), 2.18-2.04 (m, 2H), 1.91-1.78 (m, 4H), 1.47 (t, 2H), 1.37 (d, 3H); m/z=501.1 [M+H]+; t_R=1.63 (LCMS method 1). The racemic product was purified by chiral HPLC (Phenomenex Lux Cellulose, 4 μm, 21.2×250 mm; mobile phase A: hexane, mobile phase B: EtOH; isocratic elution 70(A):30(B); flow rate 15 mL/min) to provide Example 110b (peak 1; chiral HPLC t_R=3.57 min), and Example 110a (peak 2; chiral HPLC t_R=3.94 min).

Example 111: rac ethyl 4-(1-(3,4-difluorophenyl)-2-oxo-1,9-diazaspiro[5.5]undecane-9-yl)-6-(((3S,4S)-4-fluorotetrahydrofuran-3-yl)oxy)pyrimidine-2-carboxylate

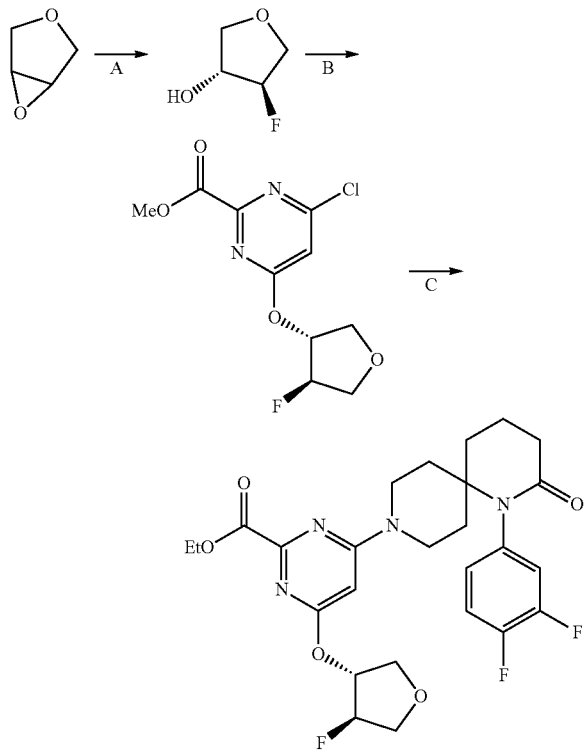

Step A: rac-(3R,4R)-4-fluorotetrahydrofuran-3-ol

Triethylaminetrihydrofluoride (60 mL) was added to 3,6-dioxabicyclo[3.1.0]hexane (10.00 g, 116.1 mmol) at RT. The mixture was then heated at 120° C. for 12 h. The reaction was quenched by ice cold water and extracted with EtOAc. The extracts were washed with brine, and dried over $Na_2SO_4$, filtered, and concentrated under reduced pressure. Purification by silica gel chromatography (100% EtOAc) provided rac-(3R,4R)-4-fluorotetrahydrofuran-3-ol (8.0 g) as a brown liquid. $^1$H NMR (300 MHz, DMSO-$d_6$) δ 5.42 (d, 1H), 5.21-5.25 (m, 1H), 3.77-3.9 (m, 2H), 3.53-3.56 (m, 1H), 3.34 (br s, 1H).

Step B: rac-methyl 4-chloro-6-(((3R,4R)-4-fluorotetrahydrofuran-3-yl)oxy)pyrimidine-2-carboxylate A mixture of methyl 4,6-dichloropyrimidine-2-carboxylate (0.150 g, 0.724 mmol), rac-(3R,4R)-4-fluorotetrahydrofuran-3-ol (0.076 g, 0.72 mmol) and $Cs_2CO_3$ (0.472 g, 1.45 mmol) in dioxane (5 mL) was stirred at RT for 3 h. The reaction was diluted with water and extracted with EtOAc. The extracts were washed with brine, dried over $Na_2SO_4$, filtered, and concentrated under reduced pressure to provide rac-methyl 4-chloro-6-(((3R,4R)-4-fluorotetrahydrofuran-3-yl)oxy)pyrimidine-2-carboxylate (0.160 g) as yellow gummy solid which as taken on without further purification. m/z=277.1 [M+H]$^+$; $t_R$=0.47 min (LCMS method 1).

Step C: rac-ethyl 4-(1-(3,4-difluorophenyl)-2-oxo-1,9-diazaspiro[5.5]undecane-9-yl)-6-(((3S,4S)-4-fluorotetrahydrofuran-3-yl)oxy)pyrimidine-2-carboxylate A mixture of 1-(3,4-difluorophenyl)-1,9-diazaspiro[5.5]undecane-2-one (Intermediate A, 0.045 g, 0.16 mmol), rac-methyl 4-chloro-6-(((3R,4R)-4-fluorotrtrahydrofuran-3-yl)oxy)pyrimidine-2-carboxylate (0.060 g, 0.22 mmol) and DIPEA (110 μL, 0.65 mmol) in EtOH (2 mL) was heated at 80° C. for 2 hours. The mixture was cooled to RT, diluted with water and extracted with EtOAc. The extracts were washed with brine, dried over $Na_2SO_4$, filtered, and concentrated under reduced pressure. Purification by preparative HPLC (LUNA Phenomenex, 5 μm, 21.2×250 mm; 0.1% HCOOH in $H_2O$:ACN elution) provided the title compound (3 mg) as an off-white solid. $^1$H NMR (400 MHz, methanol-$d_4$) δ 7.24 (m, 1H), 7.09 (m, 1H), 6.91 (m, 1H), 6.07 (s, 1H), 5.54-5.58 (m, 1H), 5.2 (d, 1H), 4.22-4.34 (m, 4H), 4.17-4.22 (m, 1H), 4.03 (s, 1H), 3.92-3.94 (m, 1H), 3.8 (d, 1H), 3.07 (t, 2H), 2.57 (t, 2H), 2.18-2.3 (m, 2H), 1.91-2.01 (m, 4H), 1.7 (brs, 2H), 1.29 (m, 3H); m/z=535.3 [M+H]$^+$; $t_R$=2.13 min (LCMS method 1).

Example 112: (R)-9-(2-amino-6-((tetrahydrofuran-3-yl)amino)pyrimidin-4-yl)-1-(3,4-difluorophenyl)-1,9-diazaspiro[5.5]undecan-2-one

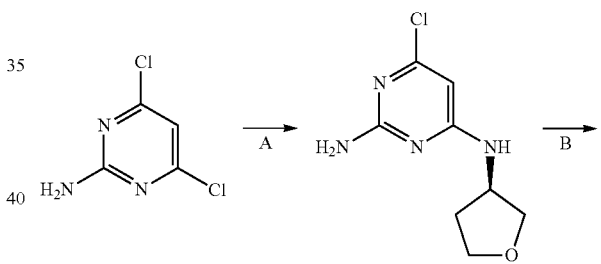

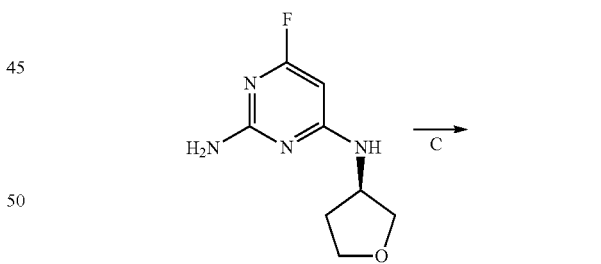

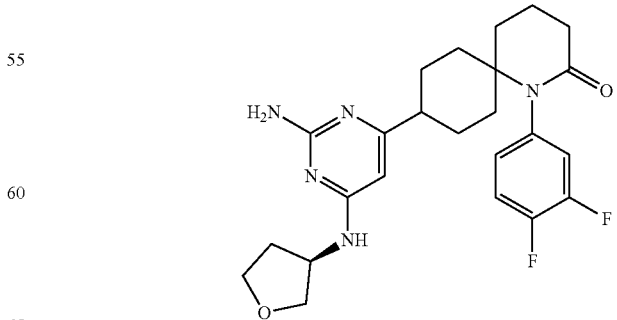

Step A: (R)-6-chloro-N4-(tetrahydrofuran-3-yl)pyrimidine-2,4-diamine

A mixture of 4,6-dichloropyrimidin-2-amine (0.300 g, 1.83 mmol), (R)-tetrahydrofuran-3-amine (0.120 g, 1.37 mmol) and DIPEA (0.96 mL, 5.5 mmol) in EtOH (5 mL) was heated at 80° C. for 12 h. The reaction mixture was cooled to RT, diluted with water and extracted twice with EtOAc. The combined organic extracts were washed with brine, dried over anhydrous Na$_2$SO$_4$, filtered, and concentrated under reduced pressure. The crude product was triturated with pentane to afford (R)-6-chloro-N4-(tetrahydrofuran-3-yl)pyrimidine-2,4-diamine (0.25 g, 64%) as an off-white solid. m/z=215.0 [M+H]$^+$; t$_R$=0.64 min (LCMS method l).

Step B: (R)-6-fluoro-N4-(tetrahydrofuran-3-yl)pyrimidine-2,4-diamine

A mixture of (R)-6-chloro-N4-(tetrahydrofuran-3-yl)pyrimidine-2,4-diamine (0.100 g, 0.465 mmol) and CsF (0.283 g, 1.86 mmol) in DMSO (5 mL) was heated at 150° C. for 24 h. The reaction mixture was cooled to RT, diluted with water and extracted twice with EtOAc. The combined organic extracts were washed with brine, dried over anhydrous Na$_2$SO$_4$, filtered, and concentrated under reduced pressure. Washing of the crude product with pentane to provided (R)-6-fluoro-N4-(tetrahydrofuran-3-yl)pyrimidine-2,4-diamine (0.15 g, crude). m/z=199.2 [M+H]$^+$; t$_R$=0.43 min (LCMS method k).

Step C: (R)-9-(2-amino-6-((tetrahydrofuran-3-yl)amino)pyrimidin-4-yl)-1-(3,4-difluorophenyl)-1,9-diazaspiro[5.5]undecan-2-one A mixture of (R)-6-fluoro-N4-(tetrahydrofuran-3-yl)pyrimidine-2,4-diamine (0.100 g, 0.502 mmol), 1-(3,4-difluorophenyl)-1,9-diazaspiro[5.5]undecan-2-one (Intermediate A, 0.106 g, 0.376 mmol) and DIPEA (0.26 mL, 1.5 mmol) in EtOH (3 mL) was heated to 80° C. for 72 h. The reaction mixture was cooled to RT, diluted with water and extracted twice with EtOAc. The combined organic extracts were washed with brine, dried over anhydrous Na$_2$SO$_4$, filtered, and concentrated under reduced pressure. Purification by preparative HPLC (Waters XSelect, 5 µm, 21.2×250 mm; mobile phase 0.02% NH$_4$OH in H$_2$O:ACN) provided the title compound as an off-white solid (20 mg). $^1$H NMR (300 MHz, DMSO-d$_6$) δ 7.43 (m, 1H), 7.24 (m, 1H), 6.92 (s, 1H), 6.34 (d, 1H), 5.46 (s, 2H), 4.94 (s, 1H), 4.26 (s, 1H), 4.01 (d, 1H), 3.6-3.82 (m, 2H), 2.87-2.56 (m, 3H), 2.32-2.54 (m, 2H), 2.16-1.92 (m, 3H), 1.6-1.76 (m, 4H), 1.44 (s, 3H), 1.32-1.5 (m, 2H); m/z=459.2 [M+H]$^+$; t$_R$=1.30 min (LCMS method j).

Example 113a: (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, or (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, and

Example 113b: (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, or (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one

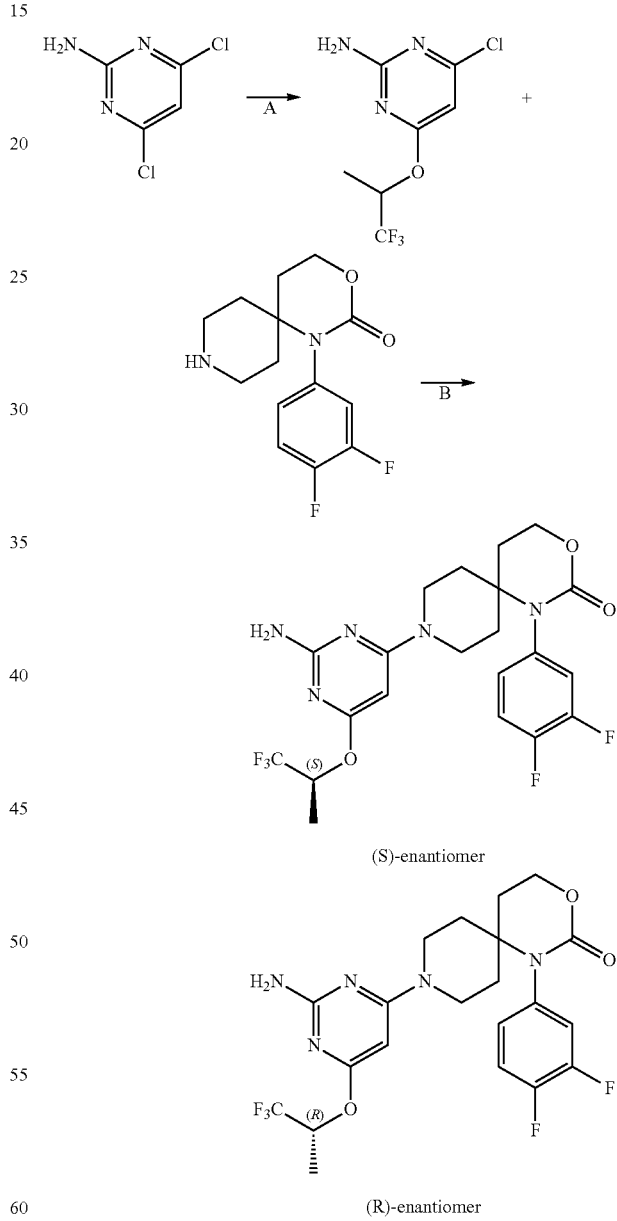

(S)-enantiomer (R)-enantiomer

Step A: rac-4-chloro-6-((1,1,1-trifluoropropan-2-yl)oxy)pyrimidin-2-amine

To a solution of 4,6-dichloropyrimidin-2-amine (5.00 g, 30.5 mmol) in 1,4-dioxane (125 mL) was added 1,1,1- trifluoropropan-2-ol (5.20 g, 45.7 mmol) and Cs₂CO₃ (29.80 g, 91.46 mmol). The mixture was stirred at 80° C. for 16 h. The reaction mixture was cooled to RT, diluted with water, and extracted with EtOAc. The combined organic extracts were washed with brine, dried over Na₂SO₄, filtered, and concentrated under reduce pressure to provide 4-chloro-6-((1,1,1-trifluoropropan-2-yl)oxy)pyrimidin-2-amine (7.40 g) as a yellow solid. m/z=242.1 [M+H]⁺; $t_R$=0.76 min (LCMS method 1).

Step B: rac-9-(2-amino-6-((1,1,1-trifluoropropan-2-yl)oxy)pyrimidin-4-yl)-1-(3,4-difluorophenyl)-3-oxa-1,9-diazaspiro[5.5]undecane-2-one To a suspension of rac-4-chloro-6-((1,1,1-trifluoropropan-2-yl)oxy)pyrimidin-2-amine (7.40 g, 29.4 mmol) in EtOH (200 mL) was added 1-(3,4-difluorophenyl)-3-oxa-1,9-diazaspiro[5.5]undecane-2-one (Intermediate E, 9.40 g, 29.4 mmol). DIEA (26.60 g, 205.7 mmol) was added dropwised at 25° C. The mixture was stirred at 80° C. for 24 h. After cooling to RT, the reaction mixture was concentrated under reduced pressure. Purification by silica gel chromatography (100% EtOAc) provided racemic 9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one (4.4 g) as a yellow solid. ¹H NMR (300 MHz, DMSO-d₆) δ 7.49-7.29 (m, 2H), 7.00-7.03 (m, 1H), 6.17 (s, 2H), 5.65-5.78 (m, 1H), 5.37 (s, 1H), 4.35 (t, 2H), 4.15 (brs, 2H), 2.83 (t, 2H), 2.30 (t, 2H), 1.84 (d, 2H), 1.47-1.35 (m, 2H), 1.32 (d, 3H); m/z=488.2 [M+H]⁺; $t_R$=0.64 min (LCMS method i). Chiral SFC (Waters UPCC; Chiralpak IG-3, 3 μm, 4.6×250 mm, 35° C.; mobile phase A: CO₂, mobile phase B: 0.1% DEA in MeOH, isocratic elution: 40% B for 7 min; flow rate 2.5 mL/min; UV detection, 210 nm) provided Example 113a (peak 1, 0.974 g; SFC $t_R$=4.41 min), and Example 113b (peak 2, 1.20 g; SFC $t_R$=5.10 min).

The synthesis of Example 114 was accomplished by employing similar methods as described for the preparation of Examples 65 and 66 using Intermediate E. The synthesis of Example 115 was accomplished by employing similar methods as described for the preparation of Example 64, using Intermediate E.

| Ex | Structure and Name | MS, m/z [M + H]⁺; $t_R$, method | ¹H NMR |
|---|---|---|---|
| 114 | 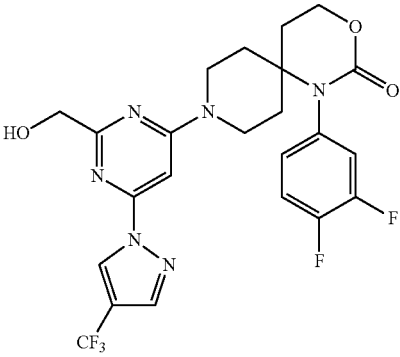 [SMILES: O=C1OCCC2(CCN(c3cc(-n4cc(C(F)(F)F)cn4)nc(CO)n3)CC2)N1c1ccc(F)c(F)c1]<br>1-(3,4-difluorophenyl)-9-(2-(hydroxymethyl)-6-(4-(trifluoromethyl)-1H-pyrazol-1-yl)pyrimidin-4-yl)-3-oxa-1,9-diazaspiro[5.5]undecan-2-one | 525.2; 0.64 min, LCMS method i | ¹H NMR (300 MHz, DMSO-d₆) δ 9.30 (s, 1H), 8.30 (s, 1H), 7.51-7.32 (m, 2H), 7.03-7.07 (m, 1H), 6.98 (s, 1H), 4.98 (brs, 1H), 4.49-4.24 (m, 5H), 3.08 (t, 2H), 2.38 (t, 3H), 1.98 (d, 2H), 1.42-1.6 (m, 2H). |
| 115 | 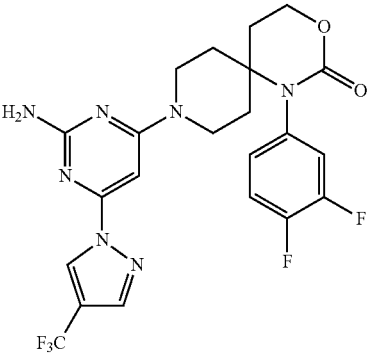 [SMILES: Nc1nc(N2CCC3(CCOC(=O)N3c3ccc(F)c(F)c3)CC2)cc(-n2cc(C(F)(F)F)cn2)n1]<br>9-(2-amino-6-(4-(trifluoromethyl)-1H-pyrazol-1-yl)pyrimidin-4-yl)-1-(3,4-difluorophenyl)-3-oxa-1,9-diazaspiro[5.5]undecan-2-one | 510.2; 0.65 min, LCMS method i | ¹H NMR (300 MHz, chloroform-d) δ 8.72 (s, 1H), 7.84 (s, 1H), 7.13-7.22 (m, 1H), 6.86-7.01 (m, 2H), 6.52 (s, 1H), 4.77 (s, 2H), 4.52-4.31 (m, 4H), 2.94-3.0 (m, 2H), 2.35 (t, 2H), 1.74-1.82 (m, 4H). |

Example 116a: (R)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one, or (S)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one and Example 116b: (S)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one, or (R)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one

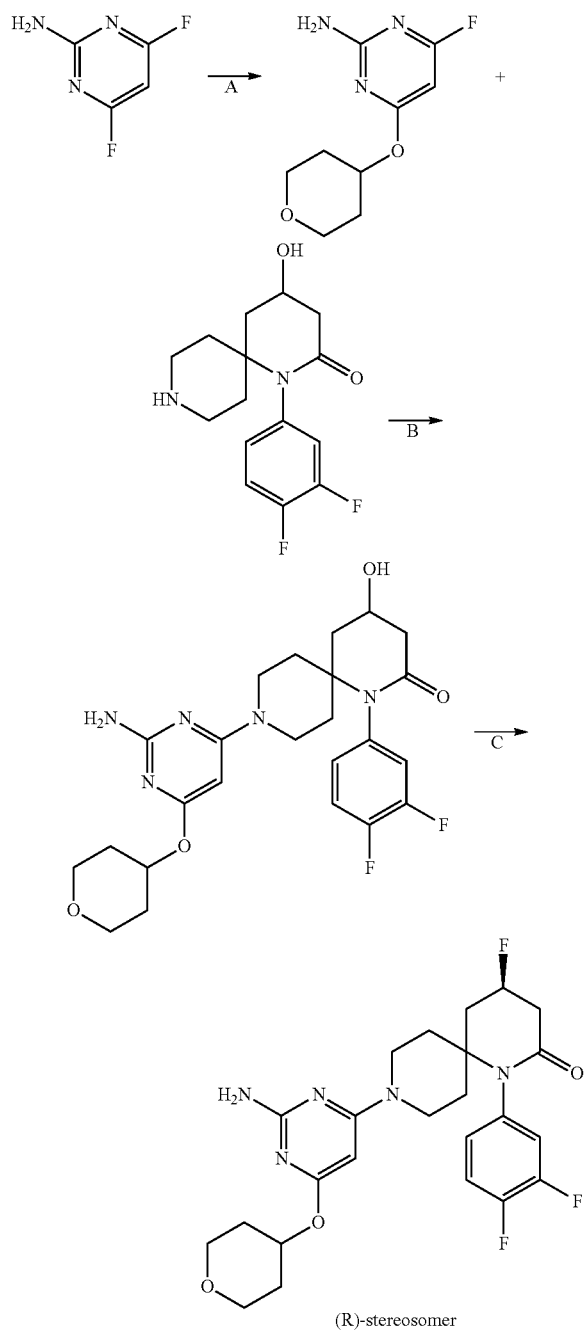

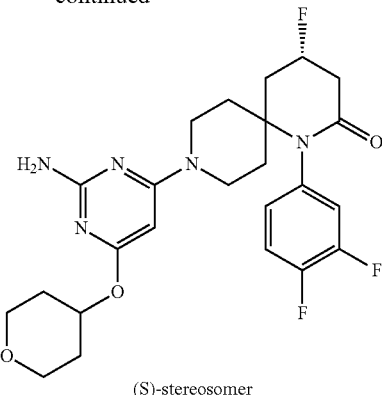

(S)-stereoisomer

Step A: 4-fluoro-6-((tetrahydro-2H-pyran-4-yl)oxy)pyrimidin-2-amine

Sodium hydride (5.48 g, 137 mmol) was added portionwise to a solution of tetrahydro-2H-pyran-4-ol (11.7 g, 114 mmol) in THF (150 mL) cooled to 0° C. 4,6-Difluoropyrimidin-2-amine (15 g, 114 mmol) was added and the mixture was stirred at RT for 12 h. The mixture was poured into water and was extracted with ethyl acetate. The combined organic extracts were washed with brine, dried over $Na_2SO_4$, filtered, and concentrated under reduced pressure. Purification by silica gel chromatography (0-20% EtOAc in petroleum ether) provided 4-fluoro-6-((tetrahydro-2H-pyran-4-yl)oxy)pyrimidin-2-amine (10.5 g, 49 mmol) as a white solid. $^1$H NMR (400 MHz, DMSO-$d_6$) δ=7.18-6.91 (m, 2H), 5.72-5.57 (m, 1H), 5.23-5.05 (m, 1H), 3.92-3.77 (m, 2H), 3.52-3.37 (m, 2H), 2.06-1.88 (m, 2H), 1.66-1.51 (m, 2H).

Step B: 9-(2-amino-6-((tetrahydro-2H-pyran-4-yl)oxy)pyrimidin-4-yl)-1-(3,4-difluorophenyl)-4-hydroxy-1,9-diazaspiro[5.5]undecan-2-one A mixture of 1-(3,4-difluorophenyl)-4-hydroxy-1,9-diazaspiro[5.5]undecan-2-one (Intermediate D, 9.3 g, 28 mmol), DIEA (1.2 mL, 70 mmol) and 4-fluoro-6-((tetrahydro-2H-pyran-4-yl)oxy)pyrimidin-2-amine (6.0 g, 28 mmol) in EtOH (70 mL) was stirred at 80° C. for 12 h. After cooling to RT the mixture was diluted with water and extracted with EA. The combined organic extracts were washed with brine, dried over $Na_2SO_4$, filtered, and concentrated under reduced pressure. Purification by silica gel chromatography (0-5% MeOH in DCM) provided 9-(2-amino-6-((tetrahydro-2H-pyran-4-yl)oxy)pyrimidin-4-yl)-1-(3,4-difluorophenyl)-4-hydroxy-1,9-diazaspiro[5.5]undecan-2-one (10 g, 20 mmol) as a white solid. $^1$H NMR (400 MHz, DMSO-$d_6$) δ=7.50-7.37 (m, 1H), 7.30-7.17 (m, 1H), 6.97-6.84 (m, 1H), 6.08-5.90 (m, 2H), 5.78-5.74 (m, 2H), 5.29-5.22 (m, 1H), 5.09 (d, 1H), 5.07-5.00 (m, 1H), 4.27-3.97 (m, 3H), 3.85-3.75 (m, 2H), 3.43-3.36 (m, 2H), 2.94-2.79 (m, 2H), 2.76-2.66 (m, 1H), 2.59 (m, 1H), 2.38-2.21 (m, 1H), 1.92-1.82 (m, 3H), 1.80-1.63 (m, 2H), 1.54-1.47 (m, 2H), 1.39-1.20 (m, 1H); m/z=490.2

Step C: 9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one DAST (3.96 g, 24.6 mmol) was added to a stirred solution of 9-(2-amino-6-((tetrahydro-2H-pyran-4-yl)oxy)pyrimidin-4-yl)-1-(3,4-difluorophenyl)-4-hydroxy-1,9-diazaspiro[5.5]undecan-2-one (6.0 g, 12 mmol) in DCM (60 mL) at 0° C. The mixture was allowed to warm to 25° C. and stir for one hour. The reaction mixture was poured into water and extracted with DCM. The combined organic extracts were washed with brine, dried over $Na_2SO_4$, filtered, and concentrated under reduced pressure. Purification by silica gel chromatography (0-5% MeOH in DCM) provided racemic 9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one (5.8 g, 11.8 mmol) as a yellow solid. $^1$H NMR (400 MHz, chloroform-d) δ=7.25-7.14 (m, 1H), 7.00-6.87 (m, 1H), 6.86-6.72 (m, 1H), 5.32-5.08 (m, 3H), 4.69-4.44 (m, 2H), 4.32-4.10 (m, 2H), 3.99-3.89 (m, 2H), 3.61-3.49 (m, 2H), 3.09-2.86 (m, 4H), 2.66-2.47 (m, 1H), 2.45-2.21 (m, 1H), 2.07-1.95 (m, 3H), 1.81-1.65 (m, 5H); m/z=492.2 [M+H]$^+$; $t_R$=0.48 min (LCMS method i). Chiral SFC (Chiralpak AD-3, 3 um, 4.6×50 mm, 35° C.; mobile phase A: $CO_2$, mobile phase B: 0.05% DEA in EtOH; isocratic elution, 40% B in A; flow rate: 3 mL/min; Detector: DAD) provided Example 116a (peak 1, 6.473 g; SFC $t_R$=1.54 min; m/z=492.2 [M+H]$^+$) and Example 116b (peak 2, 5.998 g; SFC $t_R$=3.55 min; m/z=492.2 [M+H]$^+$).

By employing similar methods as described for the preparation of Example 116, using appropriate starting materials described herein, the following compounds were prepared:

| Ex | Structure and Name | MS, m/z [M + H]$^+$; $t_R$, method | $^1$H NMR |
|---|---|---|---|
| 117 | 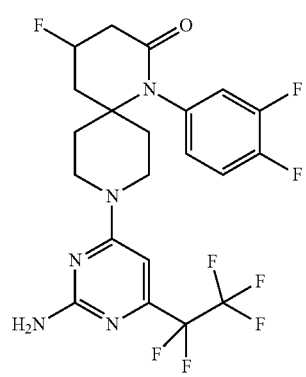 [SMILES: Nc1nc(N2CCC3(CC2)CC(F)CC(=O)N3c2ccc(F)c(F)c2)cc(C(F)(F)C(F)(F)F)n1] rac-9-(2-amino-6-(perfluoroethyl)pyrimidin-4-yl)-1-(3,4-difluorophenyl)-4-fluoro-1,9-diazaspiro[5.5]undecan-2-one | 510.2; 1.57 min, LCMS method l | $^1$H NMR (300 MHz, DMSO-$d_6$) δ 7.42 (m, 1H), 7.24 (brs, 1H), 6.93 (brs, 1H), 6.53 (brs, 2H), 6.32 (s, 1H), 5.25 (d, 1H), 4.25 (brs, 2H), 2.9-3.11 (m, 3H), 2.48-2.78 (m, 4H), 1.88 (t, 2H), 1.32-1.52 (m, 2H). |
| 118 | 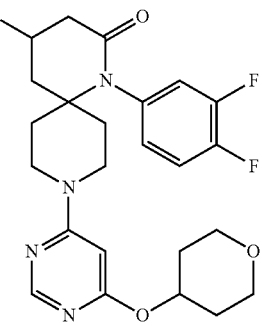 rac-1-(3,4-difluorophenyl)-4-fluoro-9-(6-((tetrahydro-2H-pyran-4-yl)oxy)pyrimidin-4-yl)-1,9-diazaspiro[5.5]undecan-2-one | 477.2; 1.99 min, LCMS method k | $^1$H NMR (300 MHz, DMSO-$d_6$) δ 8.15 (s, 1H), 7.44 (m, 1H), 7.35-7.16 (m, 1H), 6.95 (s, 1H), 6.00 (s, 1H), 5.42-5.12 (m, 2H), 4.21 (brs, 2H), 3.81 (dt, 2H), 3.55-3.34 (m, 2H), 3.14-2.88 (m, 3H), 2.58-2.7 (m, 2H), 1.8-1.95 (m, 4H), 1.38-1.6 (m, 4 H). |

Example 119: 1-(3,4-difluorophenyl)-4-fluoro-9-(6-(2,2,2-trifluoroethoxy)pyrimidin-4-yl)-1,9-diazaspiro[5.5]undecan-2-one

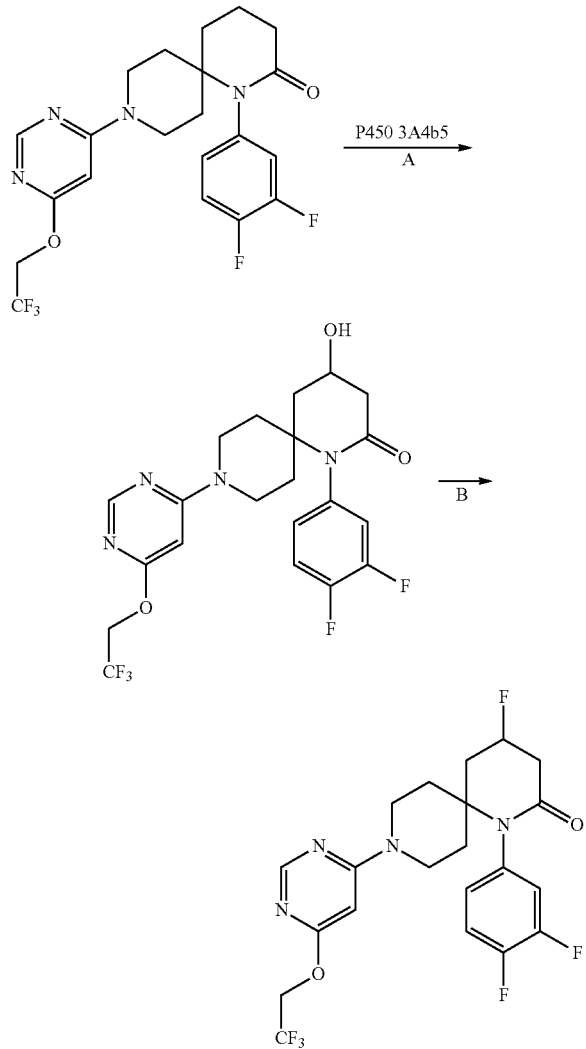

Step A: 1-(3,4-difluorophenyl)-4-hydroxy-9-(6-(2,2,2-trifluoroethoxy)pyrimidin-4-yl)-1,9-diazaspiro[5.5]undecan-2-one To 125 mL of a thawed *E. coli* expressing cytochrome P450 3 Å4b5[1] (80<$OD_{600}$<100) was added 375 mL of PSE buffer, 25 mL of sodium citrate (50 g/100 mL) and 200 mg of 1-(3,4-difluorophenyl)-9-(6-(2,2,2-trifluoroethoxy)pyrimidin-4-yl)-1,9-diazaspiro[5.5]undecan-2-one in 3 mL DMSO. The mixture was stirred in a 3 L plastic Erlenmeyer flask equipped with 4 baffles and a breathable seal. 1-Octanol (50 μL) was added as antifoam agent. The mixture was stirred in an Infors HT Multitron shaker at 30° C. at 100 rpm for 5 h. The mixture was extracted with 2×1 L EtOAc. The organic extracts were dried over $MgSO_4$, filtered, and concentrated to dryness to afford 600 mg of a blue solid. The crude material was dissolved into 4 mL DMSO and purified by preparative HPLC (Vario-Prep HPLC column VP 250/21 Nucleodur® 100-10 C18ec; mobile phase A: water+0.1% HCOOH, mobile phase B: ACN+0.1% HCOOH; flow: 40 mL/min; gradient elution 0-70% B over 25 min, 70% B for 5 min). 1-(3,4-difluorophenyl)-4-hydroxy-9-(6-(2,2,2-trifluoroethoxy)pyrimidin-4-yl)-1,9-diazaspiro[5.5]undecan-2-one was isolated with a UV purity of 82%. The isolated material was subjected to a second preparative HPLC purification (gradient elution 20-60% B over 20 min, 60% B for 5 min) which provided 1-(3,4-difluorophenyl)-4-hydroxy-9-(6-(2,2,2-trifluoroethoxy)pyrimidin-4-yl)-1,9-diazaspiro[5.5]undecan-2-one (40.5 mg, 18.6% yield, >95% UV purity). $^1$H NMR (600 MHz, DMSO-$d_6$) δ 8.21 (d, J=0.9 Hz, 1H), 7.50-7.37 (m, 1H), 7.24 (s, 1H), 6.92 (s, 1H), 6.20 (d, J=0.9 Hz, 1H), 5.10 (d, J=4.4 Hz, 1H), 4.93 (q, J=9.1 Hz, 2H), 4.24 (s, 2H), 4.13 (dt, J=13.9, 7.1 Hz, 1H), 3.00 (t, J=13.2 Hz, 2H), 2.72 (dd, J=17.1, 5.6 Hz, 1H), 2.61 (t, J=1.9 Hz, 1H), 2.36-2.28 (m, 1H), 1.93 (d, J=13.3 Hz, 1H), 1.85 (d, 1H), 1.75 (s, 1H), 1.57 (t, 1H), 1.36 (s, 1H); m/z=473.2 [M+H]$^+$; $t_R$=0.63 min (LCMS method i)

[1] Preparation of the biocatalyst, please refer to: Recombinant Human Cytochrome P450 Monooxygenases for Drug Metabolite Synthesis, Biotechnol Bioeng. 2010 Aug. 1; 106(5):699-706. doi: 10.1002/bit.22775, and Recombinant Yeast and Bacteria that Express Human P450s: Bioreactors for Drug Discovery, Development, and Biotechnology Steven P. Hanlon, Thomas Friedberg, C. Roland Wolf, Oreste Ghisalba, Matthias Kittelmann Book Editors: Prof. Dr. Rolf D. Schmid, Dr. Vlada B. Urlacher; First published: 21 Jun. 2007.

Step B: 1-(3,4-difluorophenyl)-4-fluoro-9-(6-(2,2,2-trifluoroethoxy)pyrimidin-4-yl)-1,9-diazaspiro[5.5]undecan-2-one In a 10 mL vial, 1-(3,4-difluorophenyl)-4-hydroxy-9-(6-(2,2,2-trifluoroethoxy) pyrimidin-4-yl)-1,9-diazaspiro[5.5]undecan-2-one (19 mg, 0.040 mmol) was dissolved in DCM (0.40 mL), and DAST (11 μL, 0.080 mmol) in DCM was added at 0° C. After stirring for 10 min, the reaction mixture was allowed to warm to RT and stir overnight. The mixture was quenched with sat. $NaHCO_3$, stirred 20 min, and extracted with EtOAc. The extracts were washed with brine, dried over $MgSO_4$, filtered, and concentrated. Purification by reverse phase flash chromatography (RediSep® Rf Gold® Reversed Phase C18, 0-90% ACN in water). Product-containing fractions were combined, frozen, and lyopholized to provide the title compound (10 mg, 0.020 mmol). Note than any enantiomeric excess which may have been introduced during the CYP450 oxidation in Step A was not determined. $^1$H NMR (400 MHz, methylene chloride-d2) δ 7.12 (dd, J=8.5, 4.3 Hz, 1H), 6.93-6.82 (m, 1H), 6.82-6.69 (m, 1H), 5.81 (d, J=4.2 Hz, 1H), 5.20 (d, J=23.9 Hz, 1H), 4.66 (s, 2H), 4.19 (dd, J=27.7, 13.5 Hz, 2H), 3.12-2.66 (m, 4H), 2.44 (dt, J=15.4, 7.8 Hz, 1H), 2.39-2.25 (m, 1H), 1.99-1.86 (m, 1H), 1.69 (ddd, J=24.1, 10.9, 4.2 Hz, 3H), 1.53 (d, J=20.5 Hz, 1H); m/z=475.3 [M+H]$^+$; $t_R$=0.65 min (LCMS method i).

Example 120: 9-(2-amino-6-(1,1-difluoroethyl)pyrimidin-4-yl)-1-(3,4-difluorophenyl)-1,9-diazaspiro[5.5]undecan-2-one

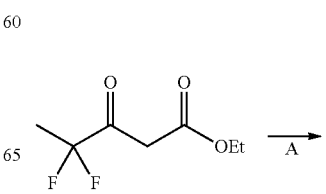

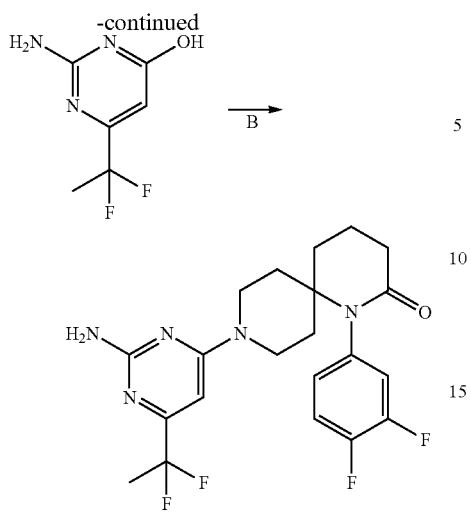

Step A: 2-amino-6-(1,1-difluoroethyl)pyrimidin-4-ol

A mixture of ethyl 4,4-difluoro-3-oxopentanoate (3.00 g, 16.6 mmol), guanidine hydrochloride (3.2 g, 33 mmol) and sodium ethoxide (2.7 g, 50 mmol) in EtOH (40 mL) was heated at 80° C. for 5 h. The reaction mixture was concentrated under reduced pressure and diluted with water and EtOAc. The organic layer was separated, dried over anhydrous $Na_2SO_4$, filtered, and concentrated under reduced pressure to provide 2-amino-6-(1,1-difluoroethyl)pyrimidin-4-ol as an off-white solid (5.4 g). m/z=176.1 $[M+H]^+$; $t_R$=0.87 min (LCMS method j).

Step B: 9-(2-amino-6-(1,1-difluoroethyl)pyrimidin-4-yl)-1-(3,4-difluorophenyl)-1,9-diazaspiro[5.5]undecan-2-one A mixture of 2-amino-6-(1,1-difluoroethyl)pyrimidin-4-ol (1.50 g, 7.75 mmol), 1-(3,4-difluorophenyl)-1,9-diazaspiro[5.5]undecan-2-one (Intermediate A, 1.08 g, 3.87 mmol), PyBrop (5.40 g, 11.6 mmol) and triethylamine (2.3 mL, 23 mmol) in dioxane (10 mL) was stirred at RT for 12 h. The reaction mixture was poured into ice cold water and extracted twice with EtOAc. The combined organic layers were washed with brine, dried over anhydrous $Na_2SO_4$, filtered, and concentrated under reduced pressure. Purification by silica gel chromatography (EtOAc) provided the title compound (0.42 g). $^1$H NMR (300 MHz, methanol-d4) δ 7.41 (m, 1H), 7.29 (m, 1H), 7.09 (m, 1H), 6.28 (s, 2H), 6.12 (s, 1H), 4.31 (brs, 2H), 2.91 (t, 2H), 2.41 (t, 2H), 2.20 (br s, 2H), 1.71-1.9 (m, 7H), 1.4-1.52 (m, 2H); m/z=438.2 $[M+H]^+$; $t_R$=0.61 min (LCMS method l).

The invention claimed is:

1. A method of treating a disease or a condition mediated by leukotriene C4 synthase (LTC4S), said method comprising administering to a patient in need of such treatment a therapeutically effective amount of a compound of Formula (I)

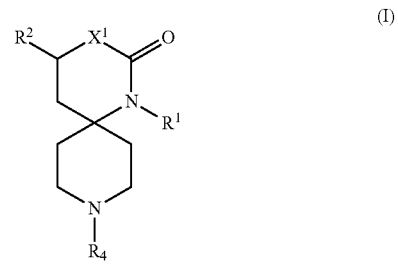

or a pharmaceutically acceptable salt thereof, wherein:
$R^1$ is phenyl optionally substituted with one or more halo substituents;
$R^2$ is H or fluoro;
$X^1$ is $CH_2$ or O;
$R^4$ is a mono or bicyclic heteroaryl, optionally substituted with one or more $R^3$ substituents;
each $R^3$ is independently selected from $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)$NH_2$, and $NR^aR^b$, wherein $R^a$ and $R^b$ are independently H, $C_{1-6}$alkyl, $C_{3-7}$cycloalkyl, $C_{3-7}$cycloalkyl-$C_{1-6}$alkyl or halo $C_{1-6}$alkyl;
wherein said aryl, heterocyclyl, heteroaryl, $C_{3-7}$cycloalkyl, $C_{3-7}$cycloalkenyl, $C_{3-7}$cycloalkoxy are further optionally substituted with one or more substituents independently selected from OH, CN, $C_{3-7}$cycloalkyl, C3-7cycloalkoxy, $NH_2$, $C_{1-6}$alkyl, $C_{1-6}$alkoxy, halo$C_{1-6}$alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$alkyl, phenyl optionally further substituted with halo; and heteroaryl optionally substituted with halo, $C_{1-6}$alkyl, halo$C_{1-6}$alkyl or $C_{3-7}$cycloalkyl;
$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_6$alkyl, phenyl, benzyl, 4-10 membered heterocyclyl, 5-10 membered heteroaryl;
wherein phenyl, heterocyclyl $C_{3-7}$cycloalkyl, and $C_{3-7}$cycloalkyl$C_{1-6}$-alkyl is optionally substituted by one or more substituents selected from $C_{1-6}$ alkyl, $C_{1-6}$alkoxy, halo, phenyl optionally further substituted with halo; heterocyclyl optionally further substituted with $C_{1-6}$alkyl or halo$C_{1-6}$alkyl;
with the proviso that when $R^2$ is F, then $X^1$ is $CH_2$; and wherein the disease or condition mediated by leukotriene C4 synthase (LTC4S) is asthma or a skin disease.

2. The method according the claim 1, comprising administering a compound of Formula (I), or a pharmaceutically acceptable salt thereof, wherein $R^4$ is selected from the group consisting of pyrimidinyl, pyrazinyl, triazolyl, triazinyl, pyridinyl, pyridine oxide, pyrimidine oxide, pyrazine oxide, quinolinyl, quinazolinyl, quinoxalinyl, indazolyl, pyrazolopyrimidinyl, pyridopyrazinyl, triazolopyridazinyl, benzooxazolyl, oxadiazolyl, tetrazolyl, thiadiazolyl, oxazolyl, and thiazolyl, each of which is optionally substituted with one or more $R^3$ substituents;
each $R^3$ is independently selected from $C_{6-10}$aryl, benzyl, $C_{1-6}$alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)$NH_2$, and $NR^aR^b$, wherein $R^a$ and $R^b$ are independently H, $C_{1-6}$alkyl, $C_{3-7}$cycloalkyl, $C_{3-7}$cycloalkyl-$C_{1-6}$alkyl or halo $C_{1-6}$alkyl;

wherein said aryl, heterocyclyl, heteroaryl, $C_{3-7}$cycloalkyl, $C_{3-7}$cycloalkenyl, $C_{3-7}$cycloalkoxy are further optionally substituted with one or more substituents independently selected from OH, CN, $C_{3-7}$cycloalkyl, C3-7cycloalkoxy, $NH_2$, $C_{1-6}$alkyl, $C_{1-6}$alkoxy, halo$C_{1-6}$alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$alkyl, phenyl optionally further substituted with halo; and heteroaryl optionally substituted with halo, $C_{1-6}$alkyl, halo$C_{1-6}$alkyl or $C_{3-7}$cycloalkyl; and wherein $R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;

wherein phenyl, heterocyclyl $C_{3-7}$cycloalkyl, and $C_{3-7}$cycloalkyl$C_{1-6}$alkyl is optionally substituted by one or more substituents selected from $C_{1-6}$ alkyl, $C_{1-6}$alkoxy, halo, phenyl optionally further substituted with halo; heterocyclyl optionally further substituted with $C_{1-6}$alkyl or halo$C_{1-6}$alkyl.

3. The method according to claim 1 comprising administering a compound of Formula (I), or a pharmaceutically acceptable salt thereof, wherein $R^4$ is selected from:

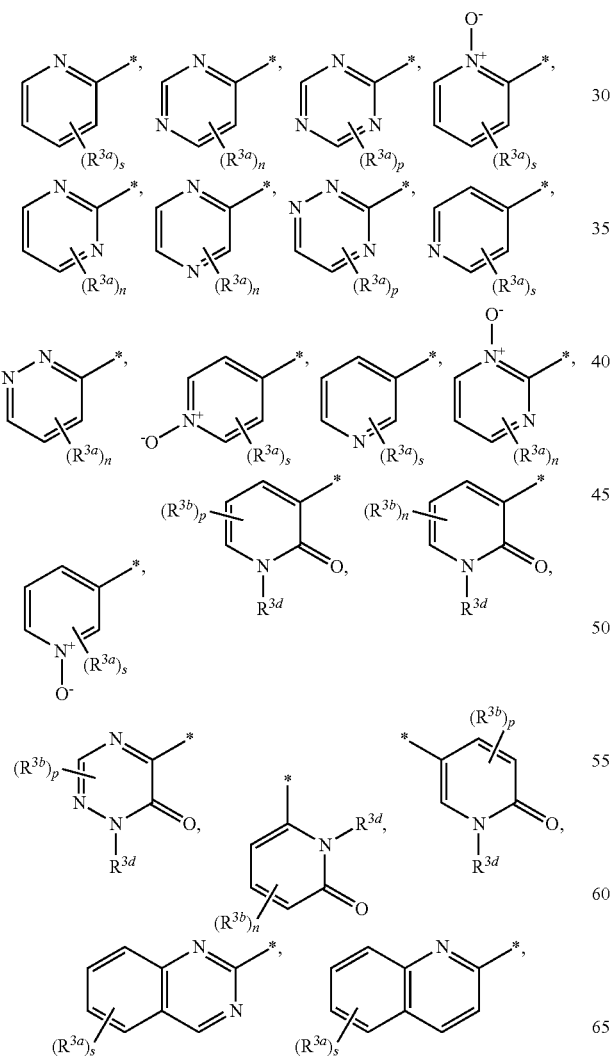

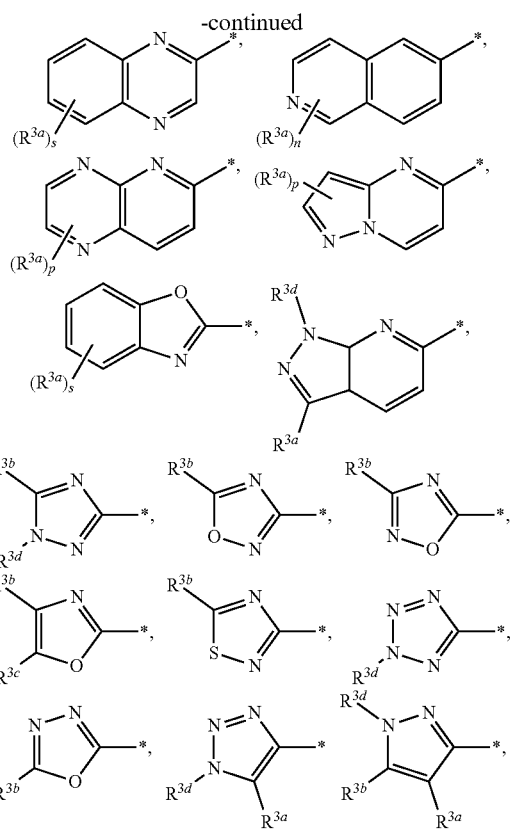

wherein the * depicts the point of attachment to the nitrogen of the spiropiperidinyl moiety; and wherein n is an integer between 1 and 3; p is 1 or 2, s is an integer between 1 and 4; and $R^{3a}$, $R^{3b}$ and $R^{3c}$ are independently selected from the group consisting of H, $C_{6-10}$aryl, benzyl, $C_{1-6}$ alkyl, $C_{3-7}$cycloalkoxy, hydroxy$C_{1-6}$alkyl, $C_{1-6}$alkoxy$C_{1-6}$alkyl, halo, halo$C_{1-6}$alkyl, $OR^5$, CN, C(O)O$C_{1-6}$alkyl, OH, $C_{3-7}$cycloalkyl, $C_{3-7}$cycloalkenyl, 5- to 10 membered heteroaryl, 4-10 membered heterocyclyl, —C(O)$NH_2$, and $NR^aR^b$, wherein $R^a$ and $R^b$ are independently H, $C_{1-6}$ alkyl, $C_{3-7}$cycloalkyl, $C_{3-7}$cycloalkyl-$C_{1-6}$alkyl or halo $C_{1-6}$alkyl;

wherein said aryl, heterocyclyl, heteroaryl, $C_{3-7}$cycloalkyl, $C_{3-7}$cycloalkenyl, $C_{3-7}$cycloalkoxy are further optionally substituted with one or more substituents independently selected from OH, CN, $C_{3-7}$cycloalkyl, C3-7cycloalkoxy, $NH_2$, $C_{1-6}$alkyl, $C_{1-6}$alkoxy, halo$C_{1-6}$alkoxy, hydroxyC1-6alkyl, —S—$C_{1-6}$alkyl; —S-(halo$C_{1-6}$alkyl), halo, halo$C_{1-6}$alkyl, —C(O)—$C_{1-6}$alkyl, phenyl optionally further substituted with halo; and heteroaryl optionally substituted with halo, $C_{1-6}$alkyl, halo$C_{1-6}$alkyl or $C_{3-7}$cycloalkyl;

$R^5$ is $C_{1-6}$alkyl, halo$C_{1-6}$alkyl, hydroxy$C_{1-6}$alkyl, alkoxy$C_{1-6}$alkyl, $C_{3-7}$cycloalkyl, $C_{3-7}$cycloalkenyl, $C_{3-7}$cycloalkyl$C_{1-6}$alkyl, phenyl, benzyl, 4-10 membered heterocyclyl, 5-10 membered heteroaryl;

wherein phenyl, heterocyclyl $C_{3-7}$cycloalkyl, and $C_{3-7}$cycloalkyl$C_{1-6}$alkyl is optionally substituted by one or more substituents selected from $C_{1-6}$ alkyl, $C_{1-6}$alkoxy, halo, phenyl optionally further substituted with halo; heterocyclyl optionally further substituted with $C_{1-6}$alkyl or halo$C_{1-6}$alkyl; and wherein R$^{3d}$ is selected from H, C$_{6-10}$aryl, C$_{1-6}$alkyl, haloC$_{1-6}$alkyl, C$_{3-6}$cycloalkyl, 5- or 6-membered heteroaryl; and wherein said aryl, cycloalkyl, heteroaryl are further optionally substituted with one or more substituents independently selected from C$_{3-6}$cycloalkyl, C$_{1-6}$alkyl, C$_{1-6}$alkoxy, haloC$_{1-6}$alkoxy, halo and haloC$_{1-6}$alkyl.

4. The method according to claim 1 comprising administering a compound of Formula (II); or a pharmaceutically acceptable salt thereof:

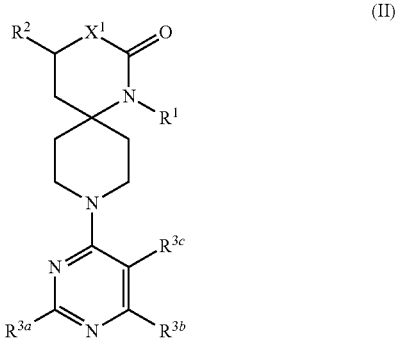

(II)

wherein R$^{3a}$, R$^{3b}$ and R$^{3c}$ are independently selected from the group consisting of H, C$_{6-10}$aryl, benzyl, C$_{1-6}$alkyl, C$_{3-7}$cycloalkoxy, hydroxyC$_{1-6}$alkyl, C$_{1-6}$alkoxyC$_{1-6}$alkyl, halo, haloC$_{1-6}$alkyl, OR$^5$, CN, C(O)OC$_{1-6}$alkyl, OH, C$_{3-7}$cycloalkyl, C$_{3-7}$cycloalkenyl, 5- to 10 membered heteroaryl, 4-10 membered heterocyclyl, —C(O)NH$_2$, and NR$^a$R$^b$, wherein R$^a$ and R$^b$ are independently H, C$_{1-6}$ alkyl, C$_{3-7}$cycloalkyl, C$_{3-7}$cycloalkyl-C$_{1-6}$alkyl or halo C$_{1-6}$alkyl;

wherein said aryl, heterocyclyl, heteroaryl, C$_{3-7}$cycloalkyl, C$_{3-7}$cycloalkenyl, C$_{3-7}$cycloalkoxy are further optionally substituted with one or more substituents independently selected from OH, CN, C$_{3-7}$cycloalkyl, C3-7cycloalkoxy, NH$_2$, C$_{1-6}$alkyl, C$_{1-6}$alkoxy, haloC$_{1-6}$alkoxy, hydroxyC1-6alkyl, —S—C$_{1-6}$alkyl; —S-(haloC$_{1-6}$alkyl), halo, haloC$_{1-6}$alkyl, —C(O)—C$_{1-6}$alkyl, phenyl optionally further substituted with halo; and heteroaryl optionally substituted with halo, C$_{1-6}$alkyl, haloC$_{1-6}$alkyl or C$_{3-7}$cycloalkyl;

R$^5$ is C$_{1-6}$alkyl, haloC$_{1-6}$alkyl, hydroxyC$_{1-6}$alkyl, alkoxyC$_{1-6}$alkyl, C$_{3-7}$cycloalkyl, C$_{3-7}$cycloalkenyl, C$_{3-7}$cycloalkylC$_{1-6}$alkyl, phenyl, benzyl, 4-10 membered heterocyclyl, 5-10 membered heteroaryl;

wherein phenyl, heterocyclyl C$_{3-7}$cycloalkyl, and C$_{3-7}$cycloalkylC$_{1-6}$alkyl is optionally substituted by one or more substituents selected from C$_{1-6}$ alkyl, C$_{1-6}$alkoxy, halo, phenyl optionally further substituted with halo; heterocyclyl optionally further substituted with C$_{1-6}$alkyl or haloC$_{1-6}$alkyl.

5. The method according to claim 4, comprising administering a compound of Formula (II), or a pharmaceutically acceptable salt thereof, wherein R$^{3a}$ is H; NH$_2$ or hydroxyC$_{1-3}$alkyl;

R$^{3b}$ is selected from the group consisting of halo, C$_{1-6}$alkyl, haloC$_{1-6}$alkyl, C$_{3-7}$cycloalkyl, OR$^5$, 4-10 membered heterocyclyl, 5- to 10-membered heteroaryl, phenyl, and wherein said heterocyclyl, heteroaryl, phenyl and cycloalkyl is further optionally substituted with one or more substituents independently selected from C$_{1-6}$alkyl, C$_{1-6}$alkoxy, haloC$_{1-6}$alkoxy, halo and haloC$_{1-6}$ alkyl; wherein R$^5$ is C$_{1-6}$alkyl, haloC$_{1-6}$alkyl, C$_{3-7}$cycloalkyl, phenyl, benzyl, 4-10 membered heterocyclyl, 5-10 membered heteroaryl;

wherein phenyl, heterocyclyl or C$_{3-7}$cycloalkyl is optionally substituted by one or more substituents independently selected from C$_{1-6}$alkyl, haloC$_{1-6}$alkyl, C$_{1-6}$alkoxy and halo; and R$^{3c}$ is H or halo.

6. The method according to claim 1, comprising administering a compound of Formula (III); or a pharmaceutically acceptable salt thereof:

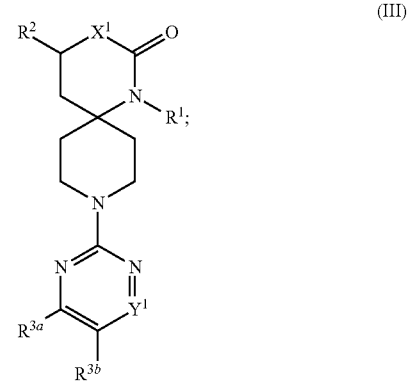

(III)

wherein wherein Y$^1$ is N or CR$^{3c}$; and wherein R$^{3a}$, R$^{3b}$ and R$^{3c}$ are independently selected from the group consisting of H, C$_{6-10}$aryl, benzyl, C$_{1-6}$alkyl, C$_{3-7}$cycloalkoxy, hydroxyC$_{1-6}$alkyl, C$_{1-6}$alkoxyC$_{1-6}$ alkyl, halo, haloC$_{1-6}$alkyl, OR$^5$, CN, C(O)OC$_{1-6}$alkyl, OH, C$_{3-7}$cycloalkyl, C$_{3-7}$cycloalkenyl, 5- to 10 membered heteroaryl, 4-10 membered heterocyclyl, —C(O)NH$_2$, and NR$^a$R$^b$, wherein R$^a$ and R$^b$ are independently H, C$_{1-6}$alkyl, C$_{3-7}$cycloalkyl, C$_{3-7}$cycloalkyl-C$_{1-6}$alkyl or halo C$_{1-6}$alkyl;

wherein said aryl, heterocyclyl, heteroaryl, C$_{3-7}$cycloalkyl, C$_{3-7}$cycloalkenyl, C$_{3-7}$cycloalkoxy are further optionally substituted with one or more substituents independently selected from OH, CN, C$_{3-7}$cycloalkyl, C$_{3-7}$cycloalkoxy, NH$_2$, C$_{1-6}$alkyl, C$_{1-6}$alkoxy, haloC$_{1-6}$alkoxy, hydroxyC1-6alkyl, —S—C$_{1-6}$alkyl; —S-(haloC$_{1-6}$alkyl), halo, haloC$_{1-6}$alkyl, —C(O)—C$_{1-6}$alkyl, phenyl optionally further substituted with halo; and heteroaryl optionally substituted with halo, C$_{1-6}$alkyl, haloC$_{1-6}$alkyl or C$_{3-7}$cycloalkyl;

R$^5$ is C$_{1-6}$alkyl, haloC$_{1-6}$alkyl, hydroxyC$_{1-6}$alkyl, alkoxyC$_{1-6}$alkyl, C$_{3-7}$cycloalkyl, C$_{3-7}$cycloalkenyl, C$_{3-7}$cycloalkylC$_{1-6}$alkyl, phenyl, benzyl, 4-10 membered heterocyclyl, 5-10 membered heteroaryl;

wherein phenyl, heterocyclyl C$_{3-7}$cycloalkyl, and C$_{3-7}$cycloalkylC$_{1-6}$alkyl is optionally substituted by one or more substituents selected from C$_{1-6}$ alkyl, C$_{1-6}$alkoxy, halo, phenyl optionally further substituted with halo; heterocyclyl optionally further substituted with C$_{1-6}$alkyl or haloC$_{1-6}$alkyl.

7. The method according to claim 1, comprising administering a compound of Formula (IV); or a pharmaceutically acceptable salt thereof:

(IV)

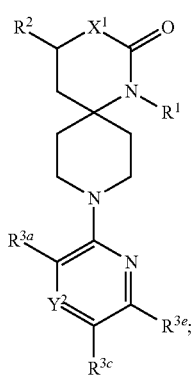

and wherein
$R^1$ is as defined in Formula I,
$Y^2$ is N or $CR^{3b}$; and wherein
$R^{3a}$, $R^{3b}$, $R^{3c}$ and $R^{3e}$ are independently selected from H, $C_{6-10}$aryl, benzyl, $C_{1-6}$alkyl, $C_{3-7}$cycloalkoxy, hydroxyC$_{1-6}$alkyl, $C_{1-6}$alkoxyC$_{1-6}$alkyl, halo, haloC$_{1-6}$alkyl, $OR^5$, CN, C(O)OC$_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein $R^a$ and $R^b$ are independently H, $C_{1-6}$alkyl, $C_{3-7}$cycloalkyl, $C_{3-7}$cycloalkyl-C$_{1-6}$alkyl or halo C$_{1-6}$alkyl;
wherein said aryl, heterocyclyl, heteroaryl, $C_{3-7}$cycloalkyl, $C_{3-7}$cycloalkenyl, $C_{3-7}$cycloalkoxy are further optionally substituted with one or more substituents independently selected from OH, CN, $C_{3-7}$cycloalkyl, $C_{3-7}$cycloalkoxy, NH$_2$, $C_{1-6}$alkyl, $C_{1-6}$alkoxy, haloC$_{1-6}$alkoxy, hydroxyC1-6alkyl, —S—C$_{1-6}$alkyl; —S-(haloC$_{1-6}$alkyl), halo, haloC$_{1-6}$alkyl, —C(O)—C$_{1-6}$alkyl, phenyl optionally further substituted with halo; and heteroaryl optionally substituted with halo, C$_{1-6}$alkyl, haloC$_{1-6}$alkyl or $C_{3-7}$cycloalkyl;
$R^5$ is $C_{1-6}$alkyl, haloC$_{1-6}$alkyl, hydroxyC$_{1-6}$alkyl, alkoxyC$_{1-6}$alkyl, $C_{3-7}$cycloalkyl, $C_{3-7}$cycloalkenyl, $C_{3-7}$cycloalkylC$_{1-6}$alkyl, phenyl, benzyl, 4-10 membered heterocyclyl, 5-10 membered heteroaryl;
wherein phenyl, heterocyclyl $C_{3-7}$cycloalkyl, and $C_{3-7}$cycloalkylC$_{1-6}$alkyl is optionally substituted by one or more substituents selected from $C_{1-6}$ alkyl, $C_{1-6}$alkoxy, halo, phenyl optionally further substituted with halo; heterocyclyl optionally further substituted with C$_{1-6}$alkyl or haloC$_{1-6}$alkyl.

8. The method according to claim 1 comprising administering a compound of Formula (V); or a pharmaceutically acceptable salt thereof:

(V)

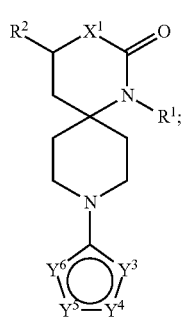

wherein
$Y^3$ is N, NR$^{3d}$ or CR$^{3a}$;
$Y^4$ is N, NR$^{3f}$ or CR$^{3b}$;
$Y^5$ is N, NR$^{3g}$ or CR$^{3c}$;
$Y^6$ is N, NR$^{3h}$ or R$^{3e}$;
wherein $R^{3a}$, $R^{3b}$, $R^{3c}$, $R^{3e}$ are independently selected from H, $C_{6-10}$aryl, benzyl, $C_{1-6}$alkyl, $C_{3-7}$cycloalkoxy, hydroxyC$_{1-6}$alkyl, $C_{1-6}$alkoxyC$_{1-6}$alkyl, halo, haloC$_{1-6}$alkyl, $OR^5$, CN, C(O)OC$_{1-6}$alkyl, OH, $C_{3-7}$cycloalkyl, $C_{3-7}$cycloalkenyl, 5- to 10 membered heteroaryl, 4-10 membered heterocyclyl, —C(O)NH$_2$, and NR$^a$R$^b$, wherein $R^a$ and $R^b$ are independently H, $C_{1-6}$alkyl, $C_{3-7}$cycloalkyl, $C_{3-7}$cycloalkyl-C$_{1-6}$alkyl or halo C$_{1-6}$alkyl;
wherein said aryl, heterocyclyl, heteroaryl, $C_{3-7}$cycloalkyl, $C_{3-7}$cycloalkenyl, $C_{3-7}$cycloalkoxy are further optionally substituted with one or more substituents independently selected from OH, CN, $C_{3-7}$cycloalkyl, C3-7cycloalkoxy, NH$_2$, $C_{1-6}$alkyl, $C_{1-6}$alkoxy, haloC$_{1-6}$alkoxy, hydroxyC1-6alkyl, —S—C$_{1-6}$alkyl; —S-(haloC$_{1-6}$alkyl), halo, haloC$_{1-6}$alkyl, —C(O)—C$_{1-6}$alkyl, phenyl optionally further substituted with halo; and heteroaryl optionally substituted with halo, C$_{1-6}$alkyl, haloC$_{1-6}$alkyl or $C_{3-7}$cycloalkyl;
$R^5$ is $C_{1-6}$alkyl, haloC$_{1-6}$alkyl, hydroxyC$_{1-6}$alkyl, alkoxyC$_{1-6}$alkyl, $C_{3-7}$cycloalkyl, $C_{3-7}$cycloalkenyl, $C_{3-7}$cycloalkylC$_{1-6}$alkyl, phenyl, benzyl, 4-10 membered heterocyclyl, 5-10 membered heteroaryl;
wherein phenyl, heterocyclyl and $C_{3-7}$cycloalkyl, and $C_{3-7}$cycloalkylC$_{1-6}$alkyl is optionally substituted by one or more substituents selected from $C_{1-6}$ alkyl, $C_{1-6}$alkoxy, halo, phenyl optionally further substituted with halo; heterocyclyl optionally further substituted with C$_{1-6}$alkyl or haloC$_{1-6}$alkyl;
wherein $R^{3d}$, $R^{3f}$, $R^{3g}$, $R^{3h}$ are independently selected from H, $C_{6-10}$aryl, C$_{1-6}$alkyl, haloC$_{1-6}$alkyl, $C_{3-6}$cycloalkyl, 5- or 6-membered heteroaryl;
and wherein said aryl, heteroaryl, $C_{3-6}$cycloalkyl are further optionally substituted with one or more substituents independently selected from $C_{3-6}$cycloalkyl, $C_{1-6}$alkyl, $C_{1-6}$alkoxy, haloC$_{1-6}$ alkoxy, halo and haloC$_{1-6}$alkyl.

9. The method according to claim 8, comprising administering a compound of Formula (V), or a pharmaceutically acceptable salt thereof, wherein the moiety:

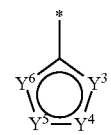

is selected from the following:

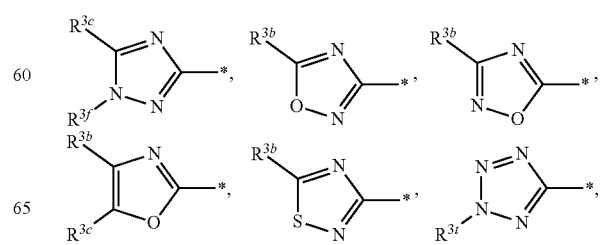

wherein $R^{3a}$, $R^{3b}$, $R^{3c}$, $R^{3e}$ and $R^{3f}$ are as defined in claim 8 and wherein * depicts the point of attachment to the nitrogen of the spiropiperidinyl moiety.

10. The method according to claim 1 comprising administering a compound of Formula (I), or a pharmaceutically acceptable salt thereof, wherein $R^1$ is phenyl optionally substituted with one or two substitutents independently selected from F and Cl.

11. The method according to claim 1 comprising administering a compound of Formula (I), or a pharmaceutically acceptable salt thereof, wherein $X^1$ is $CH_2$ and $R^2$ is F or H.

12. The method according to claim 1 comprising administering a compound of Formula (I), or a pharmaceutically acceptable salt thereof, wherein $X^1$ is O and $R^2$ is H.

13. The method according to claim 1, comprising administering a compound selected from:
- 1-(4-chloro-3-fluorophenyl)-9-(1-(4-fluorophenyl)-1H-1,2,4-triazol-3-yl)-1,9-diazaspiro[5.5]undecan-2-one;
- 1-(4-chloro-3-fluorophenyl)-9-(6-(trifluoromethyl)benzo[d]oxazol-2-yl)-1,9-diazaspiro[5.5]undecan-2-one;
- 1-(4-chloro-3-fluorophenyl)-9-(2-(trifluoromethyl)pyrazolo[1,5-a]pyrimidin-5-yl)-1,9-diazaspiro[5.5]undecan-2-one;
- 1-(3,4-difluorophenyl)-9-(6-(2,2,2-trifluoroethoxy)pyrimidin-4-yl)-1,9-diazaspiro[5.5]undecan-2-one;
- 1-(4-chloro-3-fluorophenyl)-9-(6-(2,2,2-trifluoroethoxy)pyrimidin-4-yl)-1,9-diazaspiro[5.5]undecan-2-one;
- 1-(4-chloro-3-fluorophenyl)-9-(6-(2,2-difluoroethoxy)pyrimidin-4-yl)-1,9-diazaspiro[5.5]undecan-2-one;
- 1-(4-chloro-3-fluorophenyl)-9-(5-fluoro-6-(pyrrolidin-1-yl)pyrimidin-4-yl)-1,9-diazaspiro[5.5]undecan-2-one;
- 1-(4-chloro-3-fluorophenyl)-9-(5-fluoro-6-(3-(trifluoromethyl)azetidin-1-yl)pyrimidin-4-yl)-1,9-diazaspiro[5.5]undecan-2-one;
- 1-(4-chloro-3-fluorophenyl)-9-(4-(pyrrolidin-1-yl)-1,3,5-triazin-2-yl)-1,9-diazaspiro[5.5]undecan-2-one;
- 1-(4-chloro-3-fluorophenyl)-9-(4-(2,2,2-trifluoroethoxy)pyridin-2-yl)-1,9-diazaspiro[5.5]undecan-2-one;
- 2-(1-(4-chloro-3-fluorophenyl)-2-oxo-1,9-diazaspiro[5.5]undecan-9-yl)-4-(4-fluorophenyl)pyridine 1-oxide;
- 9-(2-(5-azaspiro[2.3]hexan-5-yl)pyrimidin-4-yl)-1-(4-chloro-3-fluorophenyl)-1,9-diazaspiro[5.5]undecan-2-one;
- 9-(4-(5-azaspiro[2.3]hexan-5-yl)pyrimidin-2-yl)-1-(4-chloro-3-fluorophenyl)-1,9-diazaspiro[5.5]undecan-2-one;
- 1-(4-chloro-3-fluorophenyl)-9-(2-(3,3-dimethylazetidin-1-yl)pyrimidin-4-yl)-1,9-diazaspiro[5.5]undecan-2-one;
- 1-(4-chloro-3-fluorophenyl)-9-(5-((1R,2R/1S,2S)-2-(trifluoromethyl)cyclopropyl)-1,2,4-oxadiazol-3-yl)-1,9-diazaspiro[5.5]undecan-2-one;
- 1-(4-chloro-3-fluorophenyl)-9-(5-(3-(trifluoromethyl)bicyclo[1.1.1]pentan-1-yl)-1,2,4-oxadiazol-3-yl)-1,9-diazaspiro[5.5]undecan-2-one;
- 1-(4-chloro-3-fluorophenyl)-9-(6-hydroxy-3-(pyrrolidin-1-yl)-1,2,4-triazin-5-yl)-1,9-diazaspiro[5.5]undecan-2-one;
- 1-(4-chloro-3-fluorophenyl)-9-(6-(4-fluorophenyl)-4-methyl-3-oxo-3,4-dihydropyrazin-2-yl)-1,9-diazaspiro[5.5]undecan-2-one;
- 1-(4-chloro-3-fluorophenyl)-9-(5-cyclopentyl-1,2,4-triazin-3-yl)-1,9-diazaspiro[5.5]undecan-2-one;
- 1-(4-chlorophenyl)-9-(6-(4-fluorophenyl)pyridin-2-yl)-1,9-diazaspiro[5.5]undecan-2-one 1-(4-chloro-3-fluorophenyl)-9-(4-(trifluoromethyl)pyrimidin-2-yl)-1,9-diazaspiro[5.5]undecan-2-one;
- 1-(4-chloro-3-fluorophenyl)-9-(7-(trifluoromethyl)quinazolin-2-yl)-1,9-diazaspiro[5.5]undecan-2-one;
- 1-(4-chloro-3-fluorophenyl)-9-(5-(4-fluorophenyl)oxazol-2-yl)-1,9-diazaspiro[5.5]undecan-2-one;
- 1-(4-chloro-3-fluorophenyl)-9-(2-phenyl-2H-tetrazol-5-yl)-1,9-diazaspiro[5.5]undecan-2-one;
- 1-(4-chloro-3-fluorophenyl)-9-(5-(3,3-difluoropyrrolidin-1-yl)-1,2,4-thiadiazol-3-yl)-1,9-diazaspiro[5.5]undecan-2-one;
- 1-(4-chloro-3-fluorophenyl)-9-(3-(4-fluorophenyl)-1H-1,2,4-triazol-5-yl)-1,9-diazaspiro[5.5]undecan-2-one;
- 1-(4-chloro-3-fluorophenyl)-9-(5-cyclohexyloxazol-2-yl)-1,9-diazaspiro[5.5]undecan-2-one;
- 1-(4-chloro-3-fluorophenyl)-9-(5-(3-(trifluoromethyl)azetidin-1-yl)-1,2,4-thiadiazol-3-yl)-1,9-diazaspiro[5.5]undecan-2-one;
- 1-(4-chloro-3-fluorophenyl)-9-(5-(pyrrolidin-1-yl)-1,2,4-thiadiazol-3-yl)-1,9-diazaspiro[5.5]undecan-2-one;
- 1-(4-chloro-3-fluorophenyl)-9-(5-phenyl-1,3,4-oxadiazol-2-yl)-1,9-diazaspiro[5.5]undecan-2-one;
- 1-(4-chloro-3-fluorophenyl)-9-(1-(4-fluorophenyl)-1H-1,2,3-triazol-4-yl)-1,9-diazaspiro[5.5]undecan-2-one;
- 1-(4-chloro-3-fluorophenyl)-9-(1-(4-fluorophenyl)-1H-pyrazol-3-yl)-1,9-diazaspiro[5.5]undecan-2-one;
- 1-(4-chloro-3-fluorophenyl)-9-(2-(4-fluorophenyl)-2H-1,2,3-triazol-4-yl)-1,9-diazaspiro[5.5]undecan-2-one;
- 4-(3-chlorophenoxy)-2-(1-(3,4-difluorophenyl)-2-oxo-1,9-diazaspiro[5.5]undecan-9-yl)pyridine 1-oxide;
- 9-(4-(4-amino-4-(trifluoromethyl)piperidin-1-yl)pyrimidin-2-yl)-1-(3,4-difluorophenyl)-1,9-diazaspiro[5.5]undecan-2-one;
- 1-(3,4-difluorophenyl)-9-(4-(4-hydroxy-4-(trifluoromethyl)piperidin-1-yl)-1,3,5-triazin-2-yl)-1,9-diazaspiro[5.5]undecan-2-one;
- 9-(2-amino-5-fluoro-6-(4-hydroxy-4-(trifluoromethyl)piperidin-1-yl)pyrimidin-4-yl)-1-(3,4-difluorophenyl)-1,9-diazaspiro[5.5]undecan-2-one;
- 1-(3,4-difluorophenyl)-9-(6-(4-hydroxy-4-(trifluoromethyl)piperidin-1-yl)pyridazin-4-yl)-1,9-diazaspiro[5.5]undecan-2-one;
- 9-(6-amino-2-(3-hydroxy-3-methylazetidin-1-yl)pyrimidin-4-yl)-1-(3,4-difluorophenyl)-1,9-diazaspiro[5.5]undecan-2-one;
- 1-(4-chloro-3-fluorophenyl)-9-(6-(3,3,4,4-tetrafluoropyrrolidin-1-yl)pyrimidin-4-yl)-1,9-diazaspiro[5.5]undecan-2-one;
- 9-(6-(1,4-oxazepan-4-yl)pyrimidin-4-yl)-1-(3,4-difluorophenyl)-1,9-diazaspiro[5.5]undecan-2-one;
- rac-9-(2-amino-6-((1R,4R)-2-oxa-5-azabicyclo[2.2.1]heptan-5-yl)pyrimidin-4-yl)-1-(3,4-difluorophenyl)-1,9-diazaspiro[5.5]undecan-2-one;
- 1-(3,4-difluorophenyl)-9-(6-(4-(trifluoromethyl)-1H-pyrazol-1-yl)pyrimidin-4-yl)-1,9-diazaspiro[5.5]undecan-2-one;

1-(3,4-difluorophenyl)-9-(2-methyl-6-(1H-pyrazol-1-yl)pyrimidin-4-yl)-1,9-diazaspiro[5.5]undecan-2-one;

4-(1-(3,4-difluorophenyl)-2-oxo-1,9-diazaspiro[5.5]undecan-9-yl)-6-(1H-pyrazol-1-yl)pyrimidine-2-carbonitrile;

1-(3,4-difluorophenyl)-9-(2-methoxy-6-(1H-pyrazol-1-yl)pyrimidin-4-yl)-1,9-diazaspiro[5.5]undecan-2-one;

9-(6-(1H-pyrazol-1-yl)-2-(trifluoromethyl)pyrimidin-4-yl)-1-(3,4-difluorophenyl)-1,9-diazaspiro[5.5]undecan-2-one;

1-(3,4-difluorophenyl)-9-(2-morpholino-6-(1H-pyrazol-1-yl)pyrimidin-4-yl)-1,9-diazaspiro[5.5]undecan-2-one;

1-(3,4-difluorophenyl)-9-(2-(dimethylamino)-6-(1H-pyrazol-1-yl)pyrimidin-4-yl)-1,9-diazaspiro[5.5]undecan-2-one;

9-(6-(1H-1,2,4-triazol-1-yl)pyrimidin-4-yl)-1-(3,4-difluorophenyl)-1,9-diazaspiro[5.5]undecan-2-one;

9-(6-(4-chloro-1H-pyrazol-1-yl)pyrimidin-4-yl)-1-(3,4-difluorophenyl)-1,9-diazaspiro[5.5]undecan-2-one;

9-(6-(4-fluoro-1H-pyrazol-1-yl)pyrimidin-4-yl)-1-(3,4-difluorophenyl)-1,9-diazaspiro[5.5]undecan-2-one;

1-(3,4-difluorophenyl)-9-(6-(3-(trifluoromethyl)-1H-pyrazol-1-yl)pyrimidin-4-yl)-1,9-diazaspiro[5.5]undecan-2-one;

1-(3,4-difluorophenyl)-9-(6-(4-(trifluoromethyl)-1H-imidazol-1-yl)pyrimidin-4-yl)-1,9-diazaspiro[5.5]undecan-2-one;

9-(2-amino-5-fluoro-6-(1H-pyrazol-1-yl)pyrimidin-4-yl)-1-(3,4-difluorophenyl)-1,9-diazaspiro[5.5]undecan-2-one;

9-(4-amino-6-(4-fluoro-1H-pyrazol-1-yl)-1,3,5-triazin-2-yl)-1-(3,4-difluorophenyl)-1,9-diazaspiro[5.5]undecan-2-one;

1-(3,4-difluorophenyl)-9-(6-(oxetan-3-yloxy)-2-(trifluoromethyl)pyrimidin-4-yl)-1,9-diazaspiro[5.5]undecan-2-one;

1-(3,4-difluorophenyl)-9-(6-(oxazol-2-yl)pyrimidin-4-yl)-1,9-diazaspiro[5.5]undecan-2-one;

9-(6-amino-2-(pyridin-2-yl)pyrimidin-4-yl)-1-(3,4-difluorophenyl)-1,9-diazaspiro[5.5]undecan-2-one;

9-(2-amino-6-(4-(trifluoromethyl)-1H-pyrazol-1-yl)pyrimidin-4-yl)-1-(3,4-difluorophenyl)-1,9-diazaspiro[5.5]undecane-2-one;

1-(3,4-difluorophenyl)-9-(2-(2-hydroxypropan-2-yl)-6-(4-(trifluoromethyl)-1H-pyrazol-1-yl)pyrimidin-4-yl)1,9-diazaspiro[5.5]undecane-2-one;

1-(3,4-difluorophenyl)-9-(2-(hydroxymethyl)-6-(4-(trifluoromethyl)-1H-pyrazol-1-yl)pyrimidin-4-yl)1,9-diazaspiro[5.5]undecane-2-one;

rac-1-(3,4-difluorophenyl)-9-(2-(1-hydroxymethyl)-6-(4-(trifluoromethyl)-1H-pyrazol-1-yl)pyrimidin-4-yl)1,9-diazaspiro[5.5]undecane-2-one;

4-(1-(3,4-difluorophenyl)-2-oxo-1,9-diazaspiro[5.5]undecane-9-yl-6-(4-(trifluoromethyl)-1H-pyrazol-1-yl)pyrimidin-2-carboxamide;

9-(2-chloro-6-(4-(trifluoromethyl)-1H-pyrazol-1-yl)pyrimidin-4-yl)-1-(3,4-difluorophenyl)-1,9-diazaspiro[5.5]undecan-2-one;

(R)-9-(2-chloro-6-((tetrahydrofuran-3-yl)oxy)pyrimidin-4-yl)-1-(3,4-difluorophenyl)-1,9-diazaspiro[5.5]undecan-2-one;

(S)-9-(2-chloro-6-((tetrahydrofuran-3-yl)oxy)pyrimidin-4-yl)-1-(3,4-difluorophenyl)-1,9-diazaspiro[5.5]undecan-2-one;

(R)-9-(4-chloro-6-((tetrahydrofuran-3-yl)oxy)pyrimidin-2-yl)-1-(3,4-difluorophenyl)-1,9-diazaspiro[5.5]undecan-2-one;

1-(3,4-difluorophenyl)-9-(6-(4-fluoro-1H-pyrazol-1-yl)-2-morpholinopyrimidin-4-yl)-1,9-diazaspiro[5.5]undecan-2-one;

9-(2-amino-6-(4,4-difluorocyclohex-1-en-1-yl)pyrimidin-4-yl)-1-(3,4-difluorophenyl)-1,9-diazaspiro[5.5]undecan-2-one;

9-(2-amino-6-(4-fluorophenyl-4-yl)-1-(3,4-difluorophenyl)-1,9-diazaspiro[5.5]undecane-2-one;

9-(2-amino-6-(trifluoromethyl)pyrimidin-4-yl)-1-(3,4-difluorophenyl)-1,9-diazaspiro[5.5]undecan-2-one;

9-(2-amino-6-(perfluoroethyl)pyrimidin-4-yl)-1-(3,4-difluorophenyl)-1,9-diazaspiro[5.5]undecane-2-one;

9-(2-amino-6-(1,1,2,2-tetrafluoroethyl)pyrimidin-4-yl)-1-(3,4-difluorophenyl)-1,9-diazaspiro[5.5]undecan-2-one;

1-(3,4-difluorophenyl)-9-(2-(hydroxymethyl)-6-(perfluoroethyl)pyrimidin-4-yl)-1,9-diazaspiro[5.5]undecane-2-one;

1-(3,4-difluorophenyl)-9-(2-(2-hydroxypropan-2-yl)-6-(trifluoromethyl)pyrimidin-4-yl)-1,9-diazaspiro[5.5]undecan-2-one;

1-(4-chloro-3-fluorophenyl)-9-(4-(2,2,2-trifluoroethoxy)pyridin-2-yl)-1,9-diazaspiro[5.5]undecan-2-one;

1-(3,4-difluorophenyl)-9-(4-propoxypyrimidin-2-yl)-1,9-diazaspiro[5.5]undecan-2-one;

rac-1-(3,4-difluorophenyl)-9-(6-((1,1,1-trifluoropropan-2-yl)oxy)pyrimidin-4-yl)-1,9-diazaspiro[5.5]undecan-2-one;

1-(3,4-difluorophenyl)-9-(6-((tetrahydro-2H-pyran-4-yl)oxy)pyrimidin-4-yl)-1,9-diazaspiro[5.5]undecan-2-one;

9-(2-chloro-6-(2,2,2-trifluoroethoxy)pyrimidin-4-yl)-1-(3,4-difluorophenyl)-1,9-diazaspiro[5.5]undecan-2-one;

(S)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one;

(R)-9-(2-amino-6-(2,2,2-trifluoro-1-(oxetan-3-yl)ethoxy)pyrimidin-4-yl)-1-(3,4-difluorophenyl)-1,9-diazaspiro[5.5]undecan-2-one;

9-(2-amino-6-(3,3-difluorocyclobutoxy)pyrimidin-4-yl)-1-(3,4-difluorophenyl)-1,9-diazaspiro[5.5]undecan-2-one;

9-(2-amino-6-(2,2,2-trifluoroethoxy)pyrimidin-4-yl)-1-(3,4-difluorophenyl)-1,9-diazaspiro[5.5]undecan-2-one;

9-(2-amino-6-(2,2,2-trifluoroethoxy-1,1-d2)pyrimidin-4-yl)-1-(3,4-difluorophenyl)-1,9-diazaspiro[5.5]undecan-2-one;

9-(2-amino-6-isopropoxypyrimidin-4-yl)-1-(3,4-difluorophenyl)-1,9-diazaspiro[5.5]undecan-2-one;

9-(2-amino-6-(2-hydroxyethoxy)pyrimidin-4-yl)-1-(3,4-difluorophenyl)-1,9-diazaspiro[5.5]undecan-2-one;

rac-9-(2-amino-6-((1,1,1-trifluoropropan-2-yl)oxy)pyrimidin-4-yl)-1-(3,4-difluorophenyl)-1,9-diazaspiro[5.5]undecan-2-one;

rac-9-(2-amino-6-(2,2,2-trifluoro-1-(3-methyl oxetan-3-yl)ethoxy)pyrimidin-4-yl)-1-(3,4-difluorophenyl)-1,9-diazaspiro[5.5]undecan-2-one;

9-(2-amino-6-(2,2,3,3,3-pentafluoropropoxy)pyrimidin-4-yl)-1-(3,4-difluorophenyl)-1,9-diazaspiro[5.5]undecan-2-one;

rac-9-(2-amino-6-((4,4-difluorotetrahydrofuran-3-yl)oxy)pyrimidin-4-yl)-1-(3,4-difluorophenyl)-1,9-diazaspiro[5.5]undecan-2-one;

rac-9-(2-amino-6-(((3S,4S)-3-fluorotetrahydro-2H-pyran-4-yl)oxy)pyrimidin-4-yl)-1-(3,4-difluorophenyl)-1,9-diazaspiro[5.5]undecan-2-one;

(R)-9-(2-amino-6-((tetrahydro-2H-pyran-3-yl)oxy)pyrimidin-4-yl)-1-(3,4-difluorophenyl)-1,9-diazaspiro[5.5]undecan-2-one;

9-(2-amino-6-((tetrahydro-2H-pyran-4-yl)oxy)pyrimidin-4-yl)-1-(3,4-difluorophenyl)-1,9-diazaspiro[5.5]undecan-2-one;

rac-9-(2-amino-6-(((3R,4R)-4-fluorotetrahydrofuran-3-yl)oxy)pyrimidin-4-yl)-1-(3,4-difluorophenyl)-1,9-diazaspiro[5.5]undecan-2-one;

9-(2-amino-6-((tetrahydro-2H-pyran-4-yl-4-d)oxy)pyrimidin-4-yl)-1-(3,4-difluorophenyl)-1,9-diazaspiro[5.5]undecan-2-one;

rac-9-(2-amino-6-((3-methyltetrahydrofuran-3-yl)oxy)pyrimidin-4-yl)-1-(3,4-difluorophenyl)-1,9-diazaspiro[5.5]undecan-2-one;

rac-9-(2-amino-6-(((3S,4R)-4-fluorotetrahydrofuran-3-yl)oxy)pyrimidin-4-yl)-1-(3,4-difluorophenyl)-1,9-diazaspiro[5.5]undecan-2-one;

1-(3,4-difluorophenyl)-9-(2-(hydroxymethyl)-6-((tetrahydro-2H-pyran-4-yl)oxy)pyrimidin-4-yl)-1,9-diazaspiro[5.5]undecan-2-one;

rac-1-(3,4-difluorophenyl)-9-(6-(((3S,4R)-3-fluorotetrahydro-2H-pyran-4-yl)oxy)-2-(hydroxymethyl)pyrimidin-4-yl)-1,9-diazaspiro[5.5]undecan-2-one;

rac-1-(3,4-difluorophenyl)-9-(6-(((3R,4R)-4-fluorotetrahydrofuran-3-yl)oxy)-2-(hydroxymethyl)pyrimidin-4-yl)-1,9-diazaspiro[5.5]undecan-2-one;

(S)-1-(3,4-difluorophenyl)-9-(2-(hydroxymethyl)-6-((tetrahydrofuran-3-yl)oxy)pyrimidin-4-yl)-1,9-diazaspiro[5.5]undecan-2-one;

(S)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one;

(R)-1-(3,4-difluorophenyl)-9-(2-(hydroxymethyl)-6-((1,1,1-trifluoropropan-2-yl)oxy)pyrimidin-4-yl)-1,9-diazaspiro[5.5]undecan-2-one;

rac ethyl 4-(1-(3,4-difluorophenyl)-2-oxo-1,9-diazaspiro[5.5]undecane-9-yl)-6-(((3S,4S)-4-fluorotetrahydrofuran-3-yl)oxy)pyrimidine-2-carboxylate;

(R)-9-(2-amino-6-((tetrahydrofuran-3-yl)amino)pyrimidin-4-yl)-1-(3,4-difluorophenyl)-1,9-diazaspiro[5.5]undecan-2-one;

(R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

(S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

1-(3,4-difluorophenyl)-9-(2-(hydroxymethyl)-6-(4-(trifluoromethyl)-1H-pyrazol-1-yl)pyrimidin-4-yl)-3-oxa-1,9-diazaspiro[5.5]undecan-2-one;

9-(2-amino-6-(4-(trifluoromethyl)-1H-pyrazol-1-yl)pyrimidin-4-yl)-1-(3,4-difluorophenyl)-3-oxa-1,9-diazaspiro[5.5]undecan-2-one;

(R)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

(S)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

(S)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

(R)-9-(2-amino-6-((tetrahydro-2H-pyran-4-yl)oxy)pyrimidin-4-yl)-1-(3,4-difluorophenyl)-4-fluoro-1,9-diazaspiro[5.5]undecan-2-one;

rac-9-(2-amino-6-(perfluoroethyl)pyrimidin-4-yl)-1-(3,4-difluorophenyl)-4-fluoro-1,9-diazaspiro[5.5]undecan-2-one;

rac-1-(3,4-difluorophenyl)-4-fluoro-9-(6-((tetrahydro-2H-pyran-4-yl)oxy)pyrimidin-4-yl)-1,9-diazaspiro[5.5]undecan-2-one;

9-(2-amino-6-(1,1-difluoroethyl)pyrimidin-4-yl)-1-(3,4-difluorophenyl)-1,9-diazaspiro[5.5]undecan-2-one; and 1-(3,4-difluorophenyl)-4-fluoro-9-(6-(2,2,2-trifluoroethoxy)pyrimidin-4-yl)-1,9-diazaspiro[5.5]undecan-2-one; or a pharmaceutically acceptable salt thereof.

14. The method according to claim 1, comprising administering a compound selected from the group consisting of:

1-(3,4-difluorophenyl)-9-(6-(2,2,2-trifluoroethoxy)pyrimidin-4-yl)-1,9-diazaspiro[5.5]undecan-2-one;

9-(2-amino-6-(4-(trifluoromethyl)-1H-pyrazol-1-yl)pyrimidin-4-yl)-1-(3,4-difluorophenyl)-1,9-diazaspiro[5.5]undecane-2-one;

(R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one, (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one;

9-(2-amino-6-(1,1-difluoroethyl)pyrimidin-4-yl)-1-(3,4-difluorophenyl)-1,9-diazaspiro[5.5]undecan-2-one; and 9-(2-amino-6-(trifluoromethyl)pyrimidin-4-yl)-1-(3,4-difluorophenyl)-1,9-diazaspiro[5.5]undecan-2-one; or a pharmaceutically acceptable salt thereof.

15. The method according to claim 1, wherein the skin disease is selected from psoriasis, atopic dermatitis, eczema and chronic urticaria.

16. The method according to claim 1 comprising administering a compound which is (R)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one; or (S)-9-(2-amino-6-((1,1,1-trifluoropropan-2-yl)oxy)pyrimidin-4-yl)-1-(3,4-difluorophenyl)-3-oxa-1,9-diazaspiro[5.5]undecan-2-one; or a pharmaceutically acceptable salt thereof.

* * * * *